(12) United States Patent
Kawamura et al.

(10) Patent No.: US 9,147,847 B2
(45) Date of Patent: Sep. 29, 2015

(54) ANTHRACENE DERIVATIVE AND ORGANIC ELECTROLUMINESCENT ELEMENT USING THE SAME

(71) Applicant: IDEMITSU KOSAN CO., LTD., Tokyo (JP)

(72) Inventors: Masahiro Kawamura, Sodegaura (JP); Chishio Hosokawa, Sodegaura (JP); Masaki Numata, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 14/487,768

(22) Filed: Sep. 16, 2014

(65) Prior Publication Data

US 2015/0005512 A1   Jan. 1, 2015

Related U.S. Application Data

(63) Continuation of application No. 14/093,325, filed on Nov. 29, 2013, now Pat. No. 8,866,135, which is a continuation of application No. 13/375,020, filed as application No. PCT/JP2010/003471 on May 24, 2010, now Pat. No. 8,629,430.

(30) Foreign Application Priority Data

May 29, 2009 (JP) ................. 2009-131200

(51) Int. Cl.
| | |
|---|---|
| *H01L 21/02* | (2006.01) |
| *H01L 51/00* | (2006.01) |
| *C07D 307/79* | (2006.01) |
| *C07D 307/91* | (2006.01) |
| *C07D 307/92* | (2006.01) |
| *C07D 333/50* | (2006.01) |
| *C07D 333/74* | (2006.01) |
| *C07D 333/76* | (2006.01) |
| *C07D 493/04* | (2006.01) |
| *C07D 519/00* | (2006.01) |
| *C09K 11/06* | (2006.01) |
| *C07D 307/77* | (2006.01) |
| *H01L 51/50* | (2006.01) |

(52) U.S. Cl.
CPC .......... *H01L 51/0058* (2013.01); *C07D 307/77* (2013.01); *C07D 307/79* (2013.01); *C07D307/91* (2013.01); *C07D 307/92* (2013.01); *C07D 333/50* (2013.01); *C07D 333/74* (2013.01); *C07D 333/76* (2013.01); *C07D 493/04* (2013.01); *C07D 519/00* (2013.01); *C09K 11/06* (2013.01); *H01L 51/006* (2013.01); *H01L 51/0052* (2013.01); *H01L 51/0073* (2013.01); *H01L 51/0074* (2013.01); *C09K 2211/1011* (2013.01); *C09K 2211/1014* (2013.01); *H01L 51/5012* (2013.01)

(58) Field of Classification Search
CPC ....... H01L 51/0052–51/0068; H01L 51/51052
USPC ..................... 257/40, 103, E51.002
See application file for complete search history.

(56) References Cited

U.S. PATENT DOCUMENTS

| | | | |
|---|---|---|---|
| 6,344,284 | B1 | 2/2002 | Chou |
| 6,960,364 | B2 | 11/2005 | Suzuri et al. |
| 7,326,371 | B2 | 2/2008 | Conley et al. |
| 7,420,065 | B2 | 9/2008 | Yoshida et al. |
| 7,504,526 | B2 | 3/2009 | Kubota et al. |
| 7,833,632 | B2 | 11/2010 | Kawamura et al. |
| 8,253,129 | B2 | 8/2012 | Kawamura |
| 8,367,222 | B2 | 2/2013 | Arakane et al. |
| 8,629,430 | B2 * | 1/2014 | Kawamura et al. ............. 257/40 |
| 8,866,135 | B2 * | 10/2014 | Kawamura et al. ............. 257/40 |
| 2004/0137270 | A1 | 7/2004 | Seo et al. |
| 2004/0209118 | A1 | 10/2004 | Seo et al. |
| 2006/0235060 | A1 | 10/2006 | Yoshida et al. |
| 2007/0072002 | A1 | 3/2007 | Kim et al. |
| 2007/0247063 | A1 | 10/2007 | Murase et al. |
| 2008/0111473 | A1 | 5/2008 | Kawamura et al. |
| 2008/0152950 | A1 | 6/2008 | Je et al. |
| 2008/0297037 | A1 | 12/2008 | Vestweber et al. |
| 2008/0315754 | A1 | 12/2008 | Kawamura et al. |
| 2009/0131673 | A1 | 5/2009 | Tanabe et al. |
| 2009/0184313 | A1 | 7/2009 | Buesing et al. |

| | | | |
|---|---|---|---|
| 2009/0230855 A1 | 9/2009 | Kim et al. | |
| 2009/0247795 A1 | 10/2009 | Kawakami | |
| 2009/0261717 A1 | 10/2009 | Buesing et al. | |
| 2009/0299070 A1 | 12/2009 | Berens et al. | |
| 2010/0032658 A1 | 2/2010 | Lee et al. | |
| 2010/0033083 A1 | 2/2010 | Eum et al. | |
| 2010/0045170 A1 | 2/2010 | Lee et al. | |
| 2011/0108826 A1 | 5/2011 | Jang et al. | |
| 2011/0168992 A1 | 7/2011 | Bae et al. | |
| 2012/0037892 A1 | 2/2012 | Jang et al. | |
| 2012/0138914 A1 | 6/2012 | Kawamura et al. | |
| 2012/0319091 A1 | 12/2012 | Kato | |
| 2013/0153878 A1 | 6/2013 | Mizuki et al. | |
| 2013/0187137 A1 | 7/2013 | Mizuki et al. | |

FOREIGN PATENT DOCUMENTS

| | | |
|---|---|---|
| DE | 10 2005 058 557 | 6/2007 |
| EP | 1 437 395 | 12/2003 |
| EP | 1 593 675 A1 | 11/2005 |
| EP | 2 182 038 | 3/2009 |
| EP | 2 189 508 | 3/2009 |
| EP | 2 145 936 A2 | 1/2010 |
| EP | 2 145 936 A3 | 1/2010 |
| EP | 2189508 A2 | 5/2010 |
| EP | 2 332 931 A2 | 6/2011 |
| JP | 11-111460 | 4/1999 |
| JP | 2005-314239 | 11/2005 |
| JP | 2007-63501 | 3/2007 |
| JP | 2007-077094 | 3/2007 |
| JP | 2007-138228 | 6/2007 |
| JP | 2008-244424 | 10/2008 |
| JP | 2010-6811 | 1/2010 |
| JP | 2010-59147 | 3/2010 |
| JP | 2013-118288 | 6/2013 |
| KR | 10-2009-0065201 | 6/2009 |
| KR | 10-0910150 | 7/2009 |
| KR | 10-2009-0086015 | 8/2009 |
| KR | 10-2009-0129853 | 12/2009 |
| KR | 10-2009-0131958 | 12/2009 |
| KR | 10-2010-0002030 | 1/2010 |
| KR | 10-2010-0021367 | 2/2010 |
| KR | 10-2010-0066424 | 6/2010 |
| KR | 10-2010-0082676 | 7/2010 |
| KR | 10-2010-0094413 | 8/2010 |
| KR | 10-2011-0099195 | 9/2011 |
| WO | WO 2004/072053 A1 | 8/2004 |
| WO | 2004/078872 | 9/2004 |
| WO | WO 2005/113531 A1 | 12/2005 |
| WO | WO 2006/128800 A1 | 12/2006 |
| WO | WO 2007/068618 A1 | 6/2007 |
| WO | WO 2007/140847 A1 | 12/2007 |
| WO | WO 2008/006449 A1 | 1/2008 |
| WO | WO 2008/143229 A1 | 11/2008 |
| WO | 2010/005268 | 1/2010 |
| WO | 2010/036027 | 4/2010 |
| WO | 2010/085087 | 7/2010 |
| WO | 2010/114253 | 10/2010 |
| WO | 2010/114256 | 10/2010 |
| WO | WO 2010/114243 A2 | 10/2010 |

OTHER PUBLICATIONS

English translation of International Preliminary Report on PatentInternational Search Report issued Jun. 15, 2010, in Patent Application No. PCT/JP2010/003471. ability and Written Opinion of the International Searching Authority issued Dec. 22, 2011, in PCT/JP2010/003471.

Extended Search Report issued Nov. 16, 2012 in European Patent Application No. 10780246.4-2111.

Office Action issued Mar. 19, 2013 in Japanese Patent Application No. 2011-515879.

\* cited by examiner

*Primary Examiner* — Michael Lebentritt

(74) *Attorney, Agent, or Firm* — Oblon, McClelland, Maier & Neustadt, L.L.P.

(57) ABSTRACT

An anthracene derivative represented by the following formula (1):

In the formula (1), Z is a structure represented by the following formula (2). In the formula (2), at least one pair of adjacent two substituents of $R_{11}$ to $R_{18}$ form a ring represented by the following formula (3) or (4):

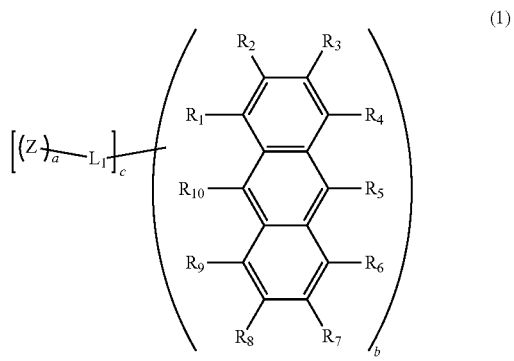

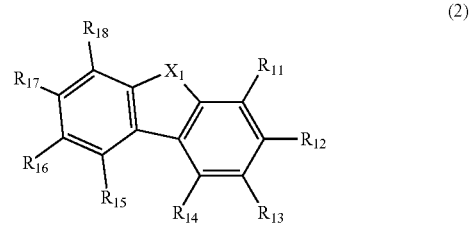

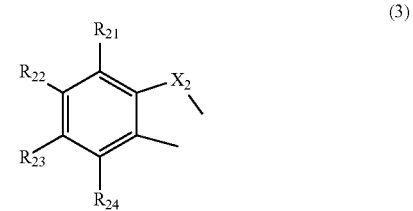

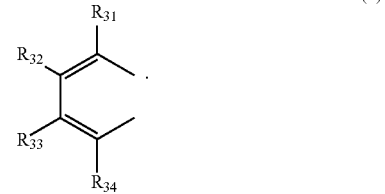

17 Claims, 1 Drawing Sheet

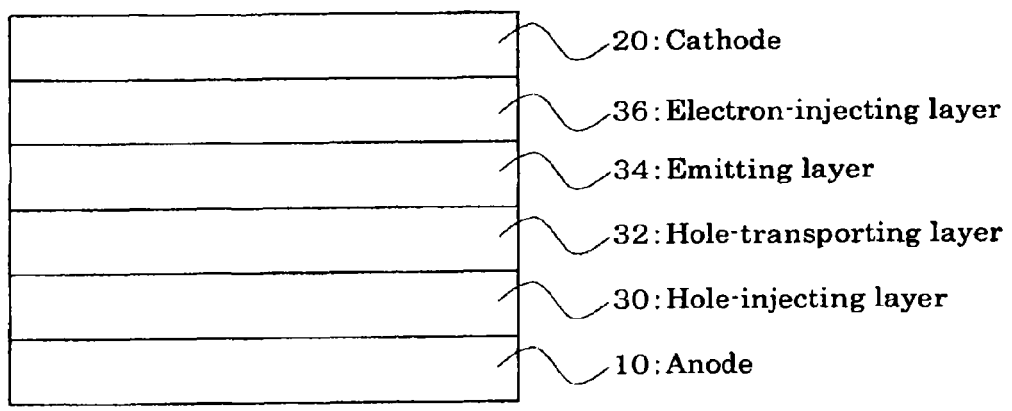

ANTHRACENE DERIVATIVE AND ORGANIC ELECTROLUMINESCENT ELEMENT USING THE SAME

This application is a continuation application of Ser. No. 14/093,325, filed on Nov. 29, 2013, which is a continuation application of Ser. No. 13/375,020, filed on Feb. 13, 2012 which is a 371 of PCT/JP10/003471, filed on May 24, 2010, now U.S. Pat. No. 8,629,430, which claims priority to JP 2009-131200, filed on May 29, 2009, the entire contents of which are incorporated herein by reference.

TECHNICAL FIELD

The invention relates to an anthracene derivative and an organic electroluminescence device using the same. In particular, the invention relates to an organic electroluminescence device having a prolonged lifetime and has a high luminous efficiency and an anthracene derivative which realizes the same.

BACKGROUND ART

An organic electroluminescence (EL) device is a promising solid-state emitting type inexpensive and large full-color display device, and has been extensively developed. In general, an organic EL device includes an emitting layer and a pair of opposing electrodes holding the emitting layer therebetween. When an electric field is applied between the both electrodes, electrons are injected from the cathode and holes are injected from the anode. The electrons recombine with the holes in the emitting layer to produce an excited state, and energy is emitted as light when the excited state returns to the ground state.

Conventional organic EL devices have a higher driving voltage than that of an inorganic light-emitting diode. The luminance or luminous efficiency thereof is also low, and their properties tend to deteriorate significantly. For these reasons, conventional organic EL devices have not been put in a practical use. Although recent organic EL devices have been improved gradually, further prolongation of lifetime, improvement in luminous efficiency or the like has been demanded.

The performance of an organic EL device has been gradually improved with improvements in emitting materials for an organic EL device. Improvement in luminous efficiency and prolongation of lifetime of an organic EL device is an important subject which leads to lowering in consumption power and improvement in durability of a display. Although luminous efficiency and lifetime of an organic EL device have been improved as a result of various studies, further improvement is demanded.

In order to solve these problems, Patent Documents 1 to 6 each disclose an organic EL device in which an anthracene derivative having dibenzofuran as a substituent is used as an emitting material. Although luminous efficiency is improved by using these materials, but the improvement was not sufficient. Further improvement in luminous efficiency and prolongation of lifetime has been required.

On the other hand, Patent Documents 4, 7 and 8 each disclose an emitting material having a fused dibenzofuran structure. However, an organic EL device using this emitting material has a defect that it has a poor efficiency and a significantly short life.

RELATED ART DOCUMENTS

Patent Documents

Patent Document 1: JP-A-H11-111460
Patent Document 2: JP-A-2005-314239
Patent Document 3: JP-A-2007-63501
Patent Document 4: WO06/128800
Patent Document 5: WO05/113531
Patent Document 6: WO08/143229
Patent Document 7: WO07/140847
Patent Document 8: WO08/6449

SUMMARY OF THE INVENTION

An object of the invention is to obtain an emitting material capable of realizing an organic EL device which has a long life and a high luminous efficiency.

According to the invention, the following anthracene derivative and the organic EL device are provided.

1. An anthracene derivative represented by the following formula (1):

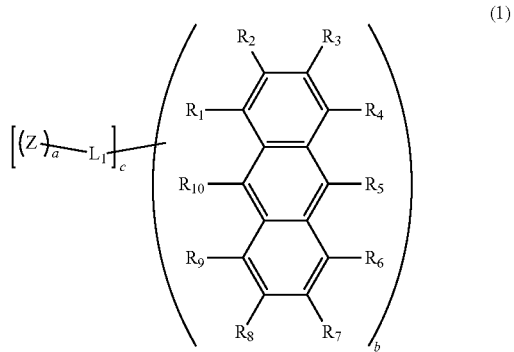

wherein in the formula (1), any one of $R_1$ to $R_{10}$ is used for bonding to $L_1$, the one used for bonding to $L_1$ is a single bond, $R_1$ to $R_{10}$ which are not used for bonding to $L_1$ are independently a hydrogen atom, a halogen atom, a hydroxyl group, a cyano group, a substituted or unsubstituted amino group, a substituted or unsubstituted alkyl group having 1 to 20 carbon atoms, a substituted or unsubstituted alkoxy group having 1 to 20 carbon atoms, a substituted or unsubstituted aryloxy group having 6 to 20 atoms that form a ring (hereinafter referred to as "ring carbon atoms"), a substituted or unsubstituted arylthio group having 6 to 20 ring carbon atoms, a substituted or unsubstituted aryl group having 6 to 50 ring carbon atoms or a substituted or unsubstituted heterocyclic group having 5 to 50 that form a ring (hereinafter referred to as "ring atoms");

$L_1$ is a single bond or a linkage group;

a, b and c are independently an integer of 1 to 4; and

Z is a structure represented by the following formula (2):

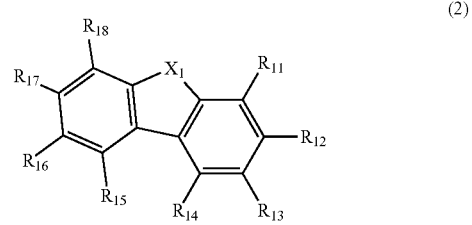

wherein in the formula (2), $R_{11}$ to $R_{18}$ are independently a hydrogen atom or a substituent and $X_1$ is an oxygen atom or a sulfur atom; and at least one pair of adjacent two substituents of $R_{11}$ to $R_{18}$ form a ring represented by the following formula (3) or (4):

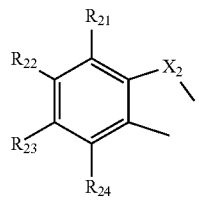
(3)

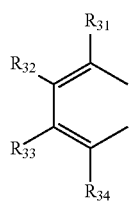
(4)

wherein in the formulas (3) and (4), $R_{21}$ to $R_{24}$ and $R_{31}$ to $R_{34}$ are independently a hydrogen atom or a substituent and $X_2$ is an oxygen atom or a sulfur atom;

any one of $R_{11}$ to $R_{18}$ which do not form a ring, $R_{21}$ to $R_{24}$ and $R_{31}$ to $R_{34}$ is used for bonding to $L_1$, and the ones used for bonding to $L_1$ are a single bond.

2. The anthracene derivative according to 1, wherein Z is represented by any of the following formulas (5) to (7):

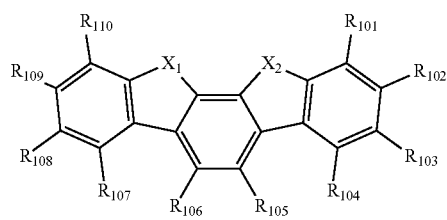
(5)

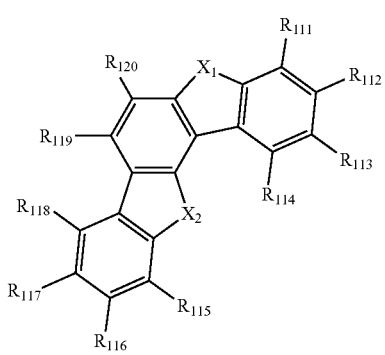
(6)

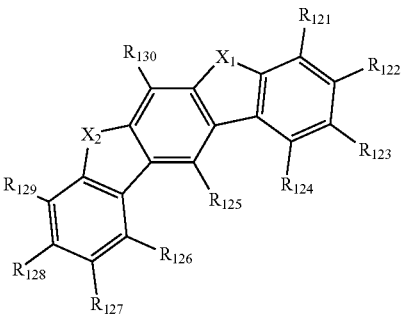
(7)

wherein in the formulas (5) to (7), $R_{101}$ to $R_{110}$, $R_{111}$ to $R_{120}$ and $R_{121}$ to $R_{130}$ are independently a hydrogen atom or a substituent; any one of $R_{101}$ to $R_{110}$, any one of $R_{111}$ to $R_{120}$, and any one of $R_{121}$ to $R_{130}$ are used for bonding to $L_1$, the ones used for bonding to $L_1$ are a single bond; and $X_1$ and $X_2$ are independently an oxygen atom or a sulfur atom.

3. The anthracene derivative according to 1, wherein Z is represented by any of the following formulas (8) to (10):

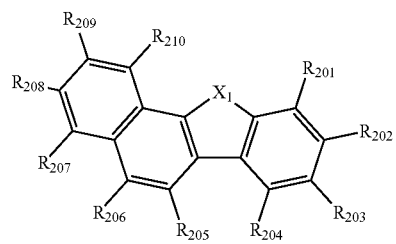
(8)

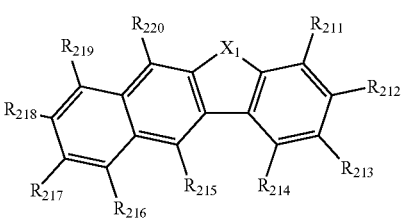
(9)

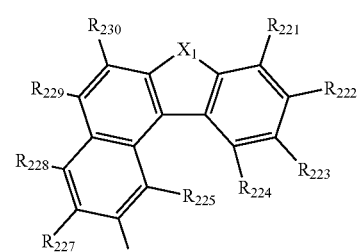
(10)

wherein in the formulas (8) to (10), $R_{201}$ to $R_{210}$, $R_{211}$ to $R_{220}$ and $R_{221}$ to $R_{230}$ are independently a hydrogen atom or a substituent; any one of $R_{201}$ to $R_{210}$, any one of $R_{211}$ to $R_{220}$ and any one of $R_{221}$ to $R_{230}$ are used for bonding to $L_1$; and the ones used for bonding to $L_1$ are a single bond; and $X_1$ is an oxygen atom or a sulfur atom.

4. The anthracene derivative according to any of 1 to 3, wherein b is 1 in the formula (1).

5. The anthracene derivative according to any of 1 to 4, wherein a is 1 or 2 in the formula (1).

6. The anthracene derivative according to any of 1 to 5, wherein $L_1$ is bonded to $R_5$ and/or $R_{10}$.
7. The anthracene derivative according to any of 1 to 5, wherein $L_1$ is bonded to any of $R_1$ to $R_4$.
8. The anthracene derivative according to 7, wherein $L_1$ is bonded to $R_2$.
9. The anthracene derivative according to any of 6 to 8, wherein $R_5$ is a group selected from a substituted or unsubstituted aryl group having 6 to 50 ring carbon atoms and a substituted or unsubstituted heterocyclic group having 5 to 50 ring atoms.
10. The anthracene derivative according to 7 or 8, wherein $R_5$ and/or $R_{10}$ is a group selected from a substituted or unsubstituted aryl group having 6 to 50 ring carbon atoms and a substituted or unsubstituted heterocyclic group having 5 to 50 ring atoms.
11. The anthracene derivative according to 9 or 10, wherein $R_5$ has a structure represented by the following formula (11):

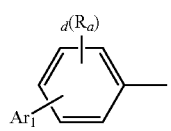

(11)

wherein in the formula (11), $Ar_1$ is a group selected from a substituted or unsubstituted aryl group having 6 to 30 ring carbon atoms and a substituted or unsubstituted heterocyclic group having 5 to 30 ring atoms; Ra is independently a hydrogen atom or a substituent; and d is an integer of 1 to 4.
12. The anthracene derivative according to 9 or 10, wherein $R_5$ is a substituted or unsubstituted fused aromatic ring having 10 to 30 ring carbon atoms.
13. The anthracene derivative according to any of 1 to 12, wherein $X_1$ and $X_2$ are oxygen atoms.
14. The anthracene derivative according to any of 1 to 13, which is a material for an organic electroluminescence device.
15. The anthracene derivative according to any of 1 to 14, which is an emitting material for an organic electroluminescence device.
16. An organic electroluminescence device which comprises between an anode and a cathode one or more organic thin film layers comprising an emitting layer, wherein at least one layer of the organic thin film layers comprises the anthracene derivative according to any of 1 to 15 singly or as a mixture component.
17. The organic electroluminescence device according to 16, wherein the emitting layer comprises the anthracene derivative.
18. The organic electroluminescence device according to 17, wherein the anthracene derivative is a host material.
19. The organic electroluminescence device according to 17 or 18, wherein the emitting layer further comprises a dopant material.
20. The organic electroluminescence device according to 19, wherein the dopant material is an arylamine compound.
21. The organic electroluminescence device according to 19, wherein the dopant material is a styrylamine compound.
22. The organic electroluminescence device according to 20, wherein the dopant material is a fused polycyclic amine derivative represented by the following formula (12):

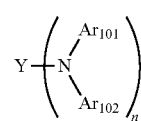

(12)

wherein in the formula (12), Y is a substituted or unsubstituted fused aryl group having 10 to 50 ring carbon atoms; $Ar_{101}$ and $Ar_{102}$ are independently an aryl group having 6 to 50 ring carbon atoms or a substituted or unsubstituted heterocyclic group having 5 to 50 ring atoms; and n is an integer of 1 to 4.
23. The organic electroluminescence device according to 22, wherein the dopant material is a fused polycyclic amine derivative which is represented by the following formula (13):

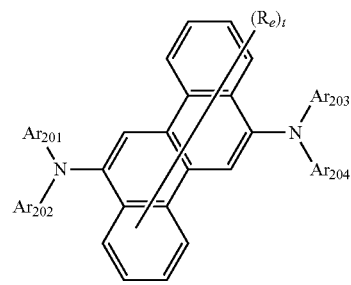

(13)

wherein in the formula (13), $R_e$ is independently a hydrogen atom, a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 50 ring carbon atoms, a substituted or unsubstituted silyl group, a substituted or unsubstituted alkylgermanium group having 1 to 50 carbon atoms or a substituted or unsubstituted arylgermanium group having 6 to 50 ring carbon atoms; t is an integer of 1 to 10; and $Ar_{201}$ to $Ar_{204}$ are independently a substituted or unsubstituted aryl group having 6 to 50 ring carbon atoms or a substituted or unsubstituted heterocyclic group having 5 to 50 ring atoms.
24. The organic electroluminescence device according to 22, wherein the dopant material is a fused polycyclic amine derivative which is represented by the following formula (14):

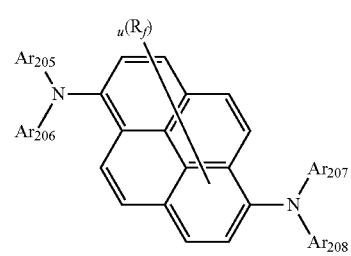

(14)

wherein in the formula (14), $R_f$ is independently a hydrogen atom, a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 50 ring carbon atoms, a substituted or unsubstituted silyl group, a substituted or unsubstituted alkylgermanium group having 1 to 50 carbon atoms or a substituted or unsubstituted arylgermanium group having 6 to 50 ring carbon atoms; u is an integer of 1 to 8; and $Ar_{205}$ to $Ar_{208}$ are independently a substituted or unsubstituted aryl group having 6 to 50 ring carbon atoms or a substituted or unsubstituted heterocylic group having 5 to 50 ring atoms.

25. The organic electroluminescence device according to 22, wherein the dopant material is a fused polycyclic amine derivative which is represented by the following formula (15):

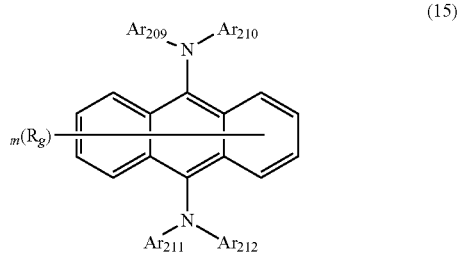

(15)

wherein in the formula (15), $R_g$ is independently a hydrogen atom, a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 50 ring carbon atoms, a substituted or unsubstituted silyl group, a substituted or unsubstituted alkylgermanium group having 1 to 50 carbon atoms or a substituted or unsubstituted arylgermanium group having 6 to 50 ring carbon atoms; m is an integer of 1 to 10; and $Ar_{209}$ to $Ar_{212}$ are independently a substituted or unsubstituted aryl group having 6 to 50 ring carbon atoms or a substituted or unsubstituted heterocyclic group having 5 to 50 ring atoms.

26. The organic electroluminescence device according to 22, wherein the dopant material is a fused polycyclic amine derivative represented by the following formula (16):

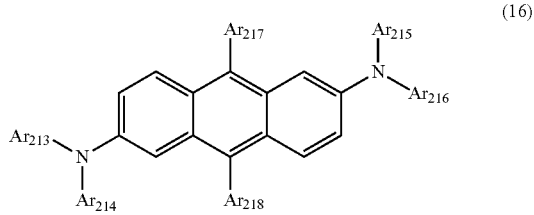

(16)

wherein in the formula (16), $Ar_{213}$ to $Ar_{218}$ are independently a substituted or unsubstituted aryl group having 6 to 50 ring carbon atoms or a substituted or unsubstituted heterocyclic group having 5 to 50 ring atoms.

By using the anthracene derivative of the invention, it is possible to provide an organic EL device which has a long life and a high luminous efficiency.

BRIEF DESCRIPTION OF THE DRAWINGS

FIG. 1 is a schematic cross-sectional view of one embodiment of the organic EL device of the invention.

MODE FOR CARRYING OUT THE INVENTION

The anthracene derivative and the organic EL device of the invention will be explained in detail below.

The anthracene derivative of the invention is represented by the following formula (1):

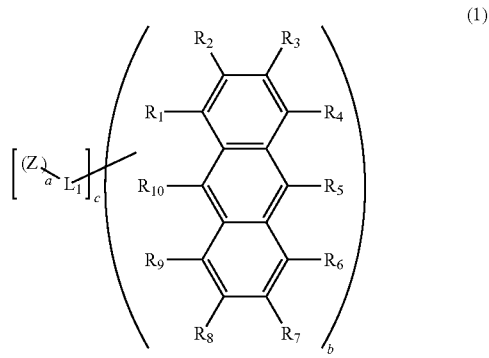

(1)

In the formula (1), any one of $R_1$ to $R_{10}$ is used for bonding to $L_1$, the one used for bonding to $L_1$ is a single bond, $R_1$ to $R_{10}$ which are not used for bonding to $L_1$ are independently a hydrogen atom, a halogen atom, a hydroxyl group, a cyano group, a substituted or unsubstituted amino group, a substituted or unsubstituted alkyl group having 1 to 20 carbon atoms, a substituted or unsubstituted alkoxy group having 1 to 20 carbon atoms, a substituted or unsubstituted aryloxy group having 6 to 20 ring carbon atoms, a substituted or unsubstituted arylthio group having 6 to 20 ring carbon atoms, a substituted or unsubstituted aryl group having 6 to 50 ring carbon atoms or a substituted or unsubstituted heterocyclic group having 5 to 50 ring atoms.

$L_1$ is a single bond or a linkage group;

a, b and c are independently an integer of 1 to 4; and

Z is a structure represented by the following formula (2):

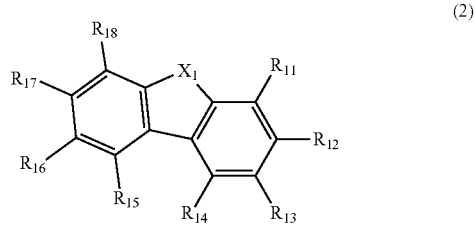

(2)

wherein in the formula (2), $R_{11}$ to $R_{18}$ are independently a hydrogen atom or a substituent and $X_1$ is an oxygen atom or a sulfur atom; and at least one pair of adjacent two substituents of $R_{11}$ to $R_{18}$ form a ring represented by the following formula (3) or (4):

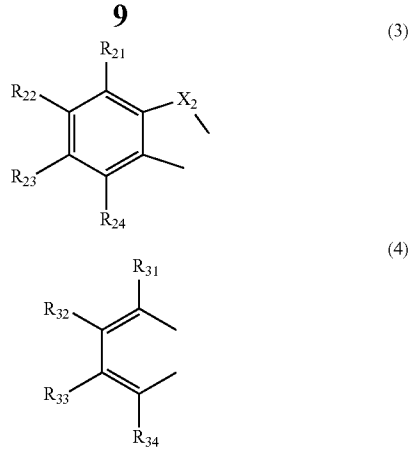

(3)

(4)

$R_{21}$ to $R_{24}$ and $R_{31}$ to $R_{34}$ are independently a hydrogen atom or a substituent and $X_2$ is an oxygen atom or a sulfur atom.

Any one of $R_{11}$ to $R_{18}$ which do not form a ring, $R_{21}$ to $R_{24}$ and $R_{31}$ to $R_{34}$ is used for bonding to $L_1$, and the one used for bonding to $L_1$ is a single bond.

It is assumed that an organic EL device having a long life and a high luminous efficiency can be obtained due to the presence of an anthracene skeleton and a structure represented by Z.

$R_{11}$ to $R_{18}$ are preferably a hydrogen atom and an alkyl group, with a hydrogen atom being more preferable.

$R_{21}$ to $R_{24}$ and $R_{31}$ to $R_{34}$ are preferably a hydrogen atom, an alkyl group or the like, with a hydrogen atom being more preferable.

In the formula (2), if the substituents of $R_{15}$ and $R_{16}$ form the ring shown by the formula (4), it is preferred that $R_{15}$ and $R_{16}$ be hydrogen atoms. If $R_{15}$ and $R_{16}$ each have a substituent, size exclusion effects occur, and hence, the distance between adjacent molecules is increased in an amorphous thin film. As a result, the driving voltage increases. Therefore, it is preferred that $R_{15}$ and $R_{16}$ be a hydrogen atom.

In the formula (2), if the substituents of $R_{13}$ and $R_{14}$ form the ring shown by the formula (4), it is preferred that $R_{15}$ and $R_{16}$ be hydrogen atoms. If $R_{13}$ and $R_{14}$ each have a substituent, size exclusion effects occur, and hence, the distance between adjacent molecules is increased in an amorphous thin film. As a result, the driving voltage increases. Therefore, it is preferred that $R_{15}$ and $R_{16}$ be a hydrogen atom.

As the divalent linkage group represented by $L_1$, a substituted or unsubstituted arylene group having 6 to 50 ring carbon atoms or a substituted or unsubstituted divalent heterocyclic group having 5 to 50 ring atoms can be mentioned.

Specific examples of the arylene group having 6 to 50 ring carbon atoms include divalent arylene groups having 6 to 50 ring carbon atoms, which are mentioned later.

Preferable arylene groups represented by $L_1$ include a phenylene group, a biphenylene group, a naphthylene group and a 9,9-dimethyfluorenylene group.

Specific examples of the divalent heterocyclic group having 5 to 50 ring atoms include a group obtained by allowing the heterocyclic groups having 5 to 50 ring carbon atoms, which will be mentioned later, to be divalent.

Preferable heterocyclic groups represented by $L_1$ include a pyridylene group, a pyrimidylene group, a dibenzofuranylene group and a carbazolylene group.

As the linkage group having 3 or more valences represented by $L_1$, a group having 3 or more valences corresponding to the above-mentioned divalent linkage group represented by $L_1$ can be mentioned.

$L_1$ can be bonded to any one of $R_1$ to $R_{10}$, preferably to any of $R_{10}$ or $R_1$ to $R_4$. It is more preferred that $L_1$ be bonded to $R_{10}$ or $R_2$.

Preferred examples of $R_1$ to $R_{10}$ include a hydrogen atom and an alkyl group. A hydrogen atom is more preferable.

It is preferred that $R_5$ be a substituted or unsubstituted aryl group having 6 to 50 ring carbon atoms or a substituted or unsubstituted heterocyclic group having 5 to 50 ring atoms.

It is more preferred that $R_5$ be a fused aryl group having 10 to 30 ring carbon atoms or a structure represented by the following formula (11):

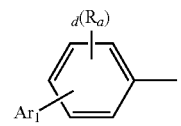

(11)

wherein in the formula (11), $Ar_1$ is a group selected from a substituted or unsubstituted aryl group having 6 to 30 ring carbon atoms and a substituted or unsubstituted heterocyclic group having 5 to 30 ring atoms.

Ra is independently a hydrogen atom or a substituent and d is an integer of 1 to 4.

Specific examples of the substituted or unsubstituted aryl group having 6 to 30 ring carbon atoms and the substituted or unsubstituted heterocyclic group having 5 to 30 ring atoms include an aryl group having 6 to 30 ring carbon atoms and a heterocyclic group having 5 to 30 ring carbon atoms, mentioned later.

$Ar_1$ is preferably a phenyl group, a naphthyl group, a phenanthryl group, a 9,9-dimethylfluorenyl group, a fluoranthenyl group, a biphenyl group, a terphenyl group, an anthryl group, a benzophenanthryl group, a chrysenyl group, a pyrenyl group, a triphenyl group, a benzochrysenyl group and a naphthacenyl group. A phenyl group, a naphthyl group, a phenanthryl group, a 9,9-dimethylfluorenyl group and a biphenyl group are particularly preferable.

Ra is preferably a hydrogen atom, a halogen atom, an alkyl group, an alkoxy group, a cyano group, a silyl group, an aryl group and a heterocylic group, with a hydrogen atom, an aryl group and a heterocylic group being particularly preferable.

Specific examples of the fused aryl group having 10 to 30 ring carbon atoms represented by $R_5$ are as mentioned later. A 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group and a 4-methyl-1-anthryl group or the like are further preferable.

For example, when $L_1$ is bonded to $R_2$, it is preferred that $R_5$ and $R_{10}$ be a substituted or unsubstituted aryl group having 6 to 50 ring carbon atoms or a substituted or unsubstituted heterocyclic group having 5 to 50 ring atoms and that $R_1$, $R_3$, $R_4$, $R_6$ to $R_9$ be a hydrogen atom. In this case, an anthracene derivative is preferably any of the following anthracene derivatives (A-1) and (A-2).

(Anthracene Derivative (A-1))

Anthracene derivative (A-1) is one in which $R_5$ and $R_{10}$ are independently a substituted or unsubstituted fused aryl group having 10 to 50 ring carbon atoms or a substituted or unsubstituted fused heterocyclic group having 8 to 50 ring atoms. As the anthracene derivative, $R_5$ and $R_{10}$ may be the same substituted or unsubstituted fused ring group or may be different substituted or unsubstituted fused ring groups. Here, the fused ring group means a fused aryl group or a fused heterocyclic group.

Specific preferable examples of the fused aryl group or the fused heterocyclic group are as mentioned later. Of them, a naphthyl group, a phenanthryl group, a benzanthryl group, a 9,9-dimethylfluorenyl group and a dibenzofuranyl group are preferable.

(Anthracene Derivative (A-2))

Anthracene derivative (A-2) is one in which $R_5$ and $R_{10}$ are independently a substituted or unsubstituted non-fused aryl group having 6 to 50 ring carbon atoms or a substituted or unsubstituted non-fused heterocyclic group having 5 to 50 ring atoms.

In a preferable mode, both $R_5$ and $R_{10}$ are substituted or unsubstituted phenyl groups. If $R_5$ and $R_{10}$ are substituted phenyl groups, the anthracene derivative (A-2) may have the structure represented by the above formula (11).

Specific examples of the preferable aryl group or the heterocyclic group as the substituent are as mentioned later. As the aryl group or the heterocyclic group as the substituent, a phenyl group, a biphenyl group, a naphthyl group, a phenanthryl group, a 9,9-dimethylfluorenyl group, a dibenzofuranyl group and a benzanthryl group are further preferable.

In another preferable mode, the following anthracene derivatives (B) to (D) can be mentioned.

(Anthracene Derivative (B))

When $L_1$ is bonded to $R_{10}$, it is preferred that $R_5$ be a substituted or unsubstituted aryl group having 6 to 50 ring carbon atoms or a substituted or unsubstituted heterocyclic group having 5 to 50 ring atoms and that $R_1$ to $R_4$ and $R_6$ to $R_9$ be a hydrogen atom.

(Anthracene Derivative (C))

When $L_1$ is bonded to $R_{10}$, it is preferred that $R_2$ and $R_5$ be a substituted or unsubstituted aryl group having 6 to 50 ring carbon atoms or a substituted or unsubstituted heterocyclic group having 5 to 50 ring atoms and that $R_1$, $R_3$, $R_4$, and $R_6$ to $R_9$ be a hydrogen atom.

(Anthracene Derivative (D))

When $L_1$ is bonded to $R_{10}$ and $R_5$, it is preferred that $R_1$, $R_3$, $R_4$, and $R_6$ to $R_9$ be a hydrogen atom. $R_2$ is a hydrogen atom, a substituted or unsubstituted aryl group or a substituted or unsubstituted heterocyclic group. In this case, the structures of Z to be bonded to $R_{10}$ and $R_5$ may be the same or different. However, it is preferred that the structures be the same.

Z is preferably a structure represented by any of the following formulas (5) to (7):

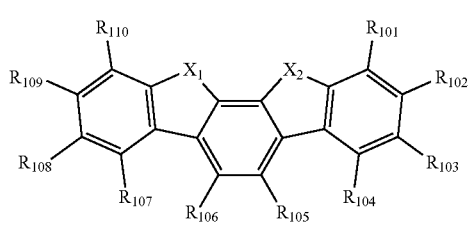

(5)

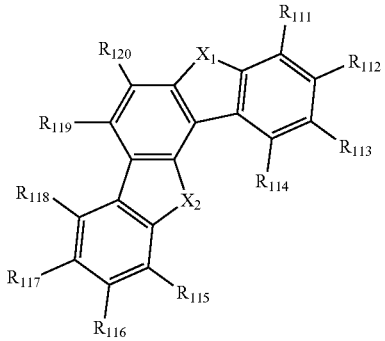

(6)

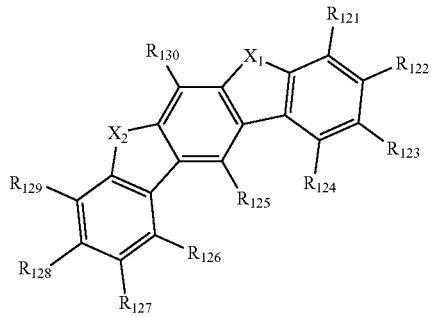

(7)

In the formulas (5) to (7), $R_{101}$ to $R_{110}$, $R_{111}$ to $R_{120}$ and $R_{121}$ to $R_{130}$ are independently a hydrogen atom or a substituent. Any one of $R_{101}$ to $R_{110}$, any one of $R_{111}$ to $R_{120}$ and any one of $R_{121}$ to $R_{130}$ is used for bonding to with $L_1$. The one used for bonding to $L_1$ is a single bond. $X_1$ and $X_2$ are independently an oxygen atom or a sulfur atom.

As preferable examples of $R_{101}$ to $R_{110}$, any one of $R_{111}$ to $R_{120}$ and any one of $R_{121}$ to $R_{130}$, a hydrogen atom, an alkyl group or the like can be mentioned, with a hydrogen atom being more preferable.

Further, it is preferred that Z be a structure represented by any of the following formulas (8) to (10):

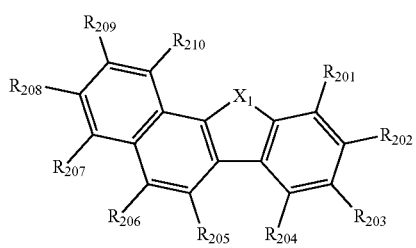

(8)

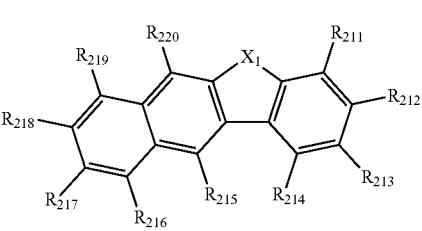

(9)

-continued

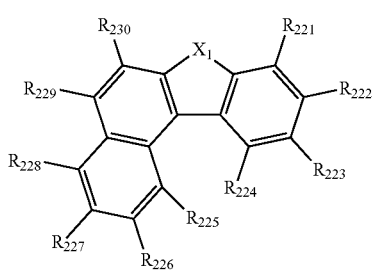

(10)

In the formulas (8) to (10), $R_{201}$ to $R_{210}$, $R_{211}$ to $R_{220}$ and $R_{221}$ to $R_{230}$ are independently a hydrogen atom or a substituent. Any one of $R_{201}$ to $R_{210}$, any one of $R_{211}$ to $R_{220}$ and any one of $R_{221}$ to $R_{230}$ is used for bonding to $L_1$. A group used for bonding to $L_1$ is a single bond. $X_1$ is an oxygen atom or a sulfur atom.

$R_{201}$ to $R_{210}$, $R_{211}$ to $R_{220}$ and $R_{221}$ to $R_{230}$, in particular, $R_{229}$ and $R_{230}$, are preferably a hydrogen atom from the viewpoint of attaining the advantageous effects of the invention easily.

It is preferred that $X_1$ in the formulas (2) and (8) to (10) and $X_1$ and $X_2$ in the formulas (3) and (5) to (7) be an oxygen atom.

As the substituent of $R_{11}$ to $R_{18}$, $R_{21}$ to $R_{24}$, $R_{31}$ to $R_{34}$, $R_{101}$ to $R_{110}$, $R_{111}$ to $R_{120}$, $R_{121}$ to $R_{130}$, $R_{201}$ to $R_{210}$, $R_{211}$ to $R_{220}$, $R_{221}$ to $R_{230}$ and Ra in the formulas (2) to (11), a halogen atom, a hydroxyl group, a cyano group, a substituted or unsubstituted amino group, a substituted or unsubstituted alkyl group having 1 to 20 carbon atoms, a substituted or unsubstituted alkoxy group having 1 to 20 carbon atoms, a substituted or unsubstituted aryloxy group having 6 to 20 ring carbon atoms, a substituted or unsubstituted arylthio group having 6 to 20 ring carbon atoms, a substituted or unsubstituted aryl group having 6 to 50 ring carbon atoms, a substituted or unsubstituted heterocyclic group having 5 to 50 ring atoms or the like can be mentioned.

a is preferably an integer of 1 or 2, more preferably an integer of 1. When a is an integer of 2 or more, plural structures of Z may be the same or different.

b is preferably 1. Therefore, $L_1$ is preferably a divalent linkage group.

c is preferably an integer of 1 or 2, more preferably an integer of 1. When c is an integer of 2 or more, plural structures of [-$L_1$-(Z)$_a$] may be the same or different.

In the specification, the "carbons that form a ring" means carbon atoms that form a saturated ring, an unsaturated ring or an aromatic ring. The "atoms that form a ring" means carbon atoms or hetero atoms that form a hetero ring (including a saturated ring, an unsaturated ring and an aromatic ring).

Unless otherwise specified, as the substituent in the "substituted or unsubstituted . . . ", a halogen atom, a cyano group, an alkyl group, a cycloalkyl group, a silyl group, an alkoxy group, an aryloxy group, an arylthio group, an aryl group, a heterocyclic group, a halogenated alkyl group, an aralkyl group or the like can be mentioned.

Further, the "unsubstituted" means that a hydrogen atom substitutes. In the invention, the hydrogen atom includes protium, deuterium and tritium.

The groups represented by $R_1$ to $R_8$, $R_{11}$ to $R_{17}$, $R_{21}$ to $R_{27}$, $R_{31}$ to $R_{37}$, $R_{41}$ to $R_{48}$, Ra and $Ar_1$ to $Ar_4$ in the above formulas (1) to (4) and the substituents in the "substituted or unsubstituted . . . " will be described below in detail.

As the halogen atom, fluorine, chlorine, bromine, iodine or the like can be mentioned, with fluorine being preferable.

As the substituted or unsubstituted amino group, an amino group substituted by an aryl group can be mentioned, and a phenylamino group is preferable. Specific examples of the aryl group which substitutes the amino group will be given later.

As the alkyl group having 1 to 20 (preferably 1 to 10, more preferably 1 to 8, and particularly preferably 1 to 4) carbon atoms, an ethyl group, a methyl group, an i-propyl group, an n-propyl group, an s-propyl group, an s-butyl group, a t-butyl group, a pentyl group, a hexyl group, a cyclopentyl group, a cyclopentyl group or the like can be given. Of these, a methyl group, an i-propyl group, a t-butyl group, a cyclohexyl group or the like can be mentioned.

As the cycloalkyl group, a cycloalkyl group having 3 to 20 (preferably 3 to 10, more preferably 3 to 8) ring carbon atoms can be mentioned. For example, a cyclopropyl group, a cyclobutyl group, a cyclopentyl group, a cyclohexyl group, a cycloheptyl group or the like can be given.

As the silyl group, an alkylsilyl group having 3 to 30 carbon atoms, an arylsilyl group having 8 to 30 ring carbon atoms or the like can be mentioned. For example, a trimethylsilyl group, a triethylsilyl group, a tert-butyldimethylsilyl group, a vinyldimethylsilyl group, a propyldimethylsilyl group, a tri-isopropylsilyl group, a triphenylsilyl group, a phenyldimethylsilyl group, a t-butyldiphenylsilyl group, a tritolylsilyl group, a trixylylsilyl group, a trinaphthylsilyl group or the like can be mentioned.

The alkoxy group having 1 to 20 (preferably 1 to 10, more preferably 1 to 8, and particularly preferably 1 to 4) carbon atoms is a group represented by —OY. As examples of Y, the same examples as those for the above-mentioned alkyl group can be given.

The aryloxy group having 6 to 20 (preferably 6 to 12) ring carbon atoms is a group represented by —OAr. Examples of Ar are the same as those for the aryl groups mentioned later.

The arylthio group having 6 to 20 (preferably 6 to 12) ring carbon atoms is a group represented by —SAr. Examples of Ar are the same as those for the aryl groups mentioned later.

As the specific examples of the aryl group having 6 to 50 (preferably 6 to 30, more preferably 6 to 20, and particularly preferably 6 to 12) ring carbon atoms, a phenyl group, a naphthyl group, a phenanthryl group, a biphenyl group, a terphenyl group, an anthryl group, a pyrenyl group, a chrysenyl group, a benzophenanthryl group, a benzanthranyl group, a benzochrysenyl group, a fluorenyl group, a fluoranthenyl group, a naphthacenyl group or the like can be given.

The "aryl group" in the specification means a hydrocarbon which is formed of an aromatic monocycle (non-fused aryl group) or a plurality of aromatic rings (fused aryl group).

The fused aryl group is a group, of the above-mentioned aryl groups, formed by fusing of two or more rings. The non-fused aryl group is a group other than the fused aryl groups of the above-mentioned aryl groups.

As the fused aryl group, a fused aryl group having 10 to 50 (preferably 10 to 30, more preferably 10 to 20) ring carbon atoms can be given. Of the specific examples of the above-mentioned aryl group, a naphthyl group, an anthryl group, a pyrenyl group, a phenanthryl group, a fluorenyl group, a fluoranthenyl group, a naphthacenyl group, a pyrenyl group or the like are preferable.

As the heterocyclic group having 5 to 50 (preferably 5 to 30, more preferably 5 to 20, particularly preferably 5 to 12) ring atoms, a pyridinyl group, a pyrazinyl group, a pyrimidinyl group, a pyridazinyl group, a triazinyl group, an indolinyl group, a quinolynyl group, an acrydinyl group, a pyrrolidinyl group, a dioxanyl group, a piperidinyl group, a morphoryl group, a piperazinyl group, a triazinyl group, a carbazolyl group, a furanyl group, a thiophenyl group, an oxazolyl group, an oxadiazolyl group, a benzoxazolyl group, a thiazolyl group, a thiadiazolyl group, a benzothiazolyl group, a triazolyl group, an imidazolyl group, a benzimidazolyl group, a benzofuranyl group, a dibenzofuranyl group or the like can be given.

The fused heterocyclic group is a group, of the above-mentioned heterocyclic groups, which is formed by fusing of two or more rings.

As the fused heterocyclic group having 8 to 50 (preferably 8 to 30, more preferably 8 to 20) ring atoms, among the specific examples of the above-mentioned heterocyclic group, a dibenzofuranyl group, a pyridinyl group, a carbazolyl group, or the like can preferably be given.

As the halogenated alkyl group, for example, one obtained by substituting at least one hydrogen atom of the above-mentioned alkyl group with a halogen atom such as fluorine, chlorine, bromine and iodine can be given. Preferable examples are the same as those of the alkyl group.

The aralykyl group is represented by —Y—Z. As examples of Y, example of alkylene corresponding to the above-mentioned examples of the alkyl can be given, and as examples of Z, the above-mentioned examples of the aryl can be given. It is preferred that the aralkyl group be an aralkyl group having 7 to 50 carbon atoms (the aryl part has 6 to 49 (preferably 6 to 30, more preferably 6 to 20 and particularly preferably 6 to 12) carbon atoms, and the alkyl part has 1 to 44 (preferably 1 to 30, more preferably 1 to 20, further preferably 1 to 10 and particularly preferably 1 to 6) carbon atoms. For example, a benzyl group, a phenylethyl group and a 2-phenylpropane-2-yl group can be given.

Examples of the anthracene derivative represented by the formula (1) are given below, though not limited thereto.

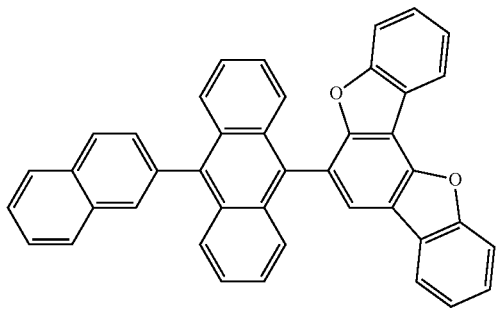

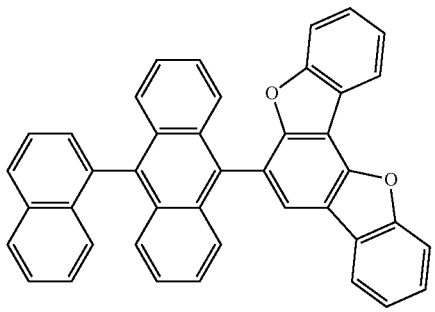

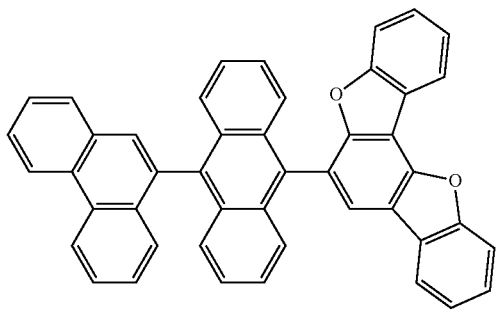

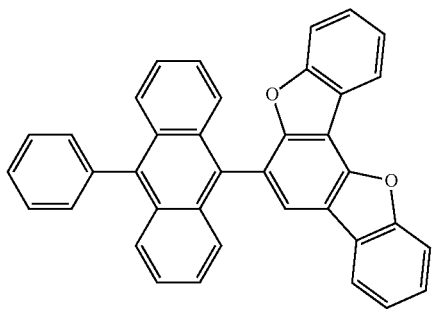

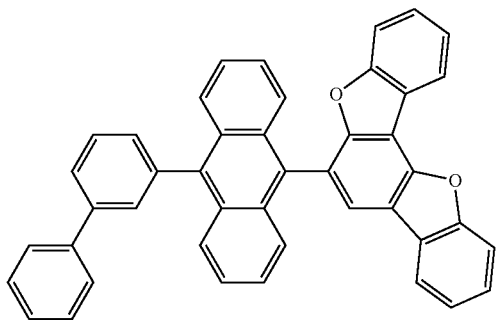

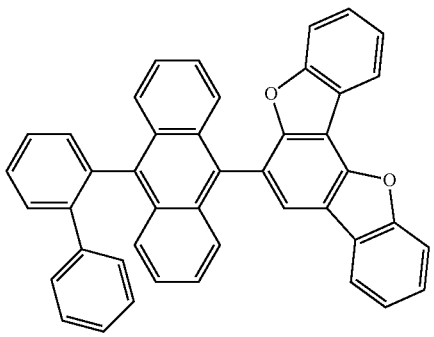

-continued
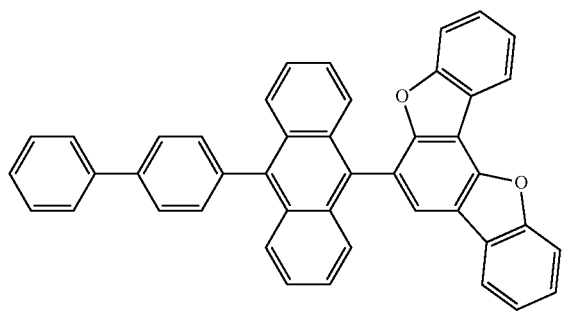
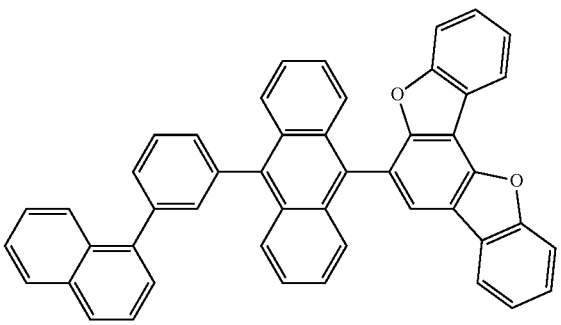
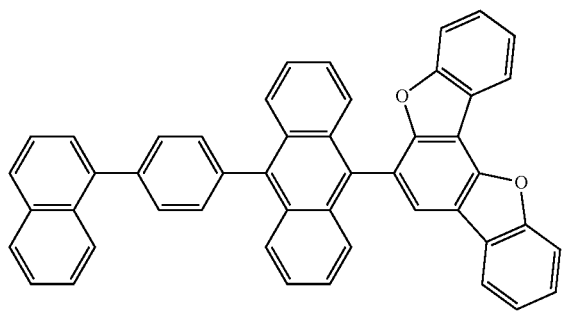
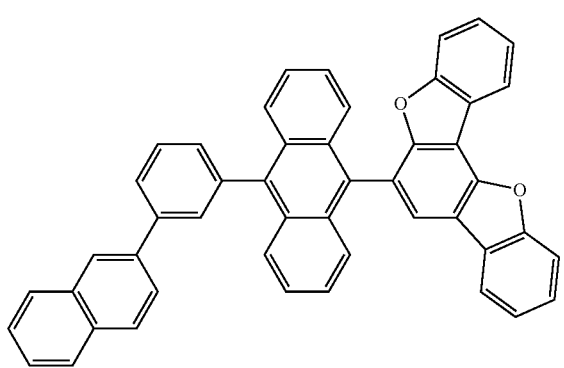
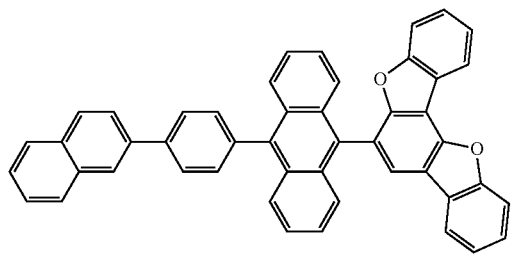
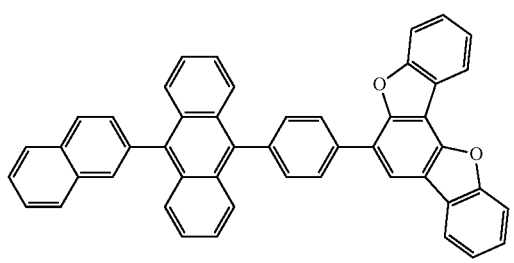
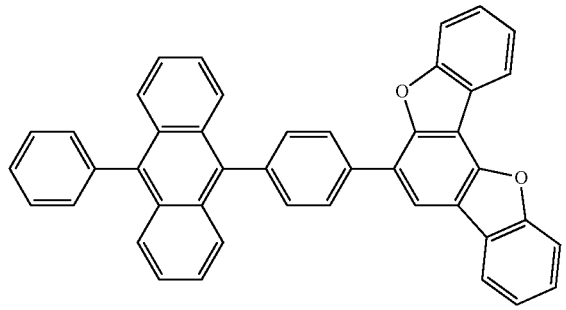
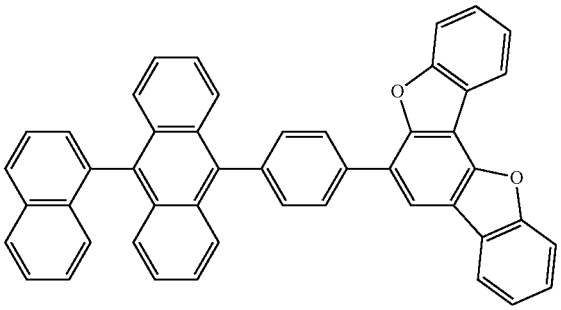
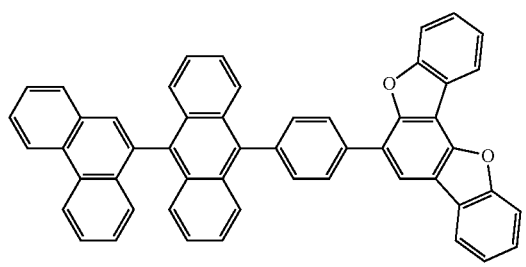
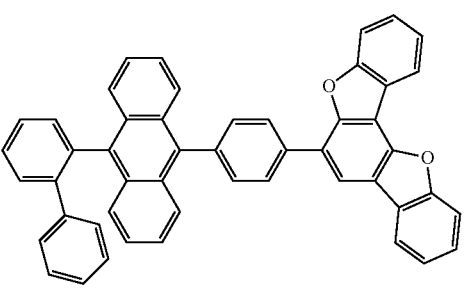

-continued
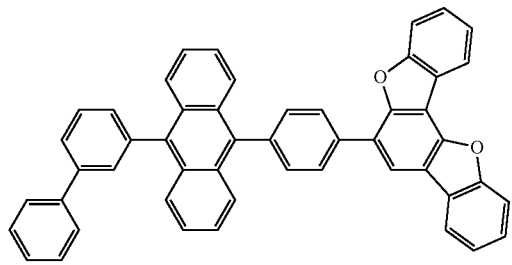
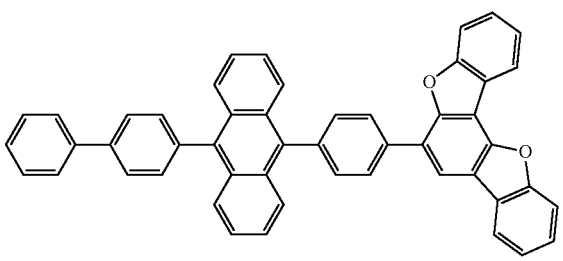
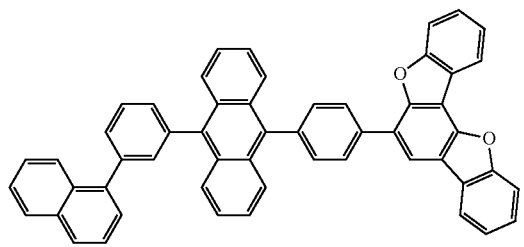
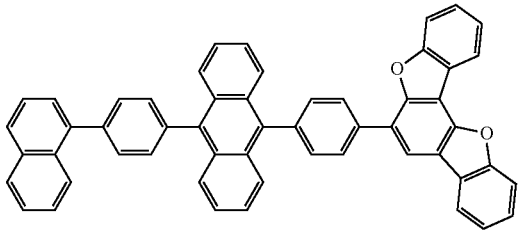
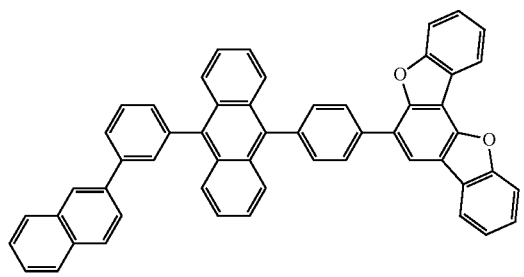
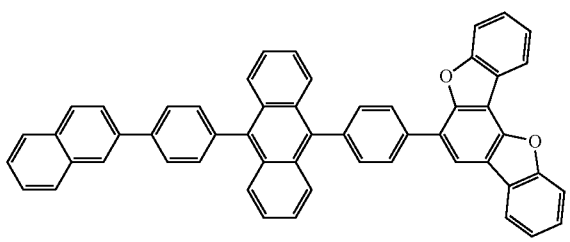
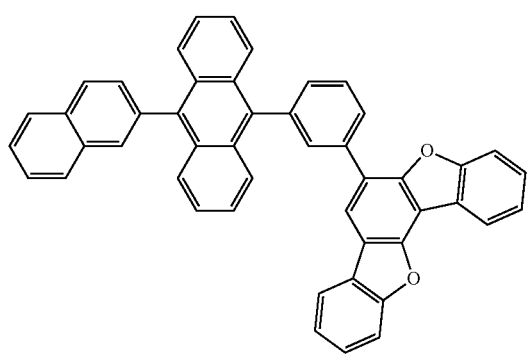
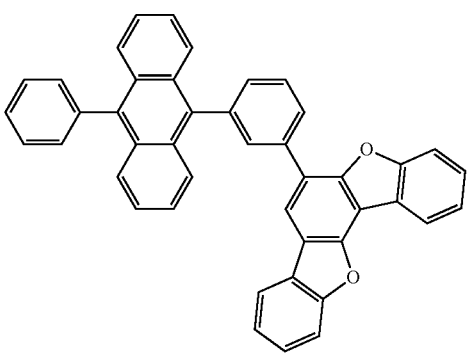
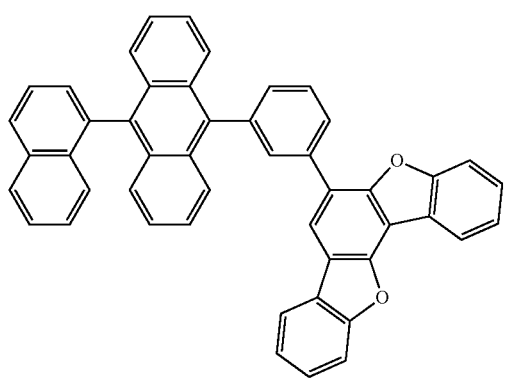
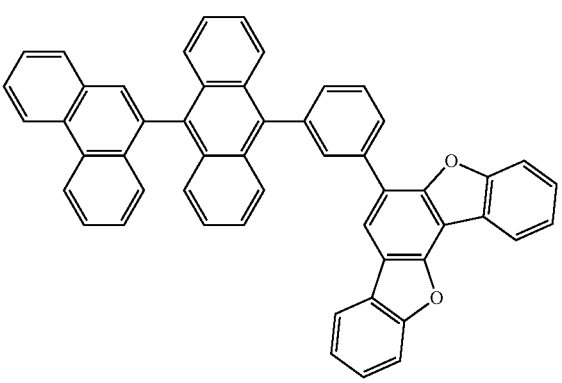

-continued
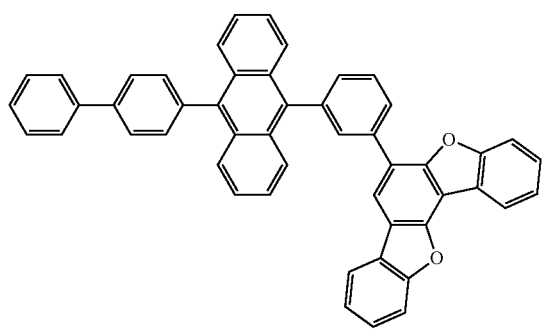
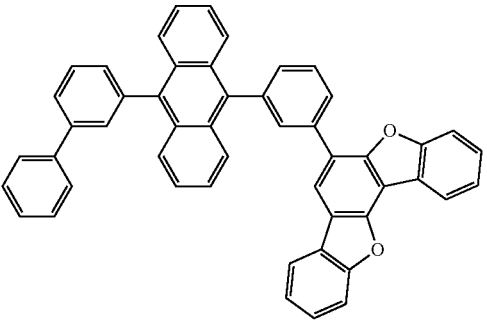
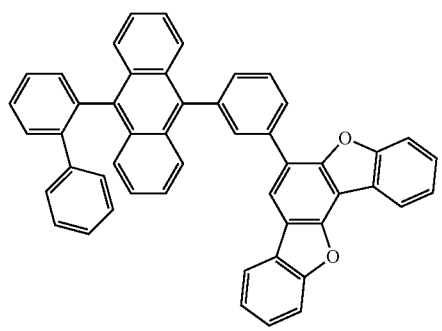
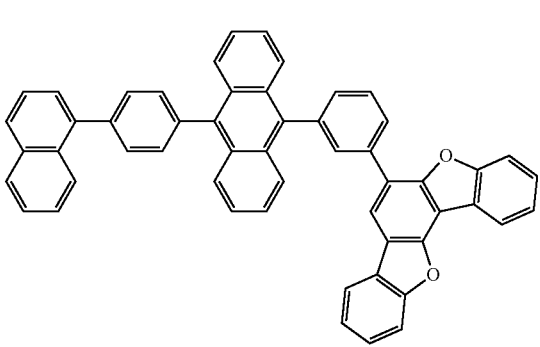
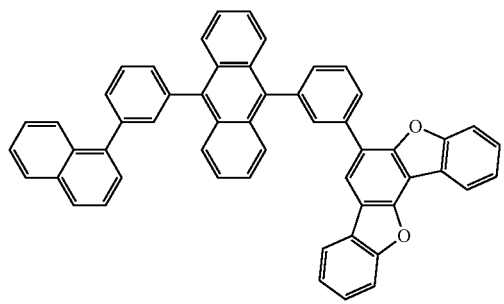
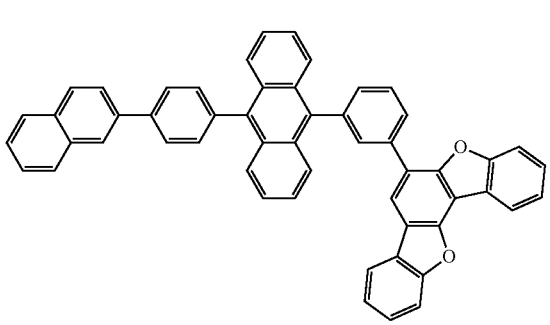
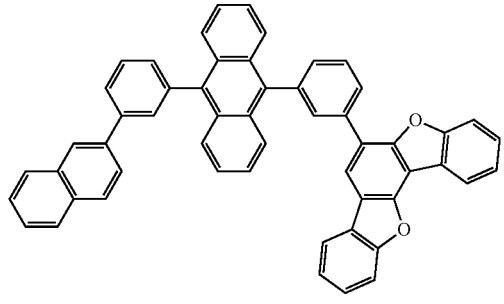
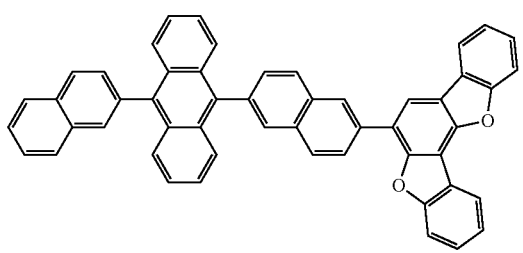
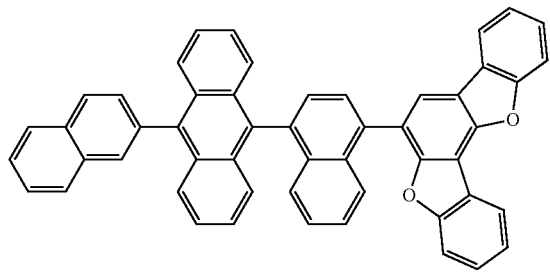
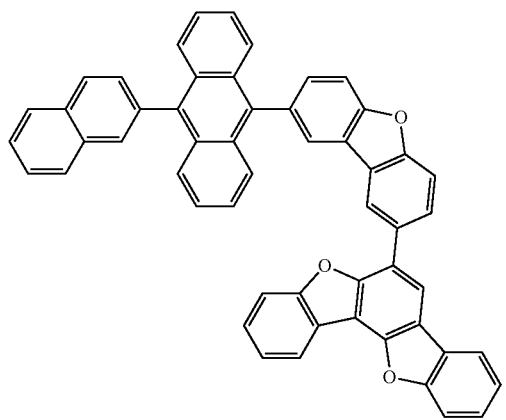

-continued
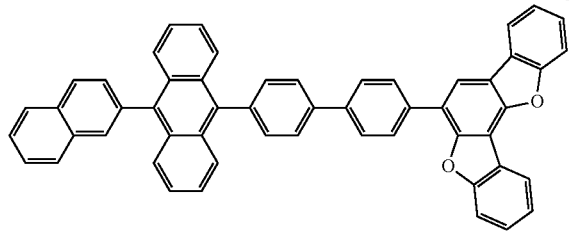
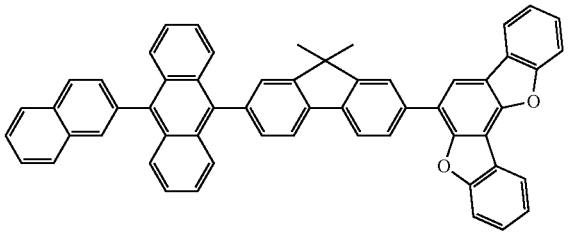
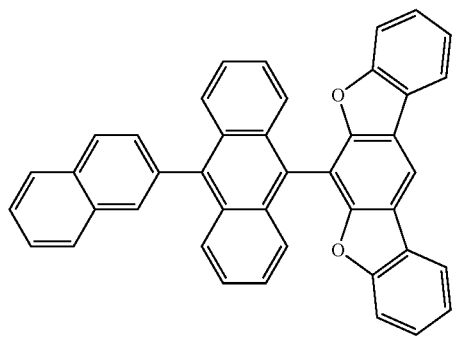
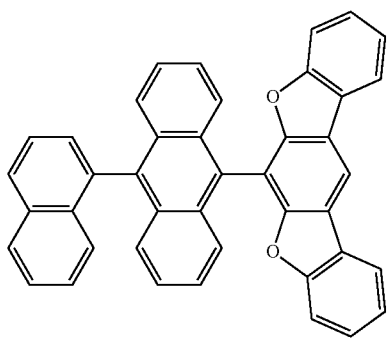
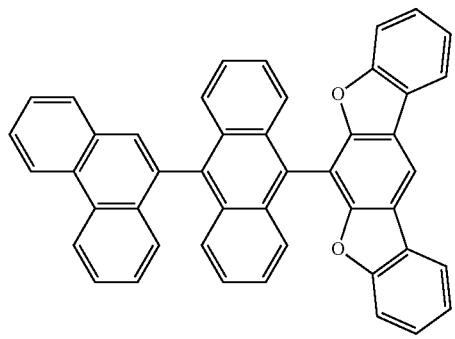
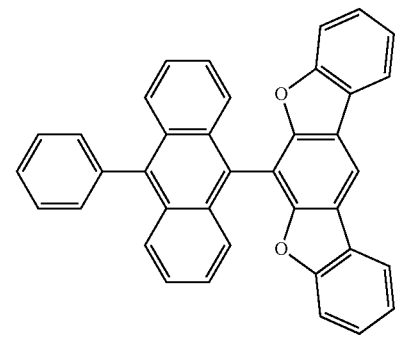
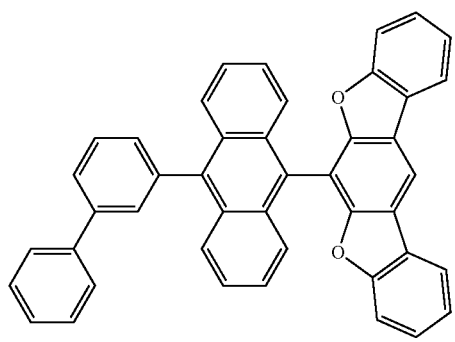
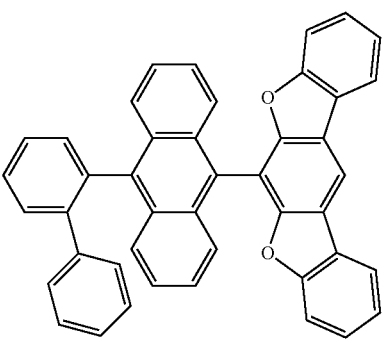
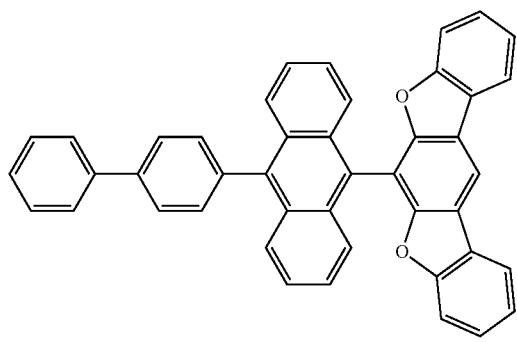
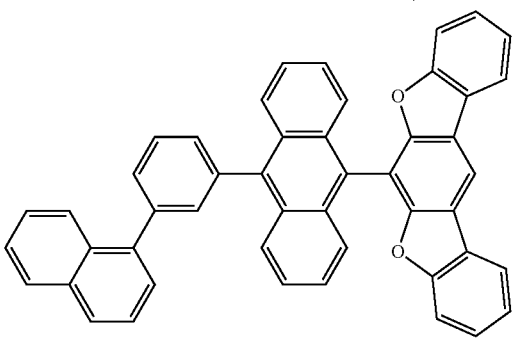

-continued
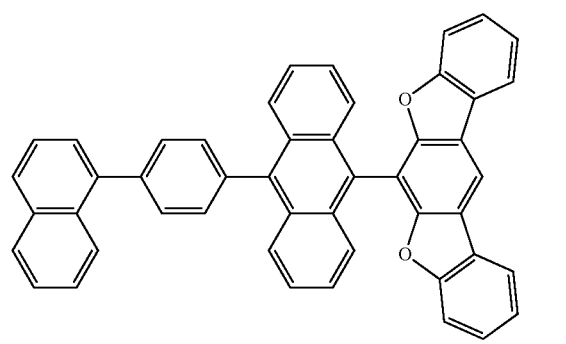 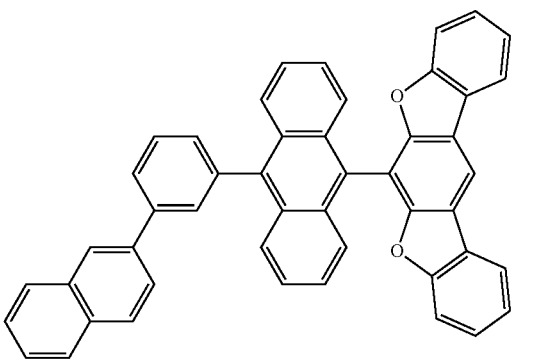
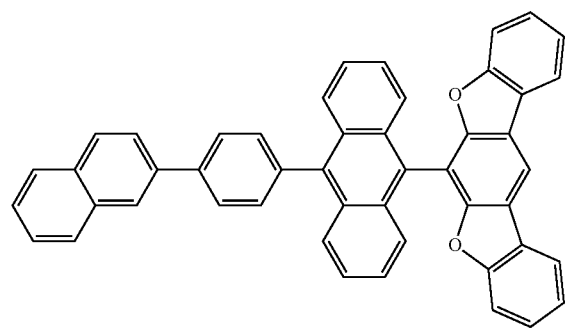 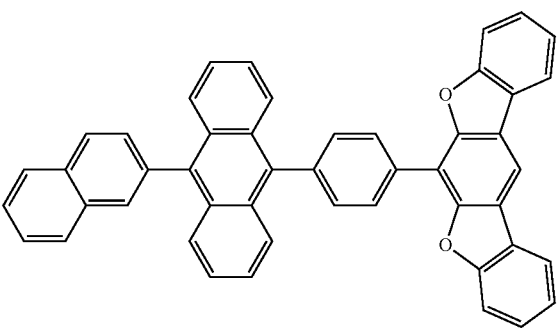
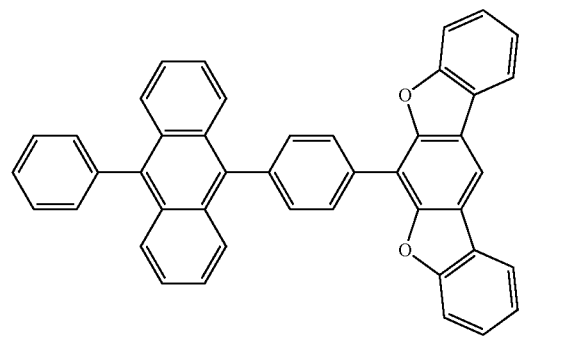 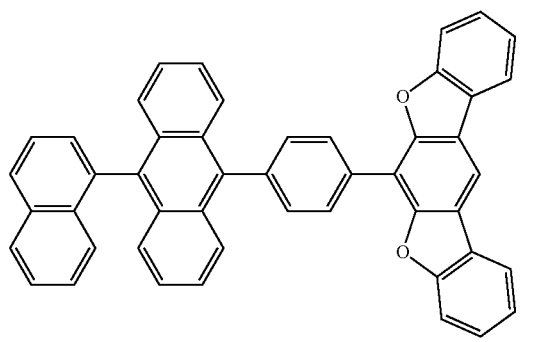
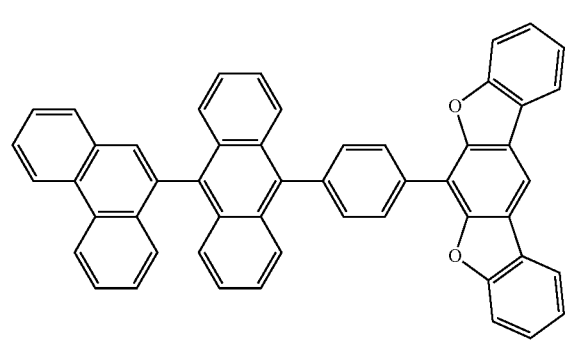 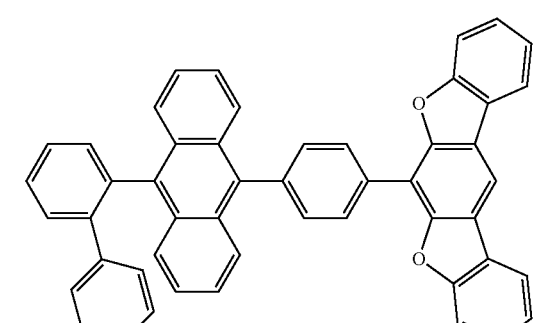
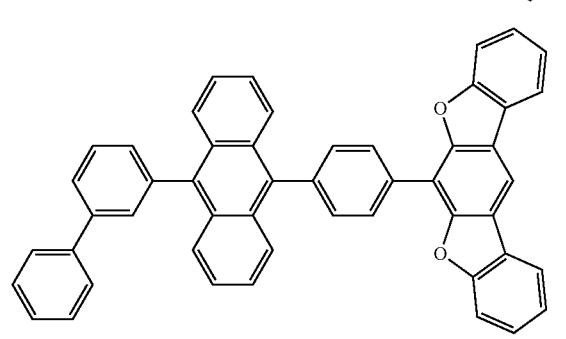 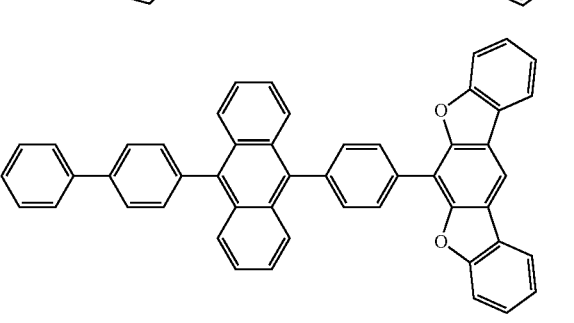

-continued
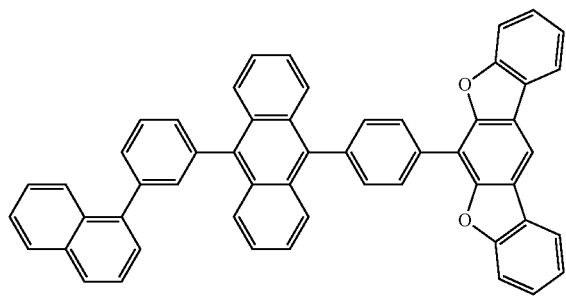
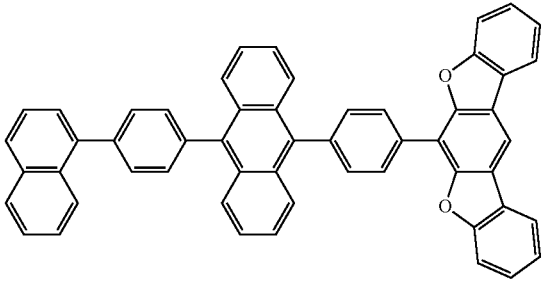
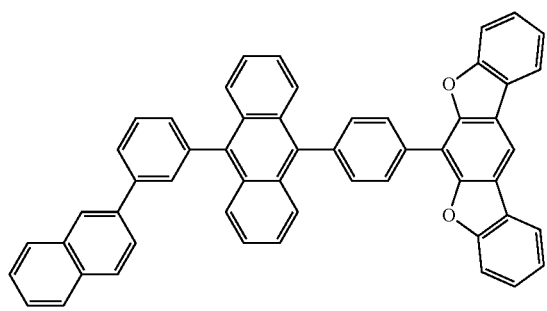
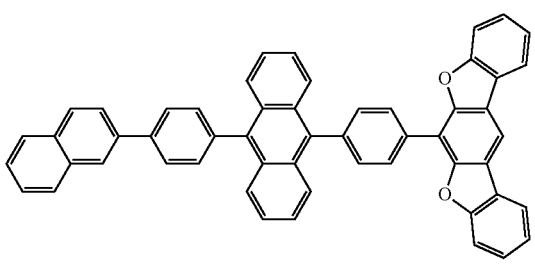
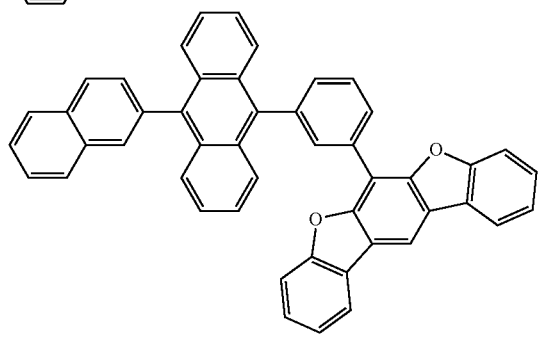
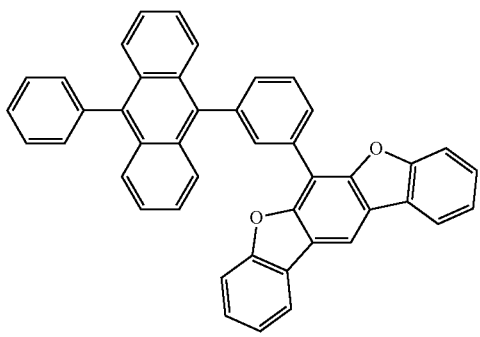
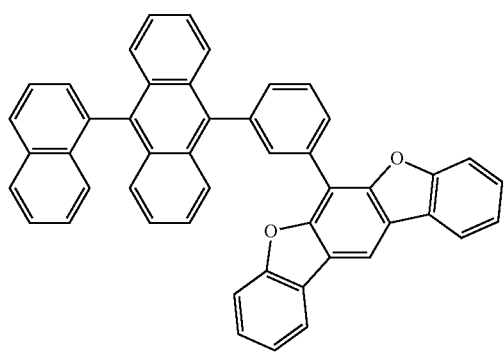
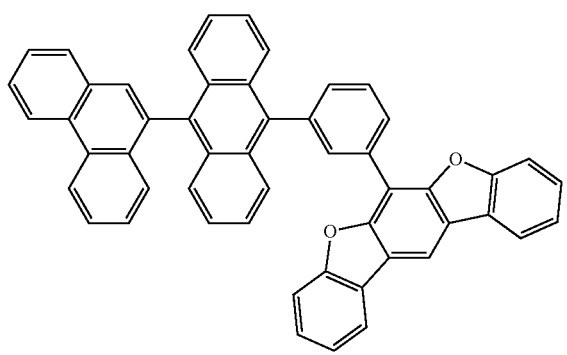
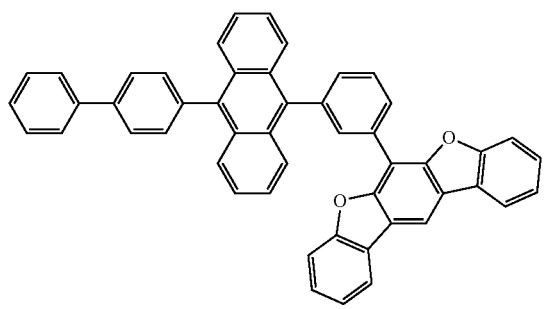
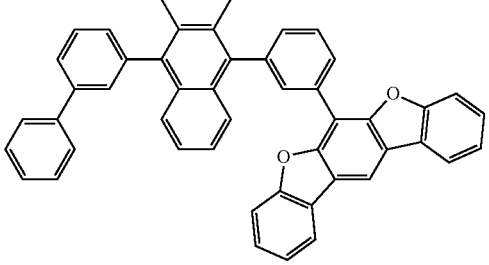

-continued
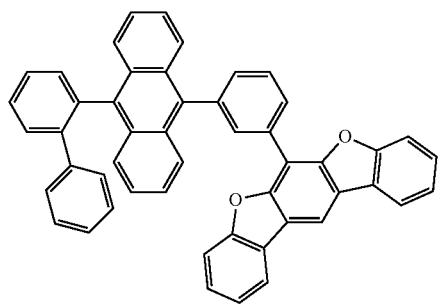
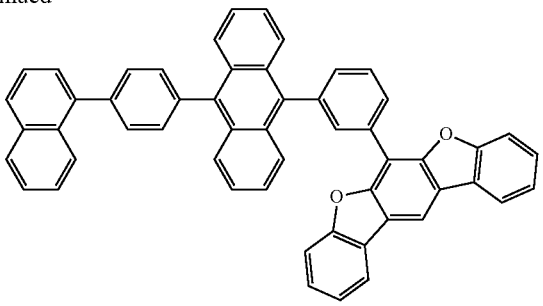
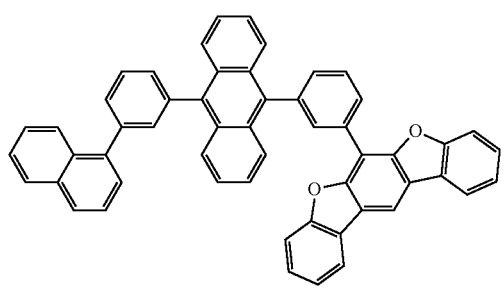
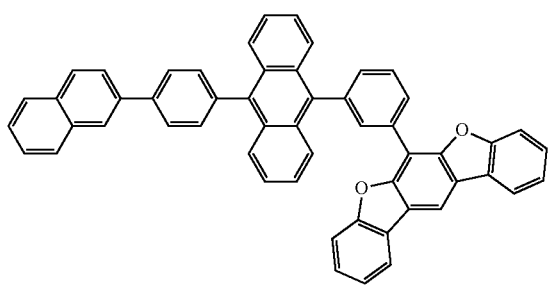
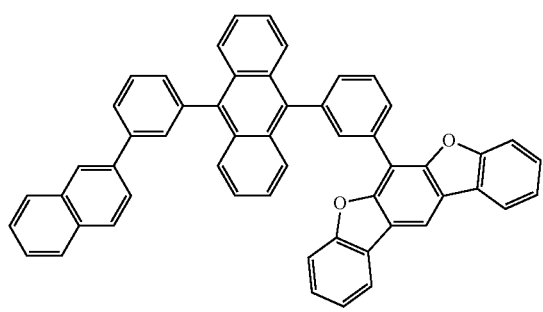
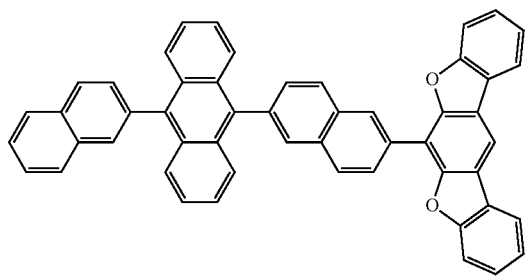
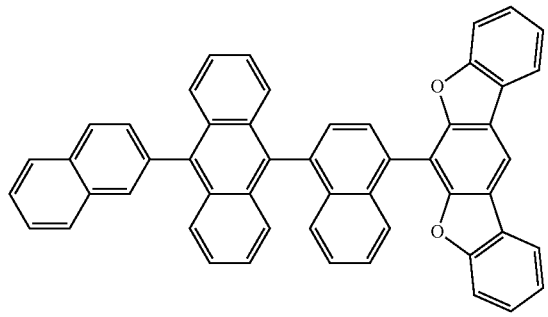
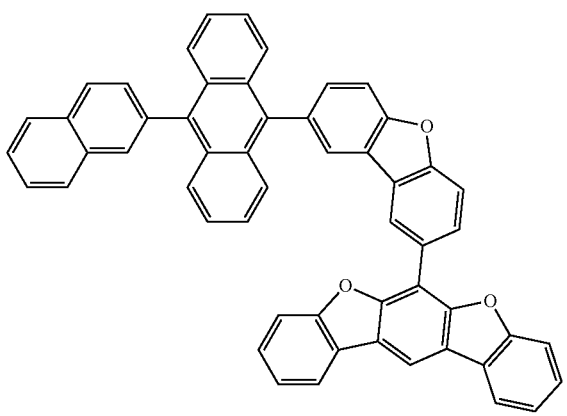
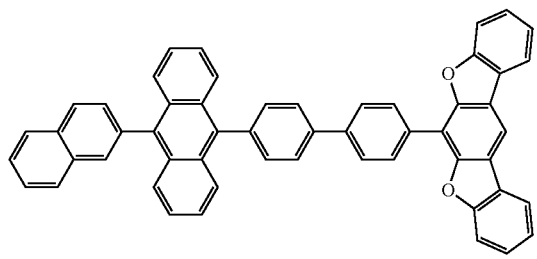
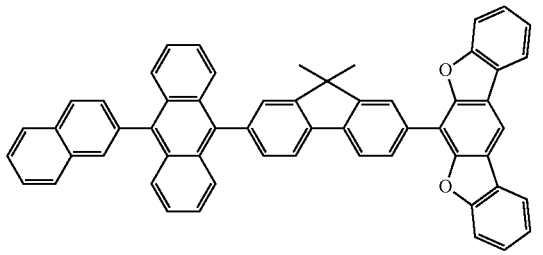

-continued
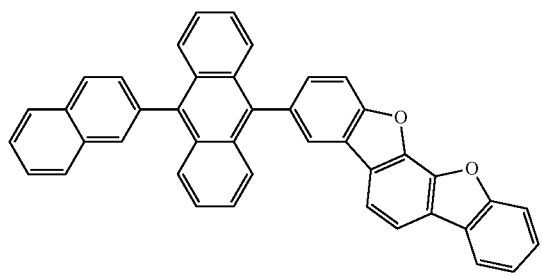
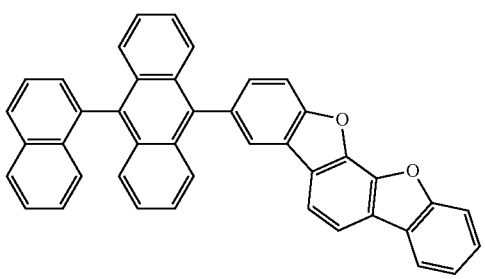
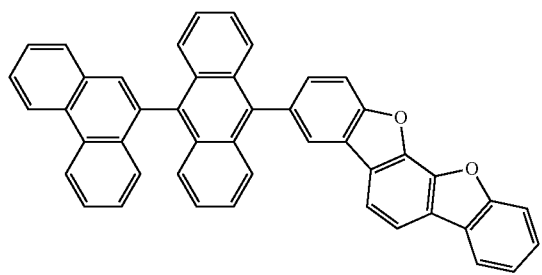
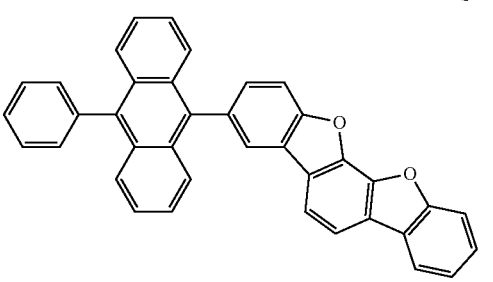
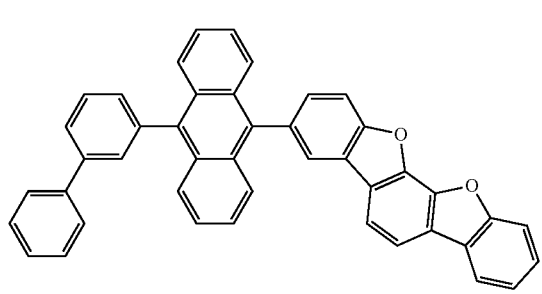
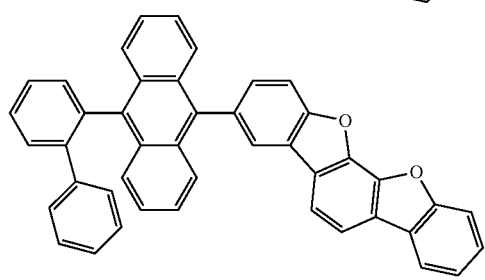
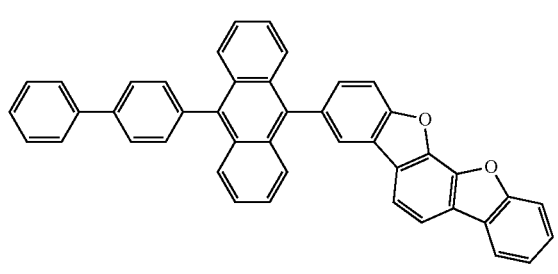
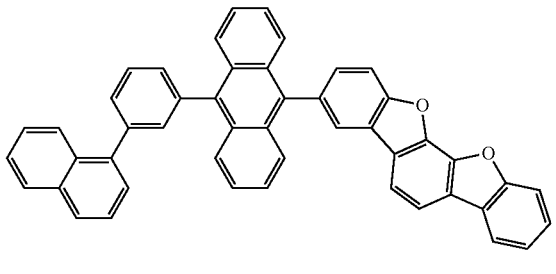
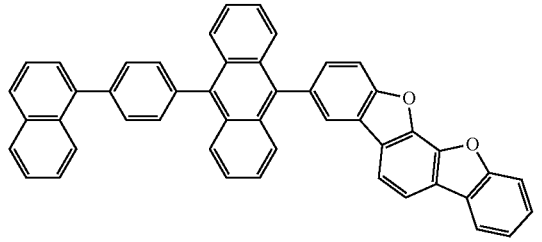
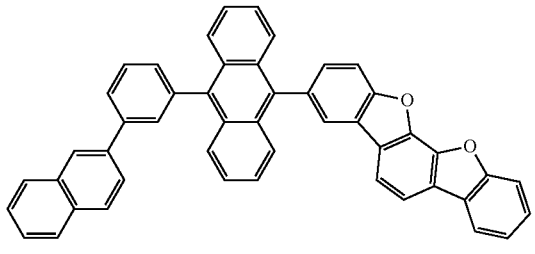
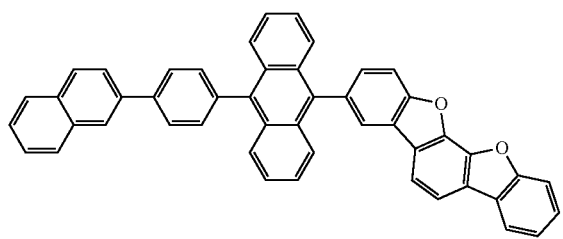
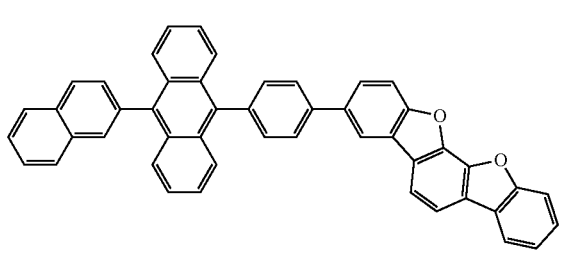

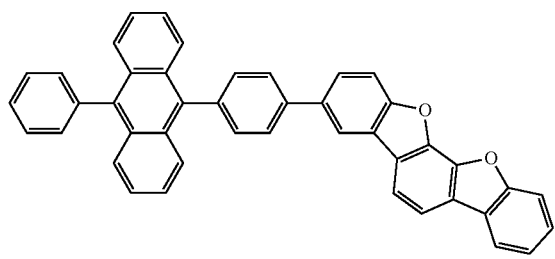

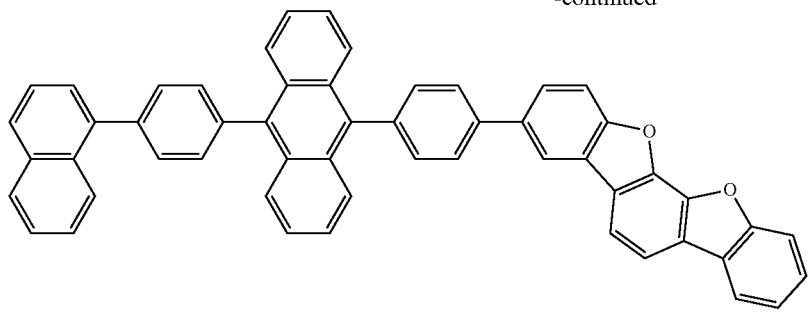
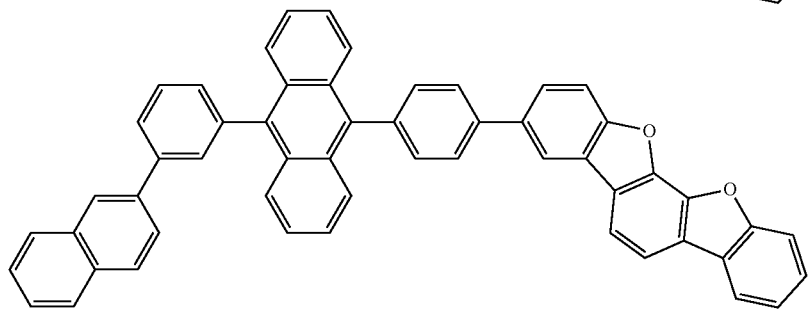
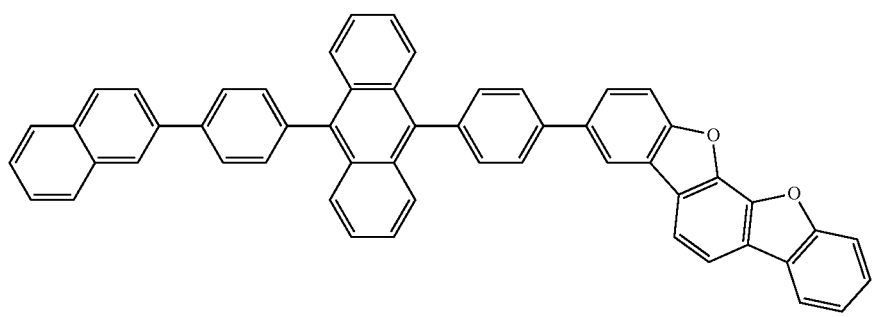
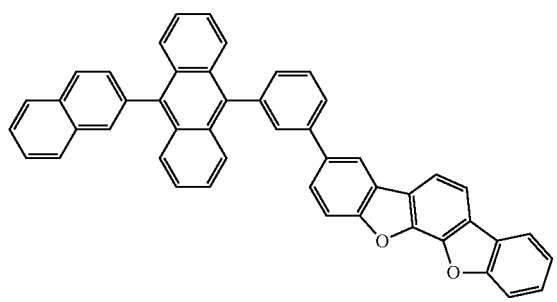
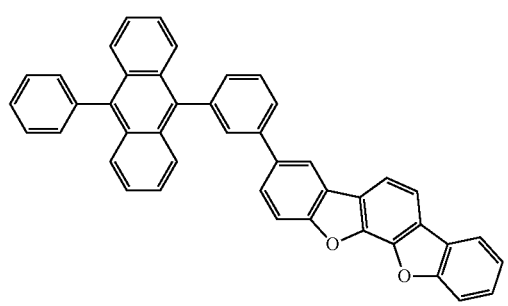
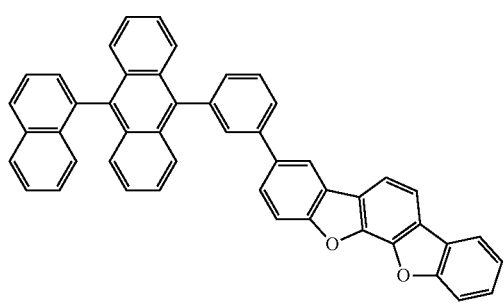
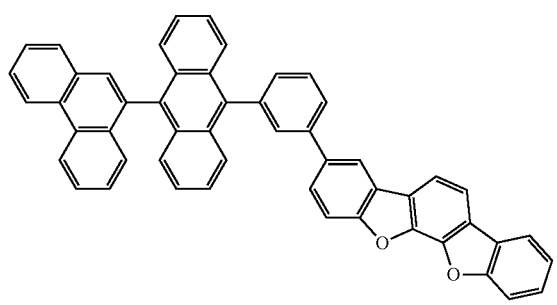

-continued
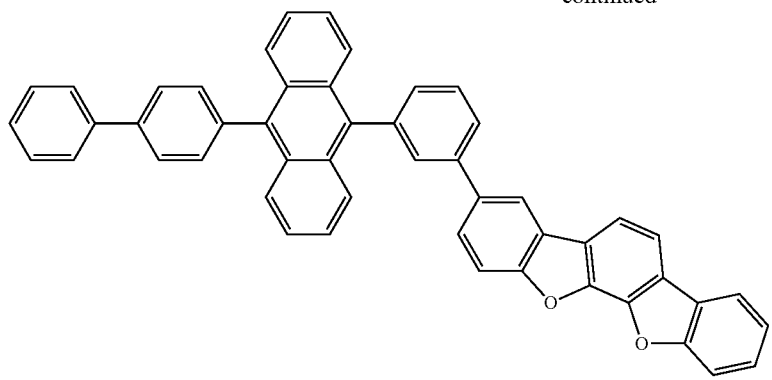
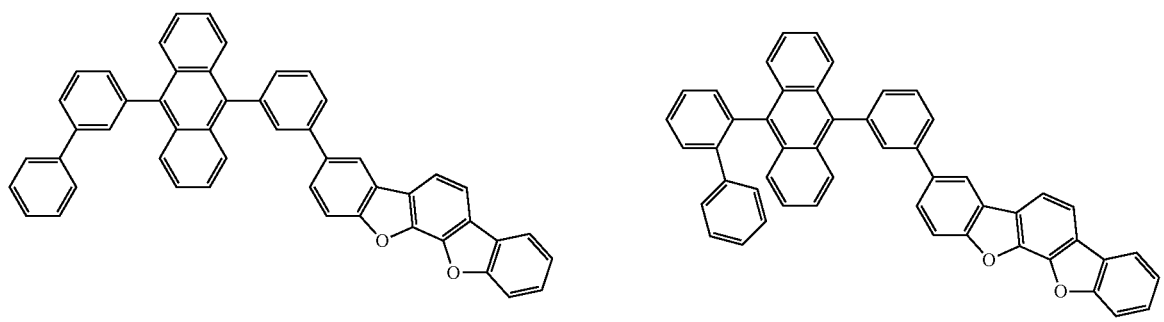
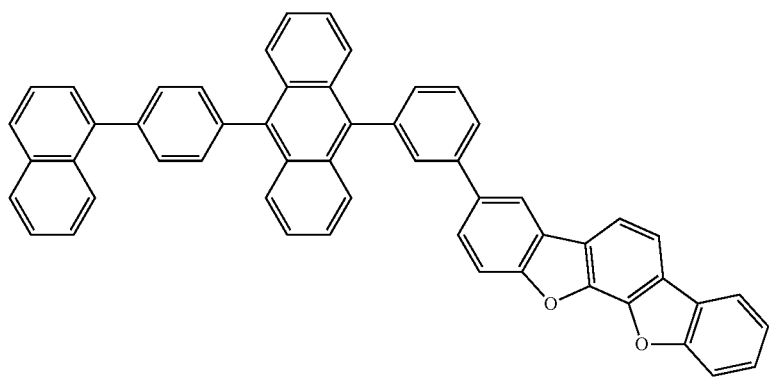
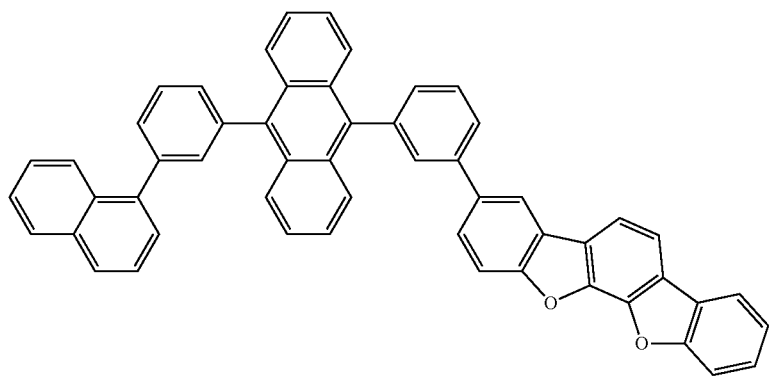

-continued
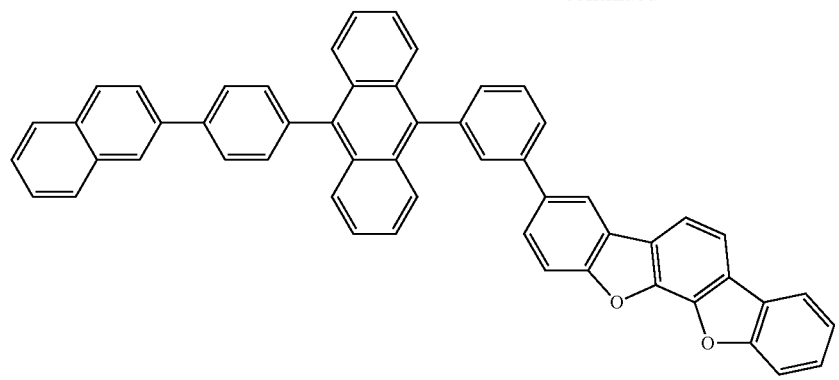
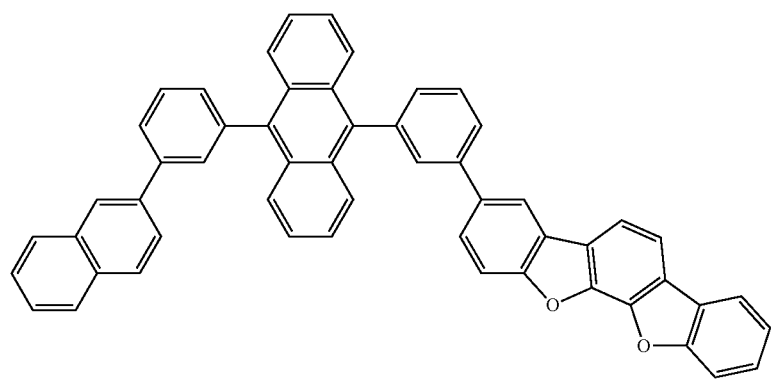
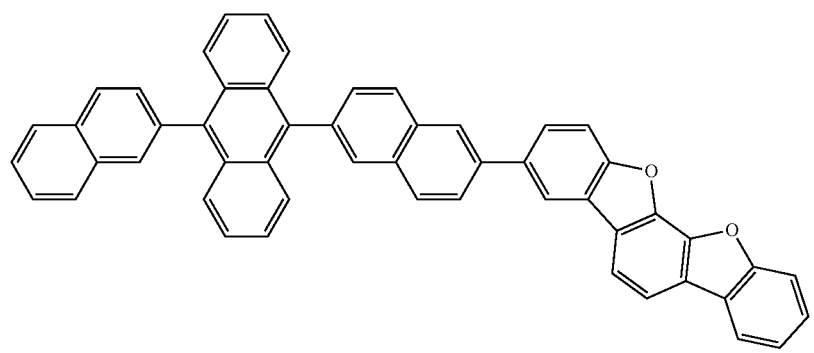
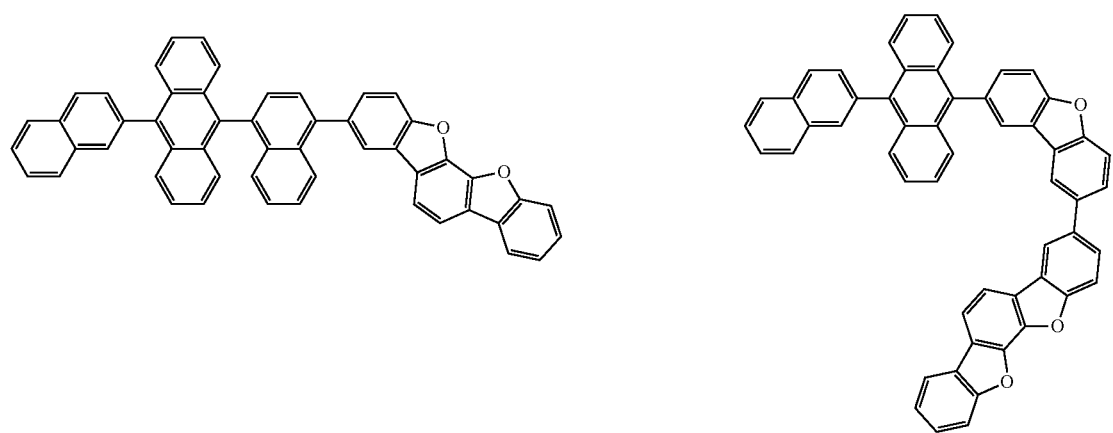

-continued
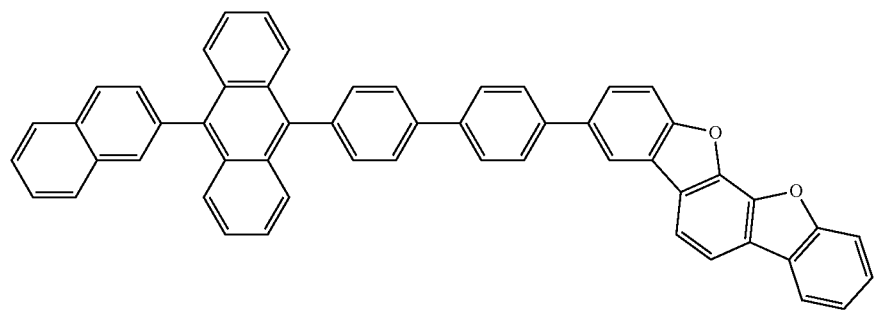
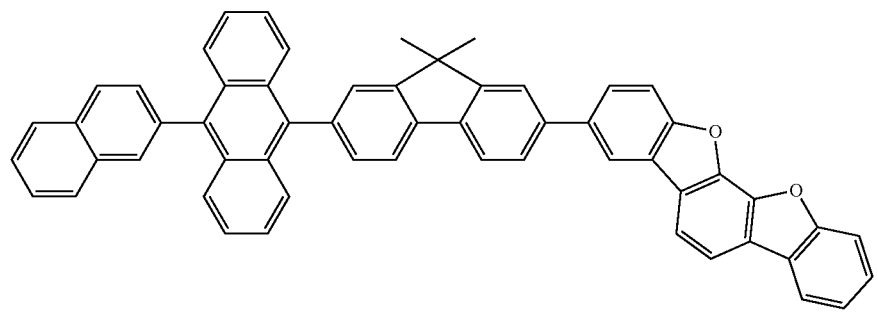
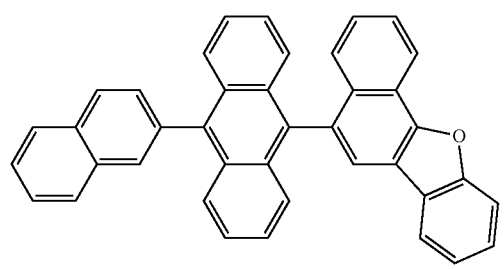
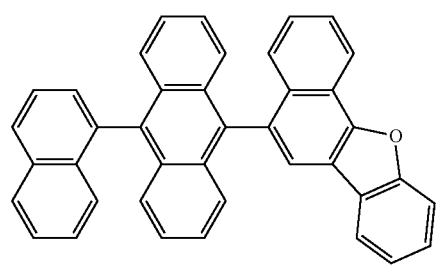
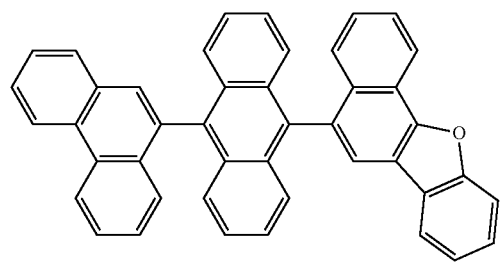
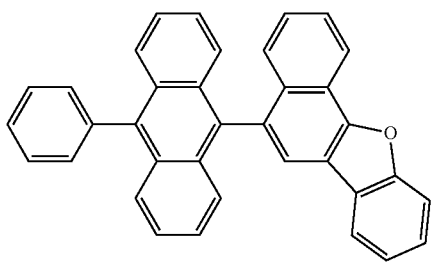
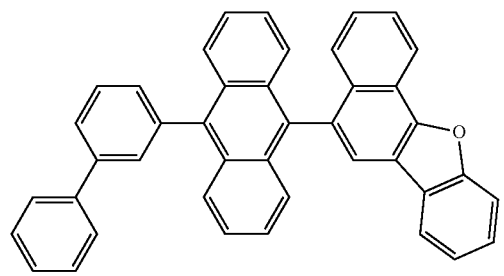
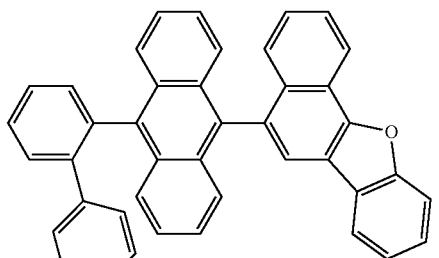
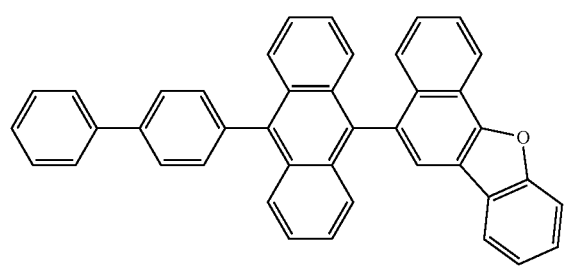
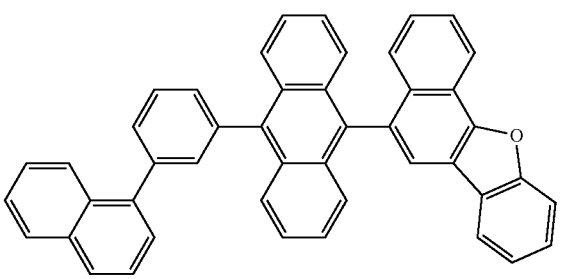

43
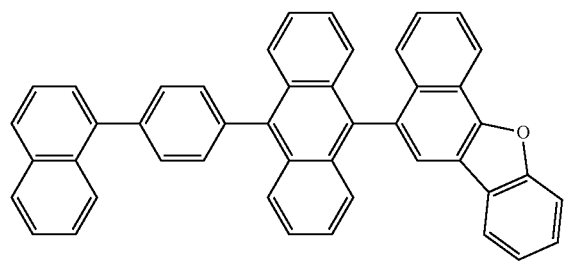
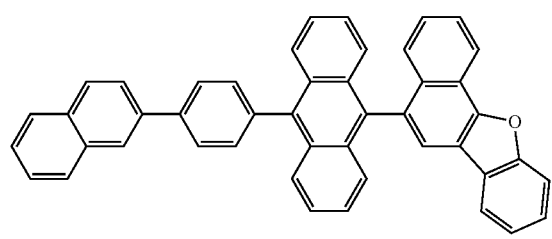
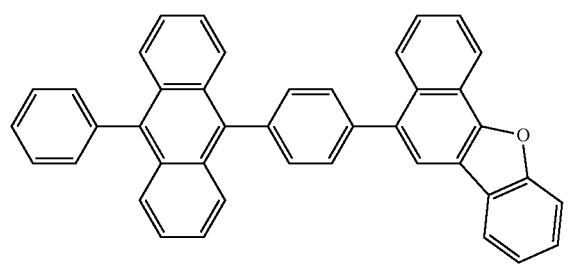
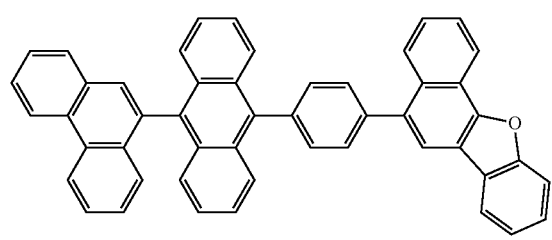
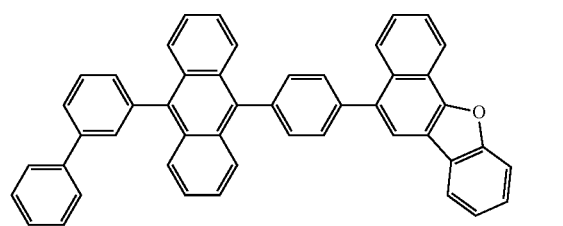
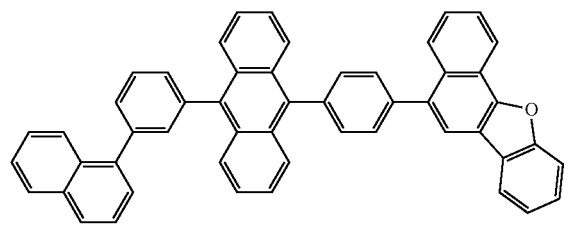
44
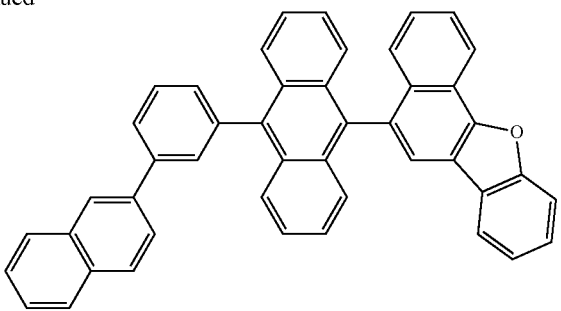
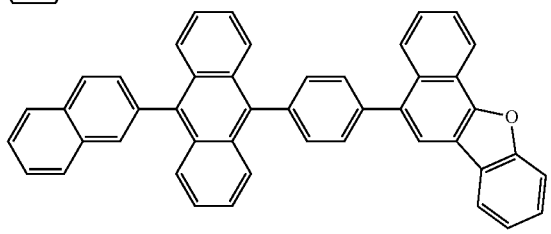
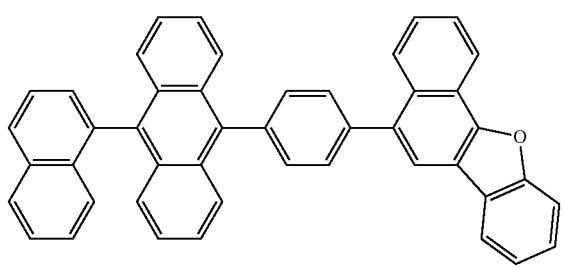
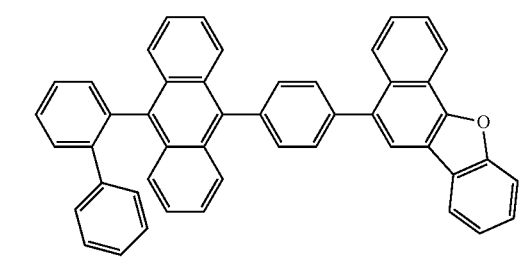
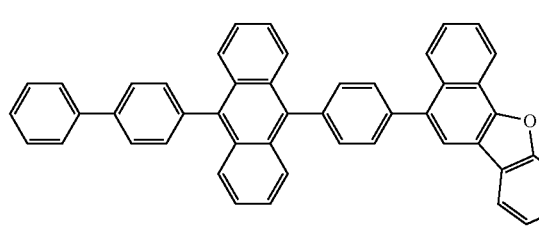
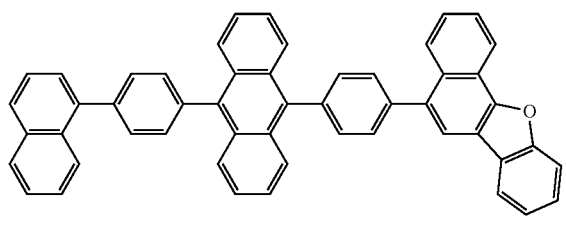

45
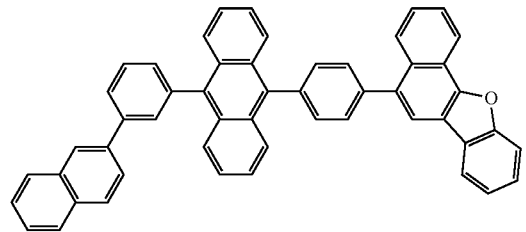
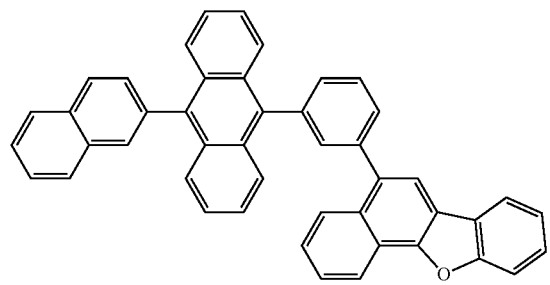
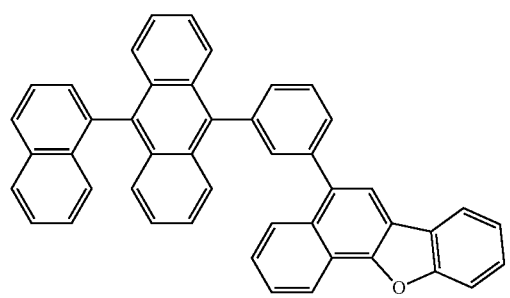
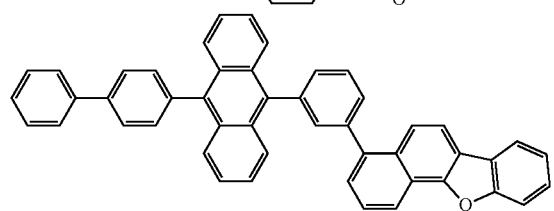
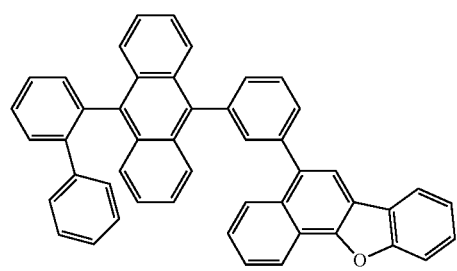
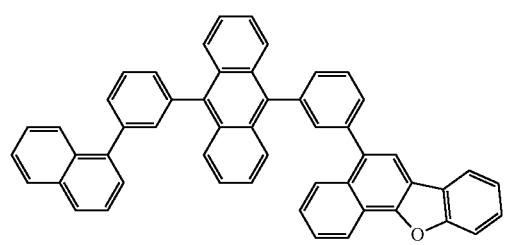
46
-continued
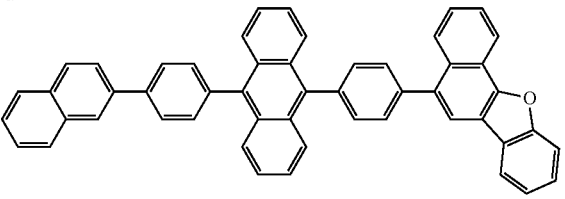
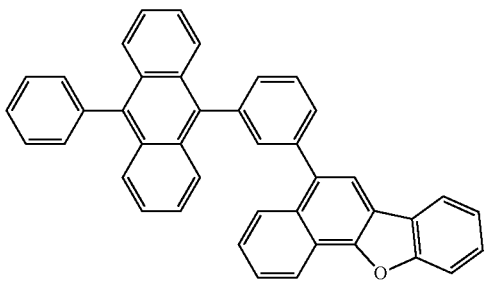
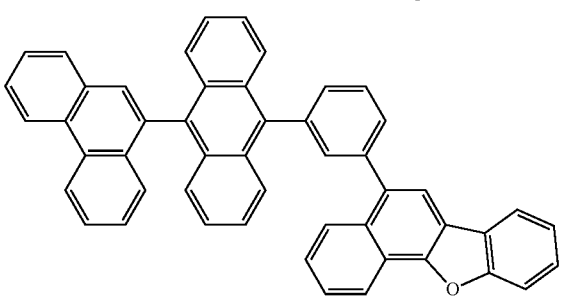
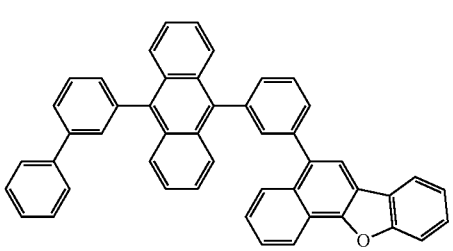
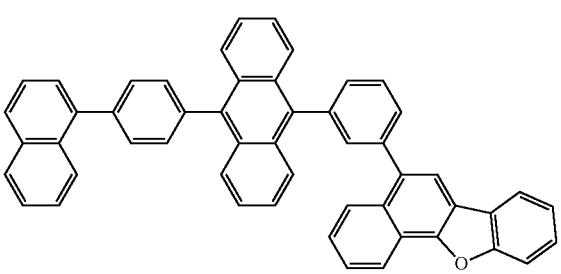
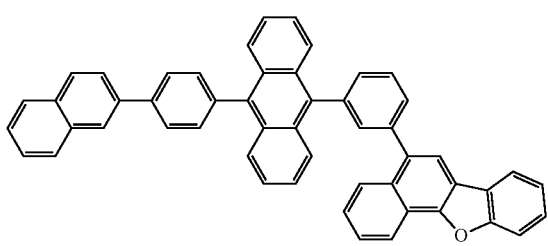

47
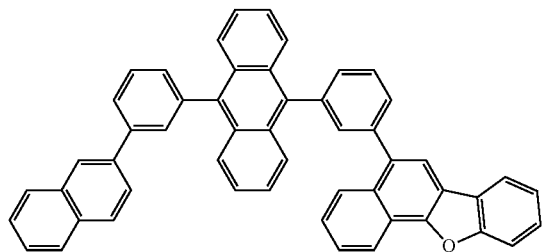
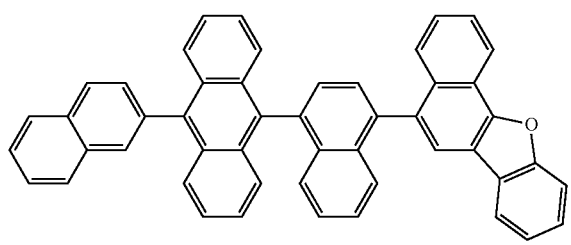
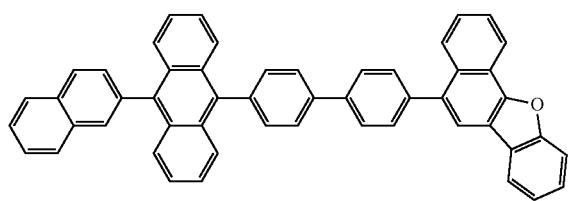
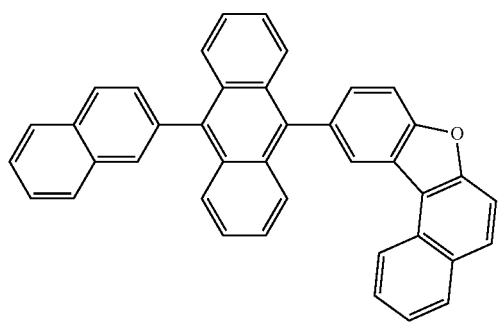
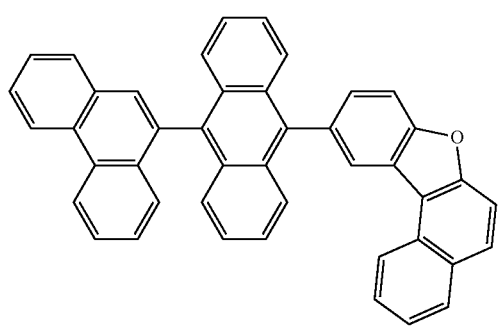
48
-continued
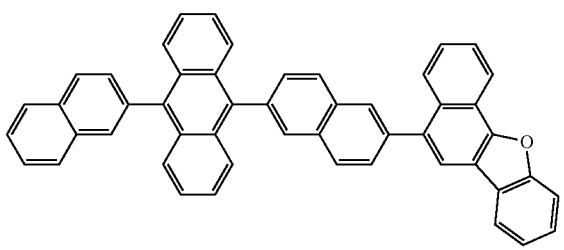
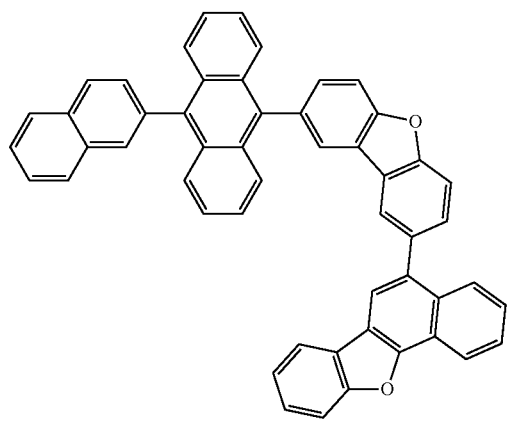
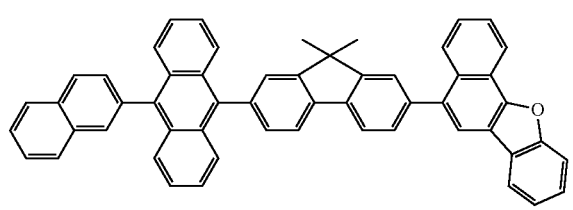
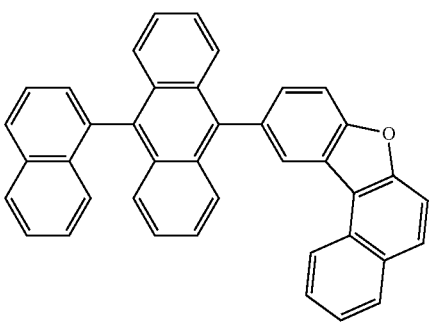
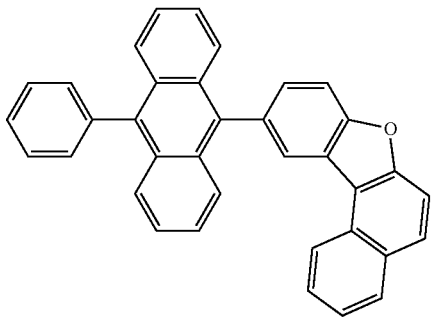

49
50
-continued
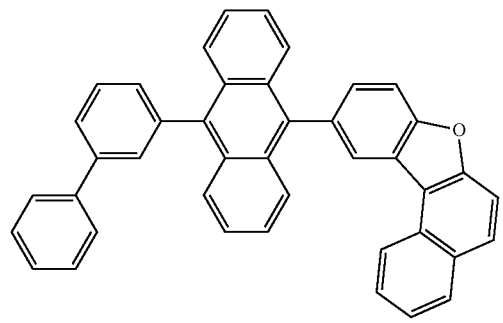
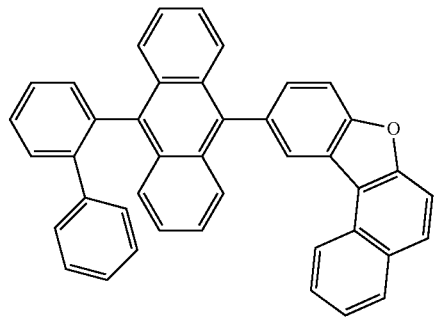
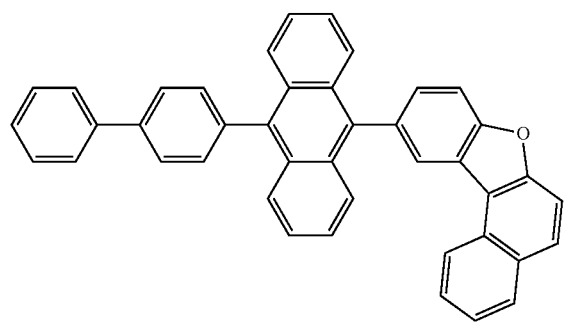
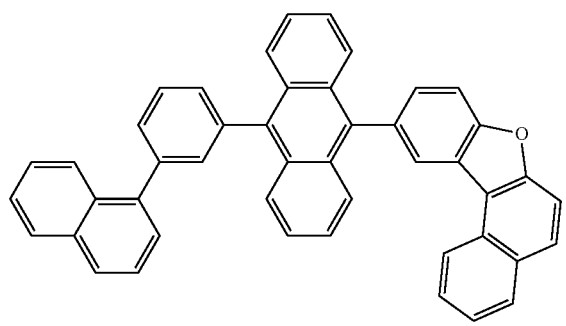
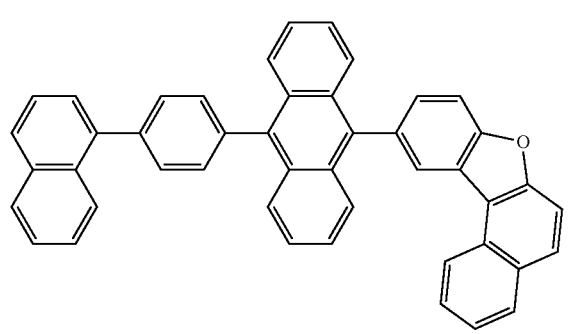
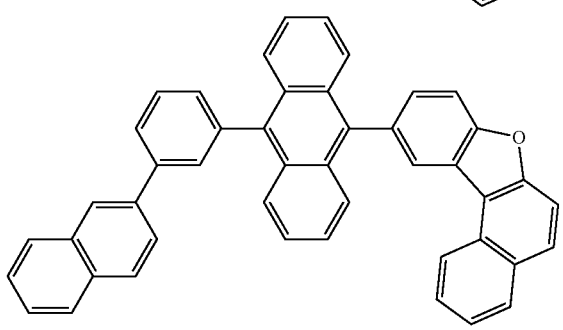
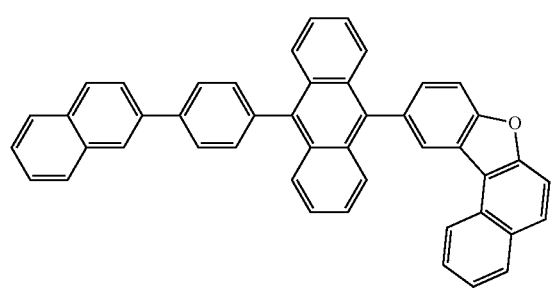
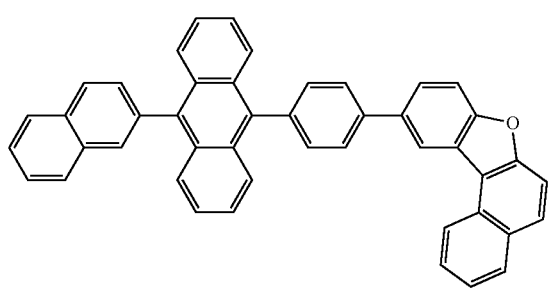
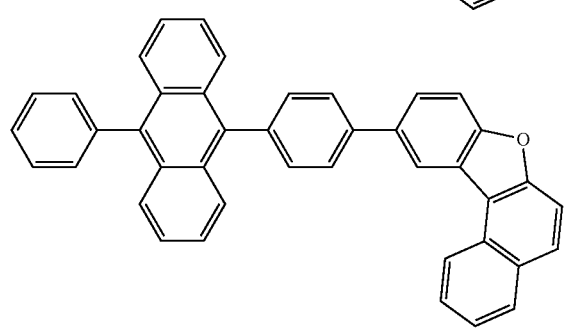
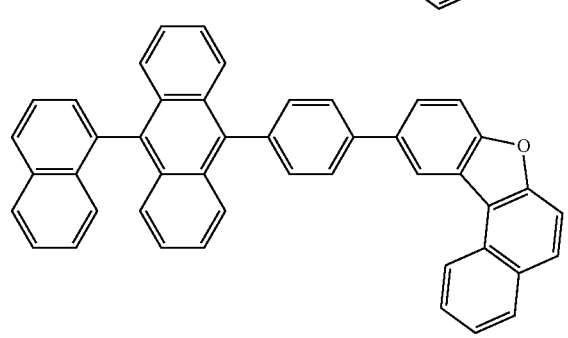

-continued
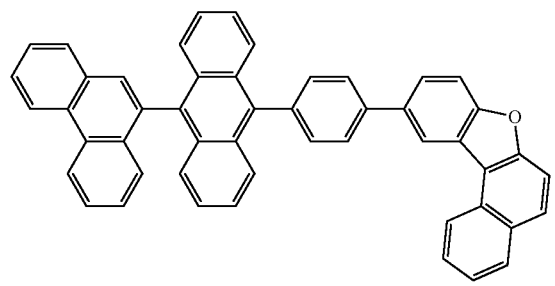
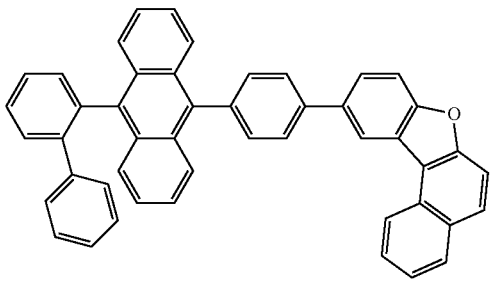
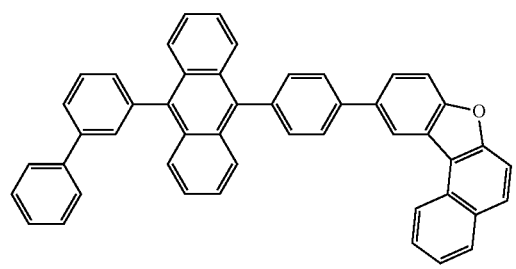
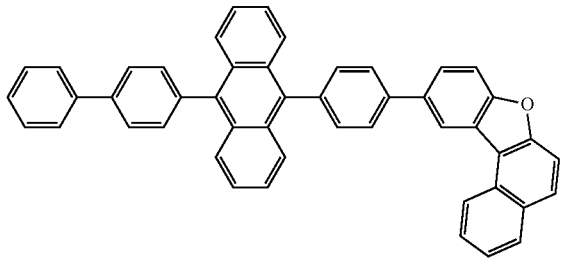
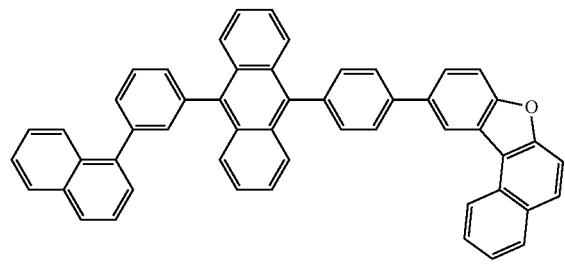
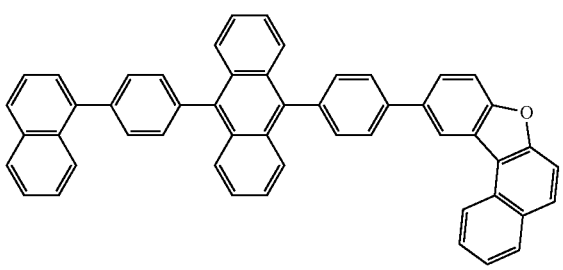
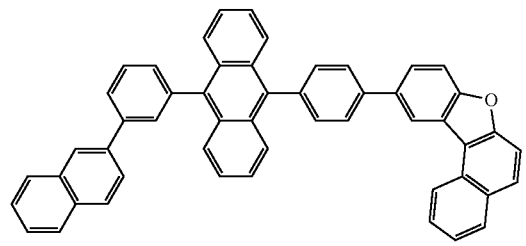
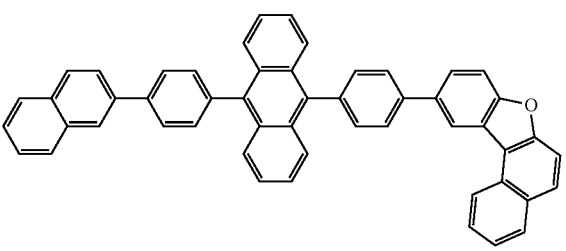
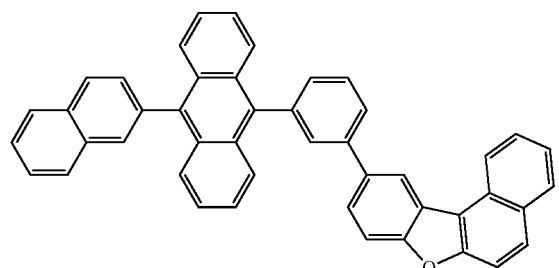
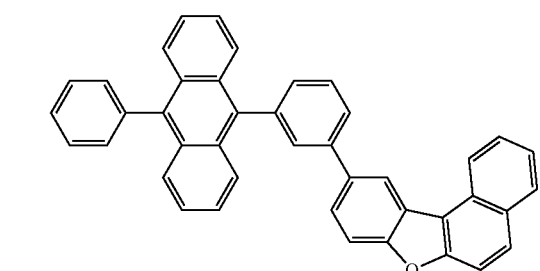
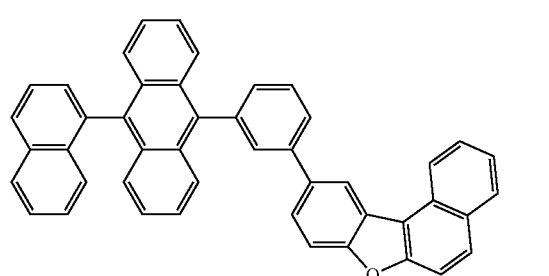
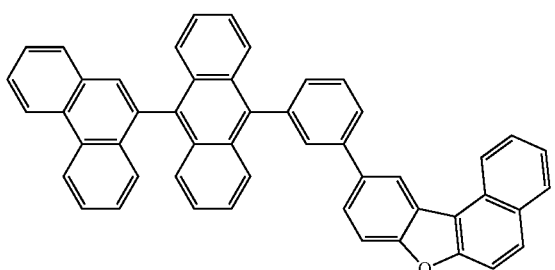

53 54
-continued
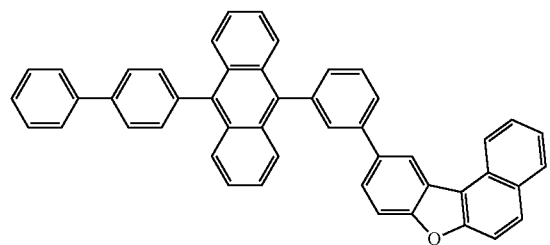
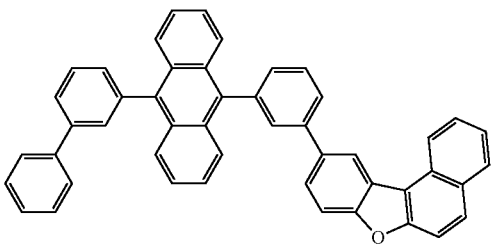
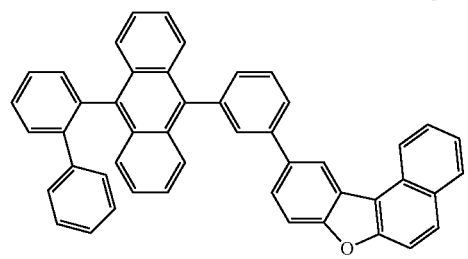
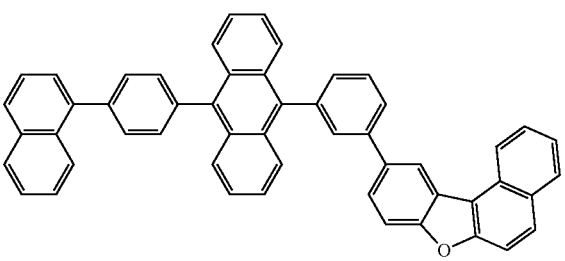
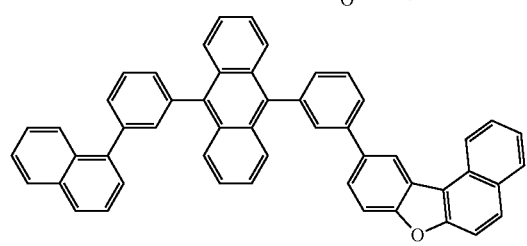
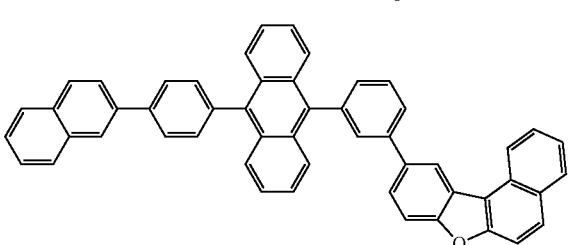
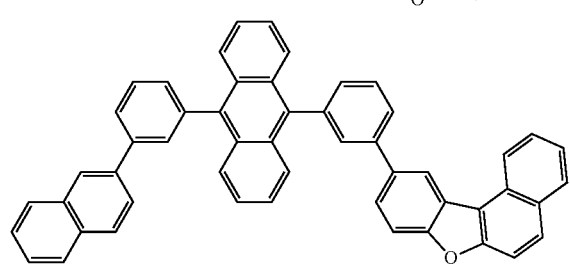
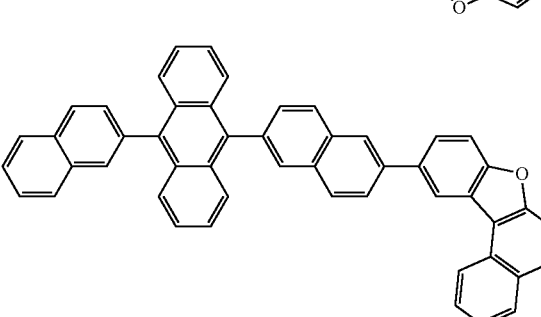
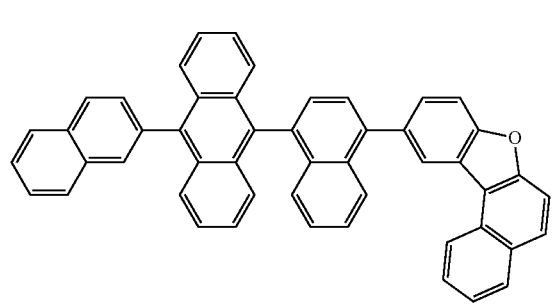
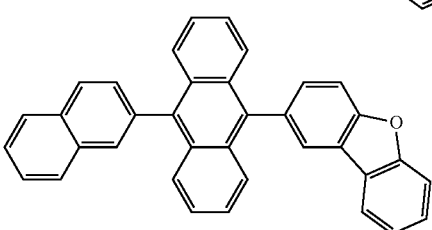
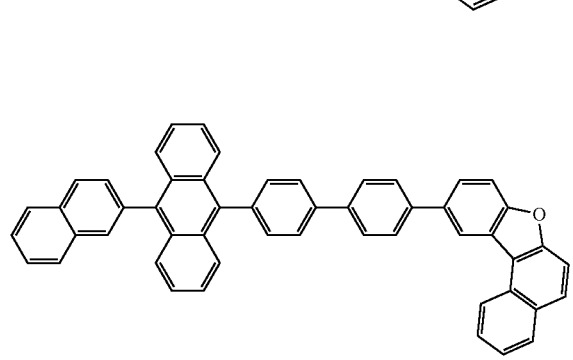
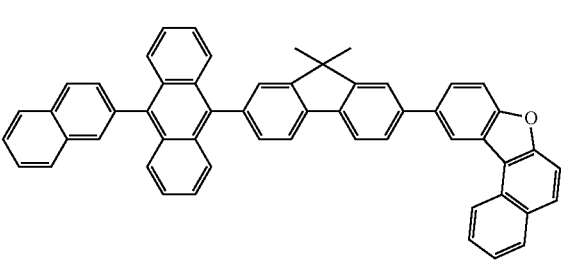

-continued
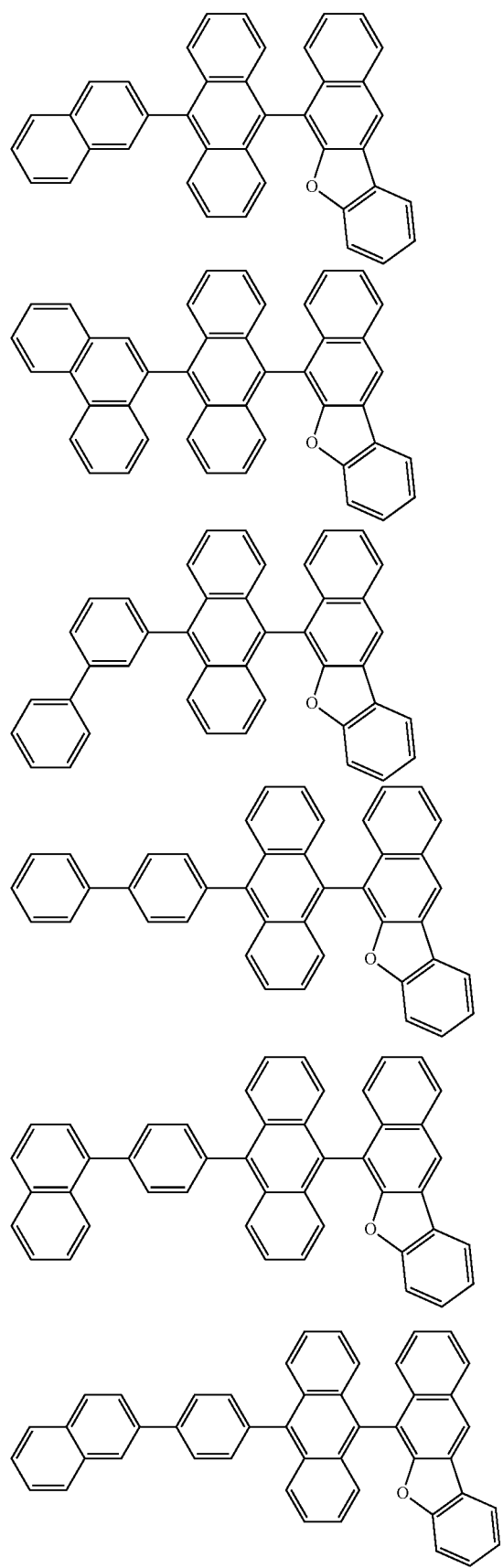
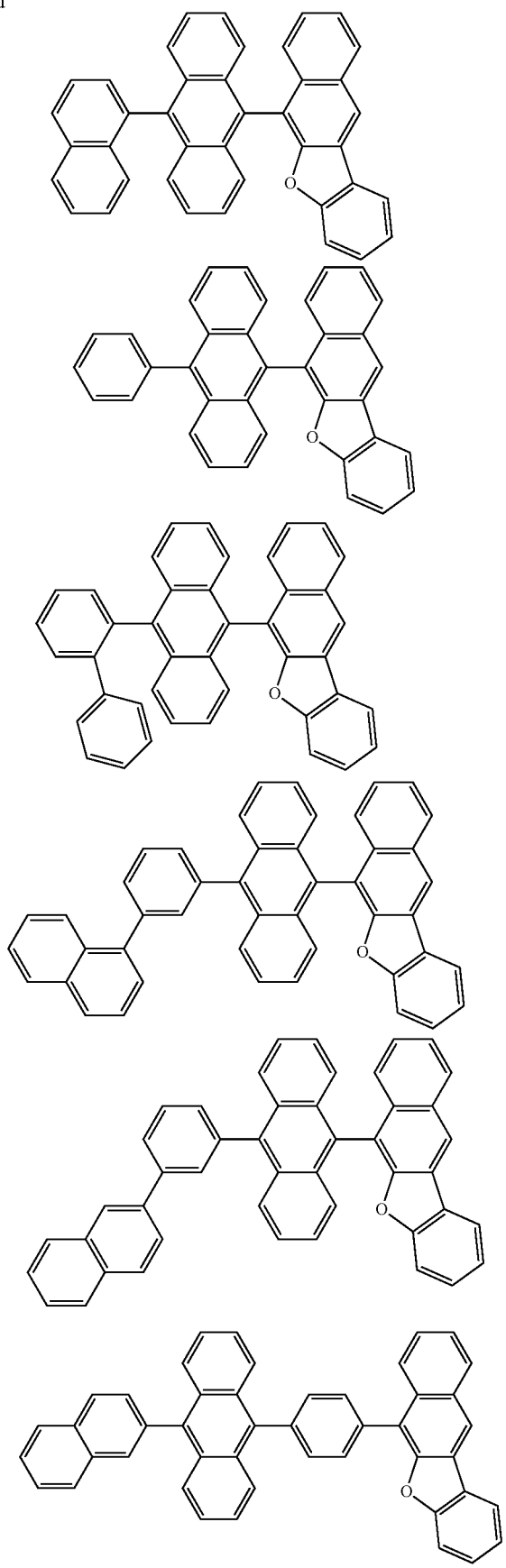

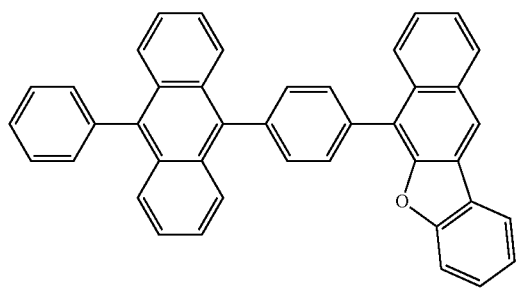
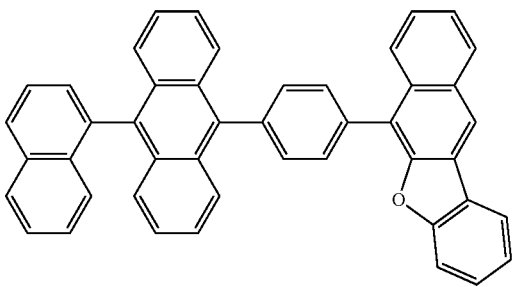
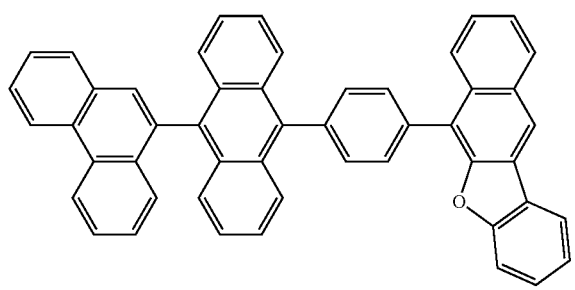
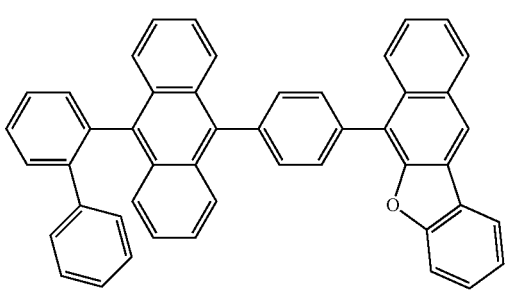
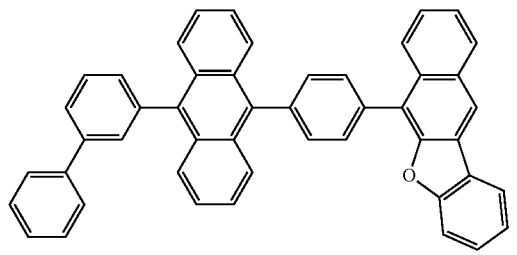
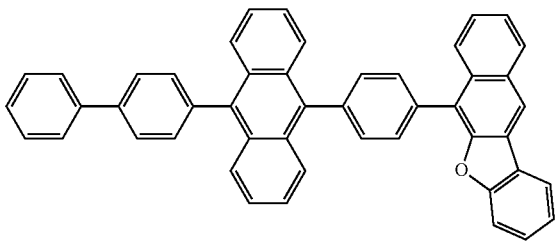
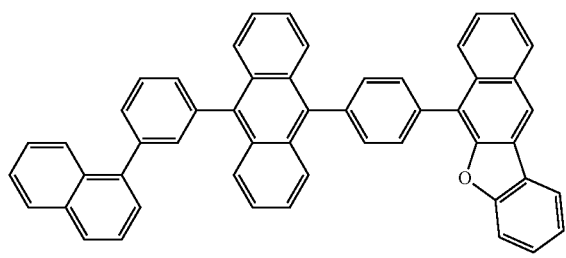
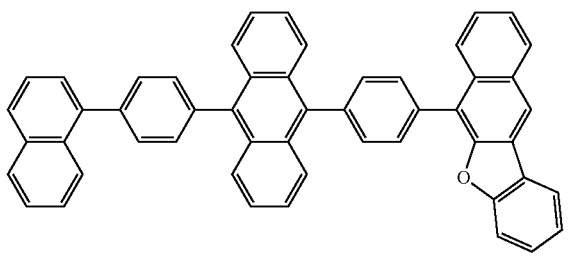
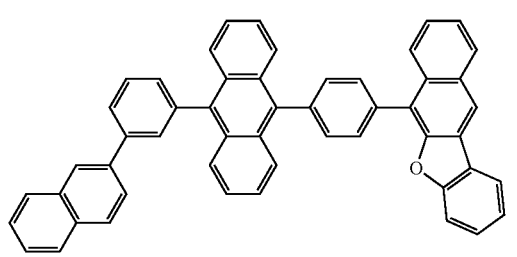
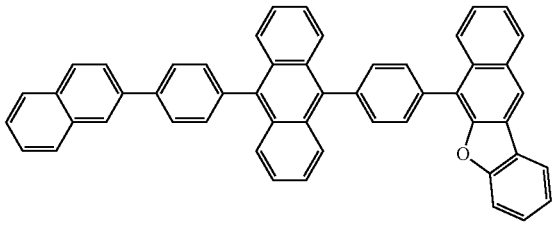

59
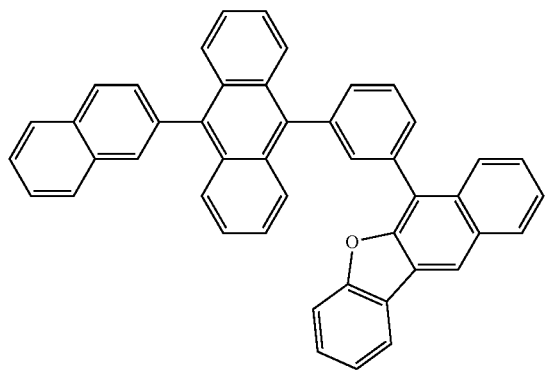
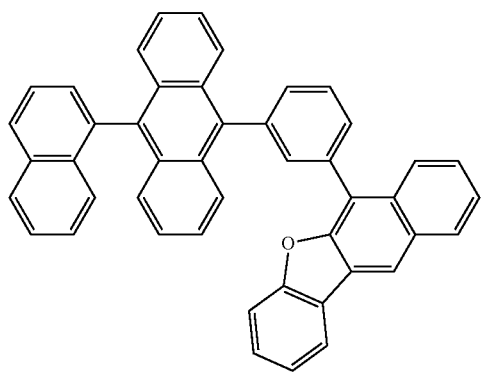
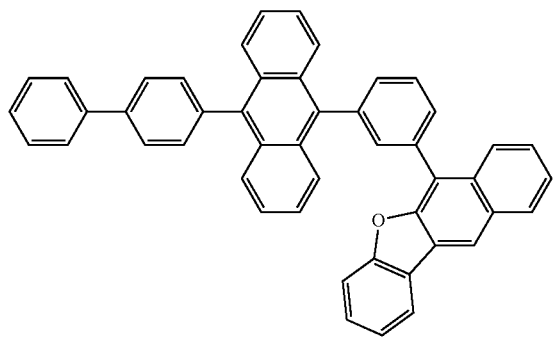
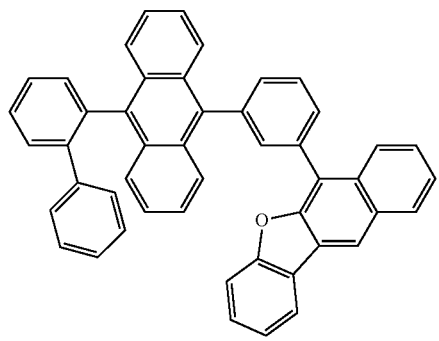
60
-continued
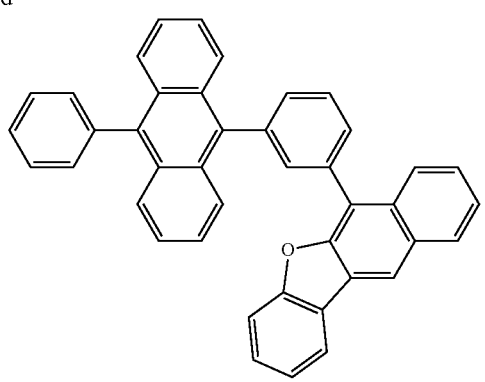
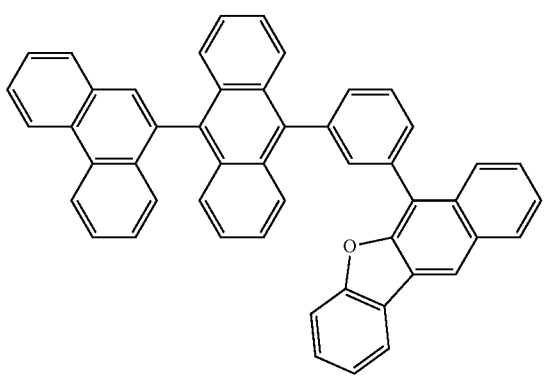
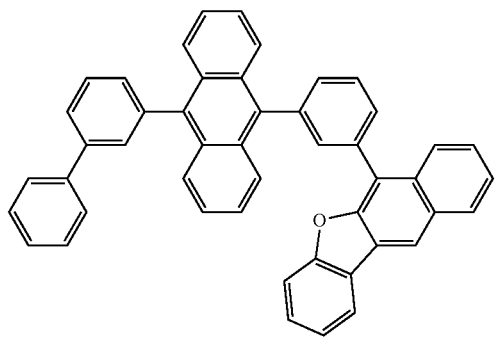
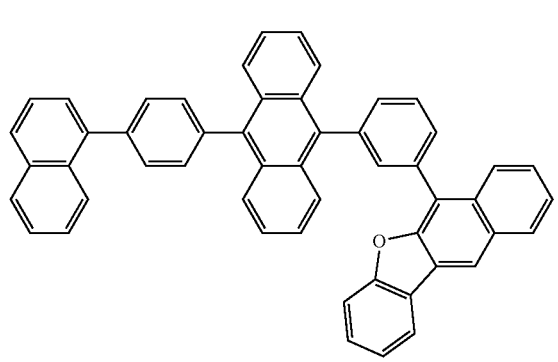

61 62
-continued
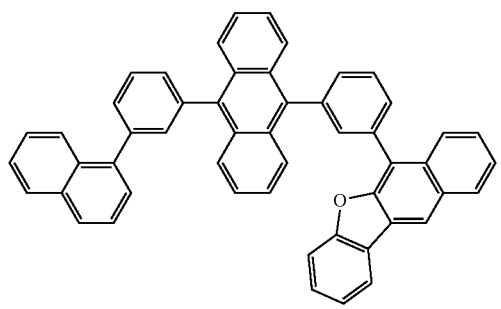 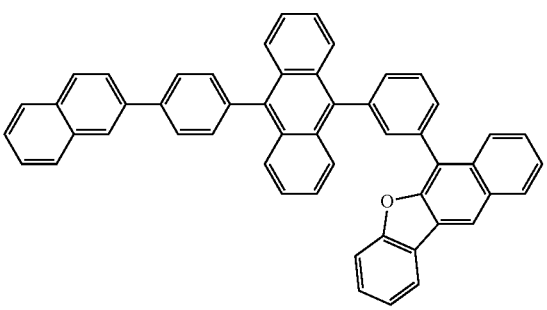
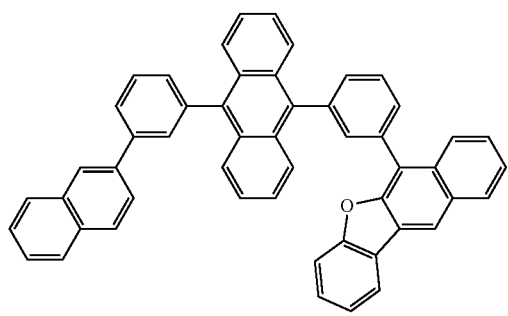 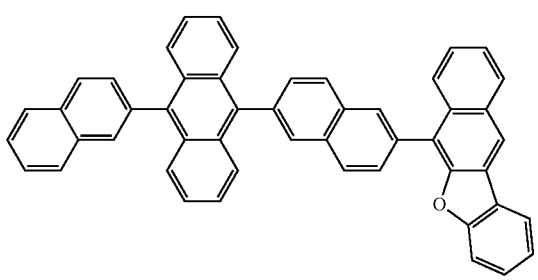
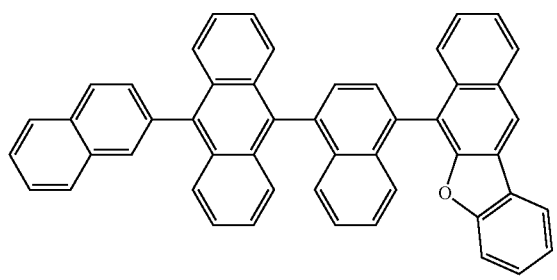 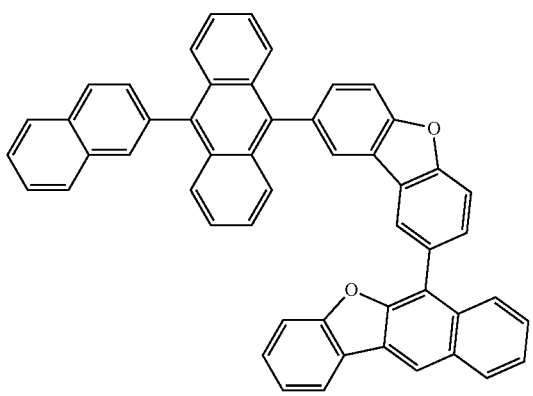
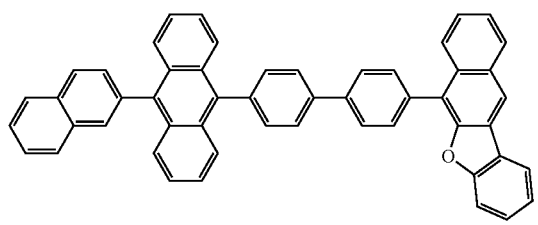 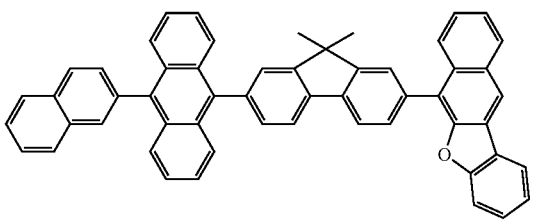
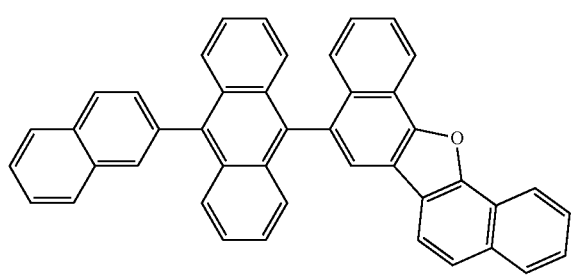 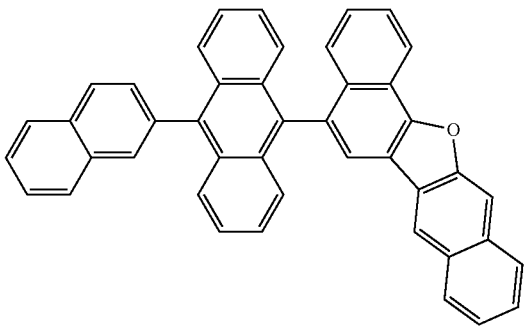

-continued
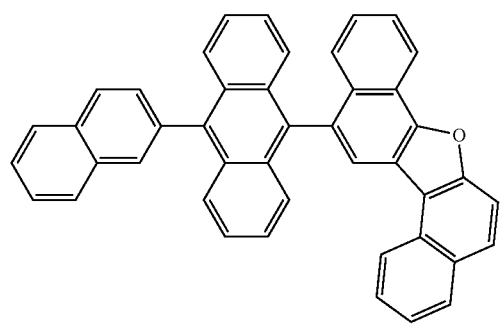
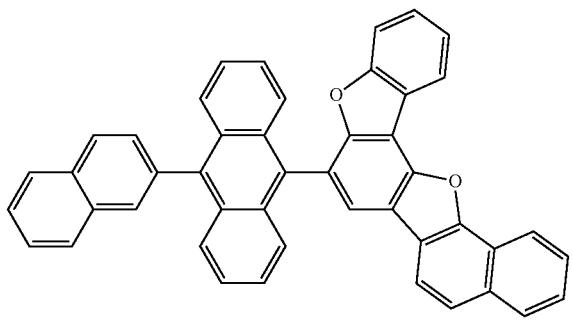
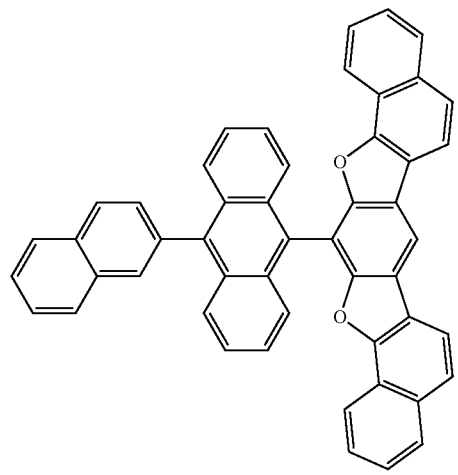
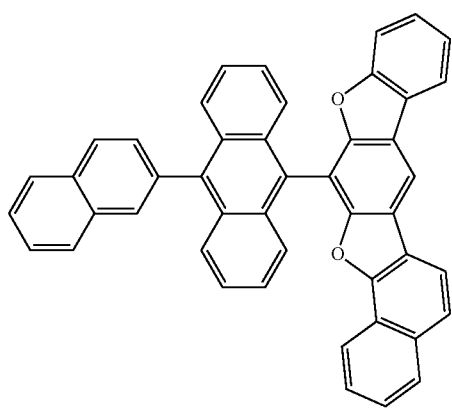
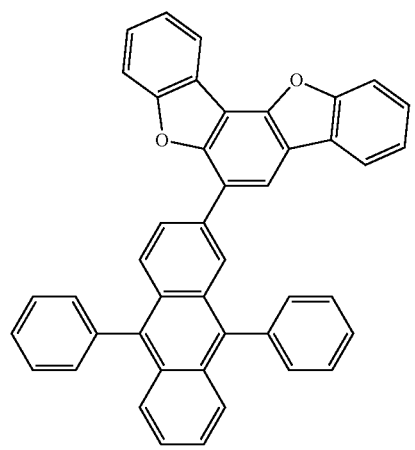
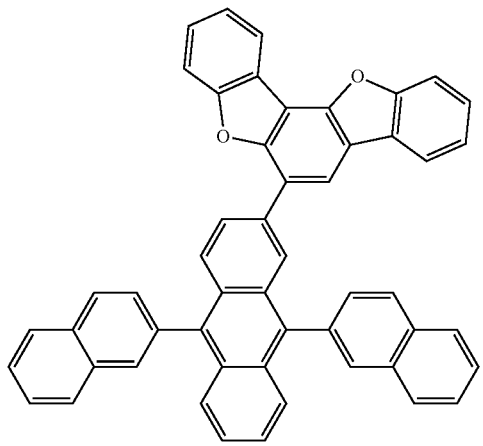
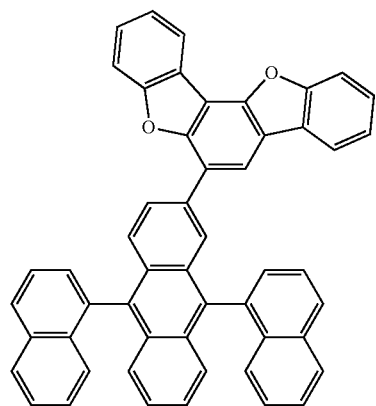
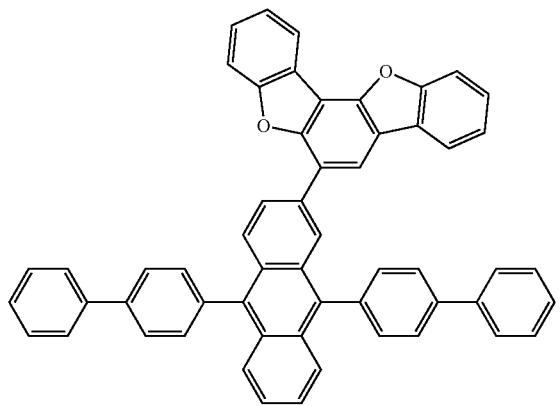

-continued
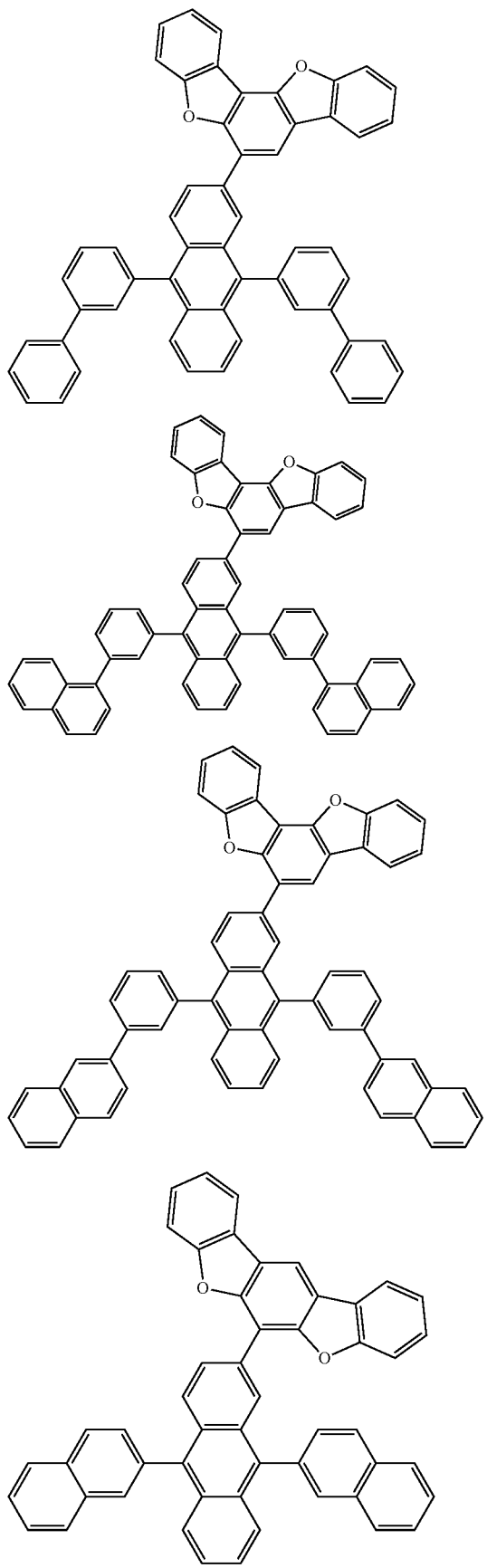
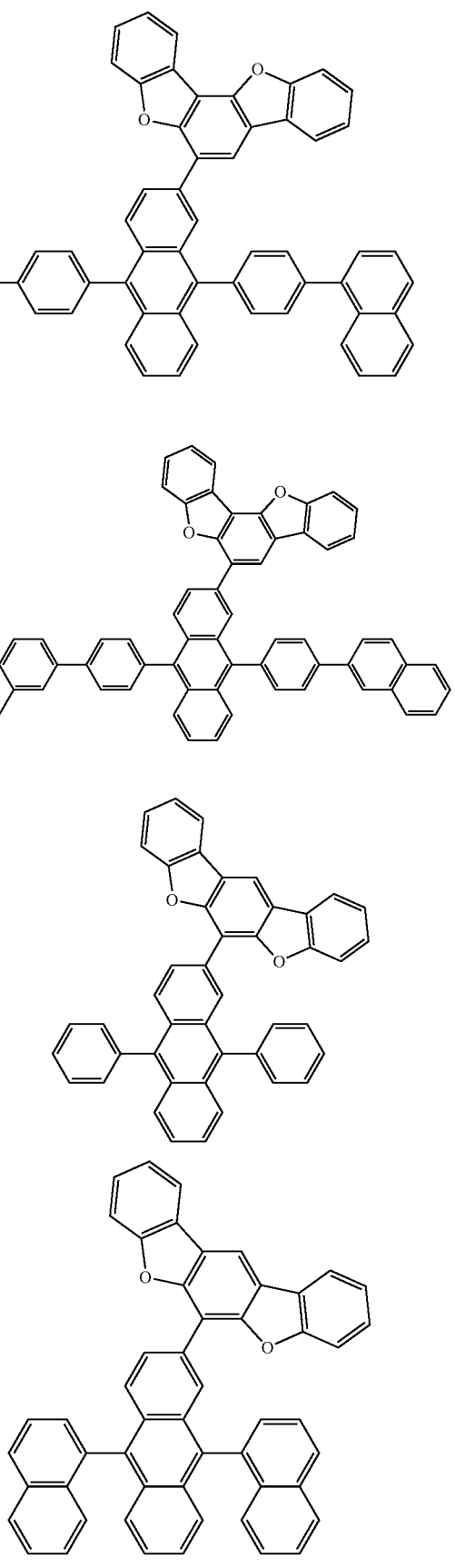

-continued
| 67 | 68 |
|---|---|
| 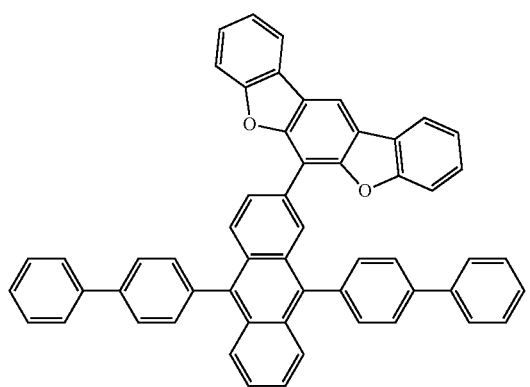 | 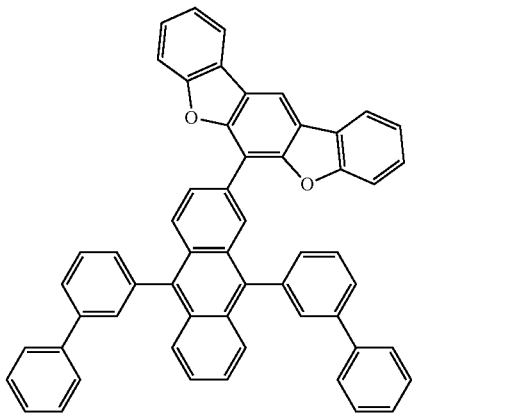 |
| 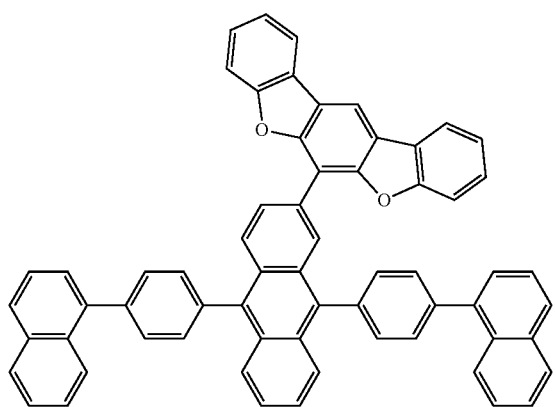 | 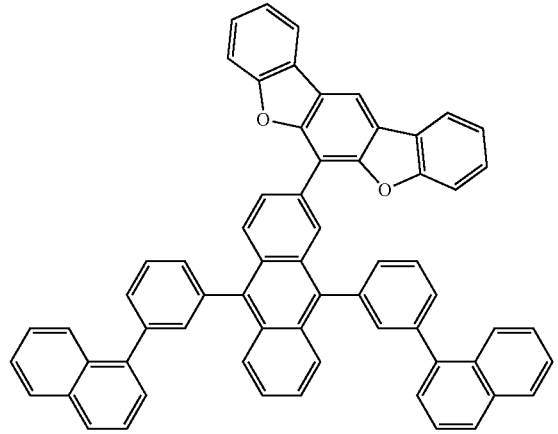 |
| 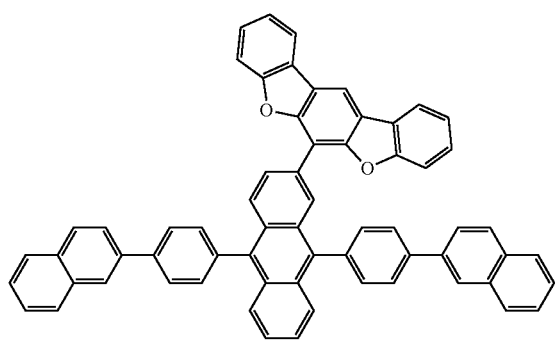 | 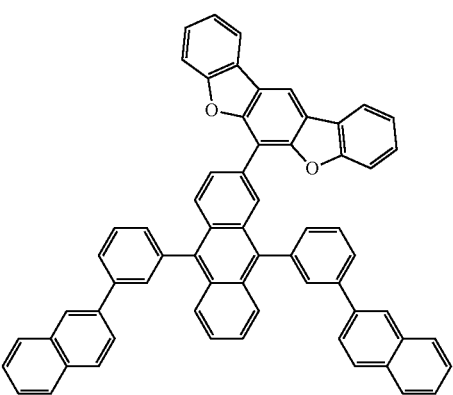 |
| 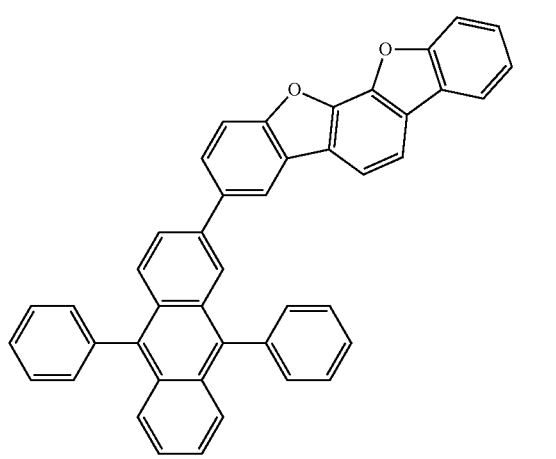 | 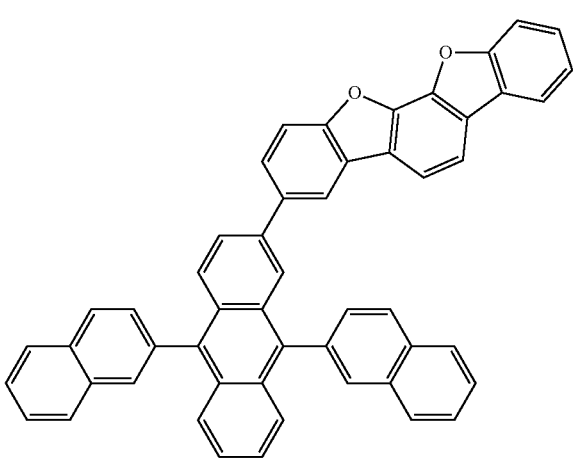 |

-continued
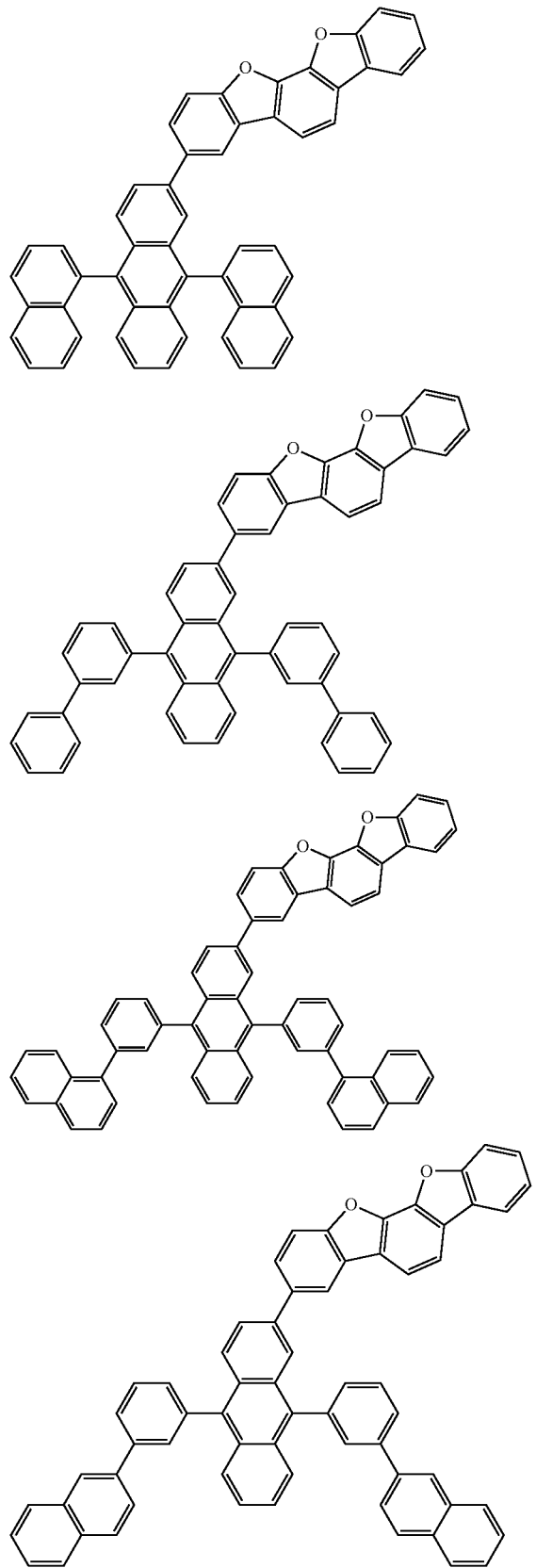
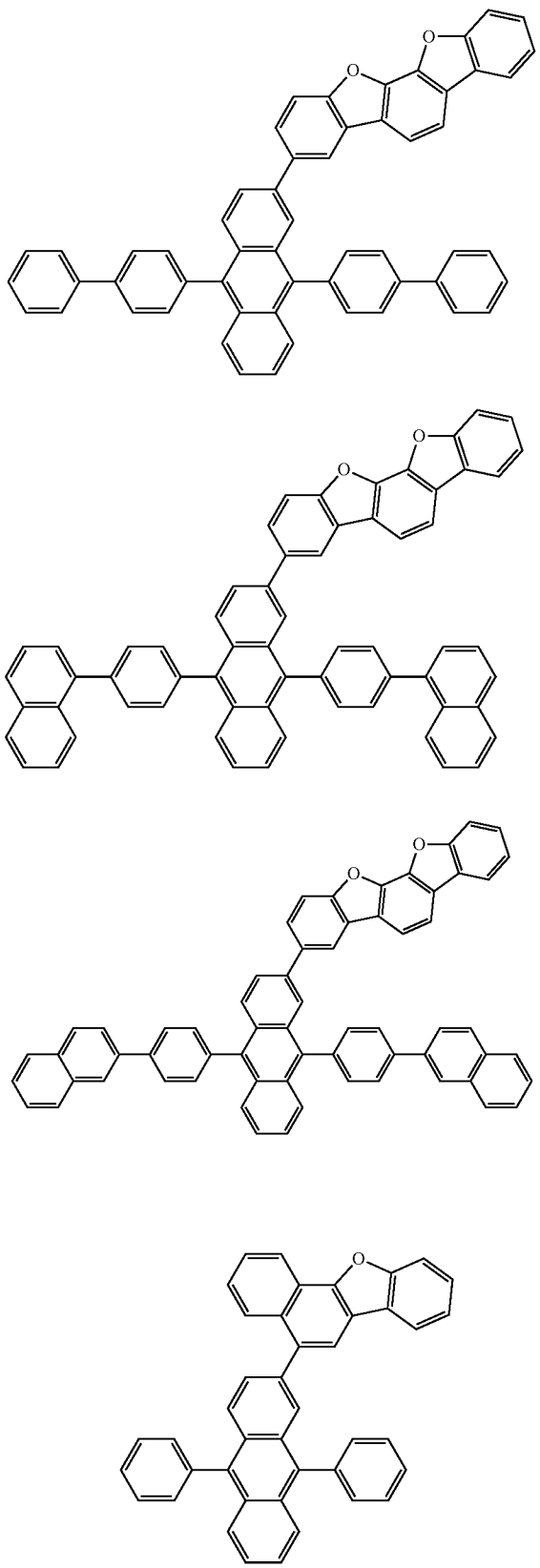

71 72
-continued
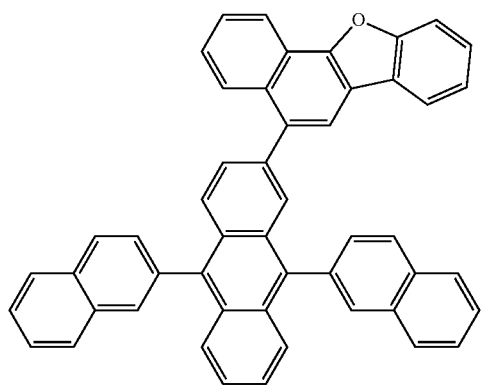
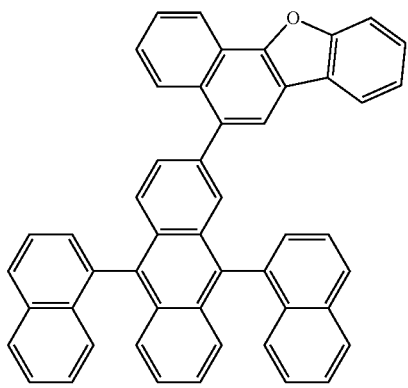
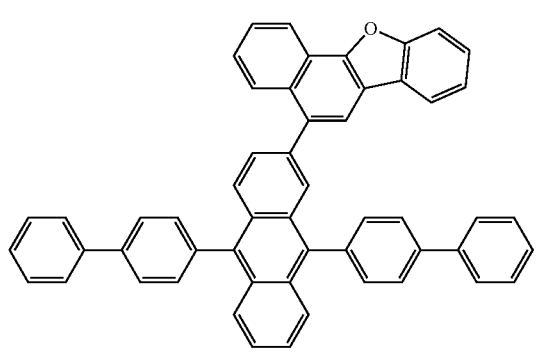
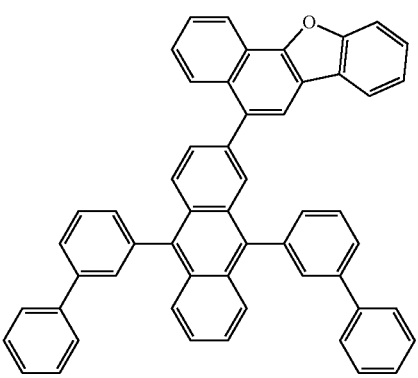
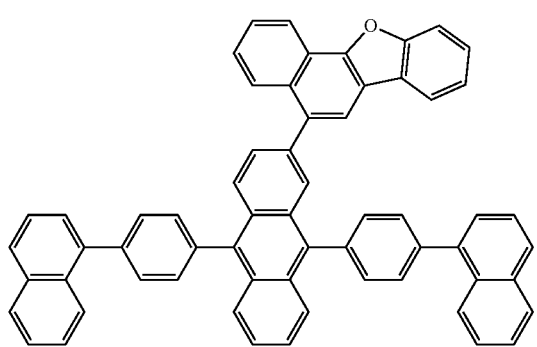
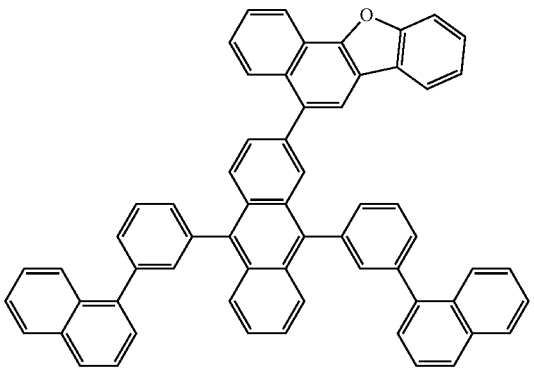
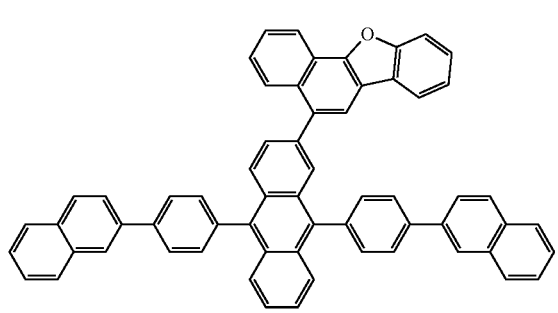
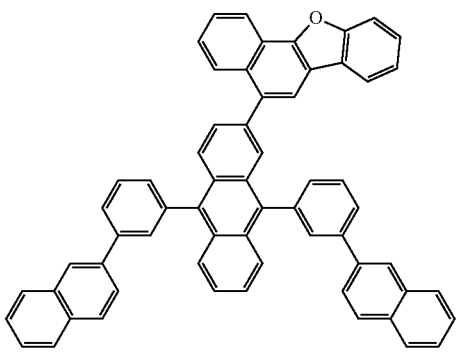

73 74
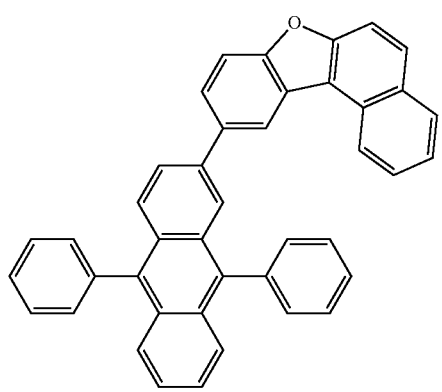
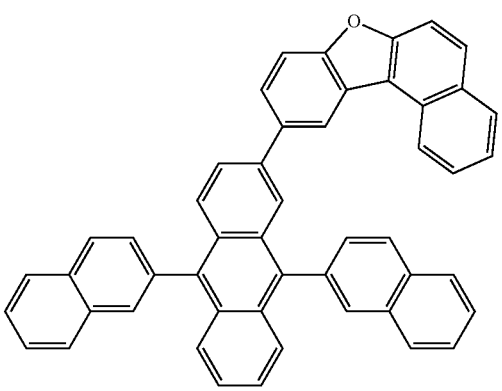
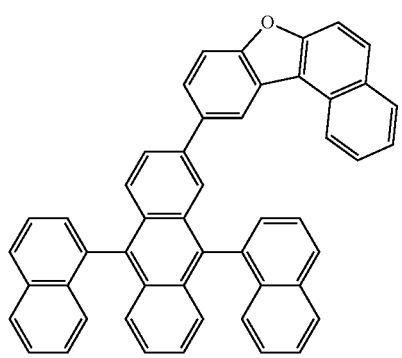
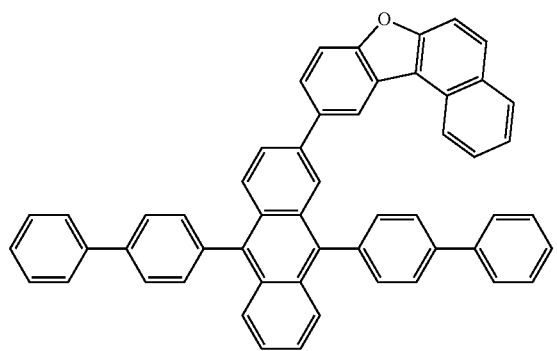
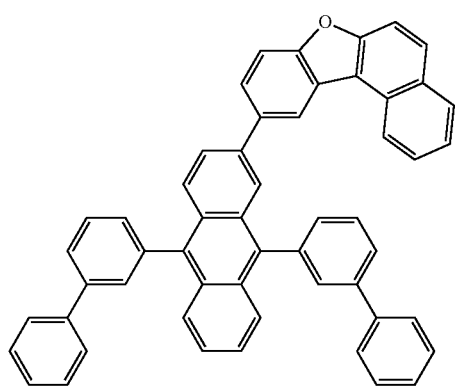
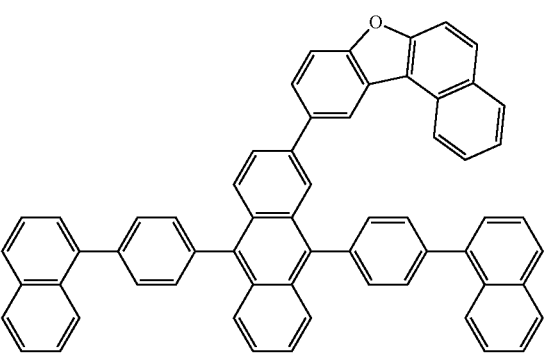
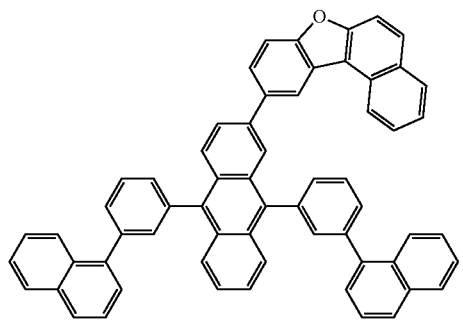
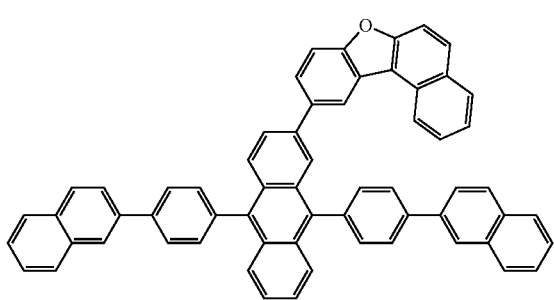

-continued
75
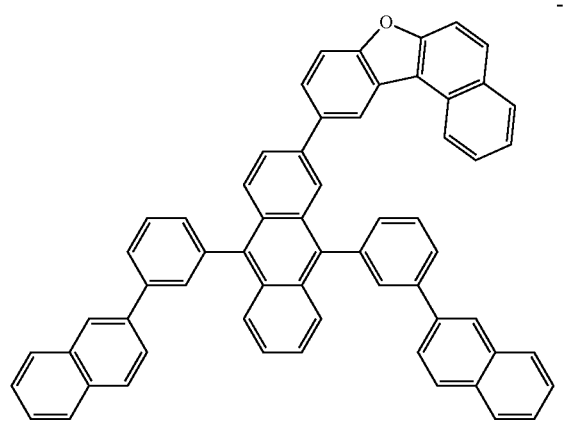
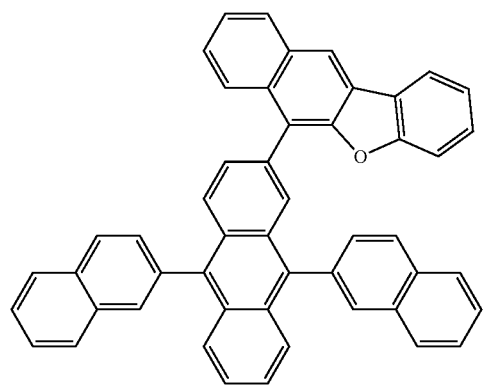
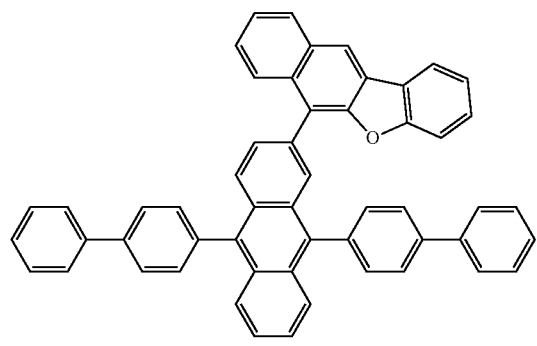
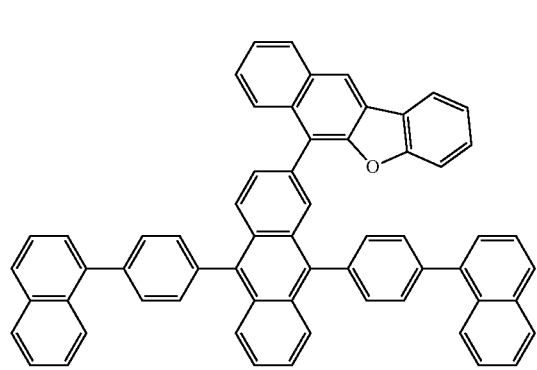
76
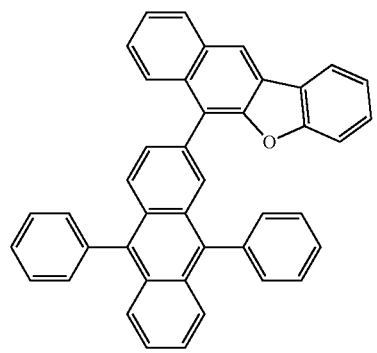
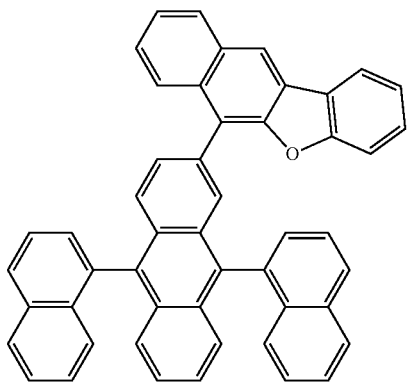
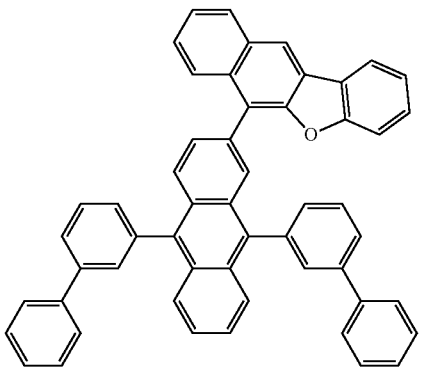
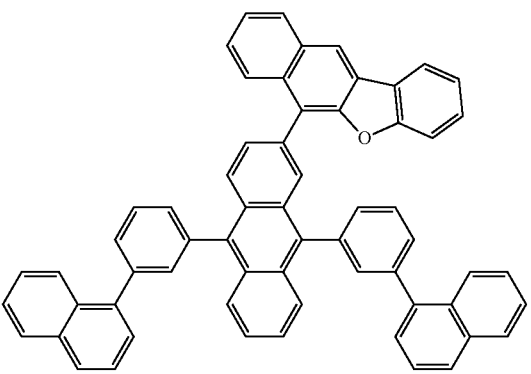

-continued
77
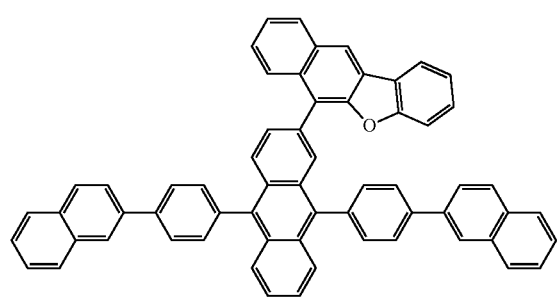
78
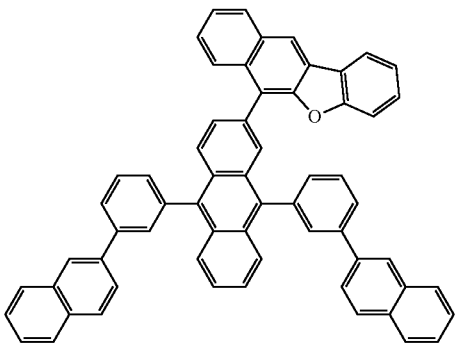
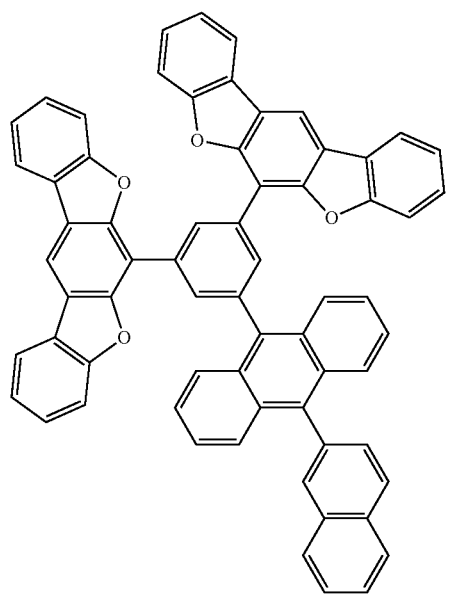
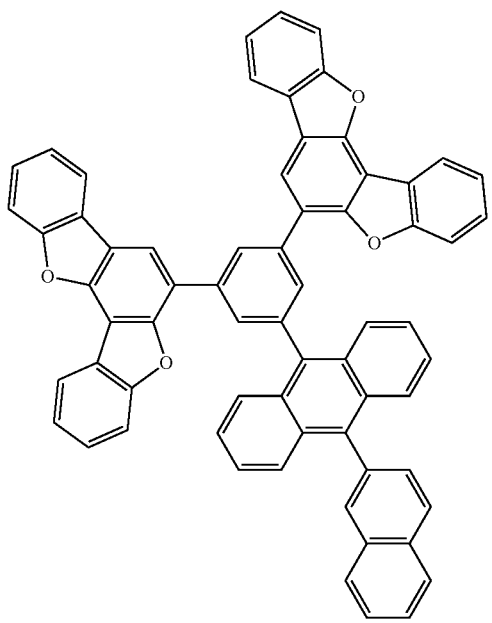
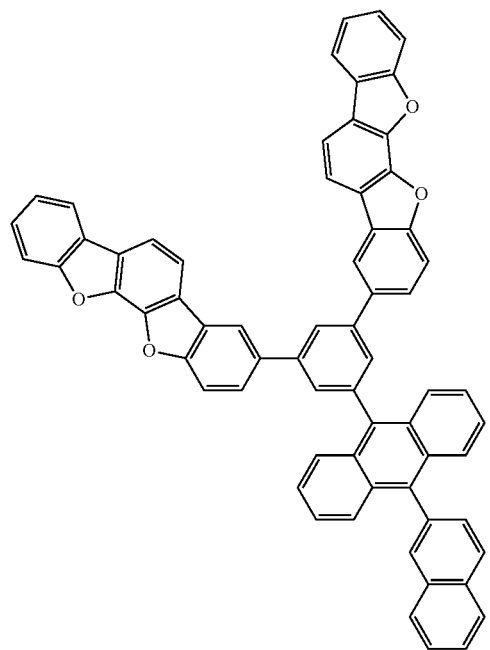
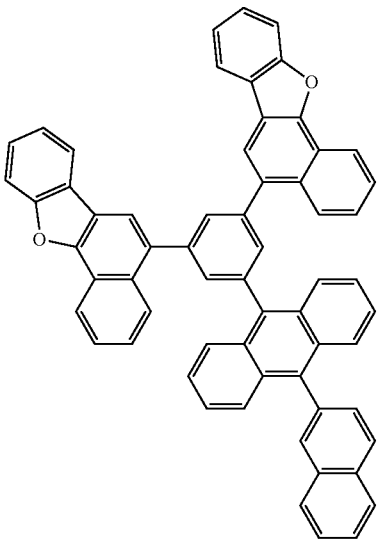

-continued
79
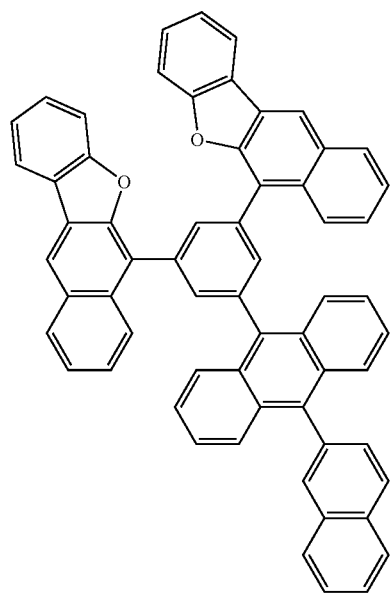
80
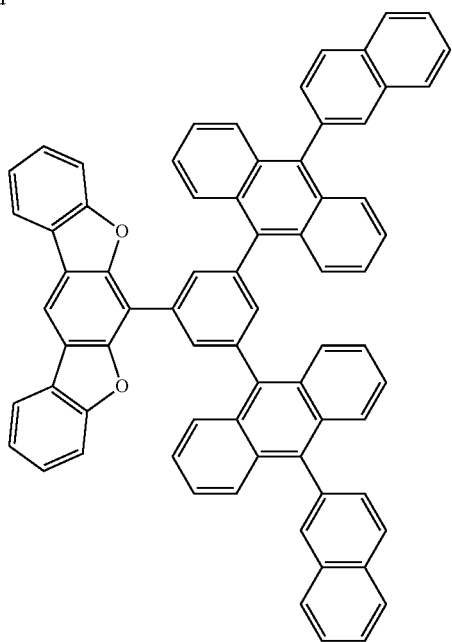
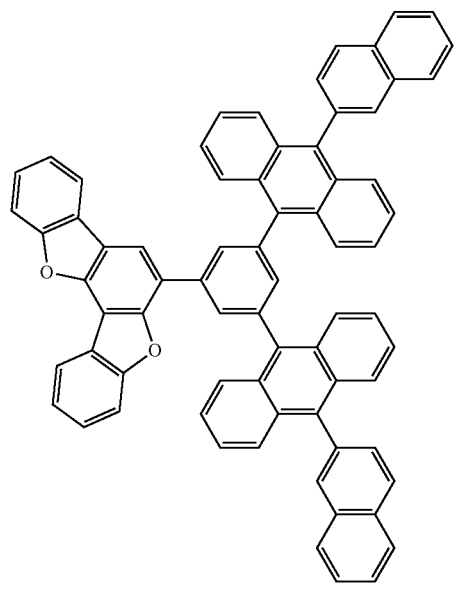
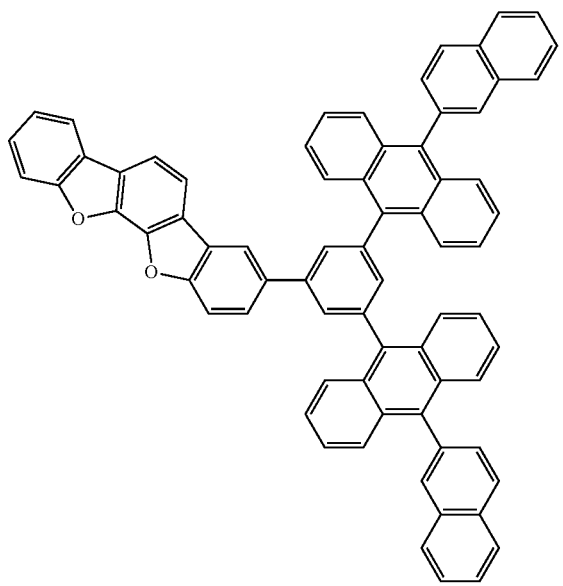

-continued
| 81 | 82 |
|---|---|
| 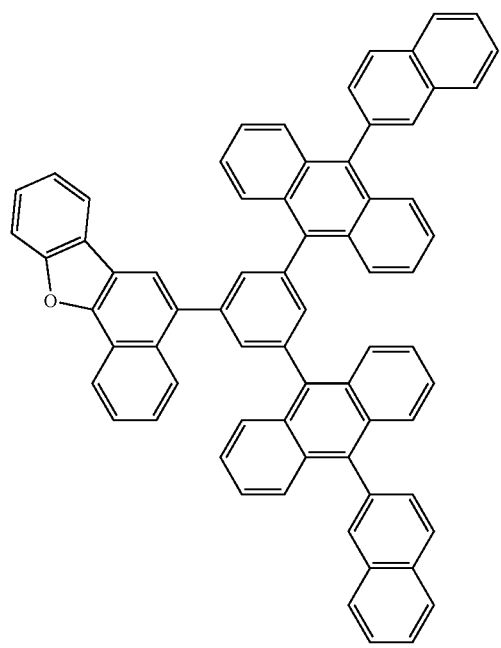 | 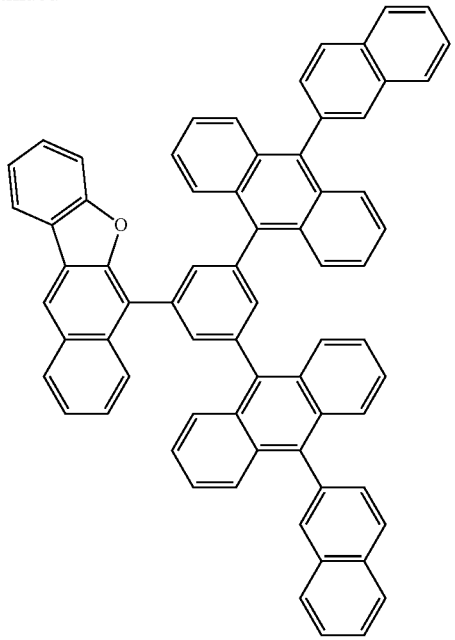 |
| 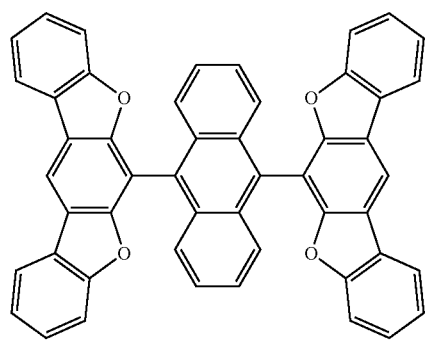 | 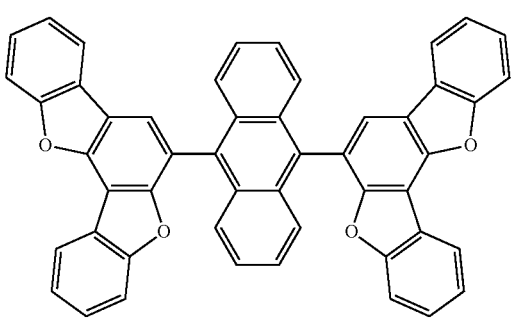 |
| 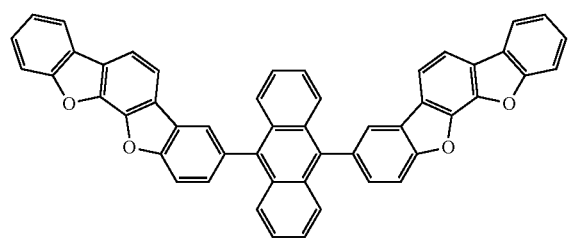 | 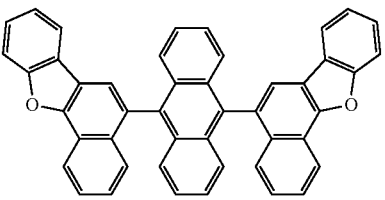 |
| 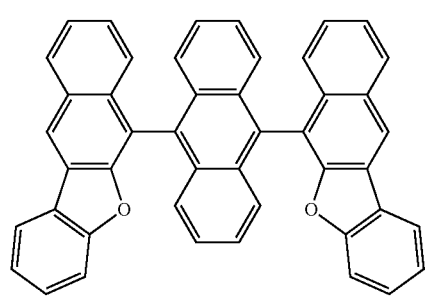 | 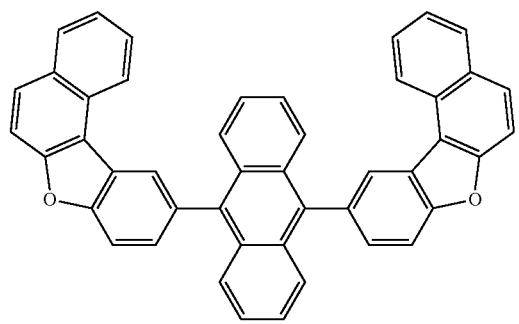 |

| 83 | 84 |
|---|---|
| 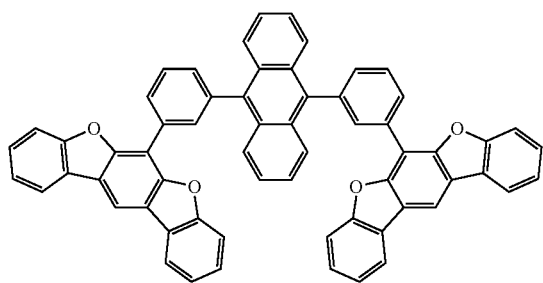 | 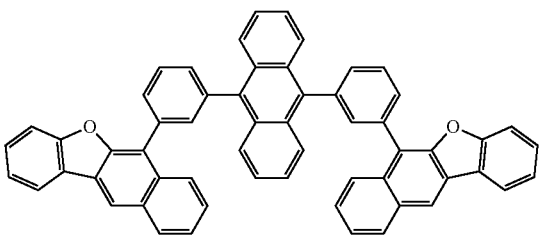 |
| 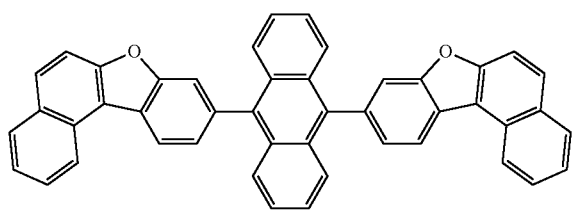 | 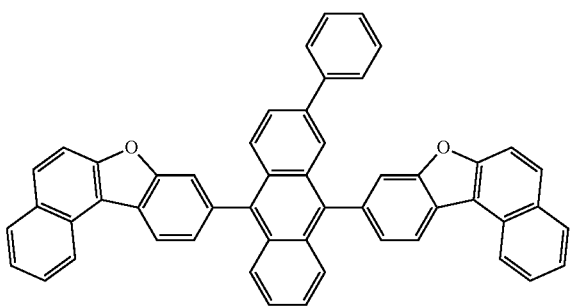 |
| 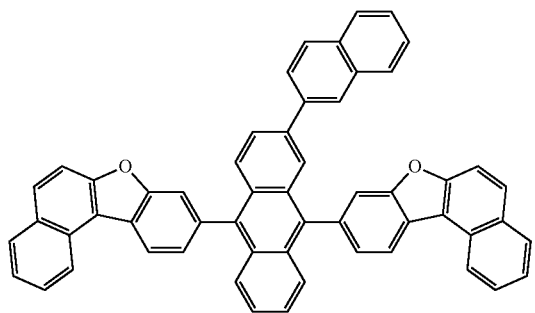 | 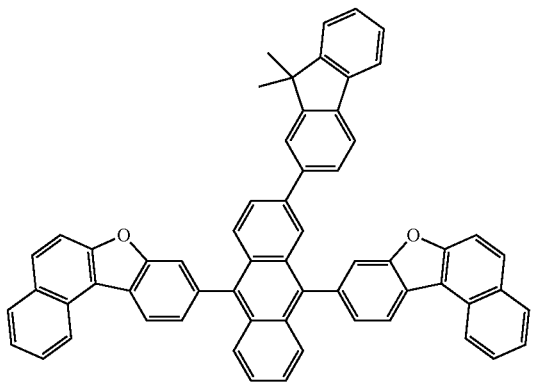 |
| 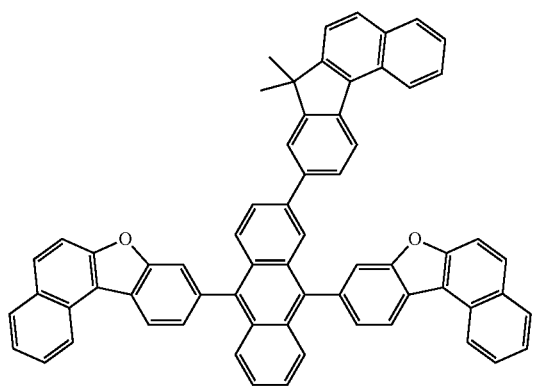 | 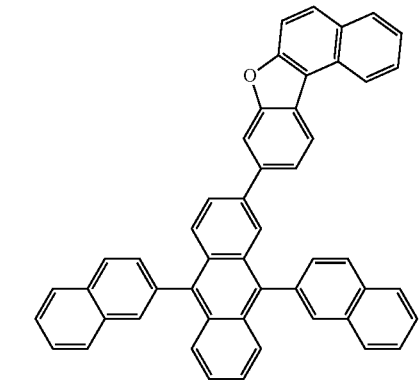 |
-continued 85
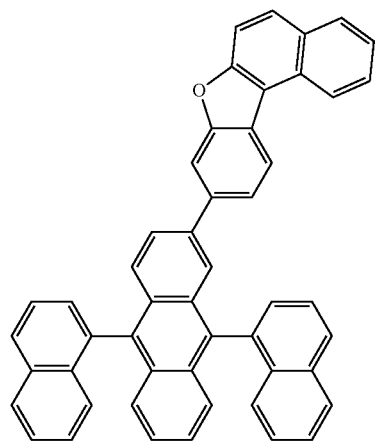
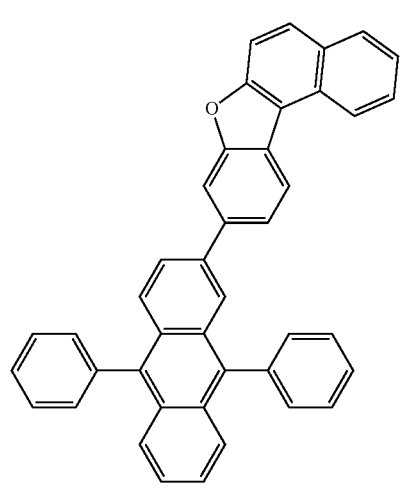
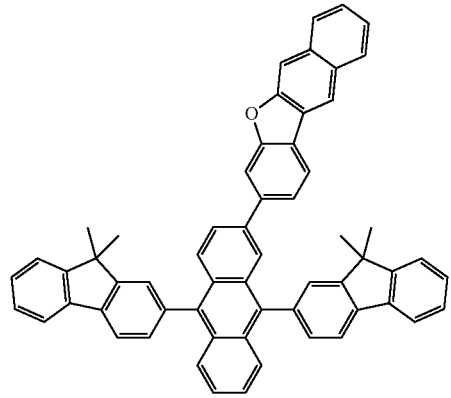
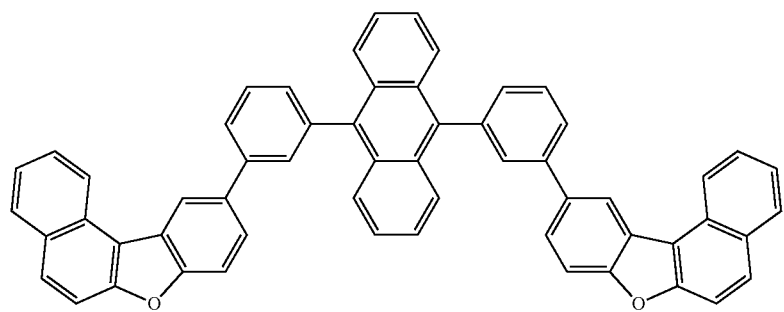
86
-continued
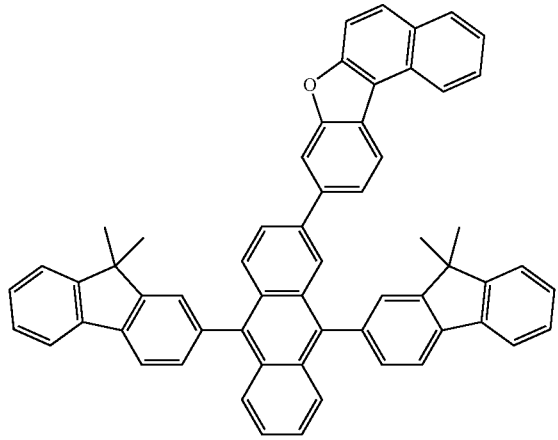
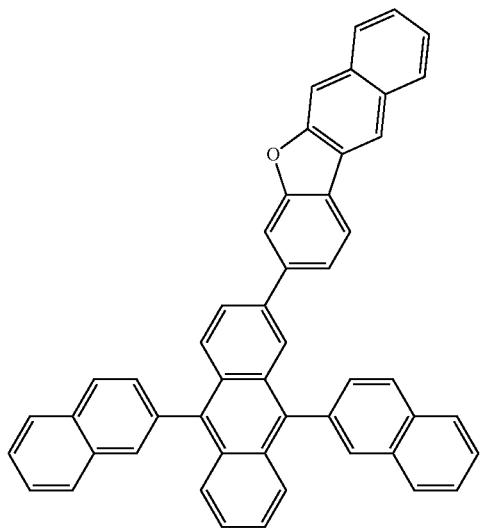
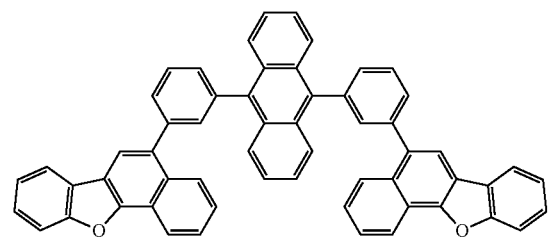

87 88
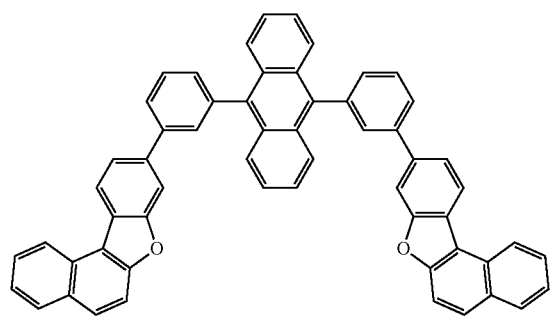 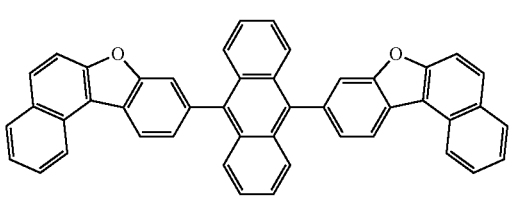
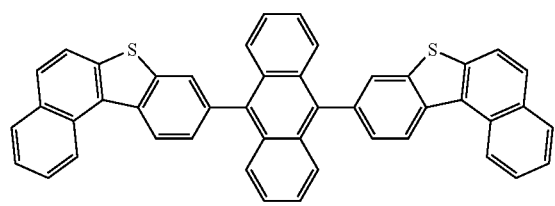 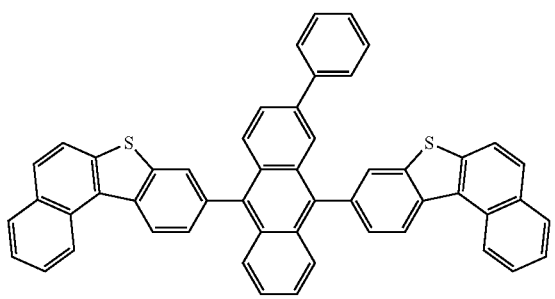
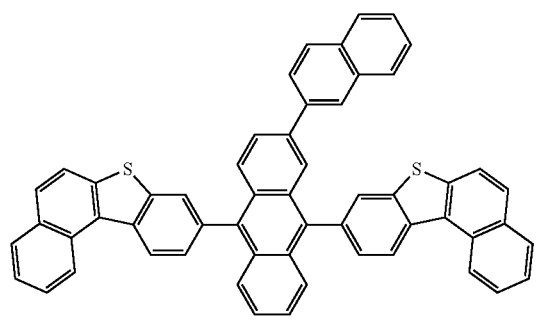 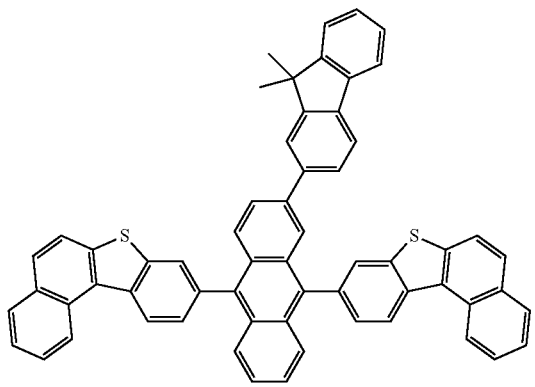
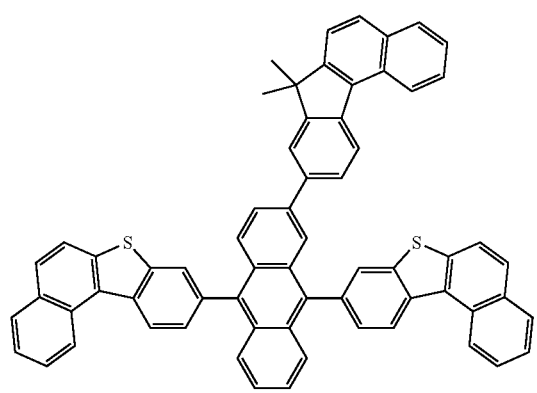 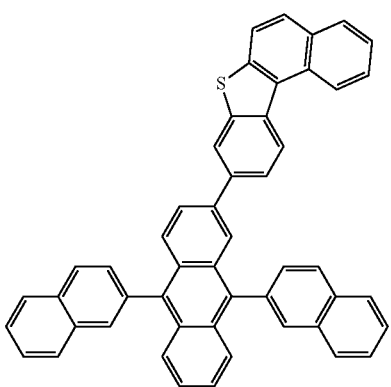

89
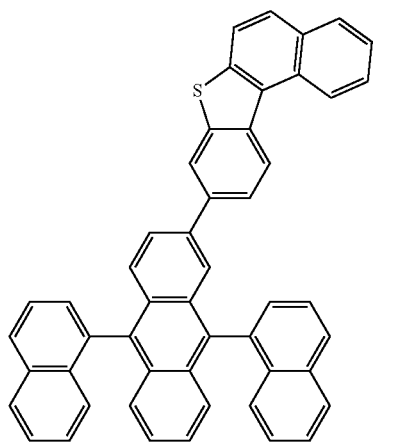
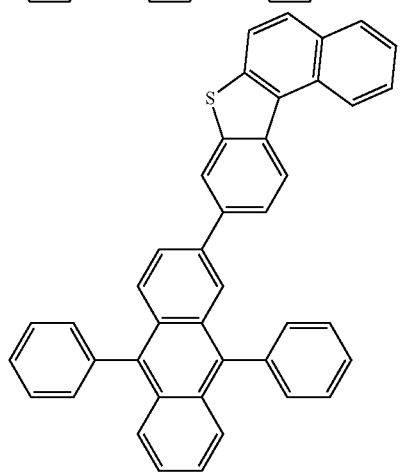
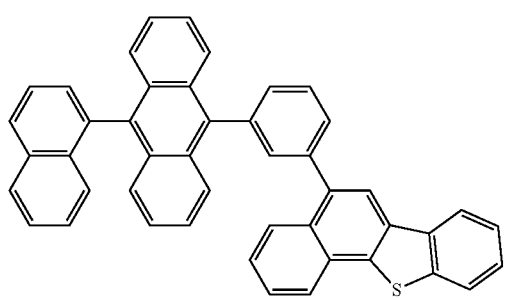
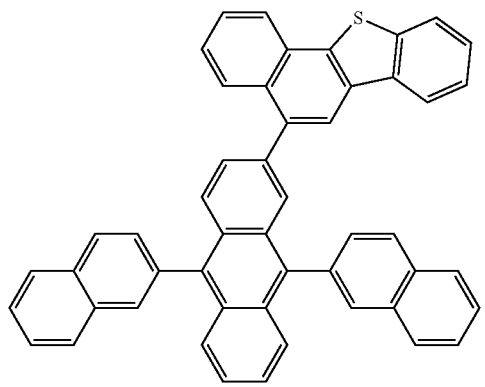
90
-continued
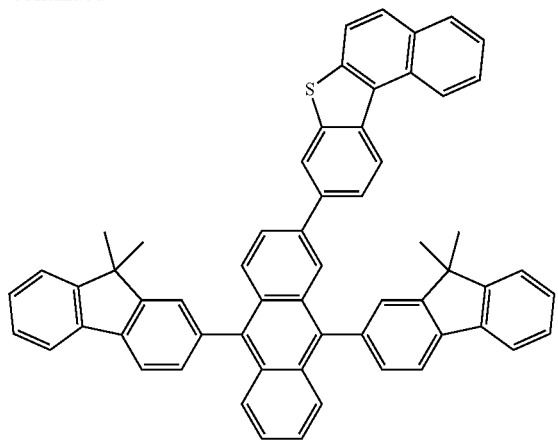
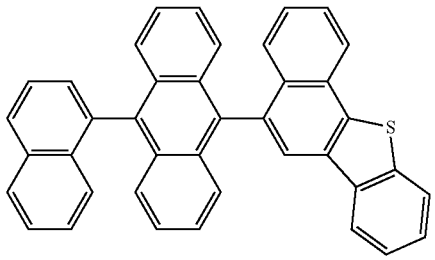
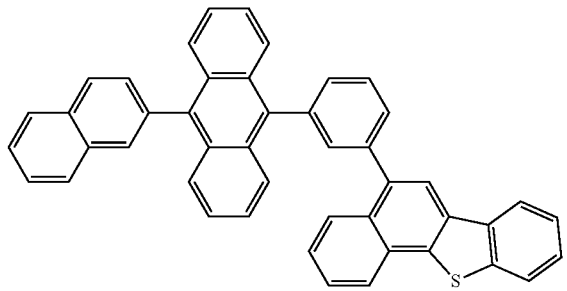
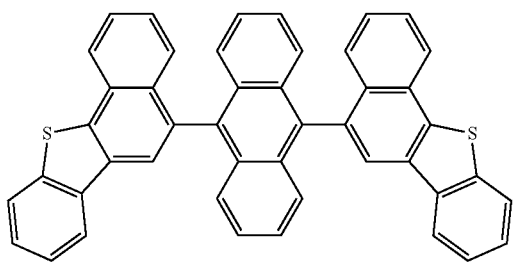

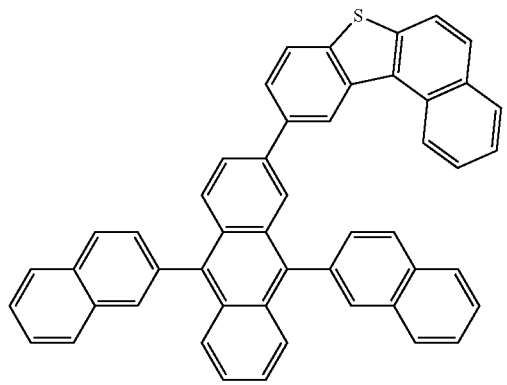
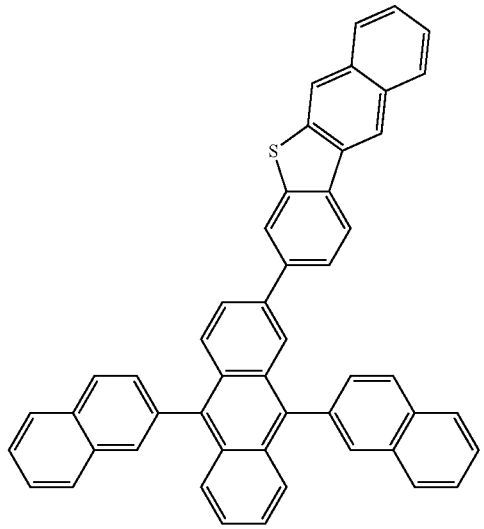

The anthracene derivative represented by the above formula (1) can be used as a material for an organic EL device, in particular, as an emitting material for an organic EL device.

The organic electroluminescence device of the invention comprises between an anode and a cathode one or more organic thin film layers comprising an emitting layer, wherein at least one layer of the organic thin film layers comprises the anthracene derivative (1).

In the organic EL device of the invention, it is preferred that the emitting layer comprise the anthracene derivative (1).

It is preferred that the anthracene derivative (1) be a host material of the emitting layer.

In the invention, as the organic EL device in which the organic thin film layer is composed of plural layers, one in which an anode, a hole-injecting layer, an emitting layer and a cathode are sequentially stacked (anode/hole-injecting layer/emitting layer/cathode), one in which an anode, an emitting layer, an electron-injecting layer and a cathode are sequentially stacked (anode/emitting layer/electron-injecting layer/cathode), one in which an anode, a hole-injecting layer, an emitting layer, an electron-injecting layer and a cathode are sequentially stacked (anode/hole-injecting layer/emitting layer/electron-injecting layer/cathode), one in which an anode, a hole-injecting layer, a hole-transporting layer, an emitting layer, an electron-injecting layer and a cathode are sequentially stacked (anode/hole-injecting layer/hole-transporting layer/emitting layer/electron-injecting layer/cathode) or the like can be given.

In the organic EL device of the invention, although the anthracene derivative (1) may be used in any of the above-mentioned organic layers, it is preferred that it be contained in the emission zone. It is particularly preferred that it be contained in the emitting layer. The content thereof is usually 30 to 100 mol %.

By allowing the organic thin film layer to be composed of plural layers, the organic EL device can be prevented from lowering of luminance or lifetime due to quenching. If necessary, an emitting material, a doping material, a hole-injecting material or an electron-injecting material can be used in combination. Further, due to the use of a doping material, luminance or luminous efficiency may be improved. The hole-injecting layer, the emitting layer and the electron-injecting layer may respectively be formed of two or more layers. In such a case, in the hole-injecting layer, a layer which injects holes from an electrode is referred to as a hole-injecting layer, and a layer which receives holes from the hole-injecting layer and transports the holes to the emitting layer is referred to as a hole-transporting layer. Similarly, in the electron-injecting layer, a layer which injects electrons from an electrode is referred to as an electron-injecting layer and a layer which receives electrons from an electron-injecting layer and transports the electrons to the emitting layer is referred to as an electron-transporting layer. Each of these layers is selected and used according to each of the factors of a material, i.e. the energy level, heat resistance, adhesiveness to the organic layer or the metal electrode or the like.

Examples of the material other than those represented by the above-mentioned formula (1) which can be used in the emitting layer together with the anthracene derivative of the invention include, though not limited thereto, fused polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, and spirofluorene and derivatives thereof, organic metal complexes such as tris(8-quinolinolate)aluminum, triarylamine derivatives, styrylamine derivatives, stilbene derivatives, coumarin derivatives, pyrane derivatives, oxazone derivatives, benzothiazole derivatives, benzoxazole derivatives, benzimidazole derivatives, pyrazine derivatives, cinnamate derivatives, diketo-pyrrolo-pyrrole derivatives, acridone derivatives and quinacridone derivatives.

In the organic EL device of the invention, if desired, the emitting layer may contain an emitting dopant (phosphoric dopant and/or fluorescent dopant) in addition to the emitting material of the invention. Further, an emitting layer containing these dopants may be stacked on the emitting layer containing the compound of the invention.

A fluorescent dopant is a compound which can emit light from a single exciton. The fluorescent dopant is preferably a compound which is selected according to a required emission color from an amine-based compound, an aromatic compound, a chelate complex such as a tris(8-quinolinolate)aluminum complex, a coumarin derivative, a tetraphenylbutadiene derivative, a bisstyrylarylene derivative, an oxadiazole derivative or the like. A styrylamine compound, a styryldiamine compound, an arylamine compound and an aryldiamine compound are more preferable, with a fused polycyclic amine derivative being further preferable. These fluorescent dopants may be used either singly or in combination of two or more.

As the fused polycyclic amine derivative, one represented by the following formula (12) is preferable.

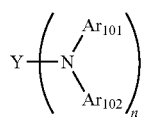
(12)

wherein in the formula (12), Y is a substituted or unsubstituted fused aryl group having 10 to 50 ring carbon atoms.

$Ar_{101}$ and $Ar_{102}$ are independently an aryl group having 6 to 50 ring carbon atoms or a substituted or unsubstituted heterocyclic group having 5 to 50 ring atoms; and n is an integer of 1 to 4. n is preferably an integer of 1 to 2.

Specific examples of Y include the above-mentioned fused aryl group. Preferably, Y is a substituted or unsubstituted anthryl group, a substituted or unsubstituted pyrenyl group or a substituted or unsubstituted chrysenyl group.

It is preferred that the above formula (12) be one represented by the following formulas (13) to (16):

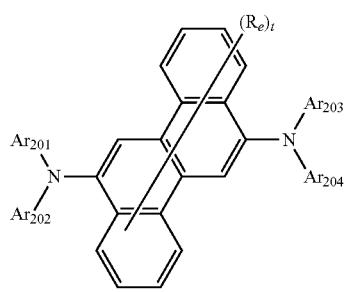
(13)

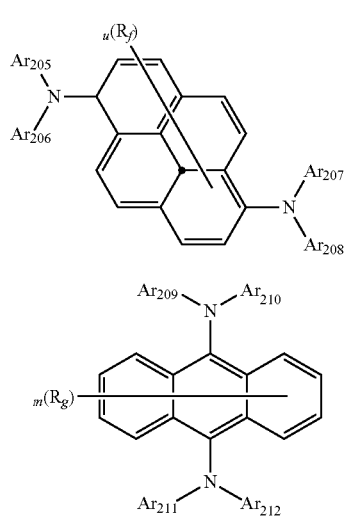
(14)

(15)

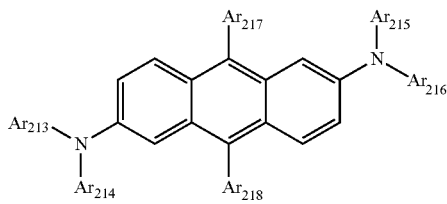
(16)

In the formulas (13) to (16), $R_e$, $R_f$ and $R_g$ are independently a hydrogen atom, a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 50 ring carbon atoms, a substituted or unsubstituted silyl group, a substituted or unsubstituted alkylgermanium group having 1 to 50 carbon atoms or a substituted or unsubstituted arylgermanium group having 6 to 50 ring carbon atoms.

Preferred examples of $R_e$, $R_f$ and $R_g$ include a substituted or unsubstituted aryl group having 6 to 50 ring carbon atoms, with a substituted or unsubstituted phenyl group, a substituted or unsubstituted naphthyl group or the like being more preferable.

t is an integer of 1 to 10. u is an integer of 1 to 8. m is an integer of 1 to 10.

$Ar_{201}$ to $Ar_{218}$ are independently a substituted or unsubstituted aryl group having 6 to 50 ring carbon atoms or a substituted or unsubstituted heterocyclic group having 5 to 50 ring atoms.

Preferred examples of $Ar_{201}$ to $Ar_{216}$ include a substituted or unsubstituted phenyl group and a substituted or unsubstituted dibenzofuranyl group. Preferred examples of $Ar_{201}$, to $Ar_{216}$ include an alkyl group, a cyano group and a substituted or unsubstituted silyl group.

As examples of the alkyl group, the alkoxy group, the aryl group, the aryloxy group and the heterocyclic group in the formulas (12) to (16), the same examples as mentioned above as the examples of the heterocyclic group can be given.

As the alkynyl group having 2 to 50 (preferably 2 to 30, more preferably 2 to 20, and particularly preferably 2 to 10) carbon atoms, a vinyl group, an allyl group, a 1-butenyl group, a 2-butenyl group, a 3-butenyl group, a 1,3-butandienyl group, a 1-methylvinyl group, a styryl group, a 2,2-diphenylvinyl group, a 1,2-diphenylvinyl group, a 1-methylallyl group, a 1,1-dimethylallyl group, a 2-methylallyl group, a 1-phenylallyl group, a 2-phenylallyl group, a 3-phenylallyl group, a 3,3-diphenylallyl group, a 1,2-dimethylallyl group, a 1-phenyl-1-butenyl group, a 3-phenyl-1-butenyl group or the like can be given. A styryl group, a 2,2-diphenylvinyl group, a 1,2-diphenylvinyl group or the like are preferably given.

As the alkynyl group having 2 to 50 (preferably 2 to 30, more preferably 2 to 20 and particularly preferably 2 to 10) carbon atoms, a propargyl group, a 3-pentynyl group or the like can be given.

As the alkylgermanium group, a methylhydrogermyl group, a trimethylgermyl group, a triethylgermyl group, a tripropylgermyl group, a dimethyl-t-butylgermyl group or the like can be given.

As the arylgermanium group, a phenyldihydrogermyl group, a diphenylhydrogermyl group, a triphenylgermyl group, a tritolylgermyl group, a trinaphthylgermyl group or the like can be given.

As the styrylamine compound and the styryldiamine compound, those represented by the following formulas (17) and (18) are preferable.

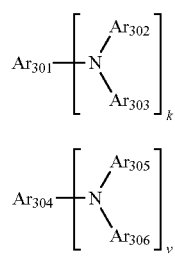

In the formula (17), $Ar_{301}$ is a k-valent group which corresponds to a phenyl group, a naphthyl group, a biphenyl group, a terphenyl group, a stilbene group, a styrylaryl group and a distyrylaryl group. $Ar_{302}$ and $Ar_{303}$ are independently an aryl group having 6 to 20 ring carbon atoms and $Ar_{301}$, $Ar_{302}$ and $Ar_{303}$ may be substituted.

k is an integer of 1 to 4. It is preferred that k be an integer of 1 to 2. Any one of $Ar_{301}$ to $Ar_{303}$ is a group having a styryl group. It is further preferred that at least one of $Ar_{302}$ and $Ar_{303}$ be substituted by a styryl group.

As the aryl group having 6 to 20 ring carbon atoms, specifically, the aryl groups as mentioned above can be given. Preferred examples include a phenyl group, a naphthyl group, an anthranyl group, a phenanthryl group and a terphenyl group.

In the formula (18), $Ar_{304}$ to $Ar_{306}$ is a v-valent substituted or unsubstituted aryl group having 6 to 40 ring carbon atoms. v is an integer of 1 to 4. It is preferred that v be an integer of 1 to 2.

Here, as the aryl group having 6 to 40 ring carbon atoms in the formula (18), specifically, the aryl groups as mentioned above can be given. Of these, a naphthyl group, an anthranyl group, a chrysenyl group, a pyrenyl group or an aryl group represented by the formula (20) are preferable.

As the preferable substituent which substitutes the above-mentioned aryl group, an alkyl group having 1 to 6 carbon atoms, an alkoxy group having 1 to 6 carbon atoms, an aryl group having 6 to 40 ring carbon atoms, an amino group which is substituted by an aryl group having 6 to 40 ring carbon atoms, an ester group having an aryl group having 5 to 40 ring carbon atoms, an ester group having an alkyl group having 1 to 6 carbon atoms, a cyano group, a nitro group, a halogen atom or the like can be given.

As the hole-injecting material, a compound which can transport holes, exhibits hole-injecting effects from the anode and excellent hole-injection effect for the emitting layer or the emitting material, and has an excellent capability of forming a thin film is preferable. Specific examples thereof include, though not limited thereto, phthalocyanine derivatives, naphthalocyanine derivatives, porphyline derivatives, benzidine-type triphenylamine, diamine-type triphenylamine, hexacyanohexaazatriphenylene, derivatives thereof, and polymer materials such as polyvinylcarbazole, polysilane and conductive polymers.

Of the hole-injecting materials usable in the organic EL device of the invention, further effective hole-injecting materials are phthalocyanine derivatives.

Examples of the phthalocyanine (Pc) derivative include, though not limited thereto, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O-GaPc, and naphthalocyanine derivatives.

In addition, it is also possible to sensitize carriers by adding to the hole-injecting material an electron-accepting substance such as a TCNQ derivative.

Preferable hole-transporting materials usable in the organic EL device of the invention are aromatic tertiary amine derivatives.

Examples of the aromatic tertiary amine derivative include, though not limited thereto, N,N'-diphenyl-N,N'-dinaphthyl-1,1'-biphenyl-4,4'-diamine, N,N,N',N'-tetrabiphenyl-1,1'-biphenyl-4,4'-diamine or an oligomer or a polymer having these aromatic tertiary amine skeletons.

As the electron-injecting material, a compound which can transport electrons, exhibits electron-injecting effects from the cathode and excellent electron-injection effect for the emitting layer or the emitting material, and has an excellent capability of forming a thin film is preferable.

In the organic EL device of the invention, further effective electron-injecting materials are a metal complex compound and a nitrogen-containing heterocyclic derivative.

Examples of the metal complex compound include, though not limited thereto, 8-hydroxyquinolinate lithium, bis(8-hydroxyquinolinate)zinc, tris(8-hydroxyquinolinate)aluminum, tris(8-hydroxyquinolinate)gallium, bis(10-hydroxybenzo[h]quinolinate)beryllium and bis(10-hydroxybenzo[h]quinolinate)zinc.

As examples of the nitrogen-containing heterocyclic derivative, oxazole, thiazole, oxadiazole, thiadiazole, triazole, pyridine, pyrimidine, triazine, phenanthroline, benzimidazole, imidazopyridine or the like are preferable, for example. Of these, a benzimidazole derivative, a phenanthroline derivative and an imidazopyridine derivative are preferable.

As a preferred mode, a dopant is further contained in these electron-injecting materials, and in order to facilitate receiving electrons from the cathode, it is further preferable to dope the vicinity of the cathode interface of the second organic layer with a dopant, the representative example of which is an alkali metal.

As the dopant, a donating metal, a donating metal compound and a donating metal complex can be given. These reducing dopants may be used singly or in combination of two or more.

In the organic EL device of the invention, the emitting layer may contain, in addition to at least one of the anthracene derivatives represented by the formula (1), at least one of an emitting material, a doping material, a hole-injecting material, a hole-transporting material and an electron-injecting material in the same layer. Moreover, for improving stability of the organic EL device obtained by the invention to temperature, humidity, atmosphere, etc. it is also possible to prepare a protective layer on the surface of the device, and it is also possible to protect the entire device by applying silicone oil, resin, etc.

As the conductive material used in the anode of the organic EL device of the invention, a conductive material having a work function of more than 4 eV is suitable. Carbon, aluminum, vanadium, iron, cobalt, nickel, tungsten, silver, gold, platinum, palladium or the like, alloys thereof, oxidized metals which are used in an ITO substrate and a NESA substrate such as tin oxide and indium oxide and organic conductive resins such as polythiophene and polypyrrole are used. As the conductive material used in the cathode, a conductive material having a work function of smaller than 4 eV is suitable. Magnesium, calcium, tin, lead, titanium, yttrium, lithium, ruthenium, manganese, aluminum, and lithium fluoride or the like, and alloys thereof are used, but not limited thereto. Representative examples of the alloys include, though not limited thereto, magnesium/silver alloys, magnesium/indium alloys and lithium/aluminum alloys. The amount ratio of the alloy is controlled by the temperature of the deposition source, atmosphere, vacuum degree or the like, and an appropriate ratio is selected. If necessary, the anode and the cathode each may be composed of two or more layers.

In the organic EL device of the invention, in order to allow it to emit light efficiently, it is preferred that at least one of the surfaces be fully transparent in the emission wavelength region of the device. In addition, it is preferred that the substrate also be transparent. The transparent electrode is set such that predetermined transparency can be ensured by a method such as deposition or sputtering by using the above-mentioned conductive materials. It is preferred that the electrode on the emitting surface have a light transmittance of 10% or more. Although no specific restrictions are imposed on the substrate as long as it has mechanical and thermal strength and transparency, a glass substrate and a transparent resin film can be given.

Each layer of the organic EL device of the invention can be formed by a dry film-forming method such as vacuum vapor deposition, sputtering, plasma ion plating, ion plating or the like or a wet film-forming method such as spin coating, dipping, flow coating or the like. Although the film thickness is not particularly limited, it is required to adjust the film thickness to an appropriate value. If the film thickness is too large, a large voltage is required to be applied in order to obtain a certain optical output, which results in a poor efficiency. If the film thickness is too small, pinholes or the like are generated, and a sufficient luminance cannot be obtained even if an electrical field is applied. The suitable film thickness is normally 5 nm to 10 μm, with a range of 10 nm to 0.2 μm being further preferable.

In the case of the wet film-forming method, a thin film is formed by dissolving or dispersing materials forming each layer in an appropriate solvent such as ethanol, chloroform, tetrahydrofuran and dioxane. Any of the above-mentioned solvents can be used.

As the solvent suited to such a wet film-forming method, a solution containing the aromatic amine derivative of the invention as an organic EL material and a solvent can be used.

It is preferred that the organic EL material contain a host material and a dopant material, that the dopant material be the aromatic amine derivative of the invention, and that the host material be at least one selected from the compounds represented by the formula (5).

In each organic thin film layer, an appropriate resin or additive may be used in order to improve film-forming properties, to prevent generation of pinholes in the film, or for other purposes.

The organic EL device of the invention can be suitably used as a planar emitting body such as a flat panel display of a wall-hanging television, backlight of a copier, a printer or a liquid crystal display, light sources for instruments, a display panel, a navigation light, or the like. The compound of the invention can be used not only in an organic EL device but also in the field of an electrophotographic photoreceptor, a photoelectric converting element, a solar cell and an image sensor.

EXAMPLES

Production Example (A) Synthesis of Intermediate (A)

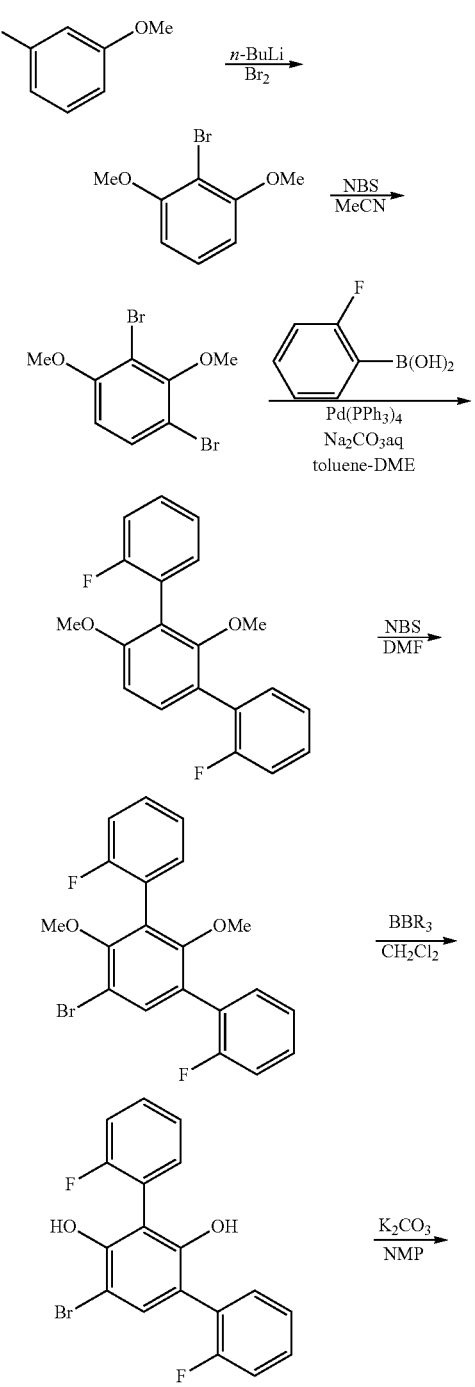

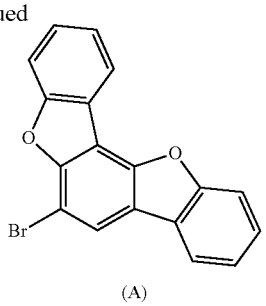

(A)

(A-1) Synthesis of 1-bromo-2,6-dimethoxybenzene

In the atmosphere of argon, 19.3 g of 1,3-dimethoxybenzene and 500 mL of anhydrous diethyl ether were placed in a flask. 105 mL (1.6M) of a hexane solution of n-butyllithium was added, and the resulting reaction solution was stirred with heating for 4 hours. After cooling to room temperature while stirring, the reaction solution was cooled to −50° C., followed by dropwise addition of 25 g of bromine. Then, while heating the reaction solution to room temperature, stirring was conducted for 2 hours. Then, 300 mL of an aqueous 10% sodium thiosulfate solution was added, and the resulting mixture was stirred for 1 hour. The reaction solution was extracted with ether, and an aqueous phase was removed, and then, an organic phase was washed with saturated saline. The organic phase was dried with magnesium sulfate and concentrated. Residues were purified by means of silica gel column chromatography. The resulting crystals were washed with hexane, whereby 17.9 g (yield: 52%) of white crystals of 1-bromo-2,6-dimethoxybenzene were obtained.

(A-2) Synthesis of 1,3-dibromo-2,6-dimethoxybenzene 17.9 g of 1-bromo-2,6-dimethoxybenzene and 200 mL of acetonitrile were placed in a flask, and the resulting mixture was cooled on ice. Then, 14.7 g of N-bromosuccinimide was added. Then, while heating the reaction solution to room temperature, stirring was conducted for 8 hours. 2.39 g of N-bromosuccinimide was further added, and stirring was conducted at room temperature for 7 hours. After completion of the stirring, the solvent was distilled off under reduced pressure. Residues were dissolved in dichloromethane, and washed sequentially with sodium thiosulfate and saturated saline. An organic phase was dried with magnesium sulfate and concentrated. Residues were purified by means of silica gel column chromatography, whereby 23.2 g (yield: 95%) of colorless oil of 1,3-bromo-2,6-dimethoxybenzene was obtained.

(A-3) Synthesis of 2,4-bis(2-fluorophenyl)-1,3-dimethoxybenzene

In the atmosphere of argon, 23.2 g of 1,3-dibromo-2,6-dimethoxybenzene, 32.9 g of 2-fluorophenylboronic acid, 5.43 g of tetrakis(triphenylphosphine)palladium(0), 150 mL of toluene, 150 mL of 1,2-dimethoxyethane and 150 mL of a 2M aqueous sodium carbonate solution were placed in a flask. The resulting mixture was stirred with heating under reflux for 24 hours. After being cooled to room temperature, an aqueous phase was removed, and an organic phase was washed with saturated saline. The organic phase was dried with magnesium sulfate and concentrated. Residues were purified by means of silica gel column chromatography. The resulting crystals were recrystallized from hexane, whereby 11.6 g (yield: 45%) of white crystals of 2,4-bis(2-fluorophenyl)-1,3-dimethoxybenzene were obtained.

(A-4) Synthesis of 1-bromo-3,5-bis(2-fluorophenyl)-2,4-dimethoxybenzene 11.6 g of 2,4-bis(2-fluorophenyl)-1,3-dimethoxybenzene and 480 mL of N,N-dimethylformamide were placed in a flask. 20 mL of a N,N-dimethylformamide solution of 6.31 g of N-bromosuccinimide was added. The reaction solution was stirred at 40° C. for 5 hours. 2.20 g of N-bromosuccinimide was further added, and the resulting mixture was stirred at 50° C. for 8 hours. After cooling to room temperature, 300 mL of water was added, and an organic substance was extracted with toluene. The toluene solution was sequentially washed with sodium thiosulfate and saturated saline. The organic phase was dried with magnesium sulfate and concentrated. Residues were purified by means of silica gel column chromatography, whereby 14.1 g (yield: 98%) of yellow oil of 1-bromo-3,5-bis(2-fluorophenyl)-2,4-dimethoxybenzene was obtained.

(A-5) Synthesis of 1-bromo-3,5-bis(2-fluorophenyl)-2,4-dihydroxybenzene

In the atmosphere of argon, 14.1 g of 1-bromo-3,5-bis(2-fluorophenyl)-2,4-dimethoxybenzene and 300 mL of anhydrous dichloromethane were placed in a flask. The resulting mixture was cooled to −78° C. with stirring. Then, 90 mL (1 M) of a dichloromethane solution of boron tribromide was added. While heating the reaction solution to room temperature, stirring was conducted for 3 hours. The reaction solution was cooled on ice, and then 150 mL of water was added. An aqueous phase was removed, and an organic phase was dried with magnesium sulfate. After concentrating the organic phase, residues were purified by using a short column, whereby 12.5 g (yield: 95%) of brown oil of 1-bromo-3,5-bis(2-fluorophenyl)-2,4-dihydroxybenzene was obtained.

(A-6) Synthesis of Intermediate (A)

In the atmosphere of argon, 12.5 g of 1-bromo-3,5-bis(2-fluorophenyl)-2,4-dihydroxybenzene, 18.3 g of potassium carbonate and 200 mL of anhydrous N-methylpyrrolidinone were placed in a flask. The resulting mixture was stirred with heating at 200° C. for 5 hours. After cooling to room temperature, 200 mL of water was added, and the resultant was diluted with toluene. An aqueous phase was removed, and an organic phase was dried with magnesium sulfate. After concentrating the organic phase, residues were purified by silica gel column chromatography, whereby 1.20 g (yield: 11%) of intermediate (A) was obtained.

(B) Synthesis of Intermediates (B) and (C)

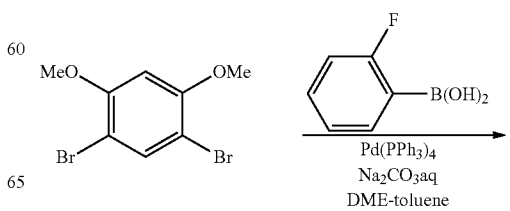

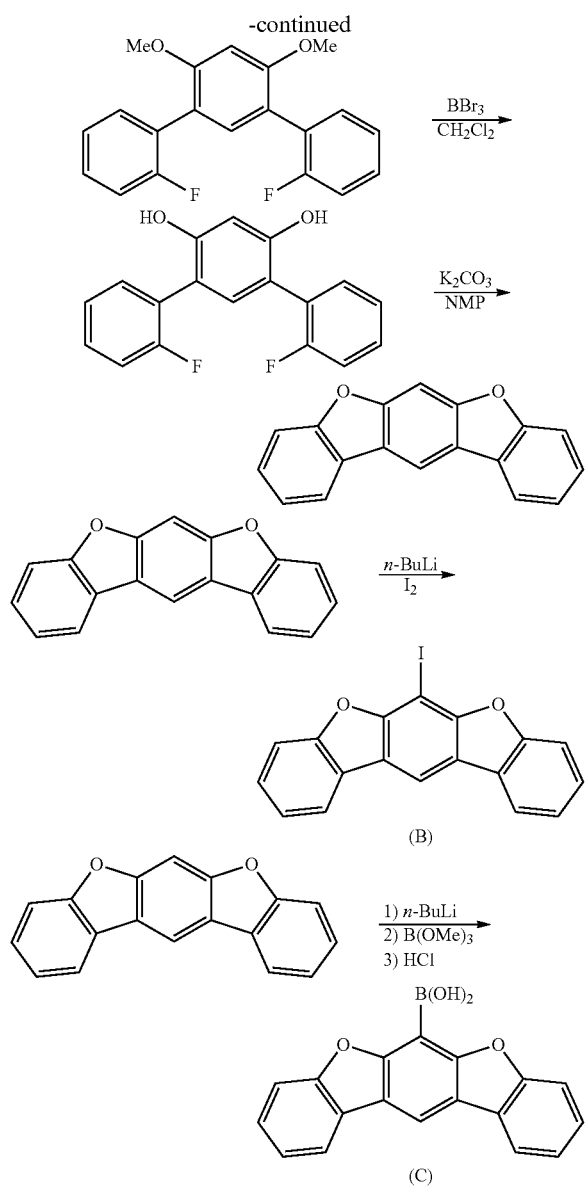

(B-1) Synthesis of
2,4-bis(2-fluorophenyl)-1,5-dimethoxybenzene 2,4-dibromo-1,5-dimethoxybenzene (88.8 g, 300 mmol, 1 eq.), 2-fluorophenylboronic acid (100.74 g, 720 mmol, 2.4 eq.), Na$_2$CO$_3$ 2M aq. (600 mL), Pd(PPh$_3$)$_4$ (6.73 g, 6 mmol, 2 mol %), 1,2-dimethoxyethane (150 mL) and toluene (150 mL) were placed in a flask, and the resulting mixture was refluxed for 36 hours.

After completion of the reaction, water (500 mL) and toluene (1 L) were added, and the mixture was transferred to a separating funnel, whereby a toluene phase was collected. After drying with MgSO$_4$, original impurities were removed by passing through a silica gel short column, thereby to concentrate the solution. The thus concentrated solution was recrystallized from a toluene/hexane mixed solvent, whereby white crystals of 86.5 g (yield: 88%) of 2,4-bis(2-fluorophenyl)-1,5-dimethoxybenzene were obtained.

(B-2) Synthesis of
2,4-bis(2-fluorophenyl)-1,5-dihydroxybenzene 1,5-dimethoxy-2,4-bis(2-fluorophenyl)benzene (48.3 g, 148 mmol, 1 eq.) and dichloromethane (dehydrated) (740 mL) were placed in a flask, and the resulting mixture was cooled to 0° C. BBr$_3$ (89.0 g, 355 mmol, 2.4 eq.) was added, and the resultant was stirred at room temperature for 24 hours.

After completion of the reaction, the solution was cooled to −78° C., and carefully deactivated with methanol, and then with a sufficient amount of water. The solution was transferred to a separating funnel, extracted with dichloromethane, and dried with MgSO$_4$. Then, original impurities were removed by passing through a silica gel short column, and the solution was concentrated. The resulting sample was dried in vacuum at 60° C. for 5 hours, whereby white solids of 44.1 g (yield: 100%) of 2,4-bis(2-fluorophenyl)-1,5-dihydroxybenzene were obtained.

(B-3) Synthesis of benzofurano[3,2-b]dibenzofuran 2,4-bis(2-fluorophenyl)-1,5-dihydroxybenzene (44.14 g, 148 mmol, 1 eq.) and N-methyl-2-pyrrolidinone (dehydrated) (888 mL) were placed in a flask. The solids were completely dissolved. K$_2$CO$_3$ (81.8 g, 592 mmol, 4 eq.) was added, followed by stirring at 200° C. for 2 hours.

After completion of the reaction, the solution was cooled to room temperature. Toluene (2 L) was added, the resulting mixture was transferred to a separating funnel, followed by washing with water. After drying with MgSO$_4$, original impurities were removed by passing through a silica gel short column, and the solution was concentrated. Then, the solution was recrystallized from a toluene/methanol mixed solvent, whereby 27.9 g (yield: 73%) of white solids of benzofurano[3,2-b]dibenzofuran was obtained.

(B-4) Synthesis of
6-iodobenzofurano[3,2-b]dibenzofuran

Benzofurano[3,2-b]dibenzofuran (2.69 g, 10.4 mmol, 1 eq.) and tetrahydrofuran (dehydrated) (62 mL) were placed in a flask, and the resulting mixture was cooled to −78° C. n-BuLi ((1.66M in hexane), 6.6 mL, 10.9 mmol, 1.05 eq.) was added, and the resulting mixture was allowed to stand at room temperature for 30 minutes. Subsequently, the mixture was again cooled to −78° C. Then, I$_2$ (2.69 g, 10.6 mmol, 1.02 eq.) was added. The resulting mixture was stirred at −78° C. for 10 minutes, and allowed to stand at room temperature for 1 hour.

After completion of the reaction, the reaction solution was deactivated by adding a small amount of water, and then concentrated by means of an evaporator. The thus concentrated solution was dispersed in and washed with water, filtered out, and dissolved in toluene. The resulting solution was dried with MgSO$_4$, and passed through a silica gel short column, thereby to concentrate this solution. This sample was recrystallized from methanol, whereby 3.77 g (yield: 94%) of white solids of 6-iodobenzofurano[3,2-b]dibenzofuran were obtained.

(C-1) Synthesis of
benzofurano[3,2-b]dibenzofuran-6-boronic acid

Benzofurano[3,2-b]dibenzofuran (12.9 g, 50 mmol, 1 eg.) and tetrahydrofuran (dehydrated) (300 mL) were placed in a flask, and the resulting mixture was cooled to −78° C. n-BuLi ((2.63M in hexane) 20.0 mL, 52.5 mmol, 1.05 eq.) was added, and the resulting mixture was allowed to stand at room temperature for one hour. Subsequently, the mixture was again cooled to −78° C. Then, B(OMe)₃ (10.4 g, 100 mmol, 2 eq.) was added. The resulting mixture was stirred at −78° C. for 10 minutes, and allowed to stand for 1 hour.

After completion of the reaction, the reaction solution was concentrated by means of an evaporator until the volume was reduced about to half. Then, 1N HCL aq. (200 mL) was added, and the resulting mixture was stirred at room temperature for 1 hour. Then, the solution was transferred to a separating funnel, and extracted with ethyl acetate.

After drying with MgSO₄, this solution was concentrated, and dispersed in and washed with a toluene/hexane mixed solvent, whereby 13.7 g (yield: 91%) of white solids of benzofurano[3,2-b]dibenzofuran-6-boronic acid were obtained.

(D) Synthesis of Intermediate D

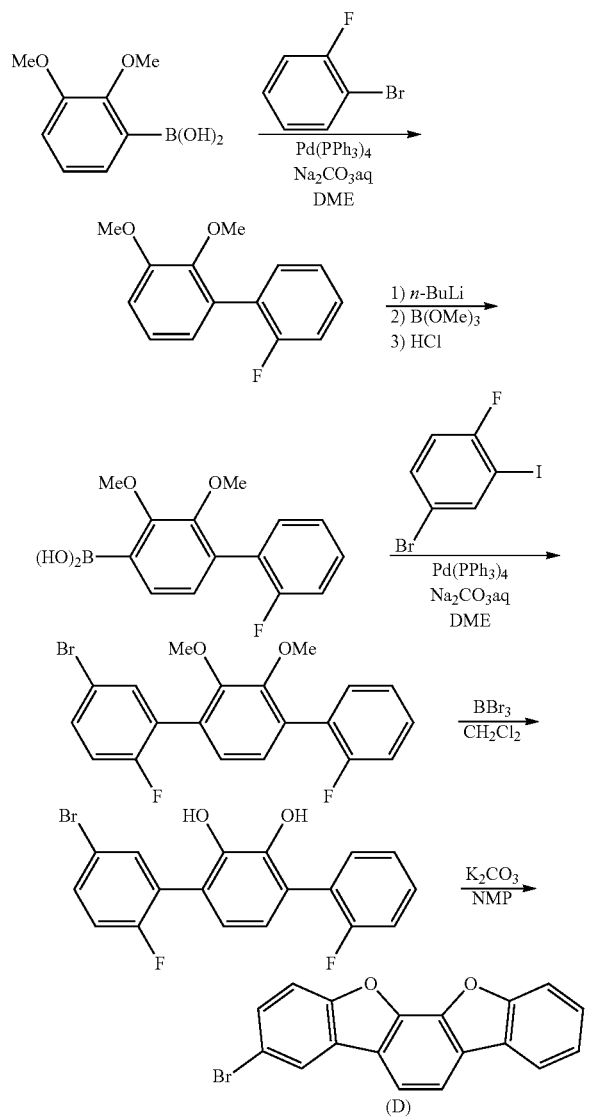

(D)

(D-1) Synthesis of 2'-fluoro-2,3-dimethoxybiphenyl

In the atmosphere of argon, 18.2 g of 2,3-dimethoxyphenylboronic acid, 17.5 g of 2-fluorobromobenzene, 2.31 g of tetrakistriphenylphosphine palladium (0), 300 mL of 1,2-dimethoxyethane and 150 mL of an aqueous 2M sodium carbonate solution were placed in a flask. The resulting mixture was stirred with heating under reflux for 8 hours. After cooling to room temperature, an aqueous phase was removed, and an organic phase was washed with saturated saline. The organic phase was dried with magnesium sulfate and then concentrated. Residues were purified by silica gel column chromatography, whereby 19.7 g of (yield 85%) of 2'-fluoro-2,3-dimethoxybiphenyl was obtained.

(D-2) Synthesis of 2'-fluoro-2,3-dimethoxybiphenyl-4-boronic acid

In the atmosphere of argon, 19.7 g of 2'-fluoro-2,3-dimethoxybiphenyl and 500 mL of anhydrous THF were placed in a flask. 56 mL of a hexane solution of 1.6M n-butyllithium was added, and the reaction solution was stirred at room temperature for 4 hours. After cooling to −78° C., 30 mL of a THF solution of 27.8 g of trimethyl borate was added dropwise. While heating to room temperature, the reaction solution was stirred for 8 hours. 200 mL of 10% HCl was added to the reaction solution, and the resulting mixture was stirred for 2 hours. The reaction solution was extracted with ether. An aqueous phase was removed, and then an organic phase was washed with saturated saline. After drying the organic phase with magnesium sulfate, the organic phase was concentrated, and residues were washed with hexane, whereby 15.2 g (yield: 65%) of 2'-fluoro-2,3-dimethoxybiphenyl-4-boronic acid was obtained.

(D-3) Synthesis of 5-bromo-2-fluoro-2',3'-dimethoxy-2''-fluoro-p-terphenyl

In the atmosphere of argon, 15.2 g of 2'-fluoro-2,3-dimethoxybiphenyl-4-boronic acid, 16.5 g of 2-fluoro-5-bromoiodobenzene, 1.27 g of tetrakistriphenylphosphine palladium (0), 180 mL of toluene and 90 mL of an aqueous 2M sodium carbonate solution were placed in a flask. The resulting solution was stirred with heating under reflux for 8 hours. After cooling to room temperature, the reaction solution was extracted with toluene. An aqueous phase was removed, and an organic phase was washed with saturated saline. The organic phase was dried with magnesium sulfate, and concentrated. Residues were purified by means of silica gel column chromatography, whereby 17.8 g (yield: 80%) of 5-bromo-2-fluoro-2',3'-dimethoxy-2''-fluoro-p-terphenyl was obtained.

(D-4) Synthesis of 5-bromo-2-fluoro-2',3'-dihydroxy-2''-fluoro-p-terphenyl 17.8 g of 5-bromo-2-fluoro-2',3'-dimethoxy-2''-fluoro-p-terphenyl and 250 mL of dichloromethane (dehydrated) were placed in a flask, and the resulting mixture was cooled to 0° C. 27.5 g of BBr₃ was added, and the resultant was stirred at room temperature for 24 hours.

After completion of the reaction, the solution was cooled to −78° C., and carefully deactivated with methanol, and then with a sufficient amount of water. The solution was transferred to a separating funnel, extracted with dichloromethane, and dried with MgSO₄. Then, original impurities were removed by passing through a silica gel short column, and the solution was concentrated. The resulting sample was dried in vacuum, whereby 16.5 g (yield: 100%) of 5-bromo-2-fluoro-2',3'-dihydroxy-2''-fluoro-p-terphenyl was obtained.

(D-5) Synthesis of 3-bromobenzofurano[3,2-c]dibenzofuran 16.5 g of 5-bromo-2-fluoro-2',3'-dihydroxy-2"-fluoro-p-terphenyl, 300 mL of N-methyl-2-pyrrolidinone (dehydrated) and 24.2 g of K₂CO₃ were placed in a flask, followed by stirring at 200° C. for 2 hours.

After completion of the reaction, the solution was cooled to room temperature. Toluene (2 L) was added, and the resulting mixture was transferred to a separating funnel and washed with water. After drying this solution with MgSO₄, original impurities were removed by passing through a silica gel short column, the solution was concentrated, recrystallized from a mixed solvent of toluene/methanol, whereby 10.1 g (yield: 70%) of white solids of 3-bromobenzofurano[3,2-c]dibenzofuran were obtained.

(E) Synthesis of Intermediate (E)

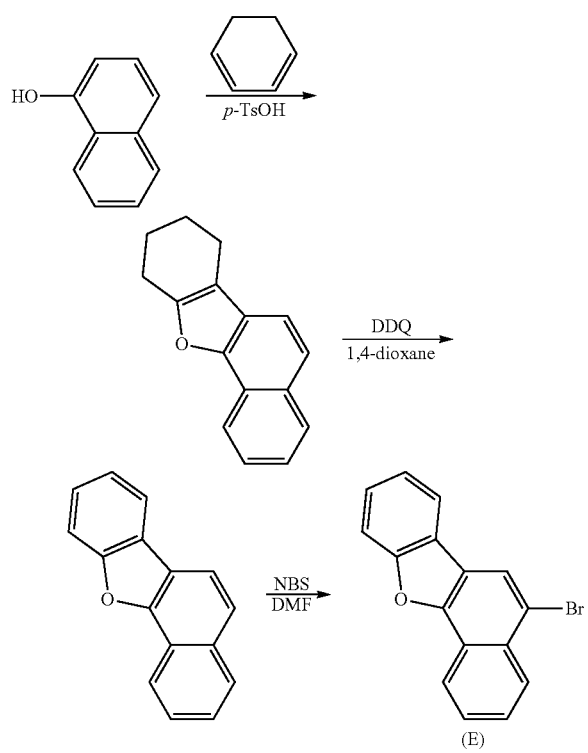

(E-1) Synthesis of 7,8,9,10-tetrahydrobenzo[b]naphtho[2,1-d]furan 144 g of 1-naphthol, 190 g of p-toluenesulfonic acid monohydrate, 80.1 g of 1,3-cyclohexadiene and 4 L of toluene were placed in a flask. The resulting mixture was stirred under reflux for 24 hours. After cooling to room temperature, the reaction solution was washed with 600 mL of water. After drying an organic phase with magnesium sulfate, the solvent was distilled off under reduced pressure. Residues were purified by silica gel column chromatography, whereby 55.5 g (yield: 25%) of 7,8,9,10-tetrahydrobenzo[b]naphtho[2,1-d]furan was obtained.

(E-2) Synthesis of benzo[b]naphtho[2,1-d]furan

In the atmosphere of argon, 55.5 g of 7,8,9,10-tetrahydrobenzo[b]naphtho[2,1-d]furan, 119 g of 2,3-dichloro-5,6-dicyano-1,4-benzoquinone and 1 L of anhydrous 1,4-dioxane were placed in a flask. The resulting mixture was stirred under reflux for 12 hours. After cooling to room temperature, the reaction solution was extracted with toluene, and deposited solids were filtered out. The filtrate was concentrated by means of a rotary evaporator, and residues were purified by silica gel column chromatography, whereby 32.7 g of (yield: 60%) of benzo[b]naphtho[2,1-d]furan was obtained.

(E-3) Synthesis of 5-bromobenzo[b]naphtho[2,1-d]furan 32.7 g of benzo[b]naphtho[2,1-d]furan was dissolved in 300 mL of N,N-dimethylformamide. Then, 50 mL of a N,N-dimethylformamide solution of 28.0 g of N-bromosuccinimide was added, and the resulting reaction solution was stirred with heating at 60° C. for 5 hours. After cooling to room temperature, the reaction solution was poured in 2 L of water. Solids thus obtained were sequentially washed with methanol, water and methanol. The resulting crude product was purified by means of silica gel column chromatography, whereby 36.5 g (yield: 82%) of 5-bromobenzo[b]naphtho[2,1-d]furan was obtained.

(F) Synthesis of Intermediate (F)

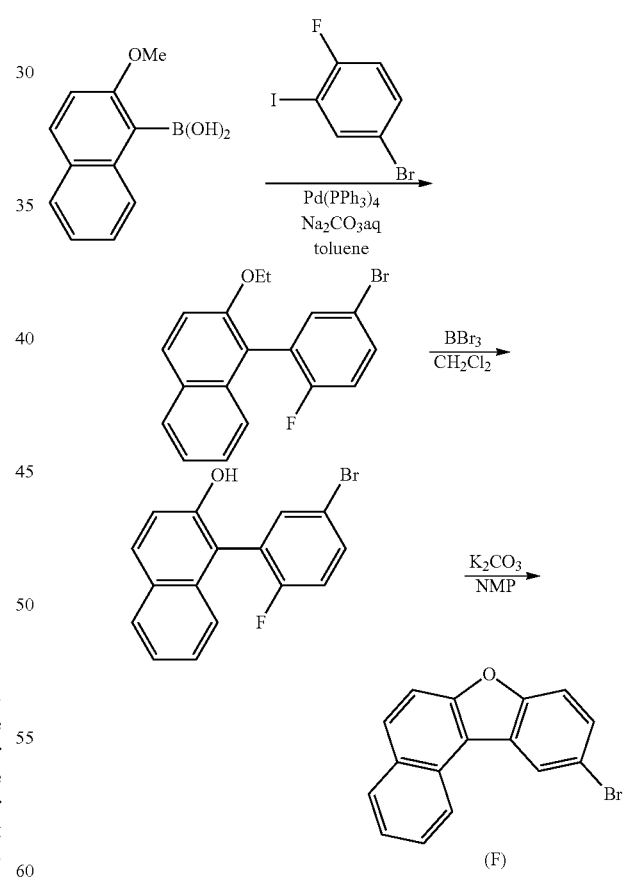

(F-1) Synthesis of 2-ethoxy-1-(2-fluoro-5-bromophenyl)naphthalene

In the atmosphere of argon, 22.7 g of 2-ethoxynaphthalene-1-boronic acid, 30.0 g of 2-fluoro-5-bromoiodobenzene, 2.31 g of tetrakistriphenylphosphine palladium (0), 300 mL of toluene and 150 mL of an aqueous 2M solution of sodium carbonate were placed in a flask, and the resulting mixture was stirred with heating under reflux for 8 hours. After cooling to room temperature, the reaction solution was extracted with toluene. An aqueous phase was removed, and then, an organic phase was washed with saturated saline. The organic phase was dried with magnesium sulfate, and concentrated. Residues were purified by means of silica gel column chromatography, whereby 24.1 g (yield: 70%) of 2-ethoxy-1-(2-fluoro-5-bromophenyl)naphthalene was obtained.

(F-2) Synthesis of 2-hydroxy-1-(2-fluoro-5-bromophenyl)naphthalene 24.1 g of 2-ethoxy-1-(2-fluoro-5-bromophenyl)naphthalene and dichloromethane (dehydrated) (200 mL) were placed in a flask. The resulting mixture was cooled to 0° C. 22.0 g of BBr₃ was added, and the resultant was stirred at room temperature for 24 hours.

After completion of the reaction, the solution was cooled to −78° C., and carefully deactivated with methanol, and then with a sufficient amount of water. The solution was transferred to a separating funnel, extracted with dichloromethane, and dried with MgSO₄. Then, original impurities were removed by passing through a silica gel short column, and the solution was concentrated. The resulting sample was dried in vacuum at 60° C. for 5 hours, whereby white solids of 22.1 g (yield: 100%) of 2-hydroxy-1-(2-fluoro-5-bromophenyl) naphthalene were obtained.

(F-3) Synthesis of Intermediate (F)

22.1 g of 2-hydroxy-1-(2-fluoro-5-bromophenyl)naphthalene, 300 mL of N-methyl-2-pyrrolidinone (dehydrated) and 19.3 g of K₂CO₃ were added, followed by stirring at 200° C. for 2 hours.

After completion of the reaction, the solution was cooled to room temperature. Toluene (2 L) was added, and the resulting mixture was transferred to a separating funnel and washed with water. After drying with MgSO₄, the solution was purified by means of silica gel column chromatography, whereby white solids of 13.5 g (yield: 65%) of intermediate (F) were obtained.

(G) Synthesis of Intermediate (G)

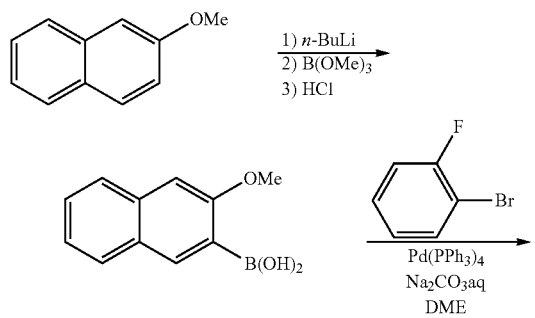

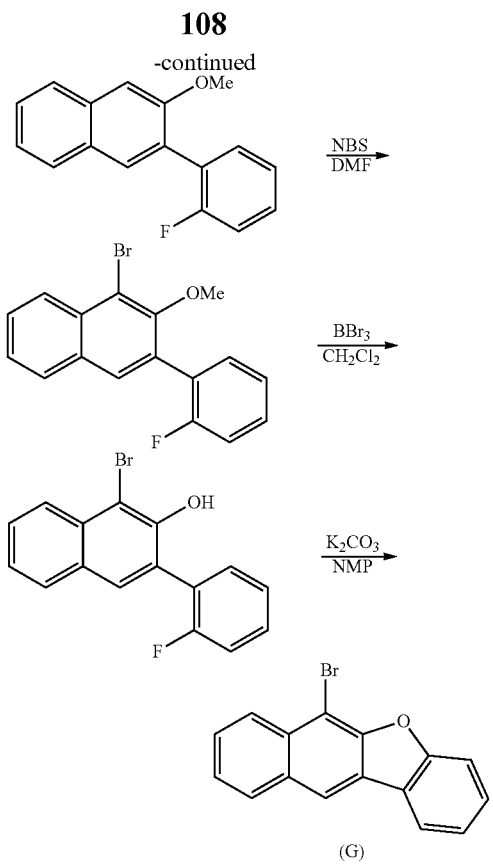

(G-1) Synthesis of 3-methoxynaphthalene-2-boronic acid 15.8 g of 2-methoxynaphthalene and 300 mL of tetrahydrofuran (dehydrated) were placed in a flask, and the resulting mixture was cooled to −78° C. 66 mL of n-BuLi (1.60M in hexane) was added, and the resulting mixture was stirred at room temperature for 4 hours. The resulting mixture was cooled to −78° C. again. Then, 27.3 of B(OMe)₃ was added, stirred at −78° C. for 10 minutes, followed by stirring at room temperature for 5 hours.

After completion of the reaction, 1N HCl aq. (200 mL) was added, and the solution was stirred at room temperature for 1 hour. Then, the solution was transferred to a separating funnel, and extracted with ethyl acetate.

This solution was dried with MgSO₄, concentrated and washed with hexane, whereby 14.3 g (yield: 71%) of white solids of 3-methoxynaphthalene-2-boronic acid were obtained.

(G-2) Synthesis of 2-methoxy-3-(2-fluorophenyl)naphthalene

In the atmosphere of argon, 14.3 g of 3-methoxynaphthalene-2-boronic acid, 12.4 g of 2-fluorobromobenzene, 1.64 g of tetrakistriphenylphosphine palladium (0), 220 mL of 1,2-dimethoxyethane, 110 mL of a 2M aqueous solution of sodium carbonate were placed in a flask, and the resulting mixture was stirred with heating under reflux for 8 hours. After cooling to room temperature, the reaction solution was extracted with toluene. An aqueous phase was removed, and then an organic phase was washed with saturated saline. The organic phase was dried with magnesium sulfate and then concentrated. Residues were purified by silica gel column chromatography, whereby 13.4 g (yield: 75%) of 2-methoxy-3-(2-fluorophenyl)naphthalene was obtained.

(G-3) Synthesis of 1-bromo-2-methoxy-3-(2-fluorophenyl)naphthalene 13.4 g of 2-methoxy-3-(2-fluorophenyl)naphthalene and 100 mL of N,N-dimethylformamide were placed in a flask. Then, 40 mL of a N,N-dimethylformamide solution of 11.3 g of N-bromosuccinimide was added. The reaction solution was stirred at 60° C. for 8 hours. After cooling to room temperature, 500 mL of water was added. Then, an organic substance was extracted with toluene. The toluene solution was sequentially washed with sodium thiosulfate and saturated saline. After drying with magnesium sulfate, the organic phase was concentrated. Residues were purified by silica gel column chromatography, whereby 15.8 g (yield: 95%) of 1-bromo-2-methoxy-3-(2-fluorophenyl)naphthalene was obtained.

(G-4) Synthesis of 1-bromo-2-hydroxy-3-(2-fluorophenyl)naphthalene 15.8 g of 1-bromo-2-methoxy-3-(2-fluorophenyl)naphthalene and 200 mL of dichloromethane (dehydrated) were placed in a flask. The resulting mixture was cooled to 0° C. 18.0 g of BBr₃ was added, and the resultant was stirred at room temperature for 24 hours.

After completion of the reaction, the solution was cooled to −78° C., and carefully deactivated with methanol, and then with a sufficient amount of water. The solution was transferred to a separating funnel, extracted with dichloromethane, and dried with MgSO₄. Then, original impurities were removed by passing through a silica gel short column, and the solution was concentrated. The resulting sample was dried in vacuum at 60° C. for 5 hours, whereby white solids of 15.1 g (yield: 100%) of 1-bromo-2-hydroxy-3-(2-fluorophenyl)naphthalene was obtained.

(G-5) Synthesis of Intermediate (G)

15.1 g of 1-bromo-2-hydroxy-3-(2-fluorophenyl)naphthalene, 150 mL of N-methyl-2-pyrrolidinone (dehydrated) and 13.2 g of K₂CO₃ were placed in a flask. The resulting mixture was stirred at 200° C. for 2 hours.

After completion of the reaction, the solution was cooled to room temperature. Toluene (200 mL) was added, and the resulting mixture was transferred to a separating funnel, followed by washing with water. After drying with MgSO₄, this solution was purified by silica gel column chromatography, whereby 2.12 g (yield: 15%) of white solids of intermediate (G) were obtained.

(H) Synthesis of Intermediate (H)

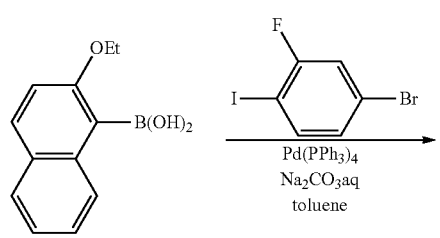

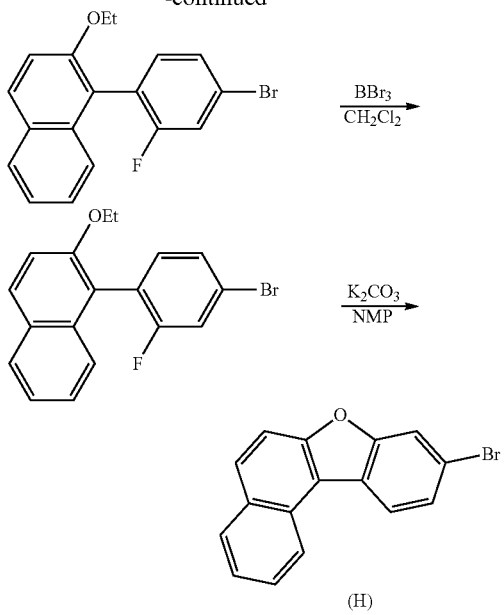

(H)

An intermediate (H) was synthesized in the same manner as in the synthesis of intermediate (F) according to the above scheme, except that 2-fluoro-4-bromoiodobenzene was used instead of 2-fluoro-5-bromoiodobenzene.

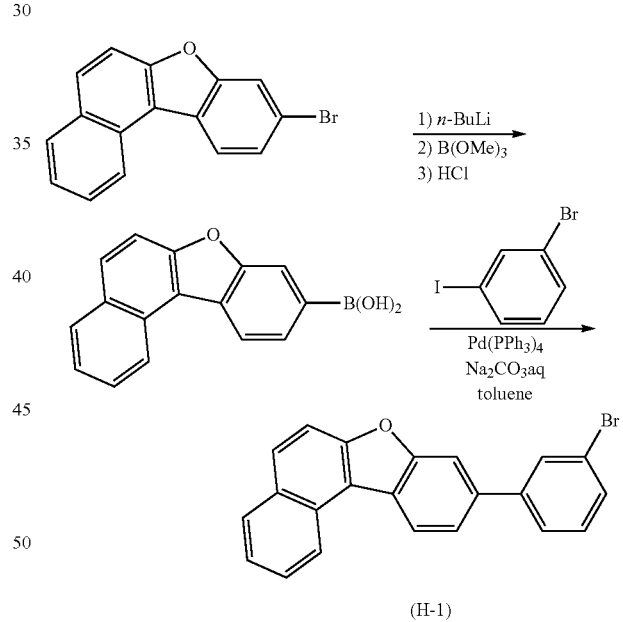

(H-1)

A derivative (H-1) of the above-mentioned intermediate (H) was synthesized in the same manner as in Example 37.

(I) Synthesis of Intermediate (I)

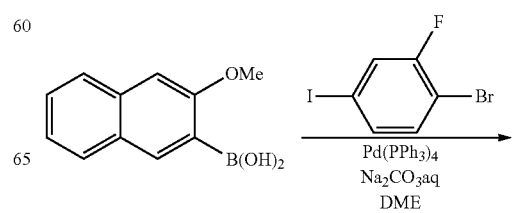

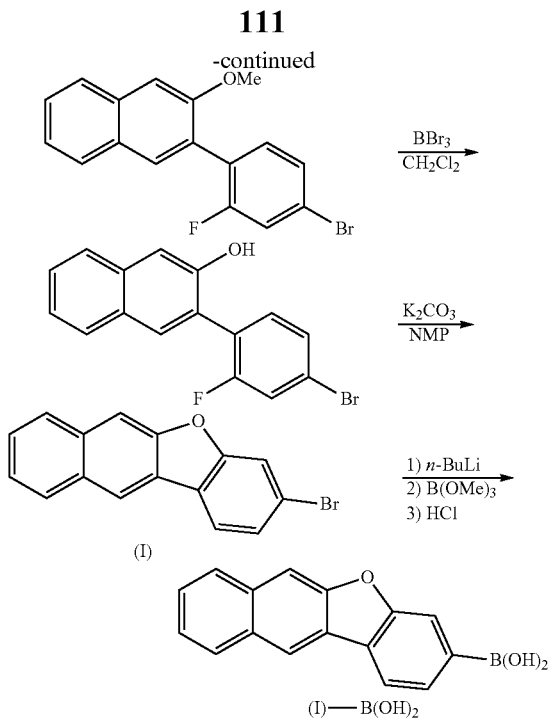

(1) Synthesis of
3-(4-bromo-2-fluorophenyl)-2-methoxynaphthalene

Synthesis was conducted in the same manner as in (G-2), except that 2-fluoro-4-bromoiodobenzene was used instead of 2-fluorobromobenzene.

(2) Synthesis of
3-(4-bromo-2-fluorophenyl)-2-hydroxynaphthalene

Synthesis was conducted in the same manner as in (G-4), except that 3-(4-bromo-2-fluorophenyl)-2-methoxynaphthalene was used instead of 1-bromo-2-methoxy-3-(2-fluorophenyl)naphthalene.

(3) Synthesis of Intermediate (I)

Synthesis was conducted in the same manner as in (G-5), except that 3-(4-bromo-2-fluorophenyl)-2-hydroxynaphthalene was used instead of 1-bromo-2-hydroxy-3-(2-fluorophenyl)naphthalene.

(4) Synthesis of Intermediate (I)—B(OH)$_2$

Synthesis was conducted in the same manner as in (37-1), except that intermediate (I) was used instead of 10-bromobenzo[b]naphtho[1,2-d]furan.

(J) Synthesis of Intermediate (J)

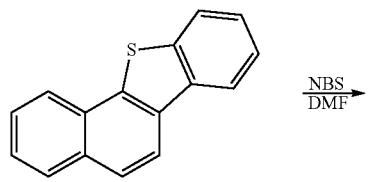

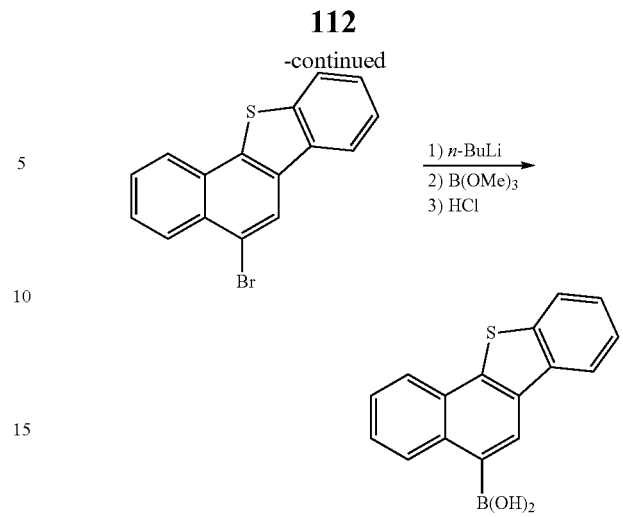

(1) Synthesis of
5-bromobenzo[b]naphtho[2,1-d]thiophene

Synthesis was conducted in the same manner as in the synthesis of intermediate (E), except that benzo[b]naphtho[2,1-d]thiophene was used instead of benzo[b]naphtho[2,1-d]furan.

(2) Synthesis of
benzo[b]naphtho[2,1-d]thiophene-5-boronic acid

Synthesis was conducted in (41-1), except that 5-bromobenzo[b]naphtho[2,1-d]thiophene was used instead of 5-bromobenzo[b]naphtho[2,1-d]furan.

Example 1

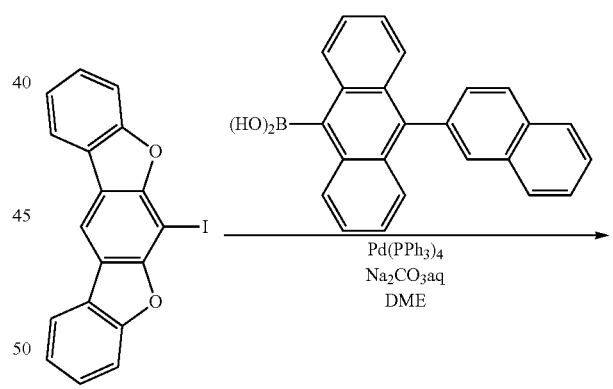

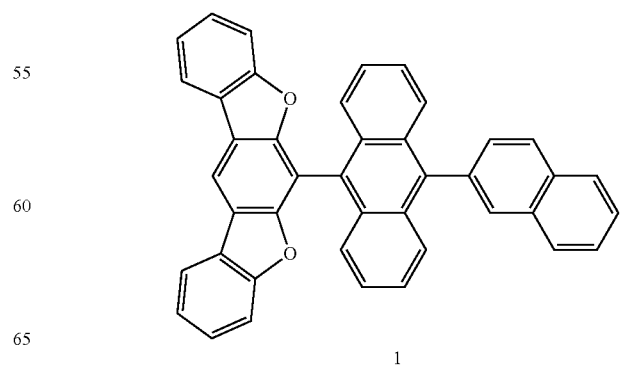

In the atmosphere of argon, 3.84 g of intermediate (B), 3.83 g of 10-(2-naphthyl)anthracene-9-boronic acid which was synthesized by a known method, 0.231 g of tetrakis(triphenylphosphine)palladium (0), 40 mL of 1,2-dimethoxyethane and 20 mL of a 2M aqueous sodium carbonate solution were charged. The resulting mixture was stirred under reflux for 8 hours. After cooling to room temperature, deposited solids were filtered out. The solids thus obtained were washed with water and methanol, recrystallized from toluene, whereby 4.20 g of pale yellow solids of compound 1 were obtained. As a result of mass spectroscopy, it was confirmed that the solids were an intended product having an m/e of 560 relative to the molecular weight of 560.18.

Example 2

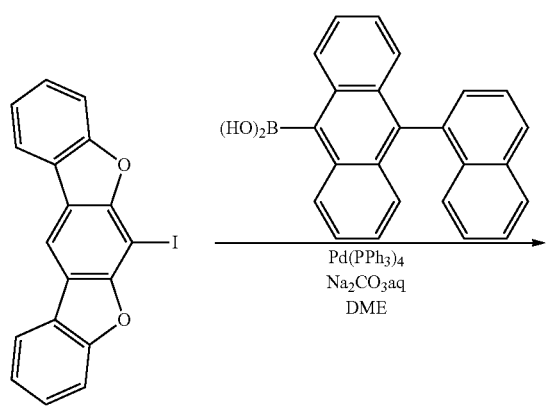

Compound 2 was obtained in the same manner as in Example 1, except that 10-(1-naphthyl)anthracene-9-boronic acid which was synthesized by a known method was used instead of 10-(2-naphthyl)anthracene-9-boronic acid. As a result of mass spectroscopy, it was confirmed that this compound was an intended product having an m/e of 636 relative to the molecular weight of 636.21.

Example 3

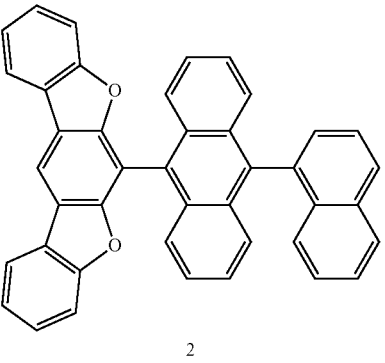

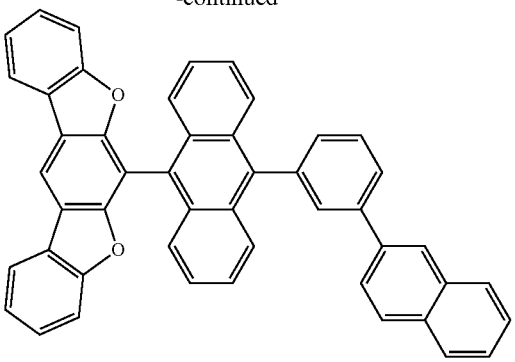

Compound 3 was obtained in the same manner as in Example 1, except that 10-[3-(2-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 636 relative to the molecular weight of 636.21.

Example 4

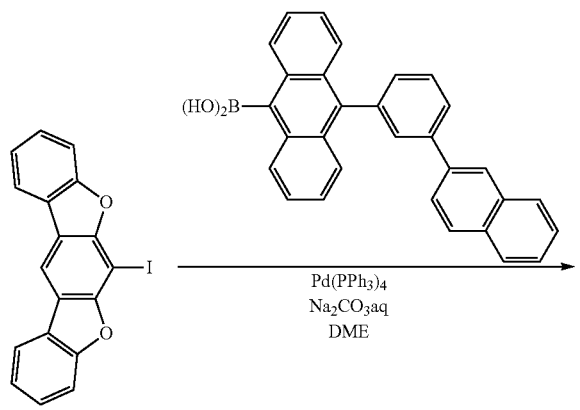

Compound 4 was obtained in the same manner as in Example 1, except that 10-[3-(1-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 636 relative to the molecular weight of 636.21.

Example 5

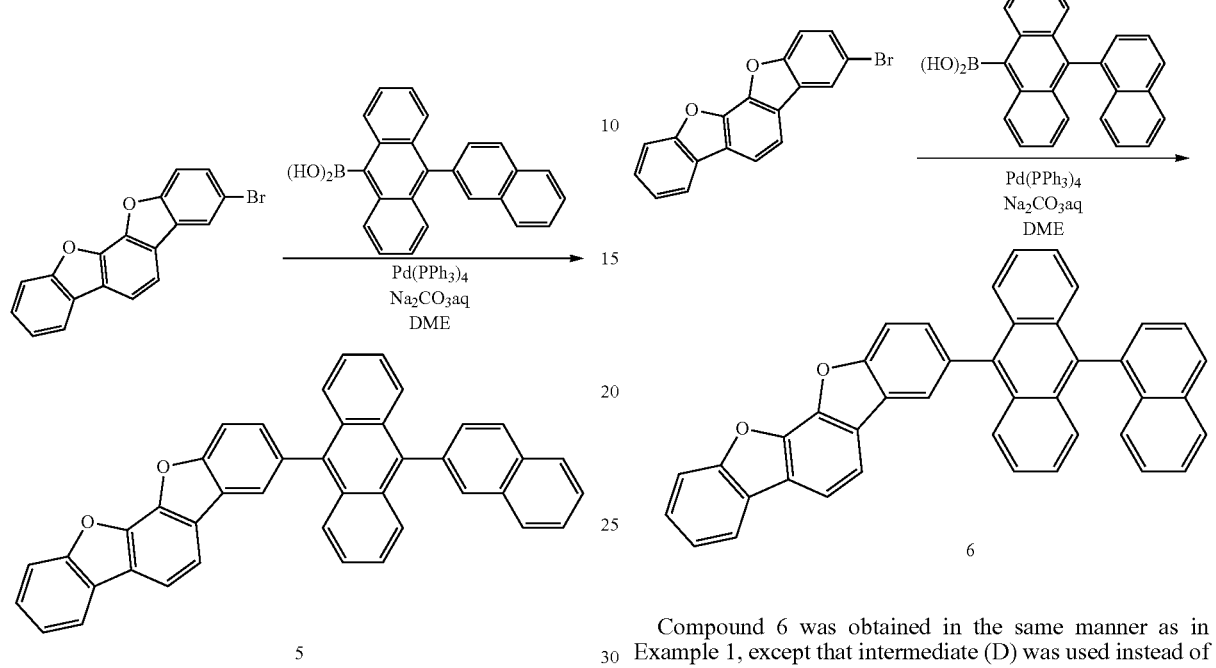

5

Compound 5 was obtained in the same manner as in Example 1, except that intermediate (D) was used instead of intermediate (B). As a result of mass spectroscopy, it was confirmed that this compound was an intended product having an m/e of 560 relative to the molecular weight of 560.18.

Example 6

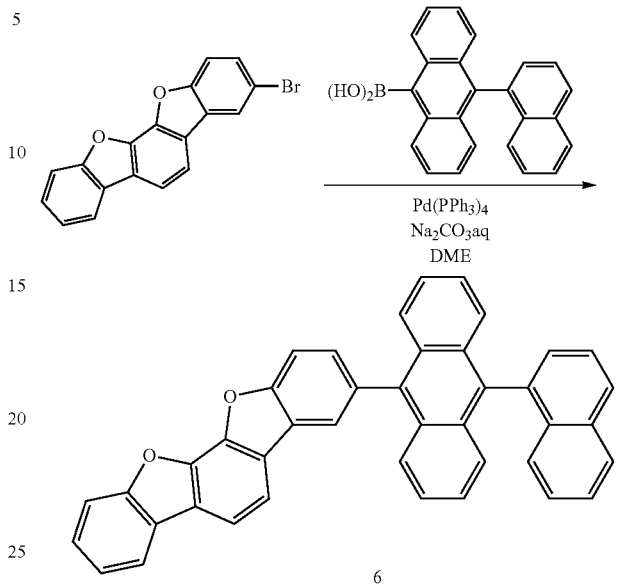

6

Compound 6 was obtained in the same manner as in Example 1, except that intermediate (D) was used instead of intermediate (B) and 10-(1-naphthyl)anthracene-9-boronic acid which was synthesized by a known method was used instead of 10-(2-naphthyl)anthracene-9-boronic acid. As a result of mass spectroscopy, it was confirmed that this compound was an intended product having an m/e of 560 relative to the molecular weight of 560.18.

Example 7

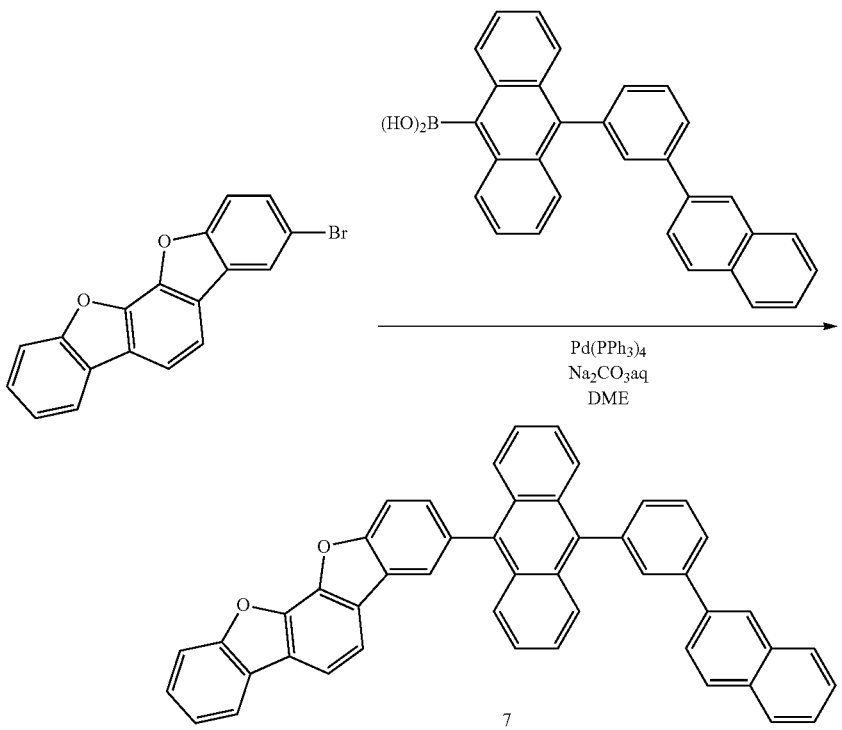

7

Compound 7 was obtained in the same manner as in Example 1, except that intermediate (D) was used instead of intermediate (B) and 10-[3-(2-naphthyl)]anthracene-9-boronic acid which was synthesized by a known method was used instead of 10-(2-naphthyl)anthracene-9-boronic acid. As a result of mass spectroscopy, it was confirmed that this compound was an intended product having an m/e of 636 relative to the molecular weight of 636.21.

Example 8

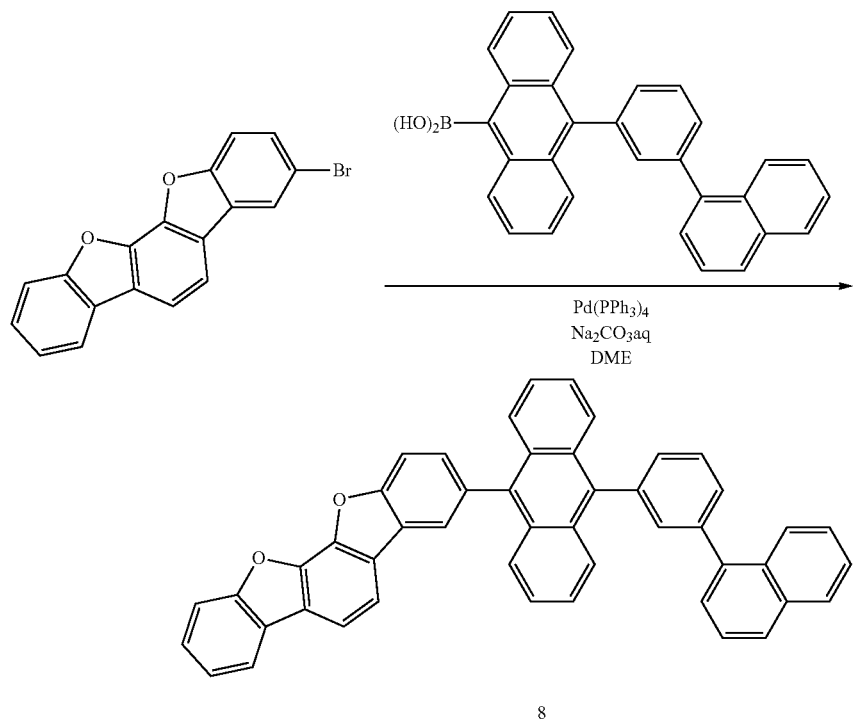

Compound 8 was obtained in the same manner as in Example 1, intermediate (D) was used instead of intermediate (B) and 10-[3-(1-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 636 relative to the molecular weight of 636.21.

Example 9

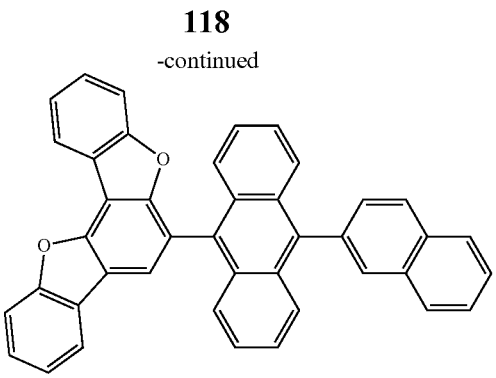

Compound 9 was obtained in the same manner as in Example 1, except that intermediate (A) was used instead of intermediate (B). As a result of mass spectroscopy, it was confirmed that this compound was an intended product having an m/e of 560 relative to the molecular weight of 560.18.

Example 10

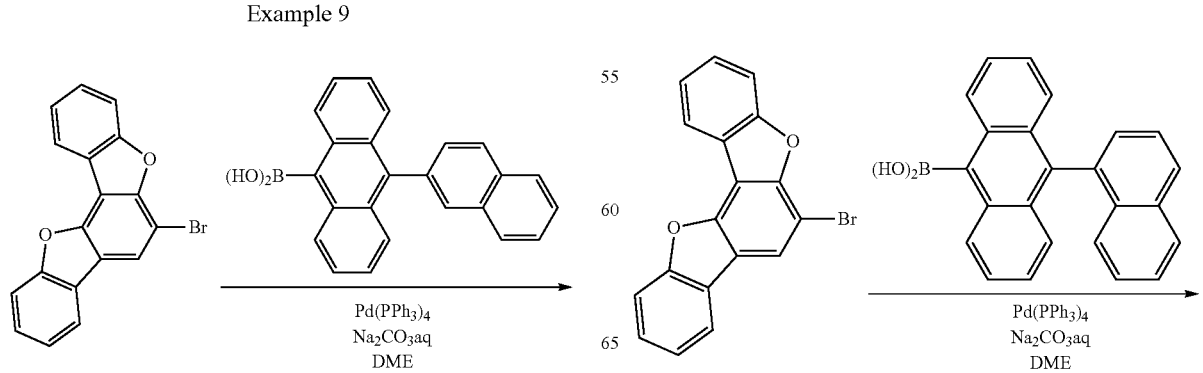

-continued

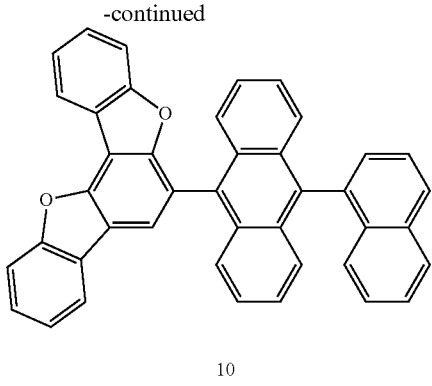

10

Compound 10 was obtained in the same manner as in Example 1, except that intermediate (A) was used instead of intermediate (B) and 10-(1-naphthyl)anthracene-9-boronic acid which was synthesized by a known method was used instead of 10-(2-naphthyl)anthracene-9-boronic acid. As a result of mass spectroscopy, it was confirmed that this compound was an intended product having an m/e of 560 relative to the molecular weight of 560.18.

Example 11

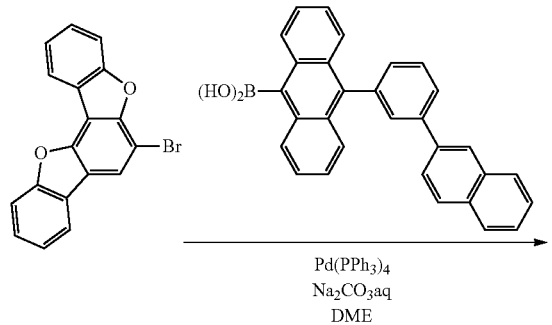

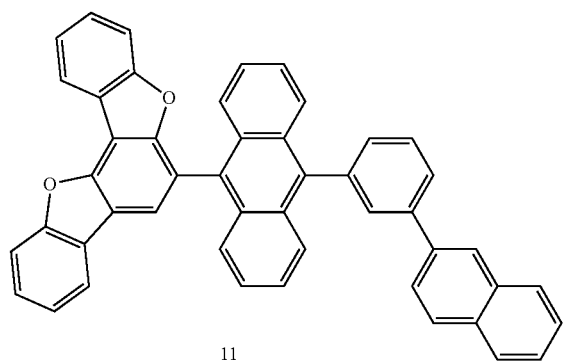

11

Compound 11 was obtained in the same manner as in Example 1, intermediate (A) was used instead of intermediate (B) and 10-[3-(2-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 636 relative to the molecular weight of 636.21.

Example 12

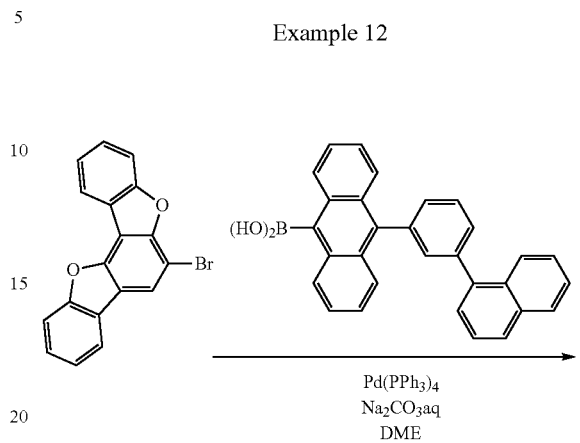

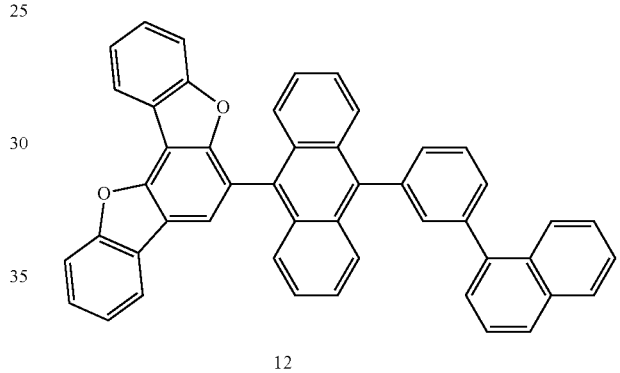

12

Compound 12 was obtained in the same manner as in Example 1, intermediate (A) was used instead of intermediate (B) and 10-[3-(1-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 636 relative to the molecular weight of 636.21.

Example 13

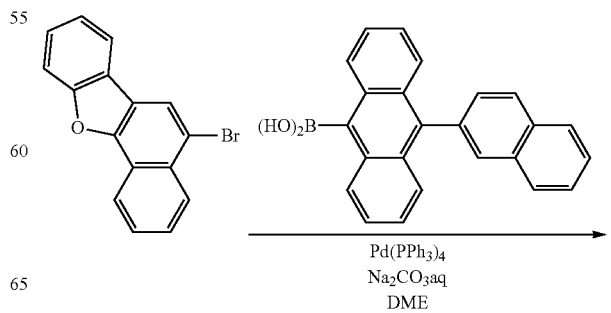

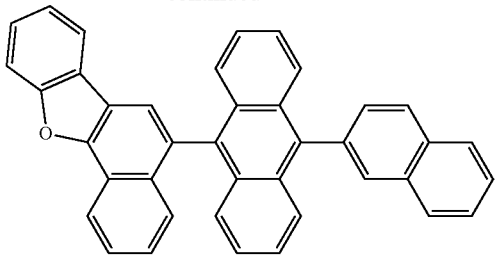

13

Compound 13 was obtained in the same manner as in Example 1, except that intermediate (E) was used instead of intermediate (B). As a result of mass spectroscopy, it was confirmed that this compound was an intended product having an m/e of 520 relative to the molecular weight of 520.18.

Example 14

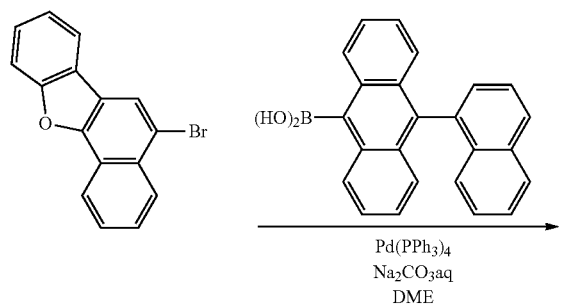

14

Compound 14 was obtained in the same manner as in Example 1, except that intermediate (E) was used instead of intermediate (B) and 10-(1-naphthyl)anthracene-9-boronic acid which was synthesized by a known method was used instead of 10-(2-naphthyl)anthracene-9-boronic acid. As a result of mass spectroscopy, it was confirmed that this compound was an intended product having an m/e of 520 relative to the molecular weight of 520.18.

Example 15

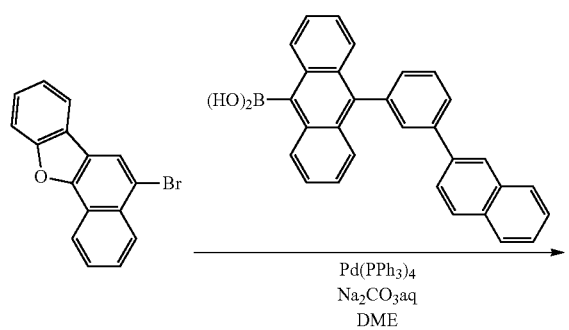

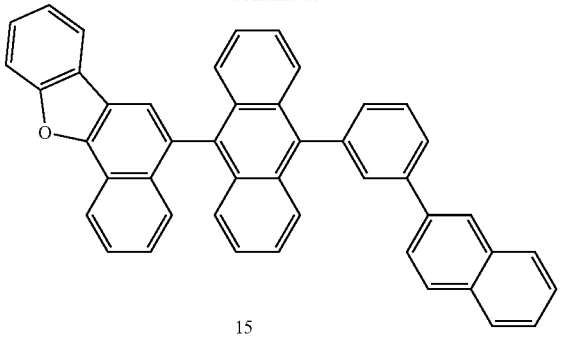

15

Compound 15 was obtained in the same manner as in Example 1, except that intermediate (E) was used instead of intermediate (B) and 10-[3-(2-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 596 relative to the molecular weight of 596.21.

Example 16

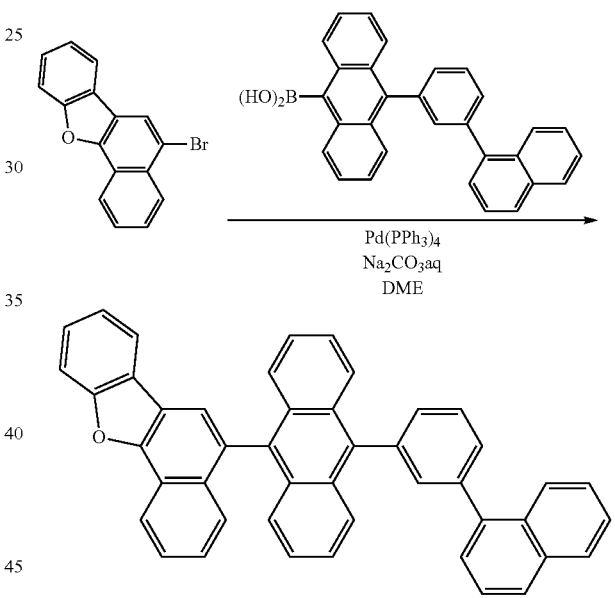

16

Compound 16 was obtained in the same manner as in Example 1, intermediate (E) was used instead of intermediate (B) and 10-[3-(1-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 596 relative to the molecular weight of 596.21.

Example 17

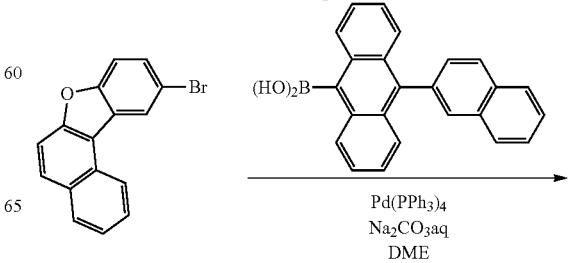

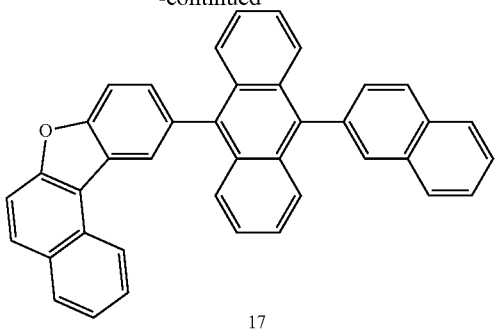

17

Compound 17 was obtained in the same manner as in Example 1, except that intermediate (F) was used instead of intermediate (B). As a result of mass spectroscopy, it was confirmed that this compound was an intended product having an m/e of 520 relative to the molecular weight of 520.18.

Example 18

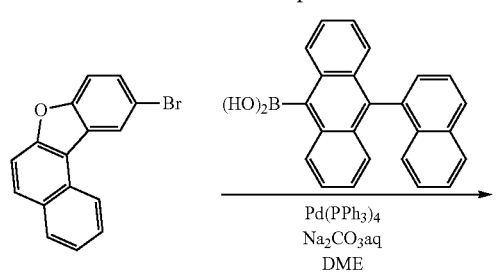

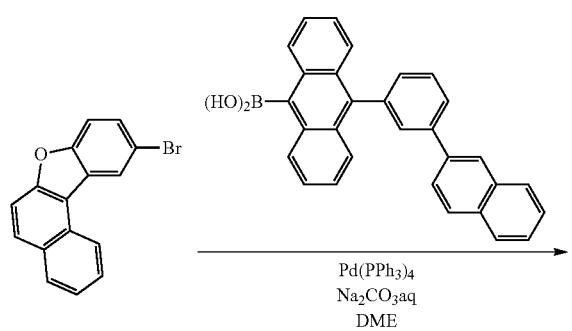

18

Compound 18 was obtained in the same manner as in Example 1, except that intermediate (F) was used instead of intermediate (B) and 10-(1-naphthyl)anthracene-9-boronic acid which was synthesized by a known method was used instead of 10-(2-naphthyl)anthracene-9-boronic acid. As a result of mass spectroscopy, it was confirmed that this compound was an intended product having an m/e of 520 relative to the molecular weight of 520. 18.

Example 19

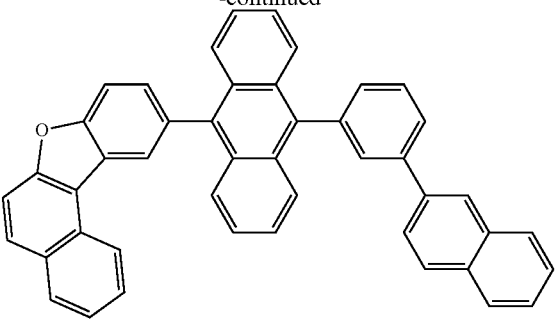

19

Compound 19 was obtained in the same manner as in Example 1, except that intermediate (F) was used instead of intermediate (B) and 10-[3-(2-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 596 relative to the molecular weight of 596.21.

Example 20

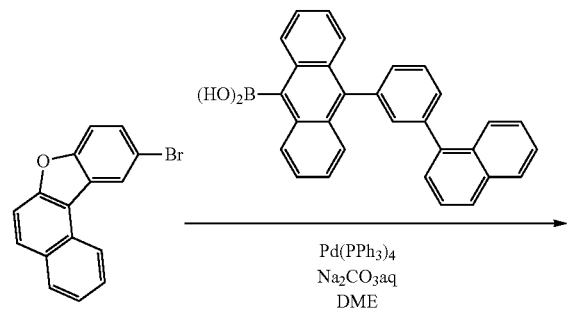

20

Compound 20 was obtained in the same manner as in Example 1, except that intermediate (F) was used instead of intermediate (B) and 10-[3-(1-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 596 relative to the molecular weight of 596.21.

Example 21

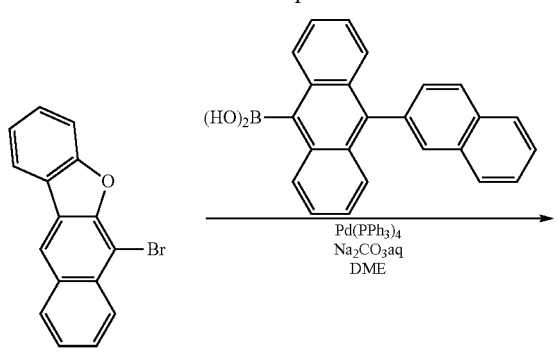

21

Compound 21 was obtained in the same manner as in Example 1, except that intermediate (G) was used instead of intermediate (B). As a result of mass spectroscopy, it was confirmed that this compound was an intended product having an m/e of 520 relative to the molecular weight of 520.18.

Example 22

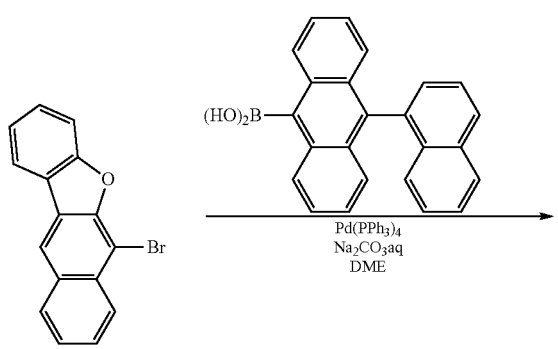

22

Compound 22 was obtained in the same manner as in Example 1, except that intermediate (G) was used instead of intermediate (B) and 10-(1-naphthyl)anthracene-9-boronic acid which was synthesized by a known method was used instead of 10-(2-naphthyl)anthracene-9-boronic acid. As a result of mass spectroscopy, it was confirmed that this compound was an intended product having an m/e of 520 relative to the molecular weight of 520. 18.

Example 23

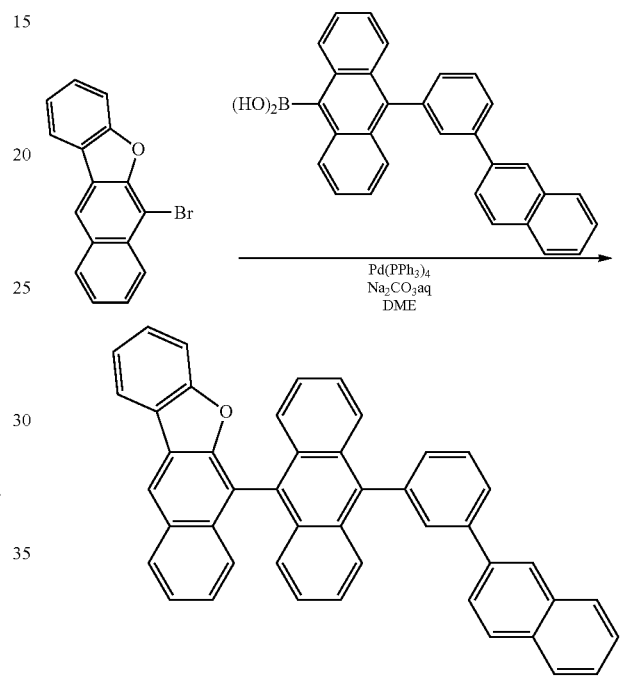

23

Compound 23 was obtained in the same manner as in Example 1, except that intermediate (G) was used instead of intermediate (B) and 10-[3-(2-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 596 relative to the molecular weight of 596.21.

Example 24

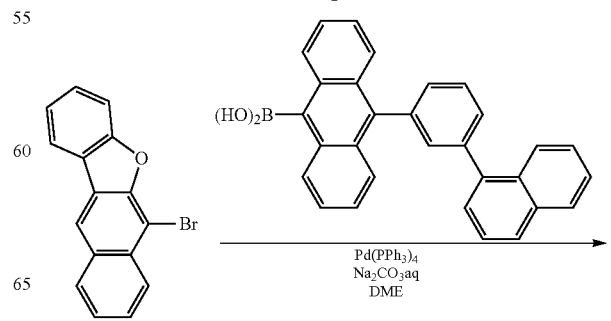

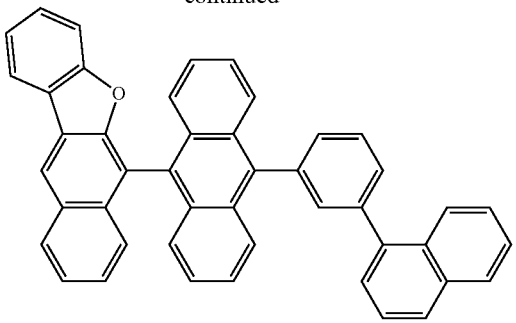

24

Compound 24 was obtained in the same manner as in Example 1, except that intermediate (G) was used instead of intermediate (B) and 10-[3-(1-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 596 relative to the molecular weight of 596.21.

Example 25

(25-1) Synthesis of 6-(3-bromophenyl)benzofurano[3,2-b]dibenzofuran

In the atmosphere of argon, 3.17 g of benzofurano[3,2-b]dibenzofuran-6-boronic acid, 2.83 g of 3-bromoiodobenzene, 0.231 g of tetrakis(triphenylphosphine)palladium (0), 40 mL of toluene and 20 mL of a 2M aqueous sodium carbonate solution were placed in a flask. The resulting mixture was stirred with heating under reflux for 8 hours. After cooling to room temperature, an aqueous phase was removed. An organic phase was extracted with toluene, dried with magnesium sulfate and concentrated. Residues were purified by silica gel column chromatography, whereby 3.39 g (yield: 82%) of 6-(3-bromophenyl)benzofurano[3,2-b]dibenzofuran was obtained.

(25-2) Synthesis of Compound 25

Compound 25 was obtained in the same manner as in Example 1, except that 6-(3-bromophenyl)benzofurano[3,2-b]dibenzofuran was used instead of intermediate (B). As a result of mass spectroscopy, it was confirmed that this compound was an intended product having an m/e of 636 relative to the molecular weight of 636.21.

Example 26

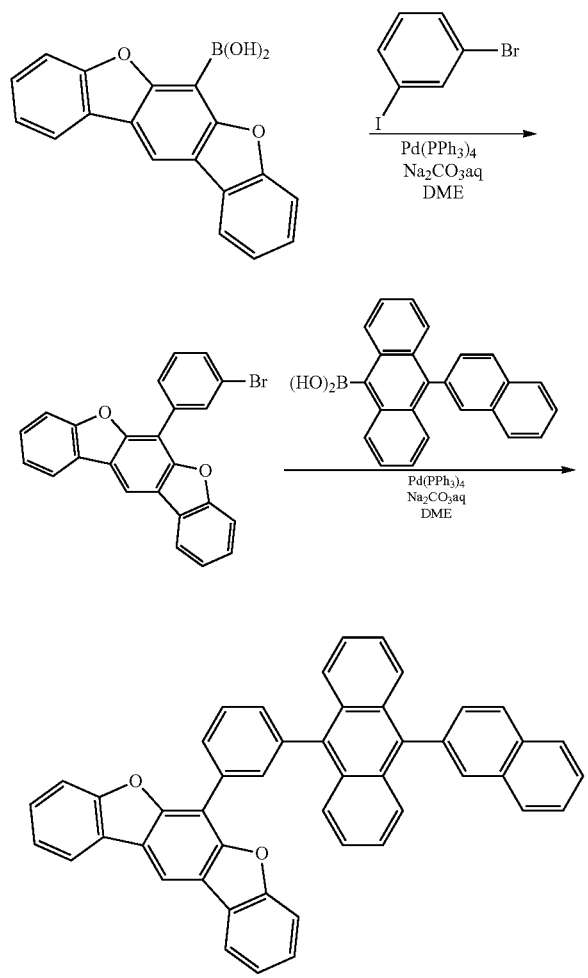

25

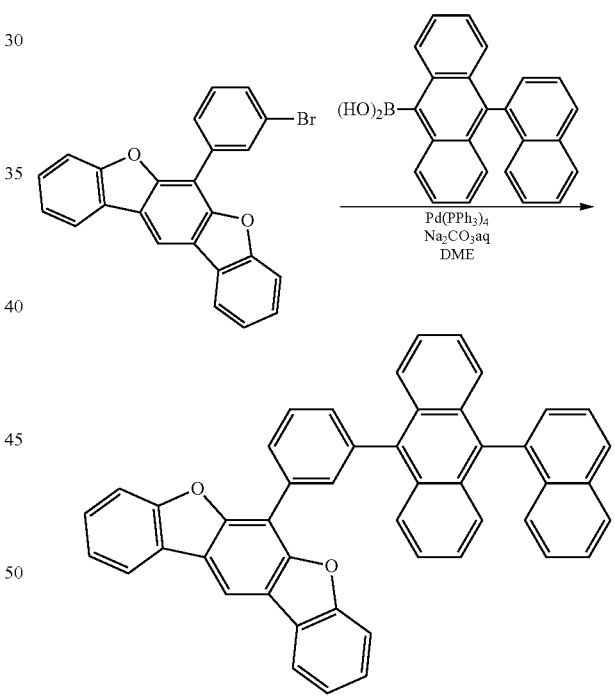

26

Compound 26 was obtained in the same manner as in Example 1, except that 6-(3-bromophenyl)benzofurano[3,2-b]dibenzofuran was used instead of intermediate (B) and 10-(1-naphthyl)anthracene-9-boronic acid which was synthesized by a known method was used instead of 10-(2-naphthyl)anthracene-9-boronic acid. As a result of mass spectroscopy, it was confirmed that this compound was an intended product having an m/e of 636 relative to the molecular weight of 636.21.

Example 27

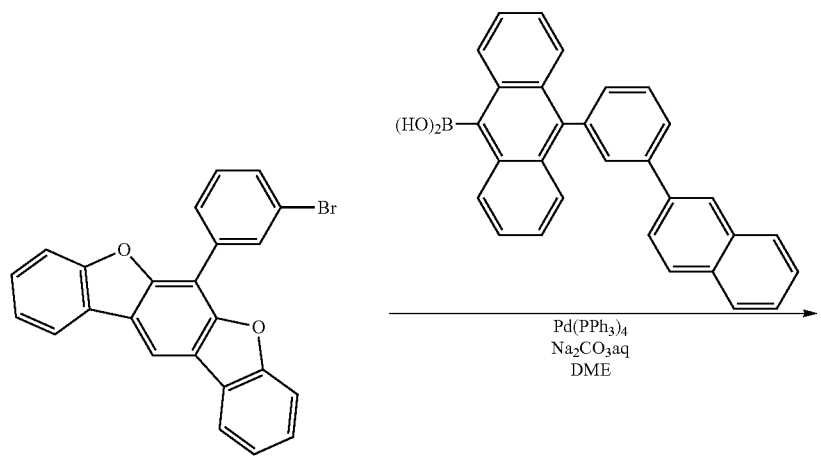

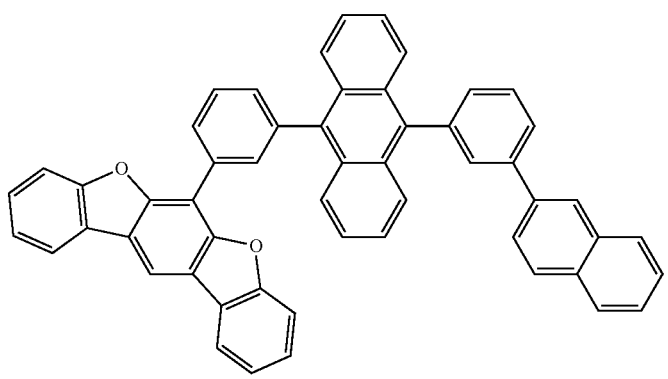

27

Compound 27 was obtained in the same manner as in Example 1, except that 6-(3-bromophenyl)benzofurano[3,2-b]dibenzofuran was used instead of intermediate (B) and 10-[(3-(2-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 712 relative to the molecular weight of 712.24.

Example 28

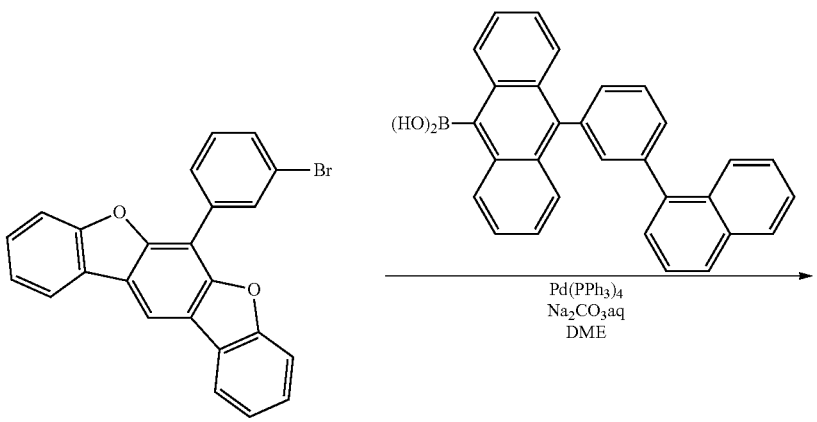

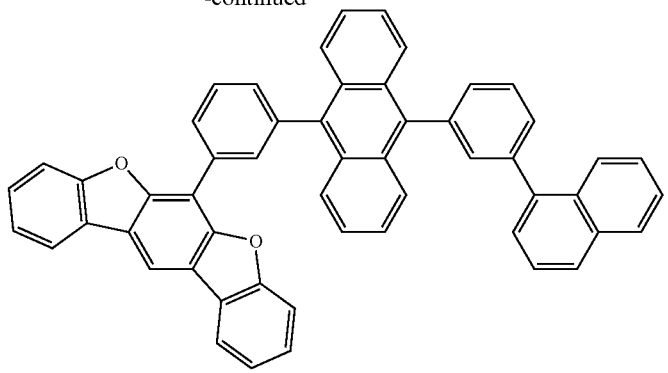

28

Compound 28 was obtained in the same manner as in Example 1, except that 6-(3-bromophenyl)benzofurano[3,2-b]dibenzofuran was used instead of intermediate (B) and 10-[(3-(1-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 712 relative to the molecular weight of 712.24.

Example 29

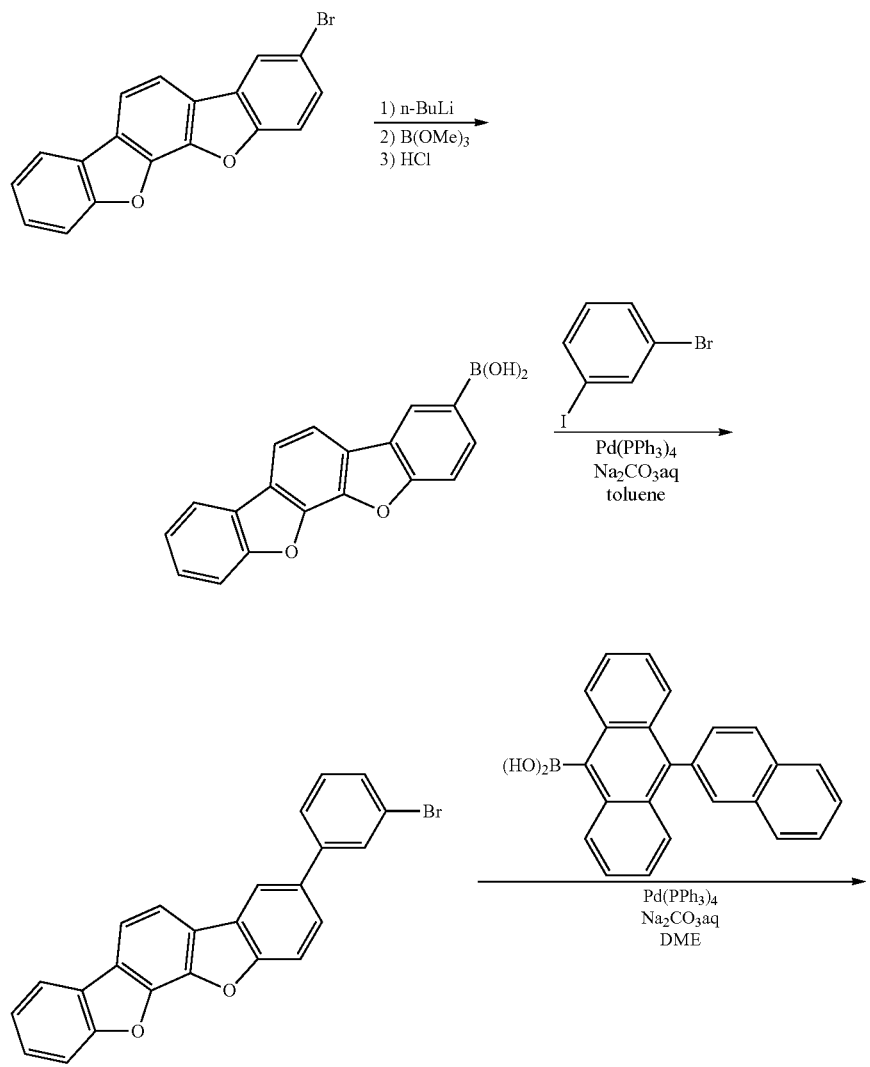

-continued

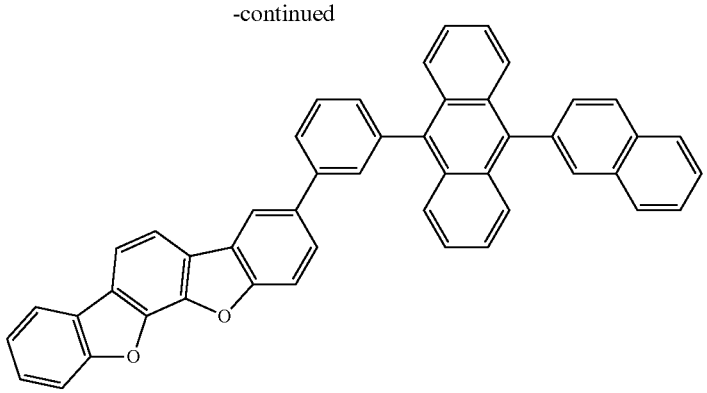

29

(29-1) Synthesis of benzofurano[3,2-c]dibenzofuran-3-boronic acid 33.5 g of 3-bromobenzofurano[3,2-c]dibenzofuran and 500 mL of tetrahydrofuran (dehydrated) were placed in a flask. The resulting mixture was cooled to −78° C. 66 mL of n-BuLi (1.60M in hexane) was added thereto. While heating to 0° C., the resulting solution was stirred for 2 hours. Then, the solution was again cooled to −78° C., and 27.3 g of B(OMe)$_3$ was added thereto. After stirring at −78° C. for 10 minutes, the solution was stirred at room temperature for 5 hours.

After completion of the reaction, 1 N HCl aq. (200 mL) was added, followed by stirring at room temperature for 1 hour. Then, the solution was transferred to a separating funnel, and extracted with ethyl acetate.

After drying with MgSO$_4$, the solution was concentrated and washed with hexane, whereby 19.6 g (yield: 65%) of white solids of 3-bromobenzofurano[3,2-c]dibenzofuran were obtained.

(29-2) Synthesis of 3-(3-bromophenyl)benzofurano[3,2-c]dibenzofuran

In the atmosphere of argon, 19.6 g of benzofurano[3,2-c]dibenzofuran-3-boronic acid, 18.4 g of 3-bromoiodobenzene, 1.50 g of tetrakis(triphenylphosphine)palladium (0), 200 mL of toluene and 100 mL of a 2M aqueous sodium carbonate solution were placed in a flask. The resulting mixture was stirred with heating under reflux for 8 hours. After cooling to room temperature, the reaction solution was extracted with toluene. An aqueous phase was removed and an organic phase was dried with magnesium sulfate and concentrated. Residues were purified by silica gel column chromatography, whereby 21.4 g of 3-(3-bromophenyl)benzofurano[3,2-c]dibenzofuran was obtained.

(29-3) Synthesis of Compound 29

Compound 29 was synthesized in the same manner as in Example 1, except that 3-(3-bromophenyl)benzofurano[3,2-c]dibenzofuran was used instead of intermediate (B). As a result of mass spectroscopy, it was confirmed that this compound was an intended product having an m/e of 636 relative to the molecular weight of 636. 21.

Example 30

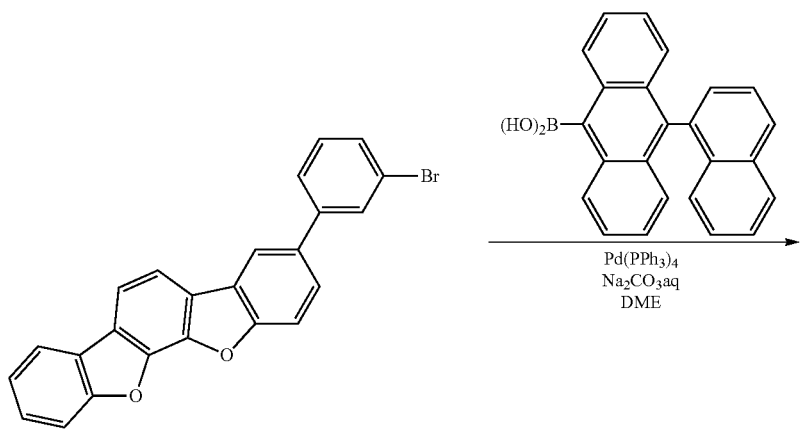

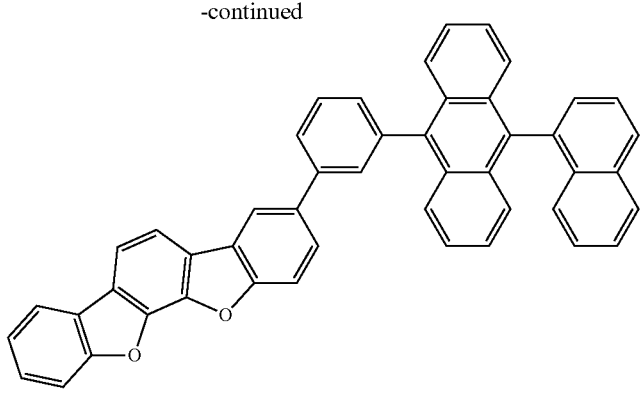

30

Compound 30 was synthesized in the same manner as in Example 1, except that 3-(3-bromophenyl)benzofurano[3,2-c]dibenzofuran was used instead of intermediate (B) and 10-(1-naphthyl)anthracene-9-boronic acid which was synthesized by a known method was used instead of 10-(2-naphthyl)anthracene-9-boronic acid. As a result of mass spectroscopy, it was confirmed that this compound was an intended product having an m/e of 636 relative to the molecular weight of 636. 21.

Example 31

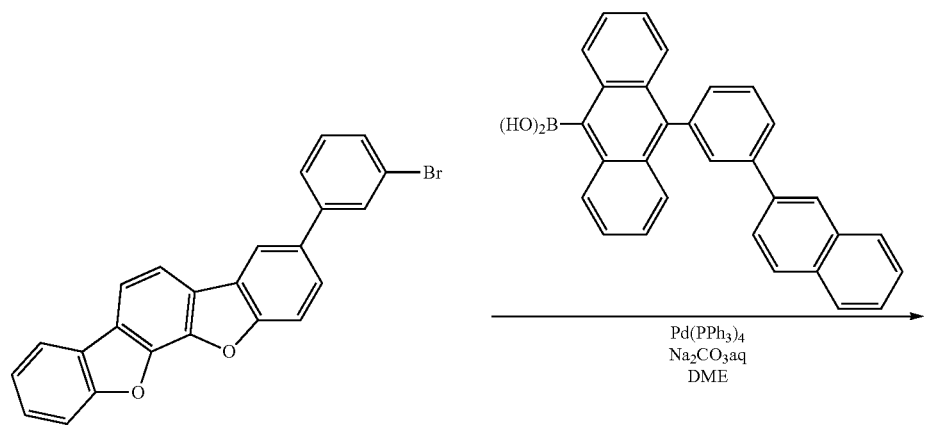

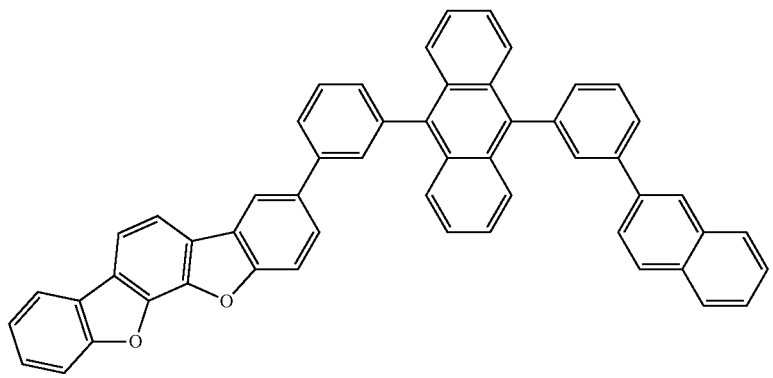

31

Compound 31 was synthesized in the same manner as in Example 1, except that 3-(3-bromophenyl)benzofurano[3,2-c]dibenzofuran was used instead of intermediate (B) and 10-[3-(2-naphthyl)phenyl]anthracene-9-boronic acid which was synthesized by a known method was used instead of 10-(1-naphthyl)anthracene-9-boronic acid. As a result of mass spectroscopy, it was confirmed that this compound was an intended product having an m/e of 712 relative to the molecular weight of 712.24.

Example 32

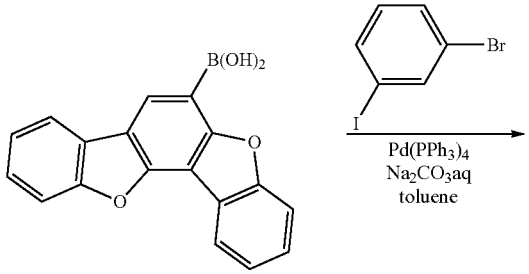

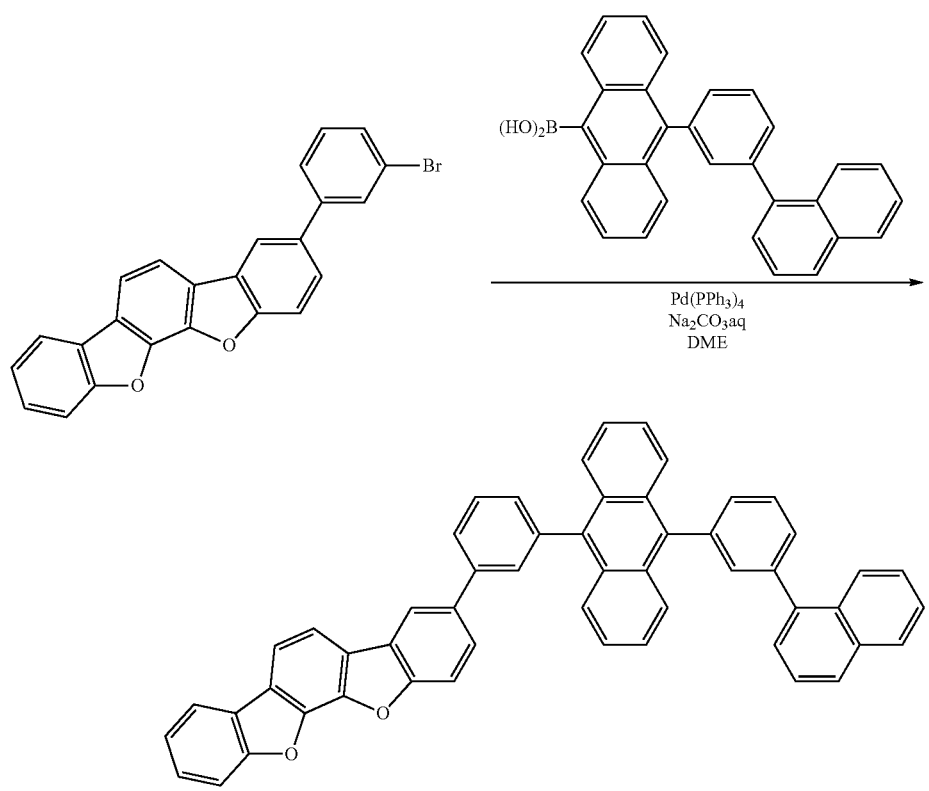

32

Compound 32 was synthesized in the same manner as in Example 1, except that 3-(3-bromophenyl)benzofurano[3,2-c]dibenzofuran was used instead of intermediate (B) and 10-[3-(1-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 712 relative to the molecular weight of 712.24.

Example 33

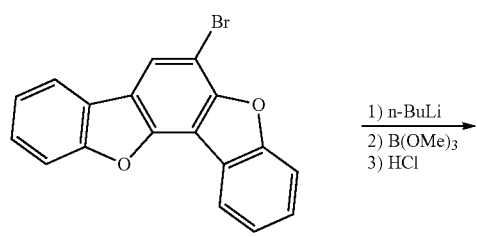

-continued

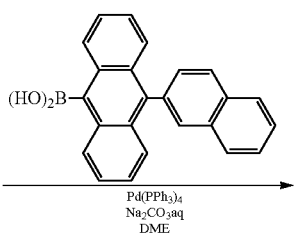

-continued

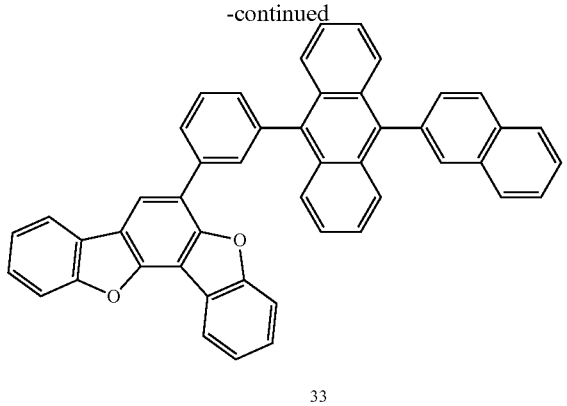

33

(33-1) Synthesis of benzofurano[2,3-c]dibenzofuran-6-boronic acid 33.5 g of 6-bromobenzofurano[2,3-c]dibenzofuran and 500 mL of tetrahydrofuran (dehydrated) were placed in a flask. The resulting mixture was cooled to −78° C. 66 mL of n-BuLi (1.60M in hexane) was added thereto. While heating to 0° C., the resulting solution was stirred for 2 hours. Then, the solution was again cooled to −78° C., and 27.3 g of B(OMe)$_3$ was added thereto. After stirring at −78° C. for 10 minutes, the solution was stirred at room temperature for 5 hours.

After completion of the reaction, 1N HCl aq. (200 mL) was added, followed by stirring at room temperature for 1 hour. Then, the solution was transferred to a separating funnel, and extracted with ethyl acetate.

After drying with MgSO$_4$, the solution was concentrated and washed with hexane, whereby 19.6 g (yield: 65%) of white solids of benzofurano[2,3-c]dibenzofuran-6-boronic acid were obtained.

(33-2) Synthesis of 6-(3-bromophenyl)benzofurano[2,3-c]dibenzofuran

In the atmosphere of argon, 19.6 g of benzofurano[2,3-c]dibenzofuran-6-boronic acid, 18.4 g of 3-bromoiodobenzene, 1.50 g of tetrakis(triphenylphosphine)palladium (0), 200 mL of toluene and 100 mL of a 2M aqueous sodium carbonate solution were placed in a flask. The resulting mixture was stirred with heating under reflux for 8 hours. After cooling to room temperature, the reaction solution was extracted with toluene. An aqueous phase was removed and an organic phase was dried with magnesium sulfate and concentrated. Residues were purified by silica gel column chromatography, whereby 21.4 g of 6-(3-bromophenyl)benzofurano[2,3-c]dibenzofuran was obtained.

(33-3) Synthesis of Compound 33

Compound 33 was synthesized in the same manner as in Example 1, except that 6-(3-bromophenyl)benzofurano[2,3-c]dibenzofuran was used instead of intermediate (B). As a result of mass spectroscopy, it was confirmed that this compound was an intended product having an m/e of 636 relative to the molecular weight of 636. 21.

Example 34

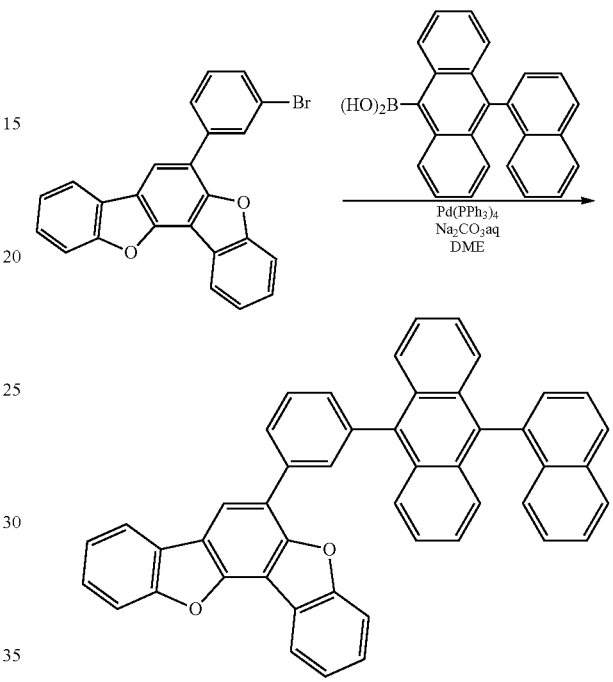

34

Compound 34 was synthesized in the same manner as in Example 1, except that 6-(3-bromophenyl)benzofurano[2,3-c]dibenzofuran was used instead of intermediate (B) and 10-(1-naphthyl)anthracene-9-boronic acid which was synthesized by a known method was used instead of 10-(2-naphthyl)anthracene-9-boronic acid. As a result of mass spectroscopy, it was confirmed that this compound was an intended product having an m/e of 636 relative to the molecular weight of 636. 21.

Example 3

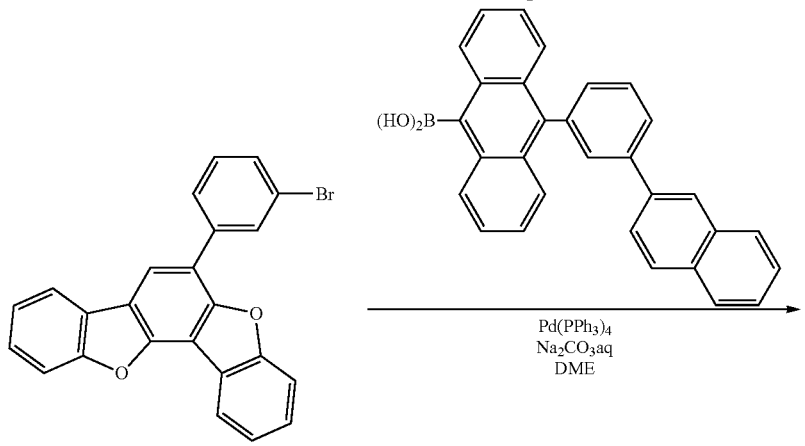

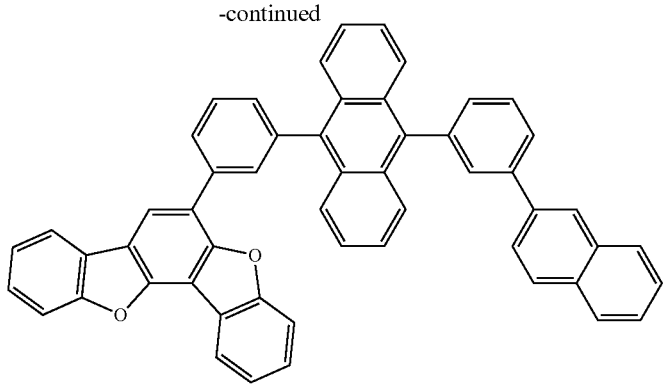

35

Compound 35 was synthesized in the same manner as in Example 1, except that 6-(3-bromophenyl)benzofurano[2,3-c]benzofuran was used instead of intermediate (B) and 10-[3-(2-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 712 relative to the molecular weight of 712. 24.

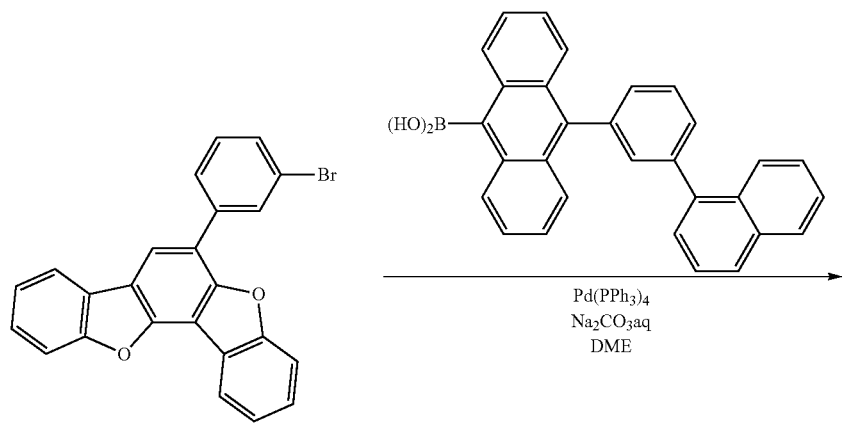

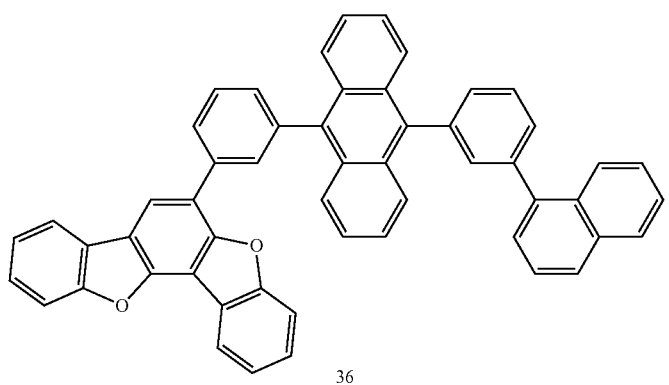

36

Compound 36 was synthesized in the same manner as in Example 1, except that 6-(3-bromophenyl)benzofurano[2,3-c]benzofuran was used instead of intermediate (B) and 10-[3-(1-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 712 relative to the molecular weight of 712. 24.

Example 37

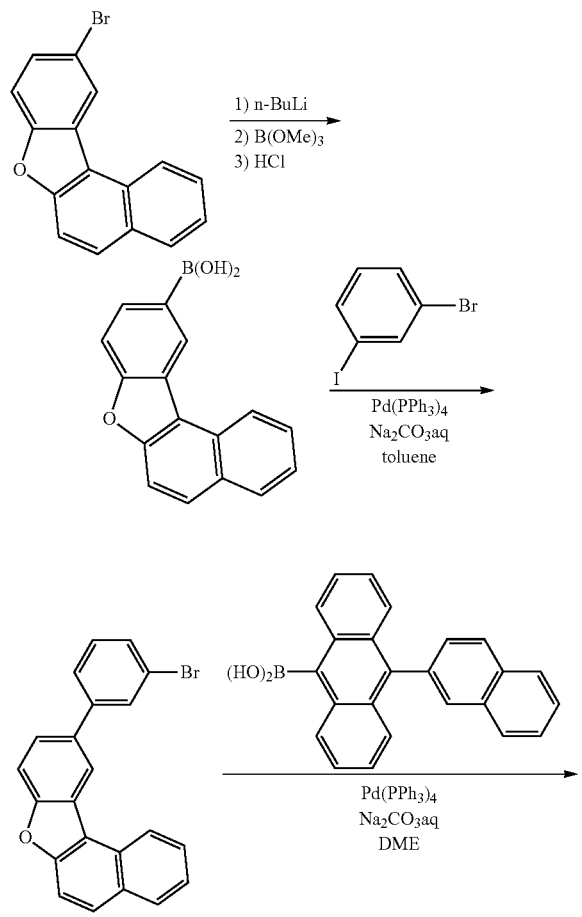

(37-1) Synthesis of benzo[b]naphtho[1,2-d]furan-10-boronic acid 29.7 g of 10-bromobenzo[b]naphtho[1,2-d]furan and 500 mL of tetrahydrofuran (dehydrated) were placed in a flask. The resulting mixture was cooled to −78° C. 66 mL of n-BuLi (1.60M in hexane) was added thereto. While heating to 0° C., the resulting solution was stirred for 2 hours. Then, the solution was again cooled to −78° C., and 27.3 g of B(OMe)$_3$ was added thereto. After stirring at −78° C. for 10 minutes, the solution was stirred at room temperature for 5 hours.

After completion of the reaction, 1N HCl aq. (200 mL) was added, followed by stirring at room temperature for 1 hour. Then, the solution was transferred to a separating funnel, and extracted with ethyl acetate.

After drying with MgSO$_4$, the solution was concentrated and washed with hexane, whereby 17.0 g (yield: 65%) of white solids of benzo[b]naphtho[1,2-d]furan-10-boronic acid were obtained.

(37-2) Synthesis of 10-(3-bromophenyl)benzo[b]naphtho[1,2-d]furan

In the atmosphere of argon, 17.0 g of benzo[b]naphtho[1,2-d]furan-10-boronic acid, 18.4 g of 3-bromoiodobenzene, 1.50 g of tetrakistriphenylphosphine palladium (0), 200 mL of toluene and 100 mL of a 2M aqueous sodium carbonate solution were placed in a flask. The resulting mixture was stirred with heating under reflux for 8 hours. After cooling to room temperature, the reaction solution was extracted with toluene. An aqueous phase was removed. An organic phase was dried with magnesium sulfate and concentrated. Residues were purified by silica gel column chromatography, whereby 21.8 g of 10-(3-bromophenyl)benzo[b]naphtho[1,2-d]furan was obtained.

(37-3) Synthesis of Compound 37

Compound 37 was obtained in the same manner as in Example 1, except that 10-(3-bromophenyl)benzo[b]naphtho[1,2-d]furan was used instead of intermediate (B). As a result of mass spectroscopy, it was confirmed that this compound was an intended product having an m/e of 596 relative to the molecular weight of 596.21.

Example 38

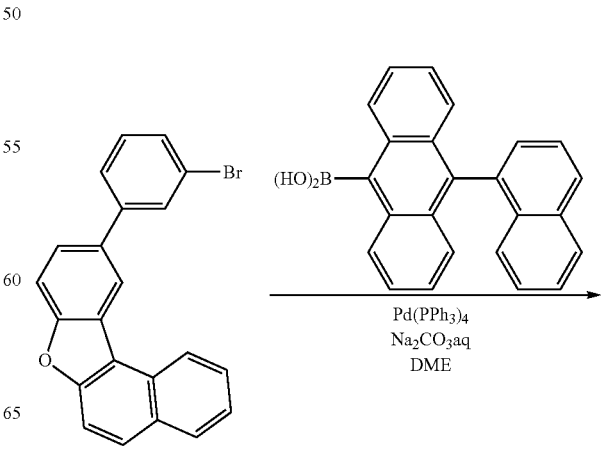

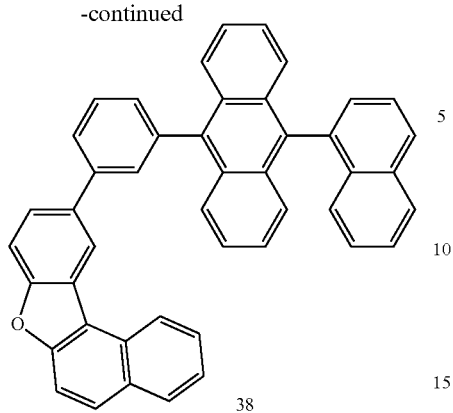

38

Compound 38 was synthesized in the same manner as in Example 1, except that 10-(3-bromophenyl)benzo[b]naphtho[1,2-d]furan was used instead of intermediate (B) and 10-(1-naphthyl)anthracene-9-boronic acid which was synthesized by a known method was used instead of 10-(2-naphthyl)anthracene-9-boronic acid. As a result of mass spectroscopy, it was confirmed that this compound was an intended product having an m/e of 596 relative to the molecular weight of 596.21.

Example 39

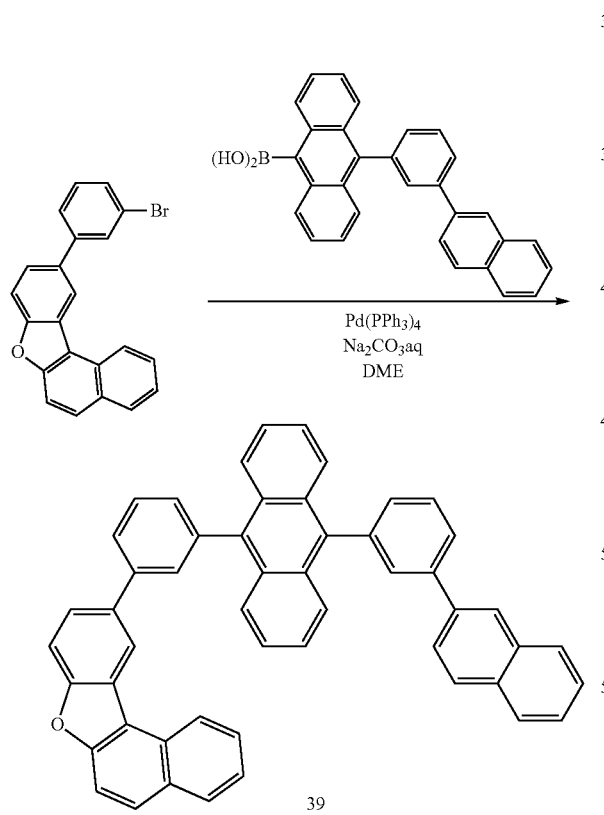

39

Compound 39 was synthesized in the same manner as in Example 1, except that 10-(3-bromophenyl)benzo[b]naphtho[1,2-d]furan was used instead of intermediate (B) and 10-[3-(2-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 672 relative to the molecular weight of 672.25.

Example 40

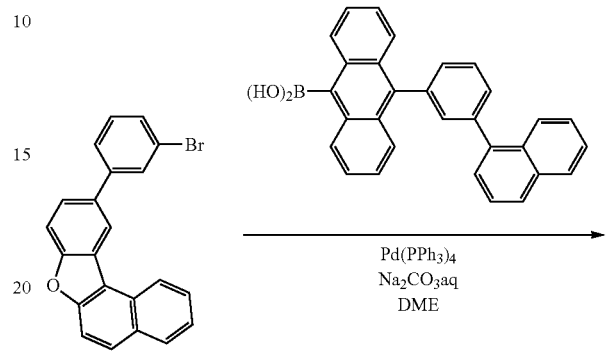

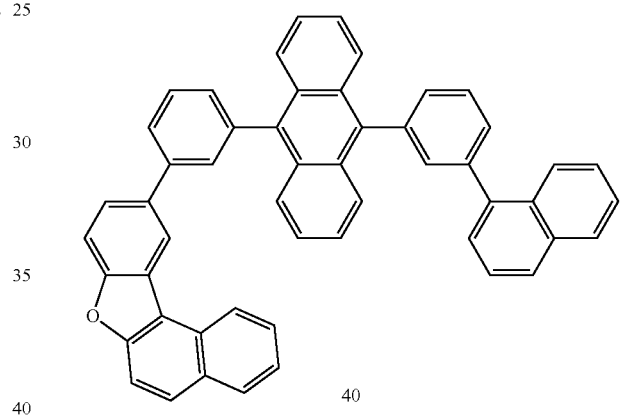

40

Compound 40 was obtained in the same manner as in Example 1, except that 10-(3-bromophenyl)benzo[b]naphtho[1,2-d]furan was used instead of intermediate (B) and 10-[3-(1-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 672 relative to the molecular weight of 672.25.

Example 41

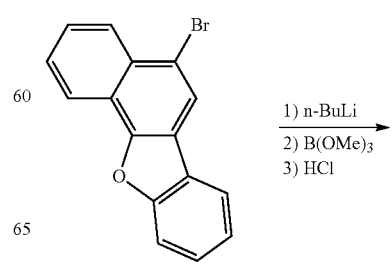

-continued

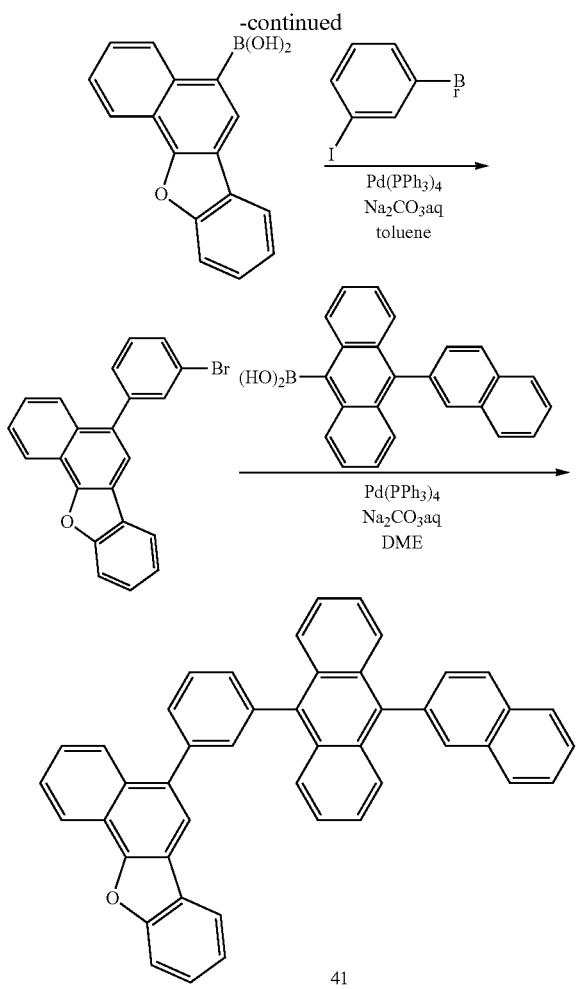

(41-1) Synthesis of benzo[b]naphtho[2,1-d]furan-5-boronic acid 29.7 g of 5-bromobenzo[b]naphtho[2,1-d]furan and 500 mL of tetrahydrofuran (dehydrated) were placed in a flask. The resulting mixture was cooled to −78° C. 66 mL of n-BuLi (1.60M in hexane) was added thereto. While heating to 0° C., the resulting solution was stirred for 2 hours. Then, the solution was again cooled to −78° C., and 27.3 g of B(OMe)$_3$ was added thereto. After stirring at −78° C. for 10 minutes, the solution was stirred at room temperature for 5 hours.

After completion of the reaction, 1N HCl aq. (200 mL) was added, followed by stirring at room temperature for 1 hour. Then, the solution was transferred to a separating funnel, and extracted with ethyl acetate.

After drying with MgSO$_4$, the solution was concentrated and washed with hexane, whereby 17.0 g (yield: 65%) of white solids of benzo[b]naphtho[2,1-d]furan-5-boronic acid were obtained.

(41-2) Synthesis of 5-(3-bromophenyl)benzo[b]naphtho[2,1-d]furan

In the atmosphere of argon, 17.0 g of benzo[b]naphtho[2,1-d]furan-5-bronic acid, 18.4 g of 3-bromoiodobenzene, 1.50 g of tetrakistriphenylphosphine palladium (0), 200 mL of toluene and 100 mL of a 2M aqueous sodium carbonate solution were placed in a flask. The resulting mixture was stirred with heating under reflux for 8 hours. After cooling to room temperature, the reaction solution was extracted with toluene. An aqueous phase was removed. An organic phase was dried with magnesium sulfate and concentrated. Residues were purified by silica gel column chromatography, whereby 21.8 g of 5-(3-bromophenyl)benzo[b]naphtho[2,1-d]furan was obtained.

(41-3) Synthesis of Compound 41

Compound 41 was synthesized in the same manner as in Example 1, except that 5-(3-bromophenyl)benzo[b]naphtho[2,1-d]furan was used instead of intermediate (B). As a result of mass spectroscopy, it was confirmed that this compound was an intended product having an m/e of 596 relative to the molecular weight of 596.21.

Example 42

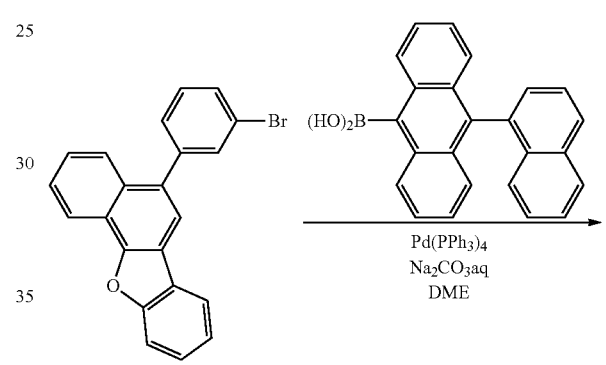

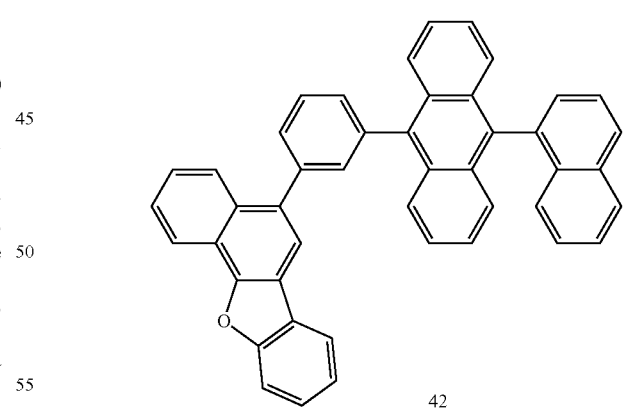

Compound 42 was synthesized in the same manner as in Example 1, except that 5-(3-bromophenyl)benzo[b]naphtho[2,1-d]furan was used instead of intermediate (B) and 10-(1-naphthyl)anthracene-9-boronic acid which was synthesized by a known method was used instead of 10-(2-naphthyl)anthracene-9-boronic acid. As a result of mass spectroscopy, it was confirmed that this compound was an intended product having an m/e of 596 relative to the molecular weight of 596.21.

Example 43

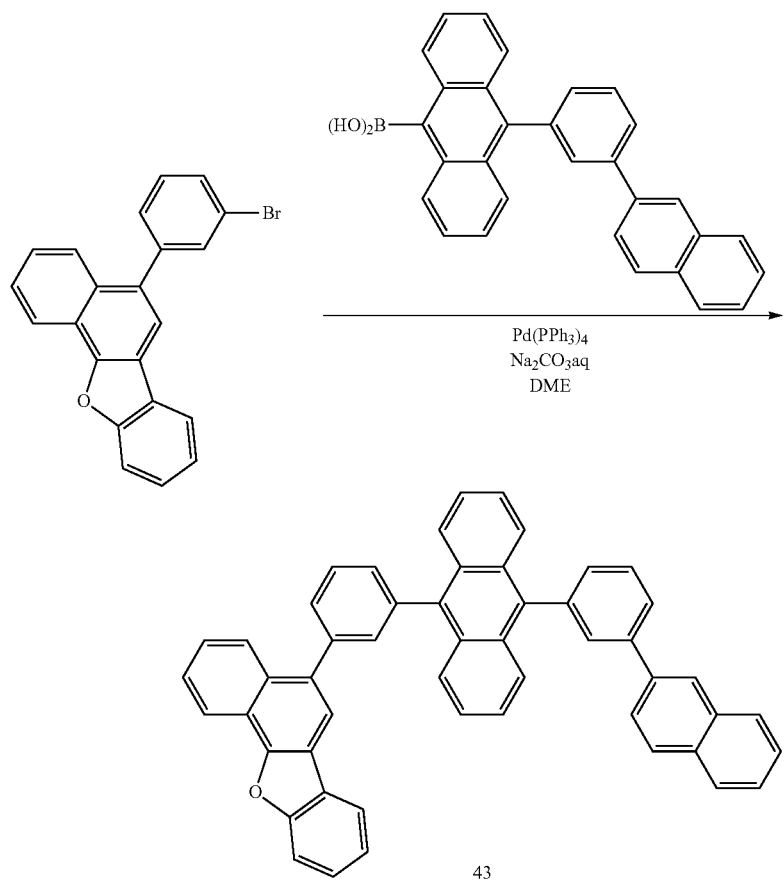

Compound 43 was synthesized in the same manner as in Example 1, except that 5-(3-bromophenyl)benzo[b]naphtho[2,1-d]furan was used instead of intermediate (B) and 10-[3-(2-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 672 relative to the molecular weight of 672.25.

Example 44

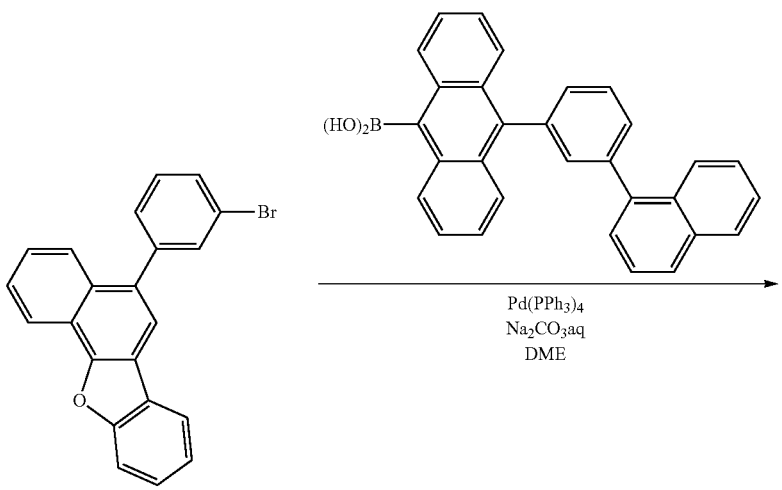

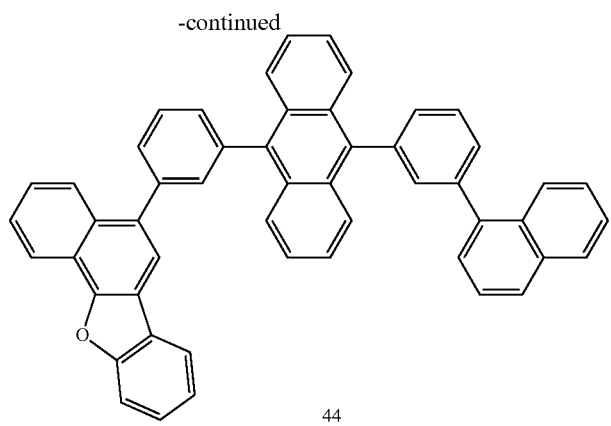

44

Compound 44 was obtained in the same manner as in Example 1, except that 5-(3-bromophenyl)benzo[b]naphtho[2,1-d]furan was used instead of intermediate (B) and 10-[3-(1-naphthyl)phenyl]anthracene-9-boronic acid which was synthesized by a known method was used instead of 10-(2-naphthyl)anthracene-9-boronic acid. As a result of mass spectroscopy, it was confirmed that this compound was an intended product having an m/e of 672 relative to the molecular weight of 672.25.

Example 45

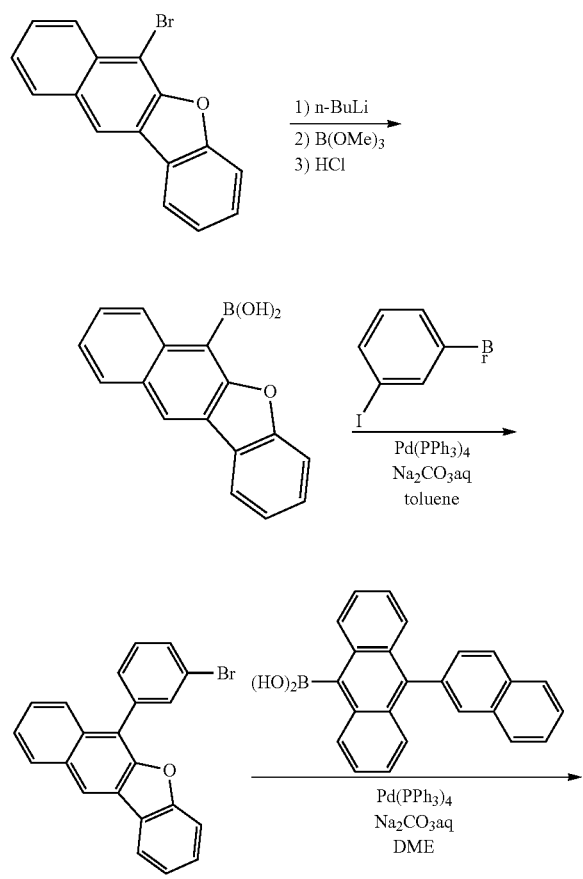

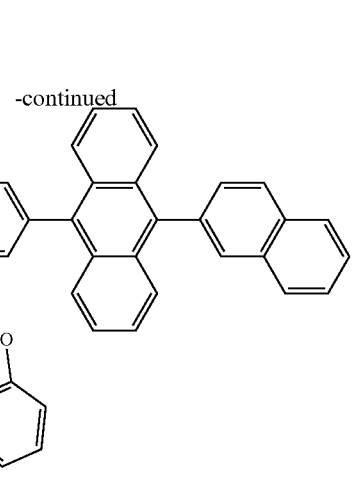

45

(45-1) Synthesis of benzo[b]naphtho[2,3-d]furan-5-boronic acid 29.7 g of 5-bromobenzo[b]naphtho[2,3-d]furan and 500 mL of tetrahydrofuran (dehydrated) were placed in a flask. The resulting mixture was cooled to −78° C. 66 mL of n-BuLi (1.60M in hexane) was added thereto. While heating to 0° C., the resulting solution was stirred for 2 hours. Then, the solution was again cooled to −78° C., and 27.3 g of B(OMe)$_3$ was added thereto. After stirring at −78° C. for 10 minutes, the solution was stirred at room temperature for 5 hours.

After completion of the reaction, 1N HCl aq. (200 mL) was added, followed by stirring at room temperature for 1 hour. Then, the solution was transferred to a separating funnel, and extracted with ethyl acetate.

After drying with MgSO$_4$, the solution was concentrated and washed with hexane, whereby 17.0 g (yield: 65%) of white solids of benzo[b]naphtho[2,3-d]furan-5-boronic acid were obtained.

(45-2) Synthesis of 5-(3-bromophenyl)benzo[b]naphtho[2,3-d]furan

In the atmosphere of argon, 17.0 g of benzo[b]naphtho[2,3-d]furan-5-boronic acid, 18.4 g of 3-bromoiodobenzene, 1.50 g of tetrakistriphenylphosphine palladium (0), 200 mL of toluene and 100 mL of a 2M aqueous sodium carbonate solution were placed in a flask. The resulting mixture was stirred with heating under reflux for 8 hours. After cooling to room temperature, the reaction solution was extracted with toluene. An aqueous phase was removed. An organic phase was dried with magnesium sulfate and concentrated. Residues were purified by silica gel column chromatography, whereby 21.8 g of 5-(3-bromophenyl)benzo[b]naphtho[2,3-d]furan was obtained.

(45-3) Synthesis of Compound 45

Compound 45 was synthesized in the same manner as in Example 1, except that 5-(3-bromophenyl)benzo[b]naphtho[2,3-d]furan was used instead of intermediate (B). As a result of mass spectroscopy, it was confirmed that this compound was an intended product having an m/e of 596 relative to the molecular weight of 596.21.

Example 46

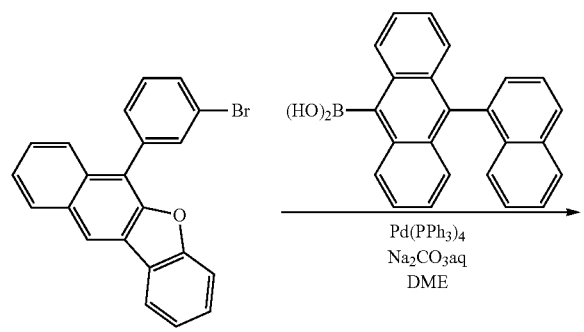

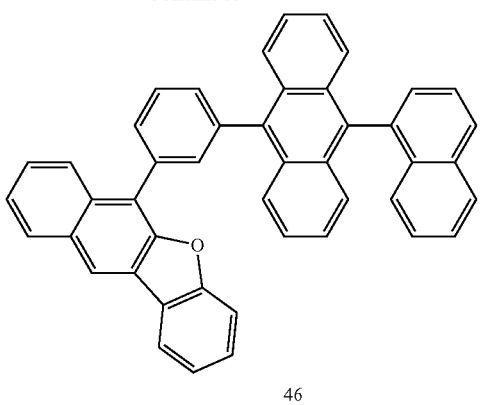

46

Compound 46 was synthesized in the same manner as in Example 1, except that 5-(3-bromophenyl)benzo[b]naphtho[2,3-d]furan was used instead of intermediate (B) and 10-(1-naphthyl)anthracene-9-boronic acid which was synthesized by a known method was used instead of 10-(2-naphthyl)-anthracene-9-boronic acid. As a result of mass spectroscopy, it was confirmed that this compound was an intended product having an m/e of 596 relative to the molecular weight of 596.21.

Example 47

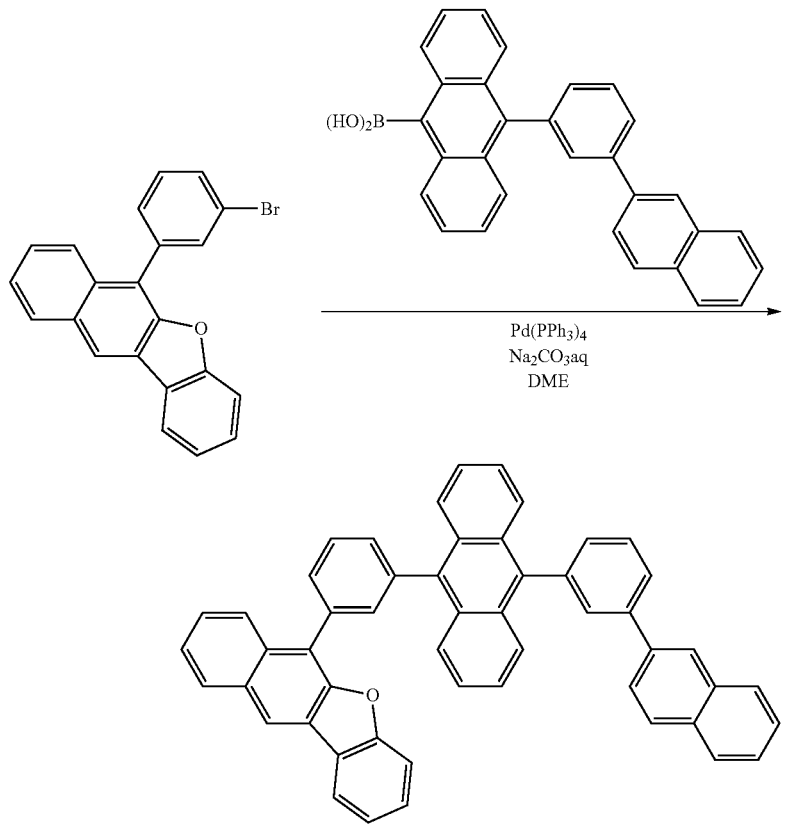

47

Compound 47 was synthesized in the same manner as in Example 1, except that 5-(3-bromophenyl)benzo[b]naphtho[2,3-d]furan was used instead of intermediate (B) and 10-[3-(2-naphthyl)phenyl]anthracene-9-boronic acid which was synthesized by a known method was used instead of 10-(2-naphthyl)-anthracene-9-boronic acid. As a result of mass spectroscopy, it was confirmed that this compound was an intended product having an m/e of 672 relative to the molecular weight of 672.25.

Example 48

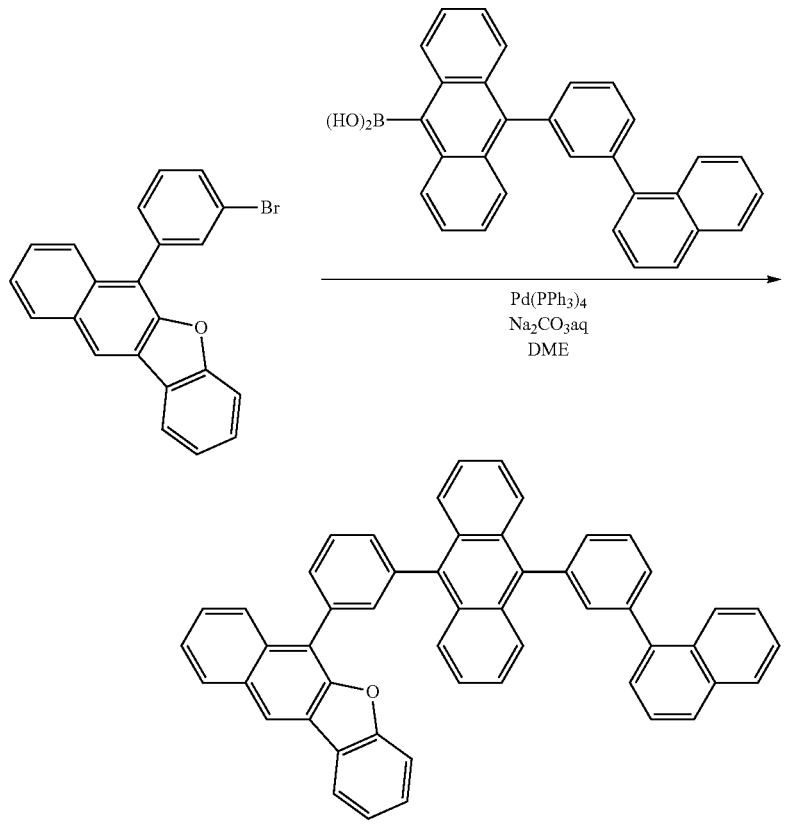

48

Compound 48 was synthesized in the same manner as in Example 1, except that 5-(3-bromophenyl)benzo[b]naphtho[2,3-d]furan was used instead of intermediate (B) and 10-[3-(1-naphthyl)phenyl]anthracene-9-boronic acid which was synthesized by a known method was used instead of 10-(2-naphthyl)-anthracene-9-boronic acid. As a result of mass intended product having an m/e of 672 relative to the molecular weight of 672.25.

Example 49

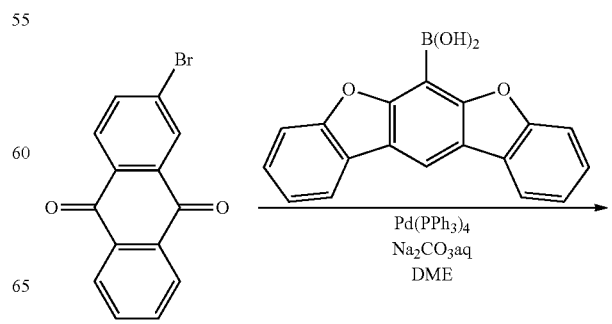

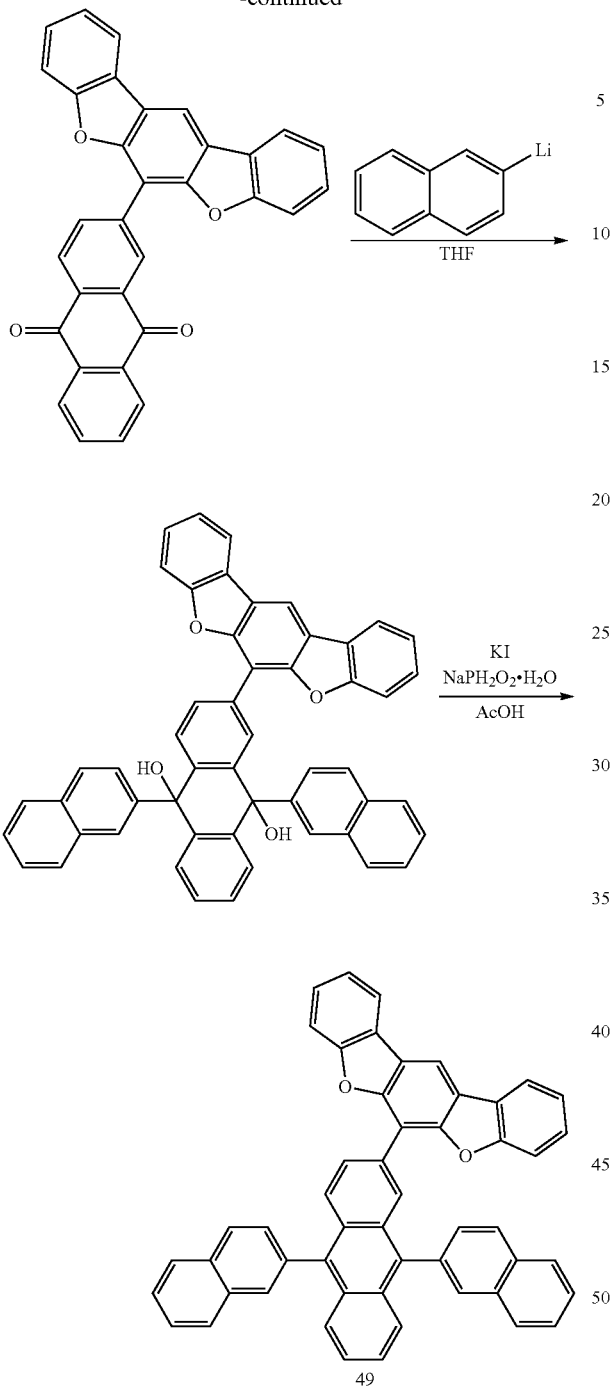

perature, and deposited solids were filtered out. The resulting solids were washed with water and methanol, and recrystallized from toluene, whereby 30.2 g (yield: 65%) of 2-[benzofurano[3,2-b]dibenzofuran-6-yl]-9,10-anthraquinone was obtained.

(49-2) Synthesis of 2-[benzofurano[3,2-b]dibenzofuran-6-yl]-9,10-dihydroxy-9,10-di(2-naphthyl)-9,10-dihydroanthracene In the atmosphere of argon, 28.2 g of 2-bromonaphthalene and 500 mL of dehydrated THF were placed in a flask. The resulting mixture was cooled to −78° C. while stirring. Then, 85 mL (1.60M) of a hexane solution of n-butyllithium was added. While heating to 0° C., the reaction solution was stirred for 2 hours. The reaction solution was again cooled to −78° C. 500 mL of a solution of 30.2 g of 2-[benzofurano[2,3-b]dibenzofuran-6-yl]-9,10-anthraquinone was added dropwise. While heating to room temperature, the reaction solution was stirred for 5 hours. 200 mL of 10% hydrochloric acid was added to the reaction solution, and the resultant was stirred for one hour. Then, the reaction solution was extracted with ethyl acetate. An aqueous phase was removed, and an organic phase was dried with magnesium sulfate. The organic phase was then concentrated, whereby 42.1 g of 2-[benzofurano[3,2-b]dibenzofuran-6-yl]-9,10-dihydroxy-9,10-di(2-naphthyl)-9,10-dihydroanthracene was obtained.

(49-3) Synthesis of Compound 49

42.1 g of 2-[benzofurano[3,2-b]dibenzofuran-6-yl]-9,10-dihydroxy-9,10-di(2-naphthyl)-9,10-dihydroanthracene, 24.3 g of potassium iodide, 7.74 g of sodium phosphinate monohydrate and 500 mL of acetic acid were placed in a flask. The resultant was stirred with heating under reflux for 8 hours. Water was added to the reaction solution, and the resulting mixture was stirred for one hour. The deposited solids were filtered out. The resulting solids were washed with methanol and recrystallized from toluene, whereby 24.0 g of yellow crystals of compound 49 were obtained. As a result of mass spectroscopy, it was confirmed that this compound was an intended product having an m/e of 686 relative to the molecular weight of 686.22.

Example 50

(49-1) Synthesis of 2-[benzofurano[3,2-b]dibenzofuran-6-yl]-9,10-anthraquinone

In the atmosphere of argon, 28.5 g of 2-bromoanthraquinone, 30.2 g of benzofurano[3,2-b]dibenzofuran-6-boronic acid, 2.31 g of tetrakistriphenylphosphine palladium (0), 400 mL of 1,2-dimethoxyethane and 200 mL of a 2M aqueous sodium carbonate solution were placed in a flask. The resulting mixture was stirred with heating under reflux for 8 hours. The resulting mixture was cooled to room tem-

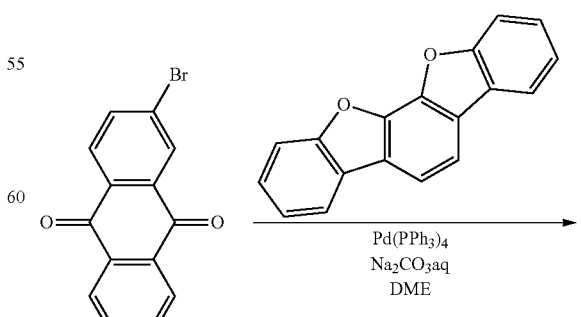

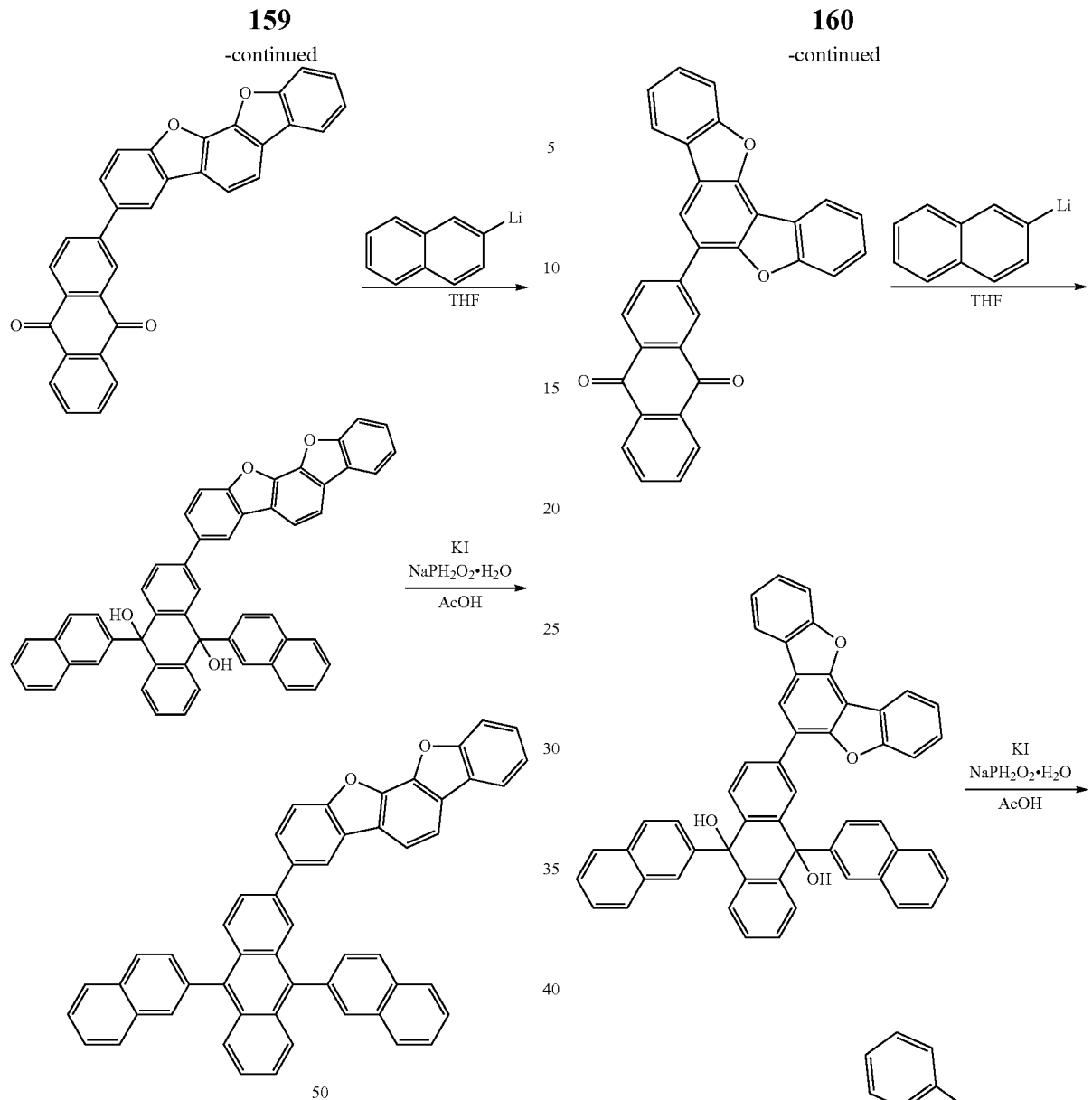

Compound 50 was synthesized in the same manner as in Example 49, except that benzofurano[3,2-c]dibenzofuran-3-boronic acid was used instead of benzofurano[3,2-b]dibenzofuran-6-boronic acid. As a result of mass spectroscopy, it was confirmed that this compound was an intended product having an m/e of 686 relative to the molecular weight of 686.22.

Example 51

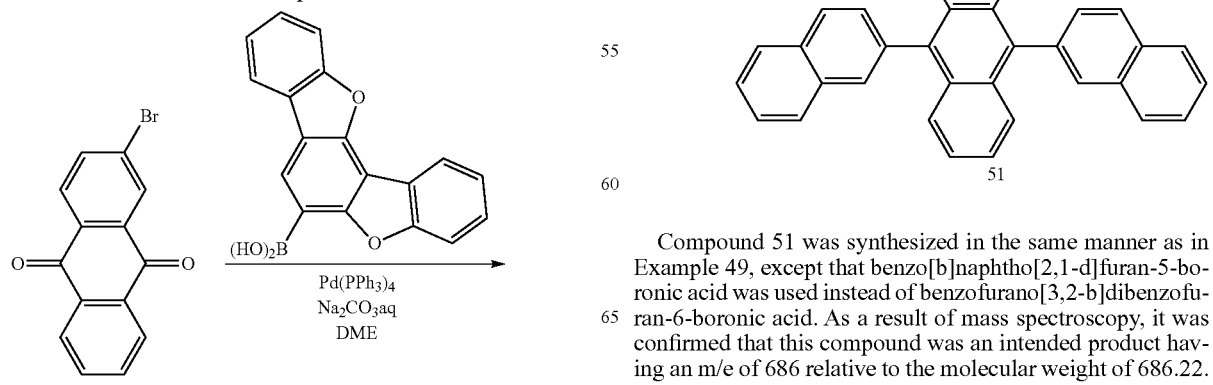

Compound 51 was synthesized in the same manner as in Example 49, except that benzo[b]naphtho[2,1-d]furan-5-boronic acid was used instead of benzofurano[3,2-b]dibenzofuran-6-boronic acid. As a result of mass spectroscopy, it was confirmed that this compound was an intended product having an m/e of 686 relative to the molecular weight of 686.22.

Example 52

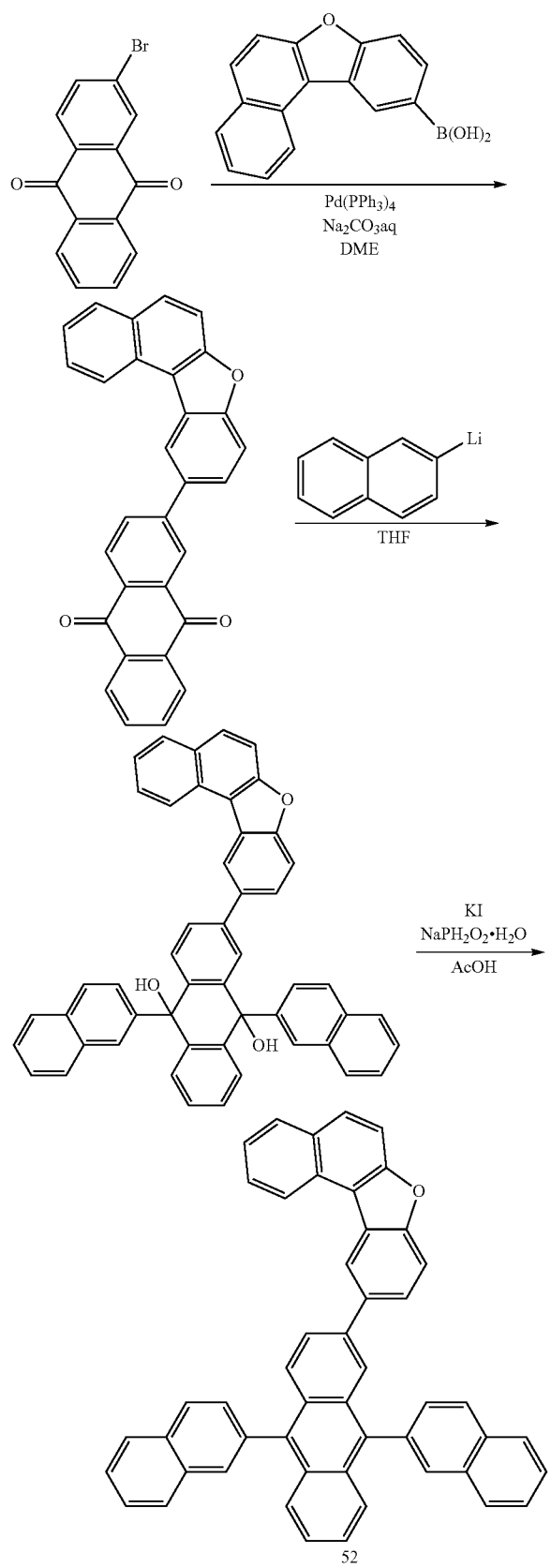

Compound 52 was synthesized in the same manner as in Example 49, except that benzo[b]naphtho[1,2-d]furan-10-boronic acid was used instead of benzofurano[3,2-b]dibenzofuran-6-boronic acid. As a result of mass spectroscopy, it was confirmed that this compound was an intended product having an m/e of 646 relative to the molecular weight of 646.23.

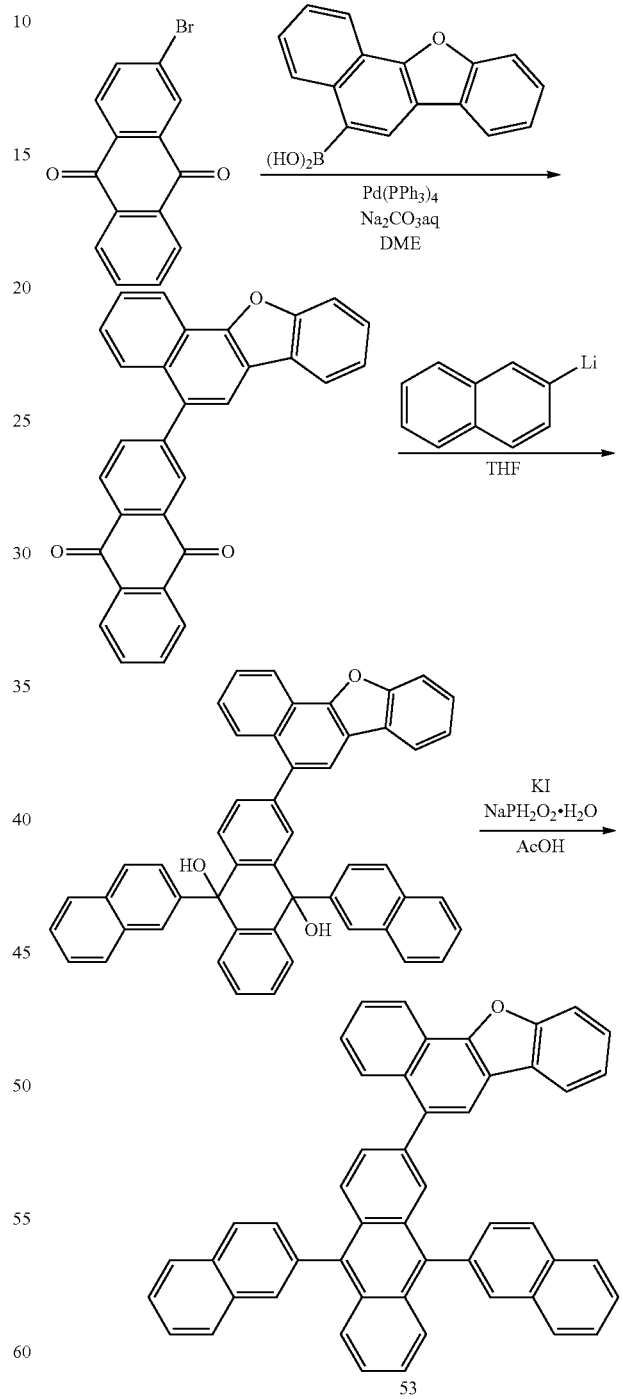

Compound 53 was synthesized in the same manner as in Example 49, except that benzo[b]naphtho[2,1-d]furan-10-boronic acid was used instead of benzofurano[3,2-b]dibenzofuran-6-boronic acid. As a result of mass spectroscopy, it was confirmed that this compound was an intended product having an m/e of 646 relative to the molecular weight of 646.23.

Example 54

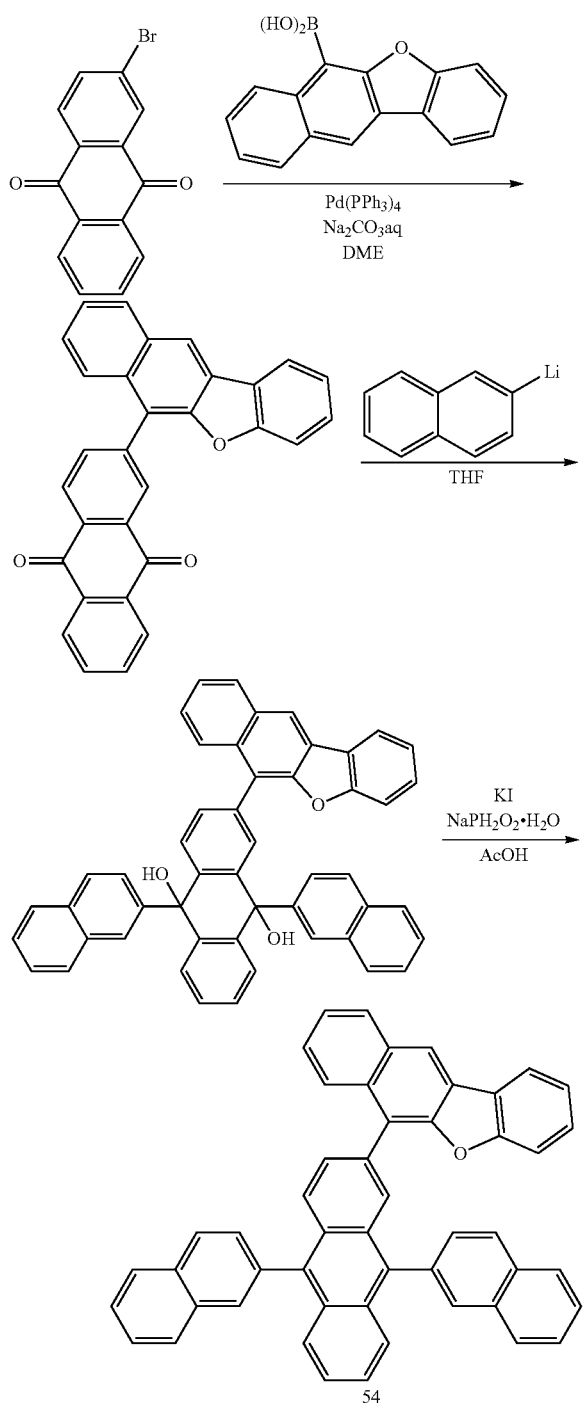

Compound 54 was synthesized in the same manner as in Example 49, except that benzo[b]naphtho[2,3-d]furan-5-boronic acid was used instead of benzofurano[3,2-b]dibenzofuran-6-boronic acid. As a result of mass spectroscopy, it was confirmed that this compound was an intended product having an m/e of 646 relative to the molecular weight of 646.23.

Example 55

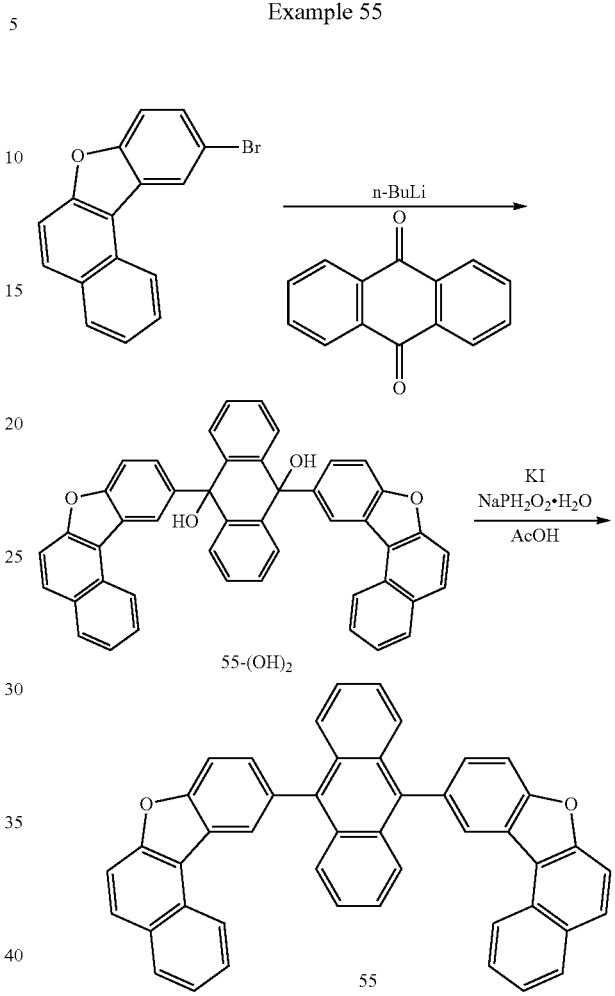

(1) Synthesis of Diol

In the atmosphere of argon, 7.43 g of intermediate (F) and 100 mL of dehydrated THF were placed in a flask. The resulting mixture was cooled to −78° C. while stirring. Then, 20 mL of (1.60M) of a hexane solution of n-butyllithium was added. While heating to 0° C., the reaction solution was stirred for 2 hours. The reaction solution was again cooled to −78° C. 50 mL of a THF solution of 2.08 g of 9,10-anthraquinone was added dropwise. While heating to room temperature, the reaction solution was stirred for 5 hours. 100 mL of 10% hydrochloric acid was added to the reaction solution. The solution was stirred for one hour, and then filtered. The resulting solids were washed with water and toluene, whereby 4.51 g of diol 55-(OH)$_2$ was obtained.

(2) Synthesis of Compound 55

4.51 g of 55-(OH)$_2$, 0.93 g of potassium iodide, 0.30 g of sodium phosphinate monohydrate and 100 mL of acetic acid were placed in a flask. The resulting mixture was stirred with heating under reflux for 8 hours. Water was added to the reaction solution, and stirred for one hour. Deposited solids were filtered out. The resulting solids were washed with methanol, recrystallized from chlorobenzene, whereby 3.20 g of yellow crystals of compound 55 were obtained. As a result of mass spectroscopy, it was confirmed that these crystals were an intended product having an m/e of 610 relative to the molecular weight of 610.19.

Example 56

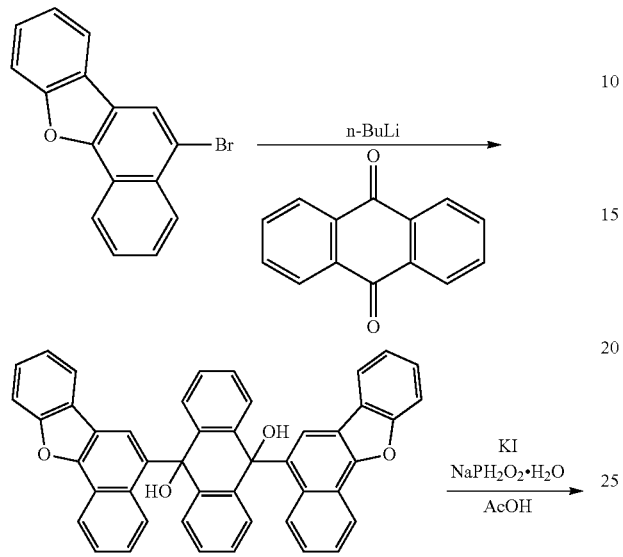

Compound 56 was synthesized in the same manner as in Example 55, except that intermediate (E) was used instead of intermediate (F). As a result of mass spectroscopy, it was confirmed that this compound was an intended product having an m/e of 610 relative to the molecular weight of 610.19.

Example 57

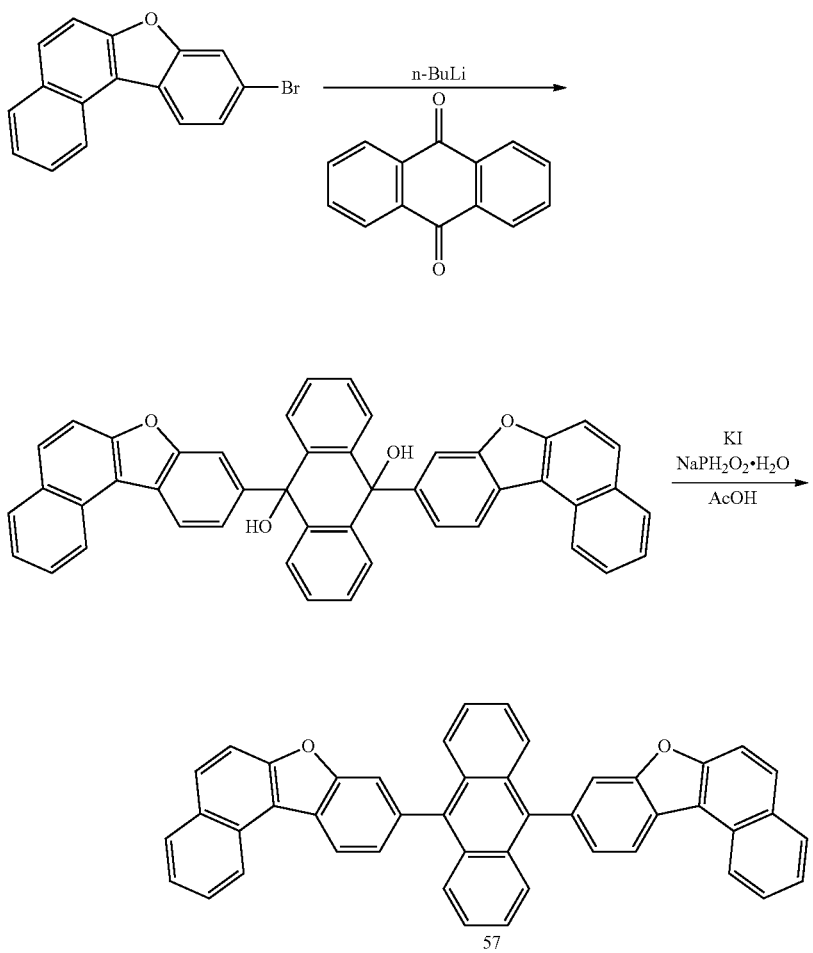

Compound 57 was synthesized in the same manner as in Example 55, except that intermediate (H) was used instead of intermediate (F). As a result of mass spectroscopy, it was confirmed that this compound was an intended product having an m/e of 610 relative to the molecular weight of 610.19.

Example 58

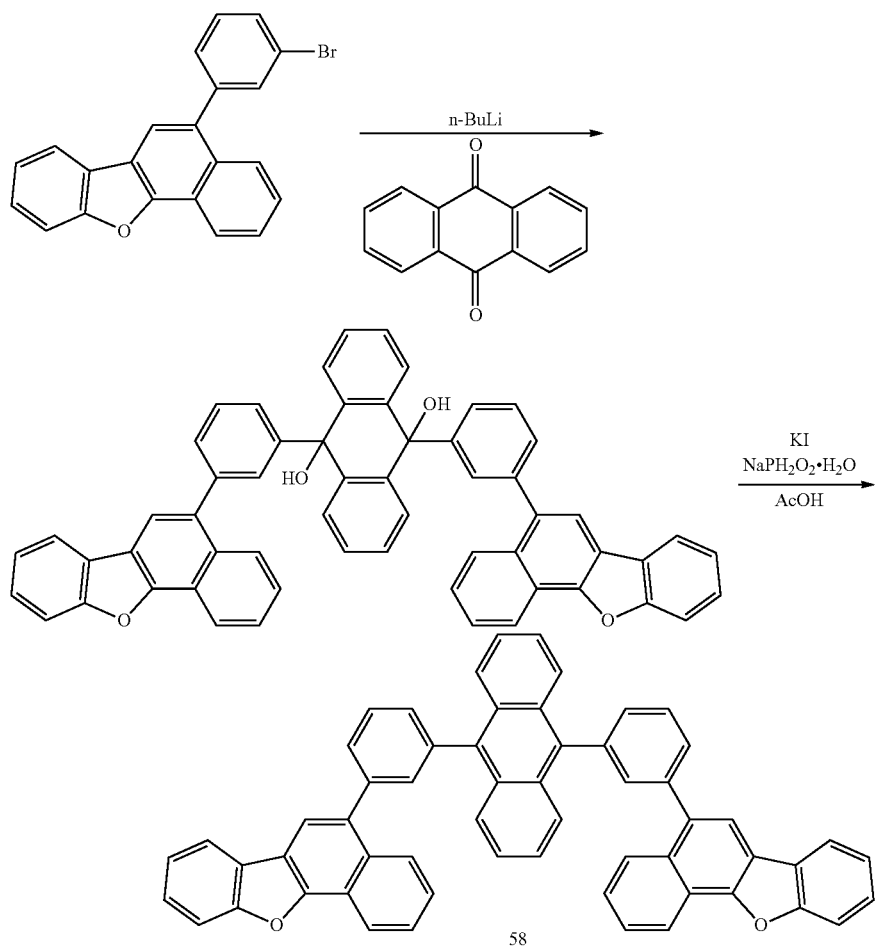

Compound 58 was synthesized in the same manner as in Example 55, except that 5-(3-bromophenyl)benzo[b]naphtho[2,1-d]furan was used instead of intermediate (F). As a result of mass spectroscopy, it was confirmed that this compound was an intended product having an m/e of 762 relative to the molecular weight of 762.26.

Example 59

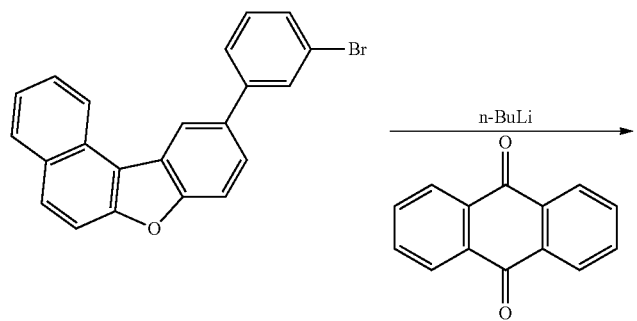

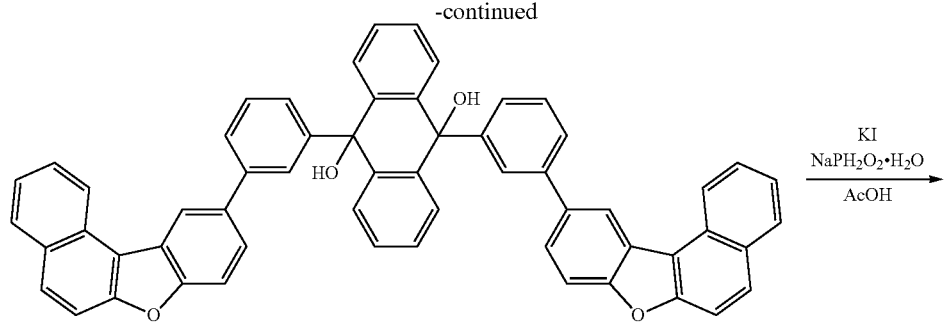
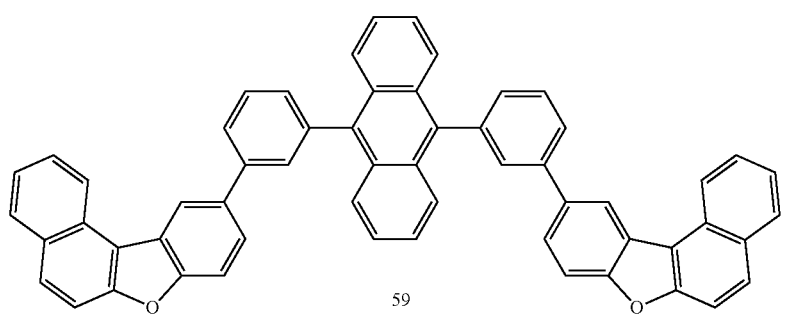
Compound 59 was synthesized in the same manner as in Example 55, except that 10-(3-bromophenyl)benzo[b]naphtho[1,2-d]furan was used instead of intermediate (F). As a result of mass spectroscopy, it was confirmed that this compound was an intended product having an m/e of 762 relative to the molecular weight of 762.26.
Example 60
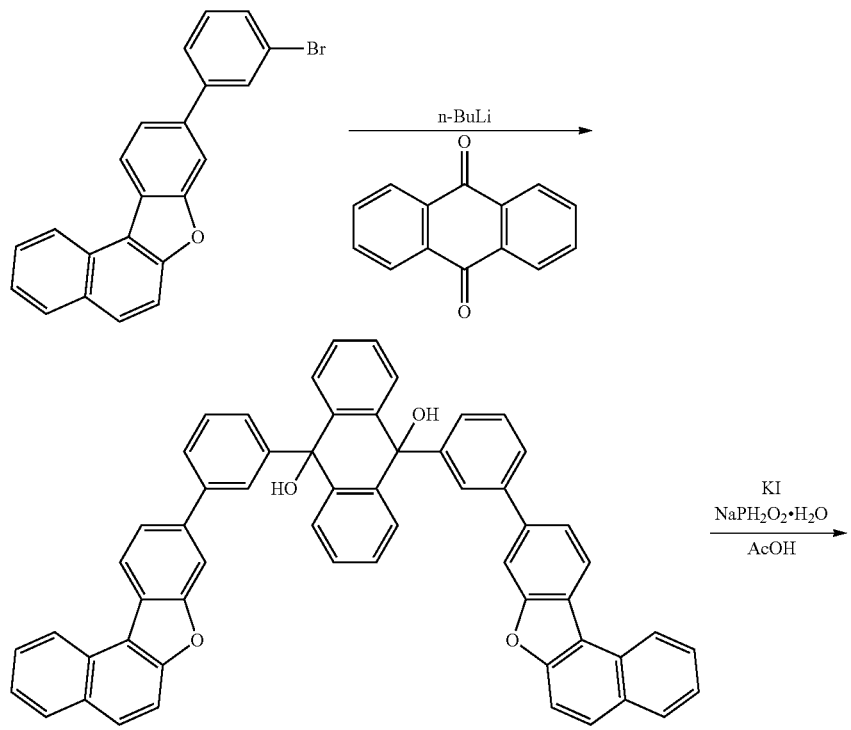

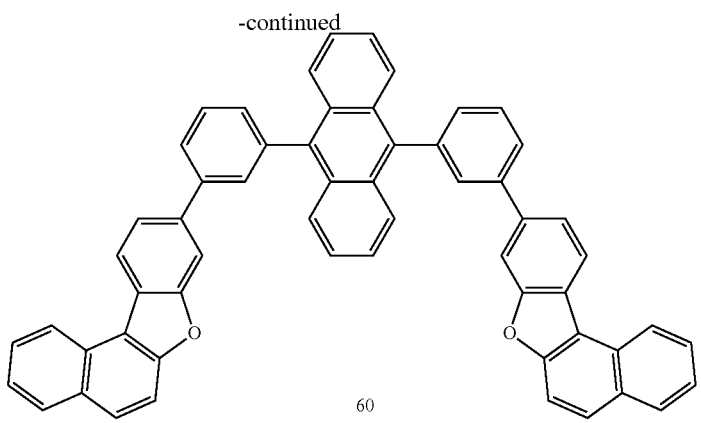

60

Compound 60 was synthesized in the same manner as in Example 55 according to the above-mentioned scheme. As a result of mass spectroscopy, it was confirmed that this compound was an intended product having an m/e of 762 relative to the molecular weight of 762.26.

Example 61

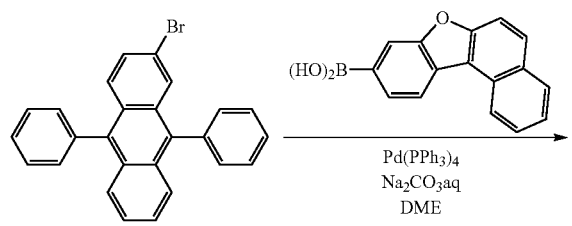

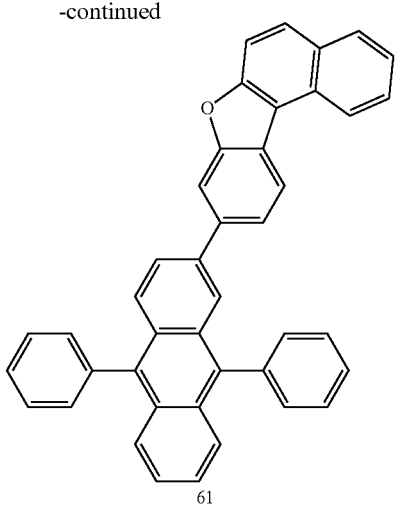

61

In the atmosphere of argon, 4.08 g of 2-bromo-9,10-diphenylanthracene, 3.14 g of a boronic acid derivative of intermediate (H), 0.231 g of tetrakis(triphenylphosphine)palladium (0), 40 mL of 1,2-dimethoxyethane and 20 mL of a 2M aqueous sodium carbonate solution were placed in a flask. The resulting mixture was stirred under reflux for 8 hours. After cooling to room temperature, deposited solids were filtered. The resulting solids were washed with water and methanol, recrystallized from toluene, whereby 4.48 g of yellow solids of compound 61 was obtained. As a result of mass spectroscopy, it was confirmed that this compound was an intended product having an m/e of 546 relative to the molecular weight of 546.20.

Example 62

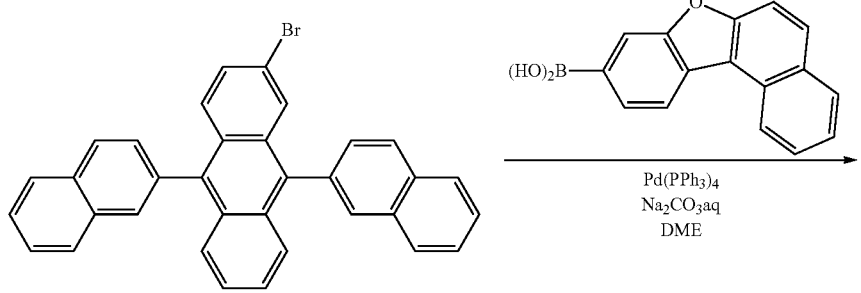

-continued

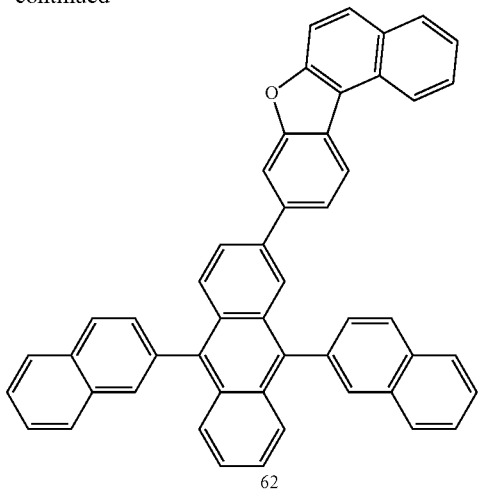
62

Compound 62 was synthesized in the same manner as in Example 61 according to the above-mentioned scheme. As a result of mass spectroscopy, it was confirmed that this compound was an intended product having an m/e of 646 relative to the molecular weight of 646.23.

Example 63

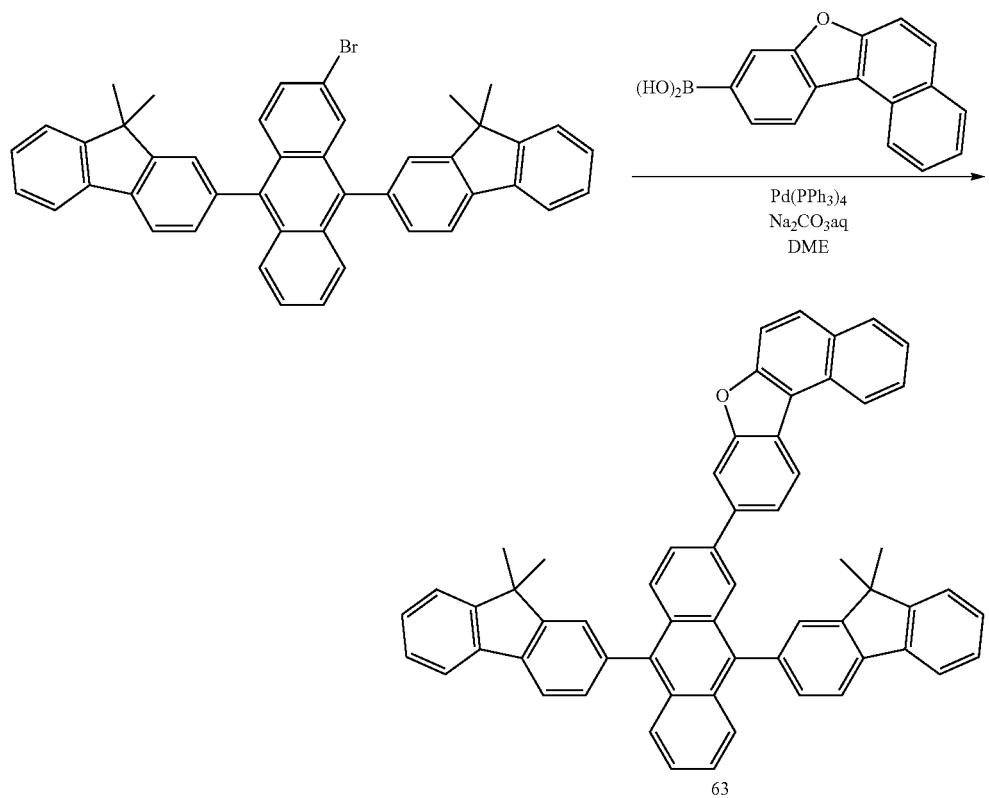

Compound 63 was obtained in the same manner as in Example 61 according to the above-mentioned scheme. As a result of mass spectroscopy, it was confirmed that this compound was an intended product having an m/e of 778 relative to the molecular weight of 778.32.

Example 64
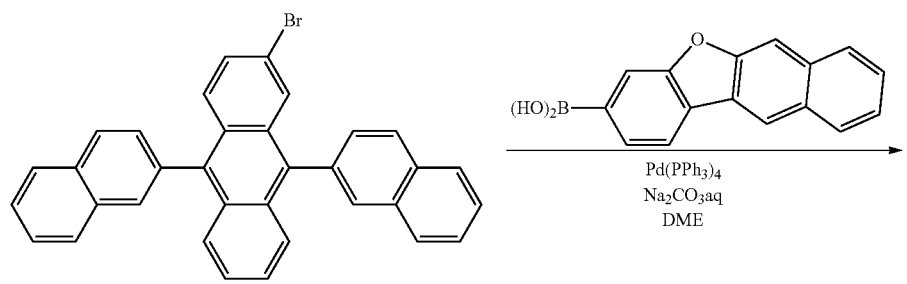
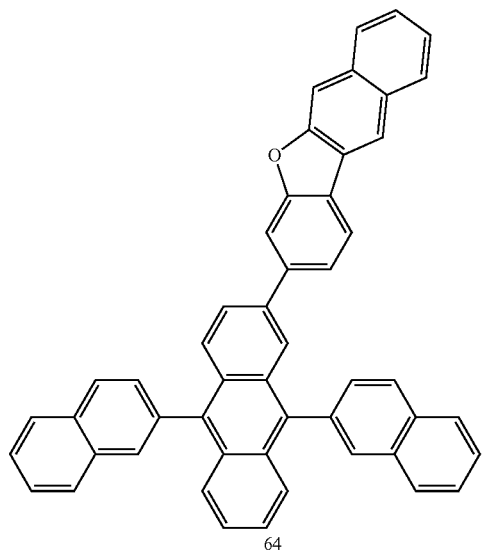
64
Compound 64 was obtained in the same manner as in Example 61 according to the above-mentioned scheme. As a result of mass spectroscopy, it was confirmed that this compound was an intended product having an m/e of 646 relative to the molecular weight of 646.23.
Example 65
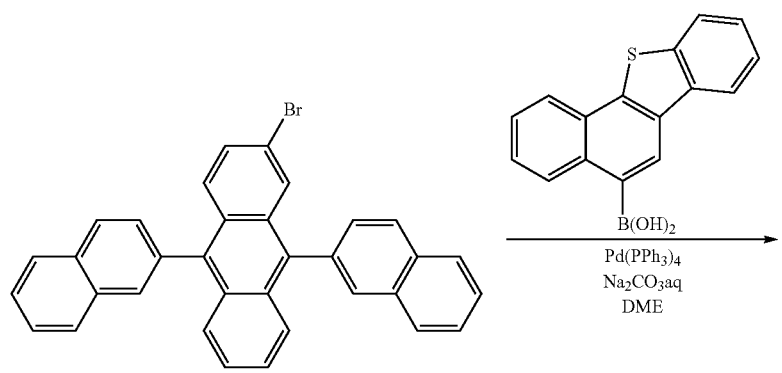

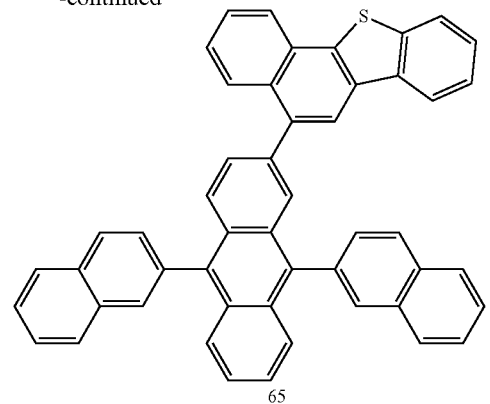

65

Compound 65 was obtained in the same manner as in Example 61 according to the above-mentioned scheme. As a result of mass spectroscopy, it was confirmed that this compound was an intended product having an m/e of 622 relative to the molecular weight of 622.21.

Examples 66 to 119

A glass substrate (GEOMATEC CO., LTD.) of 25 mm×75 mm×1.1 mm with an ITO transparent electrode (anode) was subjected to ultrasonic cleaning with isopropyl alcohol for 5 minutes, and cleaned with ultraviolet rays and ozone for 30 minutes. The resultant glass substrate with transparent electrode lines was mounted on a substrate holder in a vacuum vapor deposition apparatus. First, compound A-1 was formed into a film in a thickness of 60 nm on the surface of the transparent electrode on which the transparent electrode lines were formed so as to cover the transparent electrode. Subsequent to the formation of the A-1 film, compound A-2 was formed thereon into a film in a film thickness of 20 nm.

Further, on this A-2 film, compounds 1 to 54 produced in Examples 1 to 54 and the following dopants D-1 and D-2 were formed in a film thickness of 40 nm in a thickness ratio of 40:2. The resulting films were served as blue-emitting layers in Examples 66 to 113 and green-emitting layers in Examples 114 to 119. The anthracene derivatives and the dopants used in each example were shown in Tables 1 to 3.

On this film, as an electron-transporting layer, ET-1 having the following structure was formed into a 20 nm-thick film by deposition. Thereafter, LiF was formed into a 1 nm-thick film. Metal Al was deposited in a thickness of 150 nm as a metal cathode, thereby fabricating an organic EL device.

The organic EL device thus obtained was allowed to emit light by DC current of 10 mA/m² and the luminous efficiency was measured. In addition, the half life at the initial luminance of 1000 cd/cm² was measured by conducting a DC continuous current test. The results are shown in Tables 1 to 3.

A-1

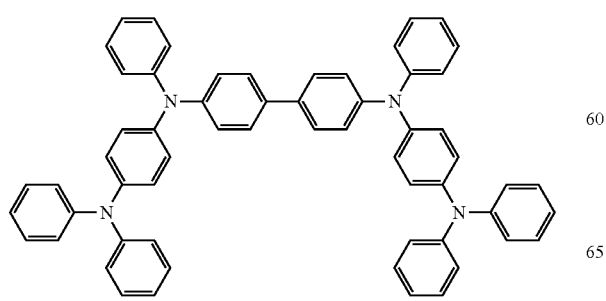

A-2

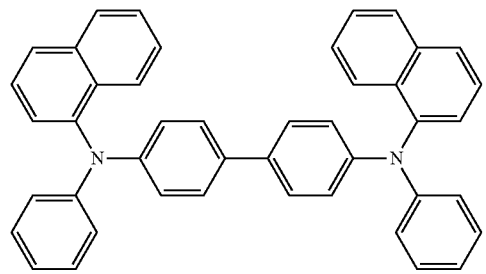

D-1

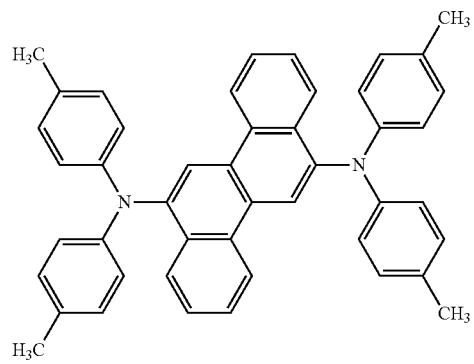

D-2

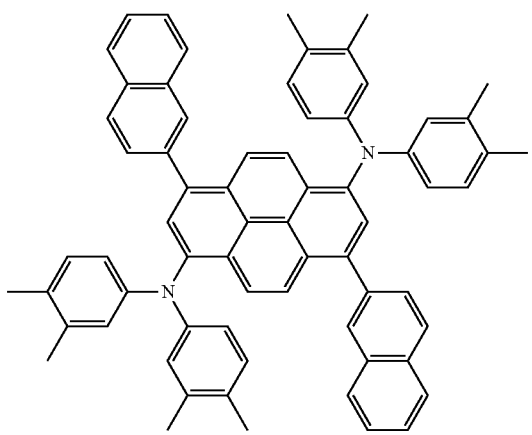

-continued

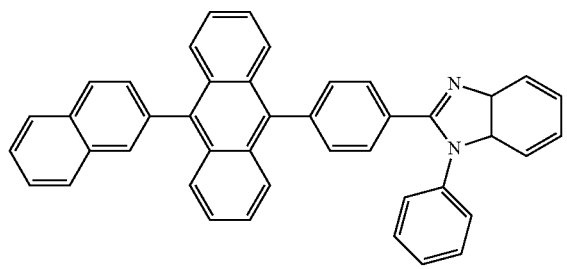

ET-1

Examples 120 to 131

A glass substrate (GEOMATEC CO., LTD.) of 25 mm×75 mm×1.1 mm with an ITO transparent electrode (anode) was subjected to ultrasonic cleaning with isopropyl alcohol for 5 minutes, and cleaned with ultraviolet rays and ozone for 30 minutes. The resultant glass substrate with transparent electrode lines was mounted on a substrate holder in a vacuum vapor deposition apparatus. First, compound A-1 was formed into a film in a thickness of 65 nm on the surface of the transparent electrode on which the transparent electrode lines were formed so as to cover the transparent electrode. Subsequent to the formation of the A-1 film, compound A-2 was formed thereon into a film in a thickness of 65 nm.

Further, on this A-2 film, compounds 52, and 61 to 65 of the invention and D-2 and D-3 were formed in a film thickness of 30 nm in a thickness ratio of 28.5:1.5. The resulting films were served as a green emitting layer. The anthracene derivatives and the dopants used in each example were shown in Table 4.

On this film, as an electron-transporting layer, ET-2 having the following structure was formed into a 20 nm-thick film by deposition. Thereafter, LIE was formed into a 1 nm-thick film. Metal Al was deposited in a thickness of 150 nm as a metal cathode, thereby fabricating an organic EL device.

The organic EL devices thus obtained were evaluated in the same manner as in Examples 66 to 119.

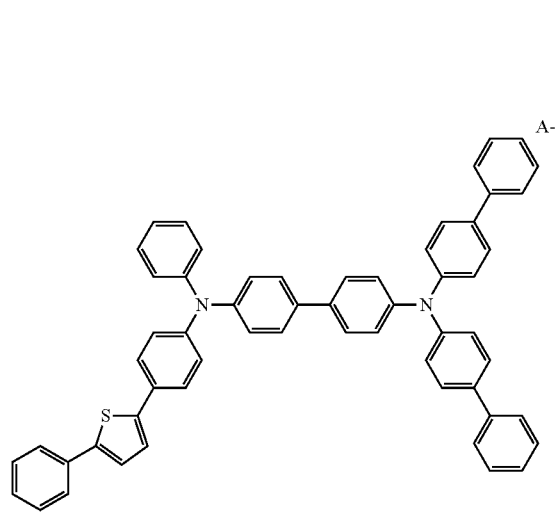

A-3

-continued

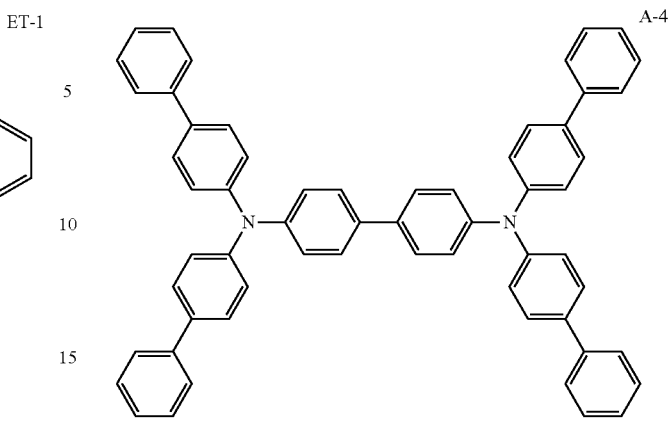

A-4

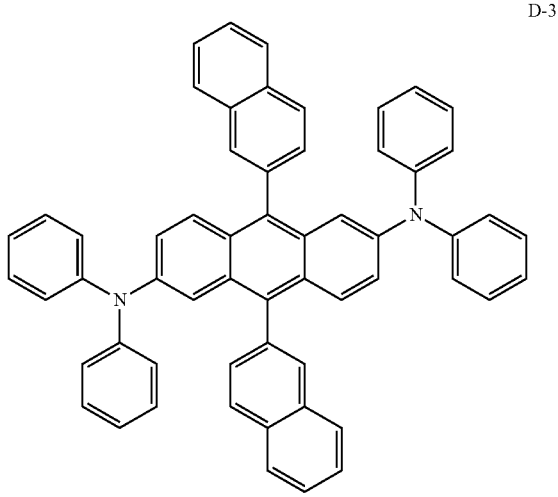

D-3

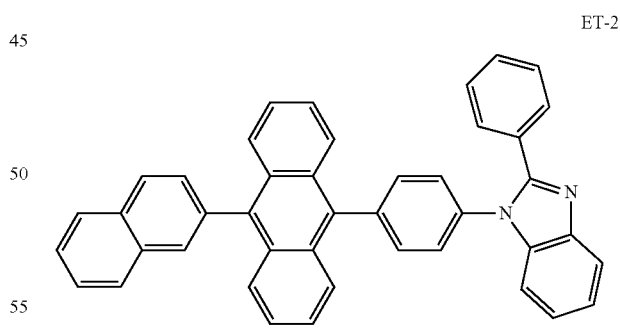

ET-2

Comparative Examples 1 to 4

Organic EL devices were fabricated and evaluated in the same manner as in Example 66, except that the compounds (A) to (D) with the following structures were used instead of compound 1. The anthracene derivatives and the dopants used in each example were shown in Tables 1 to 3. The results are shown in Tables 1 to 3.

(A)
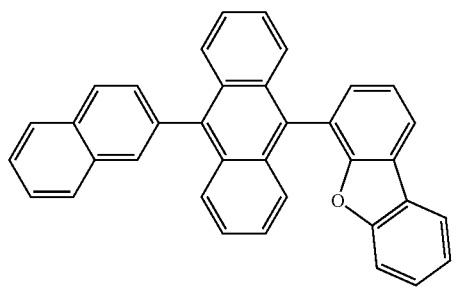

(B)
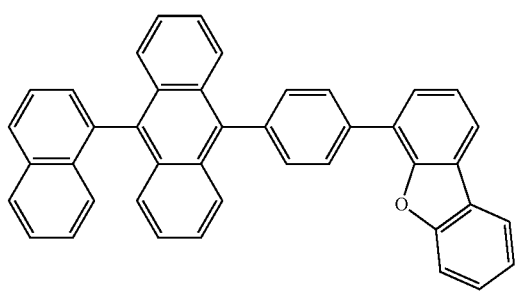

(C)
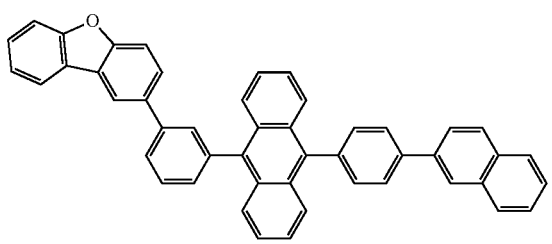

(D)
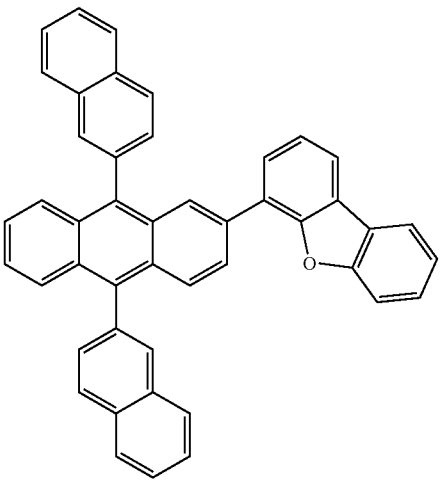

Comparative Example 5

Organic EL devices were fabricated and evaluated in the same manner as in Example 66, except that compound (E) with the following structure was used instead of compound 1 and D-2 was used instead of D-1. The results are shown in Table 3.

(E)
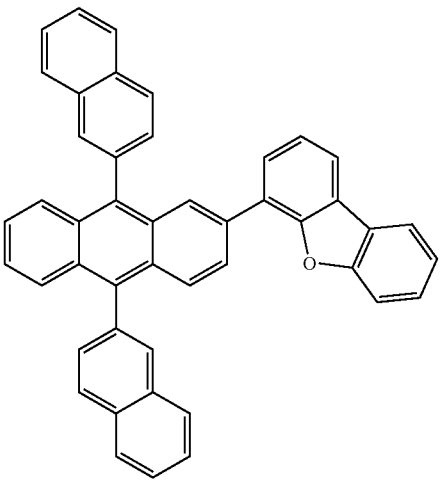

Comparative Example 6

An organic EL device was fabricated and evaluated in the same manner as in Example 120, except that compound (E) with the above structure was used instead of compound 52. The results are shown in Table 4.

Comparative Example 7

An organic EL device was fabricated and evaluated in the same manner as in Comparative Example 6, except that D-3 was used instead of D-2. The results are shown in Table 4.

TABLE 1

| Example No. | Host | Dopant | Luminous efficiency (cd/A) | Lifetime (h) | Emission color |
|---|---|---|---|---|---|
| 66 | Compound 1 | D-1 | 7.1 | 9000 | Blue |
| 67 | Compound 2 | D-1 | 7.3 | 8000 | Blue |
| 68 | Compound 3 | D-1 | 7.1 | 9000 | Blue |
| 69 | Compound 4 | D-1 | 7.1 | 9000 | Blue |
| 70 | Compound 5 | D-1 | 6.9 | 9500 | Blue |
| 71 | Compound 6 | D-1 | 7.0 | 9000 | Blue |
| 72 | Compound 7 | D-1 | 6.9 | 9500 | Blue |
| 73 | Compound 8 | D-1 | 6.9 | 9500 | Blue |
| 74 | Compound 9 | D-1 | 7.4 | 9000 | Blue |
| 75 | Compound 10 | D-1 | 7.5 | 9000 | Blue |
| 76 | Compound 11 | D-1 | 7.4 | 9000 | Blue |
| 77 | Compound 12 | D-1 | 7.4 | 9000 | Blue |
| 78 | Compound 13 | D-1 | 7.4 | 9000 | Blue |
| 79 | Compound 14 | D-1 | 7.5 | 8000 | Blue |
| 80 | Compound 15 | D-1 | 7.4 | 9000 | Blue |
| 81 | Compound 16 | D-1 | 7.4 | 9000 | Blue |
| 82 | Compound 17 | D-1 | 7.0 | 9000 | Blue |
| 83 | Compound 18 | D-1 | 7.1 | 9000 | Blue |
| 84 | Compound 19 | D-1 | 7.0 | 9000 | Blue |
| 85 | Compound 20 | D-1 | 7.0 | 9000 | Blue |
| 86 | Compound 21 | D-1 | 7.2 | 9000 | Blue |
| 87 | Compound 22 | D-1 | 7.5 | 9000 | Blue |
| 88 | Compound 23 | D-1 | 7.3 | 9000 | Blue |
| 89 | Compound 24 | D-1 | 7.2 | 9000 | Blue |
| 90 | Compound 25 | D-1 | 7.2 | 9000 | Blue |

TABLE 2

| Example No. | Host | Dopant | Luminous efficiency (cd/A) | Lifetime (h) | Emission color |
|---|---|---|---|---|---|
| 91 | Compound 26 | D-1 | 7.4 | 9000 | Blue |
| 92 | Compound 27 | D-1 | 7.5 | 8000 | Blue |
| 93 | Compound 28 | D-1 | 7.5 | 8000 | Blue |
| 94 | Compound 29 | D-1 | 7.0 | 9500 | Blue |
| 95 | Compound 30 | D-1 | 7.2 | 9000 | Blue |
| 96 | Compound 31 | D-1 | 7.1 | 9000 | Blue |
| 97 | Compound 32 | D-1 | 7.1 | 9000 | Blue |
| 98 | Compound 33 | D-1 | 7.2 | 9000 | Blue |
| 99 | Compound 34 | D-1 | 7.4 | 9000 | Blue |
| 100 | Compound 35 | D-1 | 7.4 | 9000 | Blue |
| 101 | Compound 36 | D-1 | 7.4 | 9000 | Blue |
| 102 | Compound 37 | D-1 | 7.0 | 8000 | Blue |
| 103 | Compound 38 | D-1 | 7.2 | 8000 | Blue |
| 104 | Compound 39 | D-1 | 7.1 | 8000 | Blue |
| 105 | Compound 40 | D-1 | 7.1 | 8000 | Blue |
| 106 | Compound 41 | D-1 | 7.2 | 9000 | Blue |
| 107 | Compound 42 | D-1 | 7.4 | 9000 | Blue |
| 108 | Compound 43 | D-1 | 7.3 | 9000 | Blue |
| 109 | Compound 44 | D-1 | 7.3 | 9000 | Blue |
| 110 | Compound 45 | D-1 | 7.2 | 9000 | Blue |
| 111 | Compound 46 | D-1 | 7.4 | 9000 | Blue |
| 112 | Compound 47 | D-1 | 7.3 | 9000 | Blue |
| 113 | Compound 48 | D-1 | 7.3 | 9000 | Blue |
| Com. Ex. 1 | Compound (A) | D-1 | 6.6 | 3000 | Blue |
| Com. Ex. 2 | Compound (B) | D-1 | 6.6 | 3000 | Blue |
| Com. Ex. 3 | Compound (C) | D-1 | 6.8 | 5000 | Blue |
| Com. Ex. 4 | Compound (D) | D-1 | 4.0 | 100 | Blue |

TABLE 3

| Example No. | Host | Dopant | Luminous efficiency (cd/A) | Lifetime (h) | Emission color |
|---|---|---|---|---|---|
| 114 | Compound 49 | D-2 | 25 | 40000 | Green |
| 115 | Compound 50 | D-2 | 25 | 40000 | Green |
| 116 | Compound 51 | D-2 | 25 | 40000 | Green |
| 117 | Compound 52 | D-2 | 26 | 40000 | Green |
| 118 | Compound 53 | D-2 | 26 | 40000 | Green |
| 119 | Compound 54 | D-2 | 26 | 40000 | Green |
| Com. Ex. 5 | Compound (E) | D-2 | 22 | 25000 | Green |

TABLE 4

| Example No. | Host | Dopant | Luminous efficiency (cd/A) | Lifetime (h) | Emission color |
|---|---|---|---|---|---|
| 120 | Compound 52 | D-2 | 42 | 10000 | Green |
| 121 | Compound 61 | D-2 | 42 | 80000 | Green |
| 122 | Compound 62 | D-2 | 43 | 100000 | Green |
| 123 | Compound 63 | D-2 | 42 | 90000 | Green |
| 124 | Compound 64 | D-2 | 43 | 100000 | Green |
| 125 | Compound 65 | D-2 | 40 | 60000 | Green |
| 126 | Compound 52 | D-3 | 44 | 50000 | Green |
| 127 | Compound 61 | D-3 | 44 | 40000 | Green |
| 128 | Compound 62 | D-3 | 45 | 50000 | Green |
| 129 | Compound 63 | D-3 | 44 | 45000 | Green |
| 130 | Compound 64 | D-3 | 44 | 50000 | Green |
| 131 | Compound 65 | D-3 | 41 | 30000 | Green |
| Com. Ex. 6 | Compound (E) | D-2 | 36 | 30000 | Green |
| Com. Ex. 7 | Compound (E) | D-3 | 38 | 10000 | Green |

From the above, it can be understood that the luminous efficiency can be improved and the lifetime can be prolonged by using the compound of the invention. By comparing the compounds (A) to (D) used in Comparative Examples 1 to 4, it can be confirmed that an organic EL device using an anthracene derivative having a fused dibenzofuran substituent represented by Z in Examples has a longer life and a high efficiency as compared with an organic EL device using an anthracene derivative having a dibenzofuran substituent.

Further, the derivative having a trisubstituted anthracene derivative having a fused dibenzofuran substituent represented by Z in Examples is suitable as the host material of a green organic EL device. In the green organic EL device, an organic EL device using an anthracene derivative having a fused dibenzofuran substituent or a fused dibenzothiophene substituent represented by Z (Examples 114 to 131) has a longer life and a high efficiency as compared with an organic EL device using an anthracene derivative having a dibenzofuran substituent (Comparative Examples 5 to 7). The reason therefor is assumed to be that, by allowing dibenzofuran or dibenzothiophene to have a fused ring structure, electric charges are more localized, whereby stability to holes and electrons is improved.

INDUSTRIAL APPLICABILITY

The anthracene derivative of the invention is preferably used in an organic EL device. Further, the organic EL device of the invention is useful as a planar emitting body such as a flat panel display of a wall-hanging television or light sources such as backlight of a display or the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. An organic electroluminescence device which comprises between an anode and a cathode one or more organic thin film layers comprising an emitting layer, wherein the emitting layer comprises an anthracene derivative represented by the following formula (1) as a host material and a fused polycyclic amine derivative represented by the following formula (12) as a dopant material:

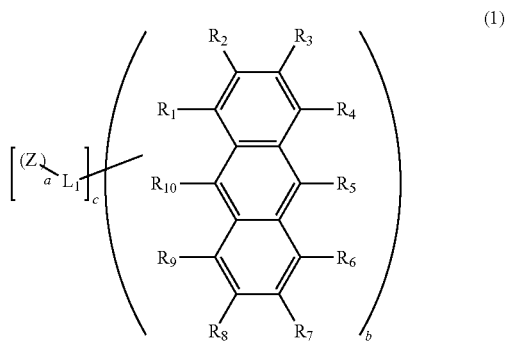

(1)

wherein in the formula (1), at least one of $R_1$ to $R_{10}$ is used for bonding to $L_1$, the one used for bonding to $L_1$ is a single bond, $R_1$ to $R_{10}$ which are not used for bonding to $L_1$ are independently a hydrogen atom, a halogen atom, a hydroxyl group, a cyano group, a substituted or unsubstituted amino group, a substituted or unsubstituted alkyl group having 1 to 20 carbon atoms, a substituted or unsubstituted alkoxy group having 1 to 20 carbon atoms, a substituted or unsubstituted aryloxy group having 6 to 20 ring carbon atoms, a substituted or unsubstituted arylthio group having 6 to 20 ring carbon atoms, a substituted or unsubstituted aryl group having 6 to 50 ring carbon atoms or a substituted or unsubstituted heterocyclic group having 5 to 50 ring atoms;

$L_1$ is a single bond or a linkage group;

a, b and c are independently an integer of 1 to 4; and

Z is represented by any of the following formulas (8) to (10):

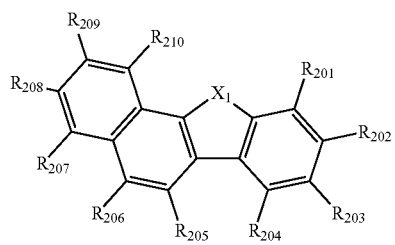
(8)

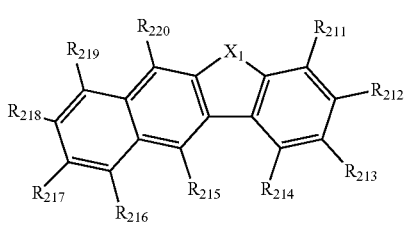
(9)

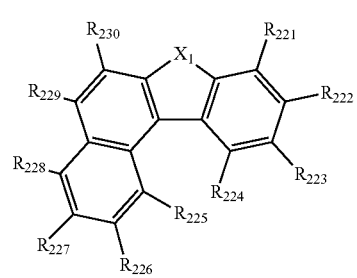
(10)

wherein in the formulas (8) to (10), $R_{201}$ to $R_{210}$, $R_{211}$ to $R_{220}$ and $R_{221}$ to $R_{230}$ are independently a hydrogen atom or a substituent; any one of $R_{201}$ to $R_{210}$, anyone of $R_{211}$ to $R_{220}$ and anyone of $R_{221}$ to $R_{230}$ are used for bonding to $L_1$; and the ones used for bonding to $L_1$ are a single bond; and $X_1$ is an oxygen atom or a sulfur atom:

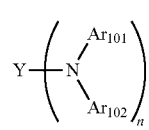
(12)

wherein in the formula (12), Y is a substituted or unsubstituted fused aryl group having 10 to 50 ring carbon atoms; $Ar_{101}$ and $Ar_{102}$ are independently an aryl group having 6 to 50 ring carbon atoms or a substituted or unsubstituted heterocyclic group having 5 to 50 ring atoms; and n is an integer of 1 to 4.

2. The organic electroluminescence device according to claim 1, wherein Z is represented by the formula (9) in the formula (1).

3. The organic electroluminescence device according to claim 2, wherein b is 1 in the formula (1).

4. The organic electroluminescence device according to claim 2, wherein a is 1 or 2 in the formula (1).

5. The organic electroluminescence device according to claim 2, wherein $L_1$ is bonded to $R_5$ and/or $R_{10}$ in the formula (1).

6. The organic electroluminescence device according to claim 2, wherein $L_1$ is bonded to any of $R_1$ to $R_4$ in the formula (1).

7. The organic electroluminescence device according to claim 6, wherein $L_1$ is bonded to $R_2$ in the formula (1).

8. The organic electroluminescence device according to claim 6, wherein $R_5$ in the formula (1) is a group selected from a substituted or unsubstituted aryl group having 6 to 50 ring carbon atoms and a substituted or unsubstituted heterocyclic group having 5 to 50 ring atoms.

9. The organic electroluminescence device according to claim 6, wherein $R_5$ and/or $R_{10}$ in the formula (1) is a group selected from a substituted or unsubstituted aryl group having 6 to 50 ring carbon atoms and a substituted or unsubstituted heterocyclic group having 5 to 50 ring atoms.

10. The organic electroluminescence device according to claim 8, wherein $R_5$ in the formula (1) has a structure represented by the following formula (11):

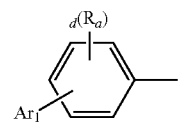
(11)

wherein in the formula (11), $Ar_1$ is a group selected from a substituted or unsubstituted aryl group having 6 to 80 ring carbon atoms and a substituted or unsubstituted heterocyclic group having 5 to 80 ring atoms; Ra is independently a hydrogen atom or a substituent; and d is an integer of 1 to 4.

11. The organic electroluminescence device according to claim 8, wherein $R_5$ in the formula (1) is a substituted or unsubstituted fused aromatic ring having 10 to 30 ring carbon atoms.

12. The organic electroluminescence device according to claim 2, wherein $X_1$ is oxygen atom in the formula (9).

13. The organic electroluminescence device according to claim 1, wherein the dopant material is a fused polycyclic amine derivative which is represented by the following formula (13):

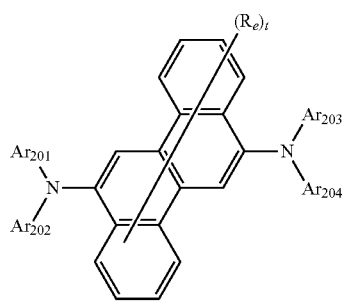
(13)

wherein in the formula (13), $R_e$ is independently a hydrogen atom, a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 50 ring carbon atoms, a substituted or unsubstituted silyl group, a substituted or unsubstituted alkylgermanium group having 1 to 50 carbon atoms or a substituted or unsubstituted arylgermanium group having 6 to 50 ring carbon atoms; t is an integer of 1 to 10; and $Ar_{201}$ to $Ar_{204}$ are independently a substituted or unsubstituted aryl group having 6 to 50 ring carbon atoms or a substituted or unsubstituted heterocyclic group having 5 to 50 ring atoms.

14. The organic electroluminescence device according to claim 1, wherein the dopant material is a fused polycyclic amine derivative which is represented by the following formula (14):

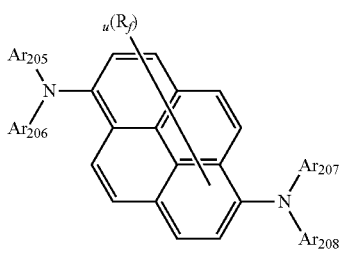

(14)

wherein in the formula (14), $R_f$ is independently a hydrogen atom, a substituted or unsubstituted alkyl group having 1 to 20 carbon atoms, a substituted or unsubstituted alkenyl group having 2 to 50 carbon atoms, a substituted or unsubstituted alkynyl group having 2 to 50 carbon atoms, a substituted or unsubstituted aralkyl group having 1 to 20 carbon atoms, a substituted or unsubstituted cycloalkyl group having 3 to 20 ring carbon atoms, a substituted or unsubstituted alkoxy group having 1 to 20 carbon atoms, a substituted or unsubstituted aryloxy group having 6 to 20 ring carbon atoms, a substituted or unsubstituted aryl group having 6 to 50 ring carbon atoms, a substituted or unsubstituted silyl group, a substituted or unsubstituted alkylgermanium group having 1 to 50 carbon atoms or a substituted or unsubstituted arylgermanium group having 6 to 50 ring carbon atoms; u is an integer of 1 to 8; and $Ar_{205}$ to $Ar_{208}$ are independently a substituted or unsubstituted aryl group having 6 to 50 ring carbon atoms or a substituted or unsubstituted heterocyclic group having 5 to 50 ring atoms.

15. The organic electroluminescence device according to claim 14, wherein $Ar_{205}$ to $Ar_{208}$ in the formula (14) are independently a substituted or unsubstituted phenyl group or a substituted or unsubstituted dibenzofuranyl group.

16. The organic electroluminescence device according to claim 1 which has a hole-injecting layer between the anode and the emitting layer.

17. The organic electroluminescence device according to claim 1, wherein Y in the formula (12) is a substituted or unsubstituted anthryl group, a substituted or unsubstituted pyrenyl group or a substituted or unsubstituted chrysenyl group.

* * * * *